United States Patent
Allen et al.

(10) Patent No.: US 10,730,880 B2
(45) Date of Patent: Aug. 4, 2020

(54) 4,6-SUBSTITUTED-PYRAZOLO[1,5-A]-PYRAZINES AS JANUS KINASE INHIBITORS

(71) Applicants: Array BioPharma Inc., Boulder, CO (US); Celgene Corporation, Summit, NJ (US)

(72) Inventors: Shelley Allen, Boulder, CO (US); Mark Laurence Boys, Boulder, CO (US); Mark J. Chicarelli, Boulder, CO (US); Jay Bradford Fell, Boulder, CO (US); John P. Fischer, Boulder, CO (US); John Gaudino, Boulder, CO (US); Erik James Hicken, Boulder, CO (US); Ronald Jay Hinklin, Boulder, CO (US); Christopher F. Kraser, Boulder, CO (US); Ellen Laird, Boulder, CO (US); John E. Robinson, Boulder, CO (US); Tony P. Tang, Boulder, CO (US); Laurence E. Burgess, Boulder, CO (US); Robert Andrew Rieger, Boulder, CO (US); Jed Pheneger, Boulder, CO (US); Yoshitaka Satoh, Poway, CA (US); Katerina Leftheris, San Diego, CA (US); Raj K. Raheja, Poway, CA (US); Brydon L. Bennett, San Diego, CA (US)

(73) Assignees: Array BioPharma Inc., Boulder, CO (US); Celgene Corporation, Summit, NJ (US)

( * ) Notice: Subject to any disclaimer, the term of this patent is extended or adjusted under 35 U.S.C. 154(b) by 0 days.

(21) Appl. No.: 16/212,493

(22) Filed: Dec. 6, 2018

(65) Prior Publication Data
US 2019/0177328 A1    Jun. 13, 2019

Related U.S. Application Data

(62) Division of application No. 15/532,937, filed as application No. PCT/US2015/064062 on Dec. 4, 2015, now Pat. No. 10,189,845.

(60) Provisional application No. 62/088,068, filed on Dec. 5, 2014.

(51) Int. Cl.
| A61K 45/06 | (2006.01) |
| C07D 487/04 | (2006.01) |
| A61K 31/4985 | (2006.01) |
| A61K 31/5377 | (2006.01) |

(52) U.S. Cl.
CPC ........ *C07D 487/04* (2013.01); *A61K 31/4985* (2013.01); *A61K 31/5377* (2013.01); *A61K 45/06* (2013.01)

(58) Field of Classification Search
CPC ............ A61K 31/4985; A61K 31/5377; A61K 45/06; C07D 487/04
See application file for complete search history.

(56) References Cited

U.S. PATENT DOCUMENTS

| 6,313,129 B1 | 11/2001 | Uckun et al. |
| 10,189,845 B2 | 1/2019 | Allen et al. |
| 2011/0152273 A1 | 6/2011 | Arikawa et al. |
| 2013/0209400 A1 | 8/2013 | Bach Taña et al. |

FOREIGN PATENT DOCUMENTS

| WO | 2009007029 A1 | 1/2009 |
| WO | 2011089400 A1 | 7/2011 |
| WO | 2011101161 A1 | 8/2011 |
| WO | 2011130146 A1 | 10/2011 |
| WO | 2013055645 A1 | 4/2013 |

(Continued)

OTHER PUBLICATIONS

Jaworska et al (2004).*
Atallah, et al., "Prospect of JAK2 inhibitor therapy in myeloproliferative neoplasms", Exp Rev Anticancer Ther 9, 663-670 (2009).
Barosi, et al., "Novel strategies for patients with chronic myeloproliferative disorders", Curr Opin Hematol 16, 129-134 (2009).
Borie, et al., "JAK3 inhibition as a new concept for immune suppression", Curr Opin Investigational Drugs 4, 1297-1303 (2003).

(Continued)

*Primary Examiner* — Shirley V Gembeh
(74) *Attorney, Agent, or Firm* — Viksnins Harris Padys Malen LLP

(57) ABSTRACT

Compounds of Formula I:

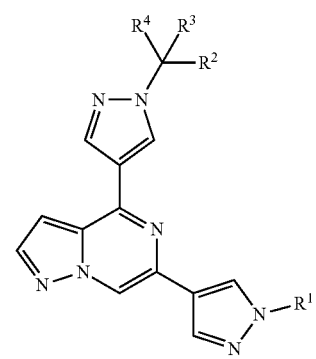

and stereoisomers and pharmaceutically acceptable salts and solvates thereof in which $R^1$, $R^2$, $R^3$ and $R^4$ have the meanings given in the specification, are inhibitors of one or more JAK kinases and are useful in the treatment of JAK kinase-associated diseases and disorders, such as autoimmune diseases, inflammatory diseases, rejection of transplanted organs, tissues and cells, as well as hematologic disorders and malignancies and their co-morbidities.

25 Claims, No Drawings

(56) References Cited

FOREIGN PATENT DOCUMENTS

| WO | WO 2013055645 | * | 4/2013 |
| WO | 2013143663 A1 | | 10/2013 |

OTHER PUBLICATIONS

Haura, et al., "Mechanisms of disease: Insights into the emerging role of signal transducers and activators of transcription in cancer", Nature Clinical Practice Oncology 2(6), 315-324 (2005).

Ihle, et al., "Jak2: normal function and role in hematopoietic disorders", Curr Opin Genet Dev 17, 8-14 (2007).

Menet, et al., "Advances in the Discovery of Selective JAK Inhibitors", Progress in Medicinal Chemistry 52, 153-223 (2013).

Murray, "The JAK-STAT signaling pathway: input and output integration", J Immunol 178(5), 2623-2629 (2007).

Ortmann, et al., "Susceptibility to Collagen-Induced Arthritis: Cytokine-Mediated Regulation", Clinical Immunology 98(1), 109-118 (2001).

O'Sullivan, et al., "Cytokine receptor signaling through the Jak-Stat-Socs pathway in disease", Molecular Immunology 44, 2497-2506 (2007).

Patent Cooperation Treaty, International Searching Authority, Search Report and Written Opinion for PCT/US2015/064062, 13 pages, dated Mar. 3, 2016.

Percy, et al., "The V617F JAK2 mutation and the myeloproliferative disorders", Hematological Oncology 23(3-4), 91-93 (2005).

Santos, et al., "Phase 2 study of CEP-701, an orally available JAK2 inhibitor, in patients with primary or post-polycythemia vera/essential thrombocythemia myelofibrosis", Blood 115(6), 1131-1136 (2010).

Sayyah, et al., "Jak2 Inhibitors: Rationale and Role as Therapeutic Agents in Hematologic Malignancies", Curr Oncol Rep 11(2), 117-124 (2009).

Shaw, et al., "A natural mutation in the Tyk2 pseudokinase domain underlies altered susceptibility of B10.Q/J mice to infection and autoimmunity", PNAS 100(20), 11594-11599 (2003).

Vainchecker, et al., "JAKs in pathology: role of Janus kinases in hematopoietic malignancies and immunodeficiencies", Semin Cell Dev Biol 9(4), 385-393 (2008).

Verma, et al., "Jak family of kinases in cancer", Cancer and Metastasis Reviews 22, 423-434 (2003).

Watford, et al., "Signaling by IL-12 and IL-23 and the immunoregulatory roles of STAT4", Immunol Rev 202, 139-156 (2004).

* cited by examiner

4,6-SUBSTITUTED-PYRAZOLO[1,5-A]PYRAZINES AS JANUS KINASE INHIBITORS

CROSS-REFERENCE TO RELATED APPLICATION(S)

This application is a Division of U.S. patent application Ser. No. 15/532,937, filed Jun. 2, 2017, which is a 35 U.S.C § 371 application of International Patent Application No. PCT/US2015/064062, filed Dec. 4, 2015, which claims the benefit of Provisional Patent Application No. 62/088,068 filed Dec. 5, 2014. The entire content of the applications referenced above are hereby incorporated by reference herein.

The present invention relates to novel compounds, to pharmaceutical compositions comprising the compounds, to processes for making the compounds, and to the use of the compounds in therapy. More particularly, it relates to 4,6-substituted-pyrazolo[1,5-a]pyrazine compounds which are inhibitors of JAK kinases. In particular, the compounds are inhibitors of Tyk2, JAK1, JAK2, and/or JAK3, and are useful in the treatment of JAK kinase-associated diseases such as autoimmune diseases, inflammatory diseases, organ, tissue and cell transplant rejection, and hematological disorders and malignancies.

The members of the Janus kinase (JAK) family of non-receptor, intracellular tyrosine kinases are components of cytokine signal transduction. Four family members have been identified: JAK1, JAK2, JAK3 and Tyk2. The JAKs play a key role in the intracellular signaling mediated through Type I and Type II cytokine receptors. Specific cytokine receptor chains are associated with particular JAK kinases (reviewed in O'Sullivan et al., Mol. Immunol., 2007, 44:2497; Murray J., Immunol., 2007, 178:2623). Upon binding of cytokines to their receptors, JAKs are activated and phosphorylate the receptors, creating docking sites for other signaling molecules, in particular members of the signal transducer and activator of transcription (STAT) family. Upon phosphorylation, STATs dimerize, translocate to the nucleus and activate expression of genes involved in development, growth, differentiation, and maintenance of a variety of cell types. The cytokine-induced responses mediated by JAK kinases are important in host defense and, when dysregulated, play a role in pathogenesis of immune or inflammatory diseases, immune deficiencies, and malignancy (O'Sullivan et al., Mol. Immunol., 2007, 44:2497). Elevated or decreased levels of JAK/STAT-utilizing cytokines have been implicated in a number of disease states. In addition, mutations or polymorphisms in Type 1 and II cytokine receptors, JAK kinases, STAT proteins, and JAK/STAT regulatory proteins such as phosphotyrosine phosphatases, SOCS proteins, PIAS proteins have been reported in a variety of diseases. When dysregulated, JAK-mediated responses can positively or negatively affect cells leading to over-activation and malignancy or immune and hematopoietic deficiencies, respectively, and suggests the utility for use of inhibitors of JAK kinases. The JAK/STAT signaling pathway is involved in a variety of hyperproliferative and cancer-related processes including cell-cycle progression, apoptosis, angiogenesis, invasion, metastasis and evasion of the immune system (Haura et al., Nature Clinical Practice Oncology, 2005, 2(6), 315-324; Verna et al., Cancer and Metastasis Reviews, 2003, 22, 423-434). In addition, the JAK/STAT signaling pathway is important in the genesis and differentiation of hematopoietic cells and regulating both pro- and anti-inflammatory and immune responses (O'Sullivan et al., Molecular Immunology 2007, 44:2497).

Because cytokines utilize different patterns of JAK kinases (O'Sullivan et al., Mol. Immunol., 2007, 44:2497; Murray J., Immunol., 2007, 178:2623), there may be utility for antagonists of JAK kinases with differing intra-family selectivity profiles in diseases associated with particular cytokines or in diseases associated with mutations or polymorphisms in the JAK/STAT pathways.

JAK3 deficient mice exhibit a severe combined immunodeficiency syndrome (scid). The failure of lymphocyte development in an otherwise healthy animal supports the utility of targeting JAK3 for diseases associated with lymphocyte activation.

In addition to the scid phenotype of the JAK3-deficient mice, the elevated expression of cytokines which signal through the JAK3-associated gamma common chain in inflammatory and immune responses suggests that inhibitors of JAK3 could impede T-cell activation and prevent rejection of grafts following transplant surgery, or to provide therapeutic benefit to patients suffering autoimmune or inflammatory disorders (reviewed in O'Sullivan et al., Mol. Immunol., 2007, 44:2497; Murray J., Immunol., 2007, 178: 2623).

Inhibitors of the tyrosine kinase JAK3 have been described to be useful as immunosuppressants (see, for example, U.S. Pat. No. 6,313,129; Borie et al., Curr. Opin. Investigational Drugs, 2003, 4:1297). JAK3 has also been shown to play a role in mast-cell mediated allergic reactions and inflammatory diseases.

JAK1-deficient and/or JAK2-deficient animals are not viable. Studies have identified a high prevalence of an acquired activating JAK2 mutation (JAK2V617F) in myleoproliferative disorders such as polycythemia vera, essential thrombocythemia and idiopathic myelofibrosis and to a lesser extent in several other diseases. The mutant JAK2 protein is able to activate downstream signaling in the absence of cytokine stimulation, resulting in autonomous growth and/or hypersensitivity to cytokines and is believed to play a role in driving these diseases (Percy, M. J. and McMullin, M. F., Hematological Oncology, 2005, 23(3-4), 91-93). Additional mutations or translocations resulting dysregulated JAK2 function have been described in other malignancies (Ihle J. N. and Gilliland D. G., Curr. Opin. Genet. Dev., 2007, 17:8; Sayyah J. and Sayeski P. P., Curr. Oncol. Rep., 2009, 11:117). Inhibitors of JAK2 have been described to be useful in myeloproliferative diseases (Santos et al., Blood, 2010, 115:1131; Barosi G. and Rosti V., Curr. Opin. Hematol., 2009, 16:129, Atallah E. and Versotvsek S., 2009 Exp. Rev. Anticancer Ther. 9:663). More rarely, mutations in JAK1 and JAK3 have been reported in hematologic malignancies (Vainchecker et al., Semin. Cell Dev. Biol., 2008, Aug. 1; 9(4):385-93). JAK family kinase inhibitors may be useful in these settings (Sayyah J. and Sayeski P. P., Curr. Oncol. Rep., 2009, 11:117). In addition, over expression of cytokines which utilize JAK2 for signaling have been implicated in disease states (JAK2 utilizing cytokines are reviewed in O'Sullivan et al., Mol. Immunol., 2007, 44:2497; Murray J., Immunol., 2007, 178:2623).

JAK1 has been reported to signal with other JAK1 molecules or in collaboration with JAK2 or JAK3 depending on the cytokine input (JAK1 utilizing cytokines reviewed in O'Sullivan 2007, Murray 2007). Elevated levels of cytokines which signal through JAK1 have been implicated in a number of immune and inflammatory diseases. JAK1 or JAK family kinase antagonists may be useful for modulating or treating in such diseases.

Tyk2-deficient animals exhibit blunted immune responses to several types of pathogens and are less susceptible to some autoimmune diseases. This phenotype supports the utility of inhibiting Tyk2 in particular disease settings. Particularly, targeting Tyk2 appears to be a promising strategy for the treatment of IL-12-, IL-23- or Type 1 IFN-mediated diseases or diseases. These include but are not limited to rheumatoid arthritis, multiple sclerosis, lupus, psoriasis, psoriatic arthritis, inflammatory bowel disease, uveitis, and sarcoidosis (Shaw, M. et al., Proc. Natl. Acad. Sci. USA, 2003, 100, 11594-11599; Ortmann, R. A., and Shevach, E. M., Clin. Immunol., 2001, 98, 109-118; Watford et al., Immunol. Rev., 2004, 202:139).

International Publication Nos. WO 2011/130146 (Array BioPharma Inc.) and WO 2013/055645 (Array BioPharma Inc.) disclose 5,7-substituted imidazo[1,2-c]pyrimidines as inhibitors of one or more JAK kinases useful in the treatment of autoimmune diseases, inflammatory diseases, rejection of transplanted organs, tissues and cells, as well as hematologic disorders and malignancies and their co-morbidities.

There remains a need for compounds and methods for the treatment of autoimmune diseases, inflammatory diseases, organ, tissue and cell transplant rejection, and hematologic disorders and malignancies.

SUMMARY OF THE INVENTION

It has now been found that 4,6-substituted-pyrazolo[1,5-a]pyrazine compounds are inhibitors of one or more JAK kinases and are useful for treating JAK kinase-associated diseases and disorders, including autoimmune diseases, inflammatory diseases, rejection of transplanted organs, tissues and cells, as well as hematologic disorders and malignancies and their co-morbidities.

More specifically, provided herein are compounds of General Formula I:

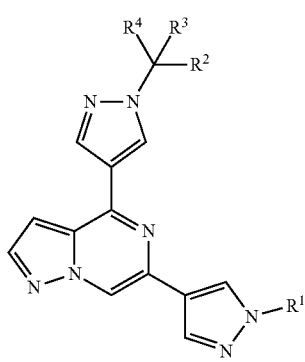

and stereoisomers and pharmaceutically acceptable salts and solvates thereof, wherein $R^1$, $R^2$, $R^3$ and $R^4$ are as defined herein.

Also provided herein are pharmaceutical compositions comprising a compound of the present invention or a pharmaceutically acceptable salt or solvate thereof, and a pharmaceutically acceptable carrier.

Also provided herein are methods of treating a disease or disorder modulated by (i.e., associated with) one or more JAK kinases, comprising administering to a subject in need of such treatment a therapeutically effective amount of a compound of General Formula I or a pharmaceutically acceptable salt or solvate thereof, or a pharmaceutical composition thereof as defined herein.

In one embodiment, provided herein is a method of treating an autoimmune disease or inflammatory disease, comprising administering to a subject in need of such treatment a therapeutically effective amount of a compound of General Formula I or a pharmaceutically acceptable salt or solvate thereof, or a pharmaceutical composition thereof as defined herein.

In one embodiment, provided herein is a method of preventing an autoimmune disease or inflammatory disease, comprising administering to a subject in need of such treatment a therapeutically effective amount of a compound of General Formula I or a pharmaceutically acceptable salt or solvate thereof, or a pharmaceutical composition thereof as defined herein.

In one embodiment, provided herein is a method of treating organ, tissue or cell transplant rejection, comprising administering to a subject in need of such treatment a therapeutically effective amount of a compound of General Formula I or a pharmaceutically acceptable salt or solvate thereof, or a pharmaceutical composition thereof as defined herein.

In one embodiment, provided herein is a method of preventing organ, tissue and cell transplant rejection, comprising administering to a subject in need of such treatment a therapeutically effective amount of a compound of General Formula I or a pharmaceutically acceptable salt or solvate thereof, or a pharmaceutical composition thereof as defined herein.

In another embodiment, provided herein is a method of treating hematological disorders and malignancies, comprising administering to a subject in need of such treatment a therapeutically effective amount of a compound of General Formula I or a pharmaceutically acceptable salt or solvate thereof, or a pharmaceutical composition thereof as defined herein.

Also provided herein are compounds of General Formula I, or pharmaceutically acceptable salts or solvates thereof, or pharmaceutical compositions thereof, as defined herein, for use in therapy, e.g., for use in the treatment of a JAK kinase-associated disease or disorder.

Also provided herein are compounds of General Formula I, or pharmaceutically acceptable salts or solvates thereof, or pharmaceutical compositions thereof, as defined herein, for use in the treatment of autoimmune diseases and inflammatory diseases.

Also provided herein are compounds of General Formula I, or pharmaceutically acceptable salts or solvates thereof, or pharmaceutical compositions thereof, as defined herein, for use in the treatment of organ, tissue and cell transplant rejection.

Also provided herein are compounds of General Formula I, or pharmaceutically acceptable salts or solvates thereof, or pharmaceutical compositions thereof, as defined herein, for use in the treatment of hematological disorders and malignancies.

Also provided herein is the use of a compound of General Formula I or a pharmaceutically acceptable salt or solvate thereof, or a pharmaceutical composition thereof, in the manufacture of a medicament for the treatment of a JAK kinase-associated disease or disorder, such as autoimmune diseases, inflammatory diseases, and organ, tissue and cell transplant rejection, and hematological disorders and malignancies.

Also provided herein is the use of a compound of General Formula I or a pharmaceutically acceptable salt or solvate thereof, or a pharmaceutical composition thereof, in the manufacture of a medicament for the treatment of hematological disorders and malignancies.

Also provided herein is a method for inhibiting JAK kinase activity in a cell, the method comprising contacting the cell with a compound of Formula I or pharmaceutically acceptable salt or solvate thereof, or a pharmaceutical composition thereof, wherein said contacting is in vitro or in vivo. In one embodiment, the cell is a mammalian cell.

Also provided herein is a pharmaceutical combination for treating a JAK kinase-associated disease or disorder in a subject in need thereof, which comprises (a) a compound of General Formula I or a pharmaceutically acceptable salt or solvate thereof, (b) an additional therapeutic agent, and (c) optionally at least one pharmaceutically acceptable carrier, for simultaneous, separate or sequential use for the treatment of a JAK kinase-associated disorder, wherein the amounts of the compound of General Formula I or pharmaceutically acceptable salt or solvate thereof and the additional therapeutic agent are together effective in treating the JAK kinase-associated disease or disorder. Also provided herein is a pharmaceutical composition comprising such a combination. Also provided herein is the use of such a combination for the preparation of a medicament for the treatment of a JAK kinase-associated disorder. Also provided herein is a commercial package or product comprising such a combination for simultaneous, separate or sequential use.

Also provided herein are intermediates for preparing compounds of General Formula I.

Also provided herein are methods of preparing, methods of separation, and methods of purification of the compounds of this invention.

DETAILED DESCRIPTION OF THE INVENTION

Provided herein are compounds, and pharmaceutical compositions thereof, which are useful in the treatment of JAK kinase-associated diseases or disorders, for example autoimmune diseases, inflammatory diseases, organ, tissue and cell transplant rejection, and hematological disorders and malignancies.

Accordingly, one embodiment of this invention provides a compound of the general Formula I

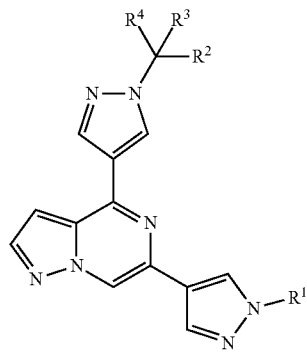

I or a stereoisomer or pharmaceutically acceptable salt or solvate thereof, wherein:
$R^1$ is hydroxy(1-6C)alkyl, $HOCH_2$(cyclopropylidine)$CH_2$—, (1-4C alkoxy)(1-6C)hydroxyalkyl, (hydroxy)trifluoro(1-6C)alkyl, dihydroxy(2-6C)alkyl, $H_2N$(3-6C)hydroxyalkyl, (1-3C alkyl)NH(3-6C)hydroxyalkyl, (1-3C alkyl)$_2$N(3-6C)hydroxyalkyl, $H_2N$(1-4C alkoxy)(3-6C)alkyl, $Cyc^1(CH_2)_m$—, hetCyc$^1$, hetCyc$^2CH_2$—, $R^aR^bNC(=O)CH_2$—, hetCyc$^{3a}$(1-3C)alkyl, hetCyc$^{3b}$(2-3C)hydroxyalkyl, $R^cR^dN$(2-3C)alkyl, (1-3C alkyl)$_2NSO_2$(2-3C) alkyl, hetCyc$^4$, (1-6C)alkyl or $CH_3SO_2$(1-6C)alkyl;

$Cyc^1$ is a 4-6 membered cycloalkyl substituted with 1-2 substituents independently selected from the group consisting of HO, $HOCH_2$—, (1-3C)alkyl, $H_2NHC(=O)$—, (1-3C alkyl)$_2NC(=O)$— and $HOCH_2CH_2NHC(=O)$—;

m is 0 or 1;

hetCyc$^1$ is a 4-6 membered heterocyclic ring having a ring heteroatom selected from N, O and S wherein the S is optionally oxidized to $SO_2$, wherein said heterocyclic ring is optionally substituted with a substituent selected from the group consisting of OH, (1-3C alkyl)C(=O)—, (1-3C alkyl)$SO_2$—, (1-3C alkyl)NHC(=O)— and $NH_2CH_2C(=O)$—;

hetCyc$^2$ is a 4-6 membered heterocyclic ring having a ring S atom, wherein the S is oxidized to $SO_2$;

$R^a$ and $R^b$ are independently H or (1-3C)alkyl, or $R^a$ and $R^b$ together with the nitrogen atom to which they are attached form a 4-6 membered ring optionally having a ring oxygen atom;

hetCyc$^{3a}$ and hetCyc$^{3b}$ are independently a 4-6 membered heterocyclic ring having 1-2 ring heteroatoms independently selected from N and O, wherein said heterocyclic ring is optionally substituted with 1-2 substituents independently selected from the group consisting of halogen, OH, (1-4C) alkoxy, $HOCH_2$—, (1-3C alkyl)C(=O)— and oxo;

$R^c$ is H or (1-3C)alkyl;

$R^d$ is (1-3C)alkyl, (1-3C alkyl)$SO_2$—, hetCyc$^a$, or (3-6C) cycloalkyl optionally substituted with $HOCH_2$—;

hetCyc$^a$ is a 5-6 membered azacyclic ring optionally substituted with 1-2 substituents independently selected from oxo and (1-3C)alkyl;

hetCyc$^4$ is azetidinyl substituted with $((CH_3)_2N)_2P(=O)$— or Y—C(=O)—;

Y is $R^eR^fN(CH_2)_n$—, hetCyc$^bCH_2$—, $Cyc^2$, hydroxy(1-3C)alkyl, (1-3C alkyl)$_2NC(=O)$—, (1-3C)alkyl$SO_2$- or (1-3C)alkyl;

n is 0 or 1;

$R^e$ and $R^f$ are independently H or (1-3C)alkyl;

hetCyc$^b$ is a 4-5 membered azacyclic ring optionally substituted with OH;

$Cyc^2$ is a (3-6C)cycloalkyl optionally substituted with OH;

$R^2$ is (1-6C)alkyl, trifluoro(1-6C)alkyl, difluoro(1-6C) alkyl, fluoro(1-6C)alkyl, hydroxy(1-6C)alkyl, (1-6C)alkoxy, (3-6C)cycloalkyl (optionally substituted with one or two halogens), (3-6C)cycloalkylCH$_2$—, HOC(=O)— or phenyl, and $R^3$ is (1-6C)alkyl or (3-6C)cycloalkyl, or $R^2$ and $R^3$ together with the carbon atom to which they are attached form a 3-7 membered cycloalkyl ring optionally substituted with one or two substituents independently selected from OH, (1-6C)alkyl and hydroxy(1-6C)alkyl, or $R^2$ and $R^3$ together with the carbon atom to which they are attached form a 4-membered saturated azacyclic ring substituted with $SO_2CF_3$; and $R^4$ is hydrogen or (1-6C)alkyl.

In one embodiment of Formula I, $R^1$ is hydroxy(1-6C) alkyl. Non-limiting examples include the structures:

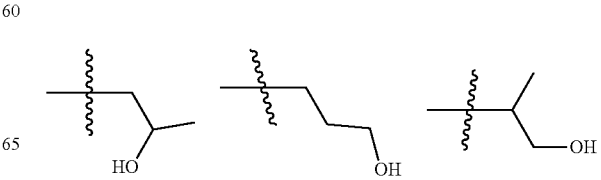

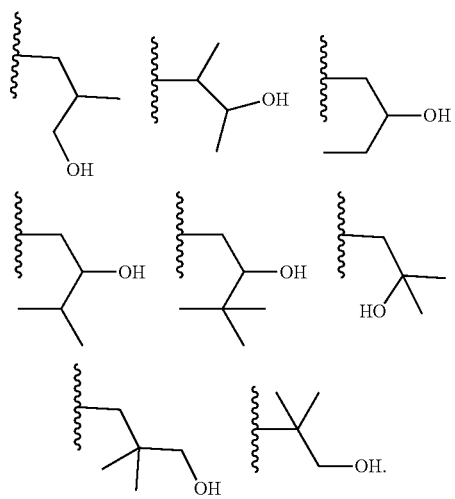

In one embodiment, $R^1$ is HOCH$_2$(cyclopropylidine)CH$_2$— having the structure:

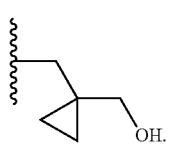 [SMILES: *CC1(CO)CC1]

In one embodiment, $R^1$ is (hydroxy)trifluoro(1-6C)alkyl, that is, a (1-6C)alkyl as defined herein, wherein one of the hydrogen atoms is replaced with hydroxy, and three of the hydrogen atoms are replaced by fluorine. A non-limiting example is the structure:

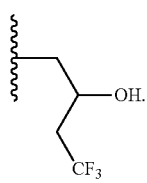

In one embodiment, $R^1$ is (1-4C alkoxy)(1-6C)hydroxyalkyl, that is, a (1-6C)alkyl as defined herein, wherein one of the hydrogen atoms is replaced with hydroxy, and one of the hydrogen atoms is replaced with a (1-4C alkoxy) group. A non-limiting example is the structure:

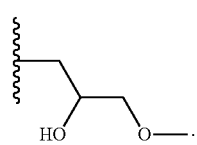

In one embodiment, $R^1$ is dihydroxy(2-6C)alkyl, that is, a (2-6C)alkyl as defined herein, wherein two of the hydrogen atoms are replaced with a OH group, provided that the two OH groups are not on the same carbon. Non-limiting examples include the structures:

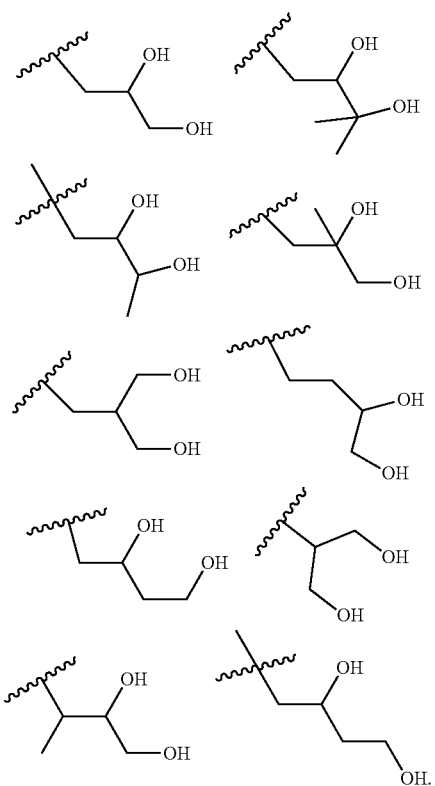

In one embodiment, $R^1$ is H$_2$N(3-6C)hydroxyalkyl, (1-3C alkyl)NH(3-6C)hydroxyalkyl or (1-3C alkyl)$_2$N(3-6C)hydroxyalkyl, that is, a (3-6C)alkyl group as defined herein, wherein one of the hydrogen atoms is replace with hydroxy, and another hydrogen atom is replaced with an H$_2$N—, (1-3C alkyl)NH— or (1-3C alkyl)$_2$N— group, respectively, provided that the hydroxy group and the amine-containing group are not on the same carbon. Non-limiting examples include the structures:

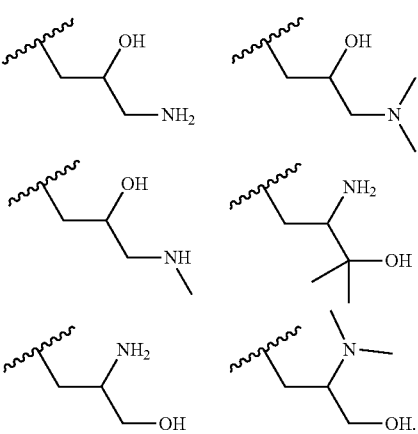

In one embodiment, $R^1$ is H$_2$N(1-4C alkoxy)(3-6C)alkyl, that is, a (3-6C)alkyl group, wherein one of the hydrogen atoms is replaced with an H$_2$N— group, and another hydrogen atom is replaced with a (1-4C)alkoxy group, provided the H$_2$N— group and (1-4C)alkoxy group are not on the same carbon. A non-limiting example is the structure:

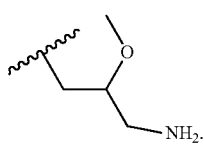 [SMILES: *CC(CN)OC]

In one embodiment, $R^1$ is $Cyc^1(CH_2)_m-$, where m is 0 or 1 and $Cyc^1$ is a 4-6 membered cycloalkyl substituted with 1-2 substituents independently selected from the group consisting of HO, $HOCH_2-$, (1-3C)alkyl, $H_2NHC(=O)-$, (1-3C alkyl)$_2NC(=O)-$ and $HOCH_2CH_2NHC(=O)-$. Non-limiting examples of $R^1$ when represented by $Cyc^1(CH_2)_m-$ include the structures:

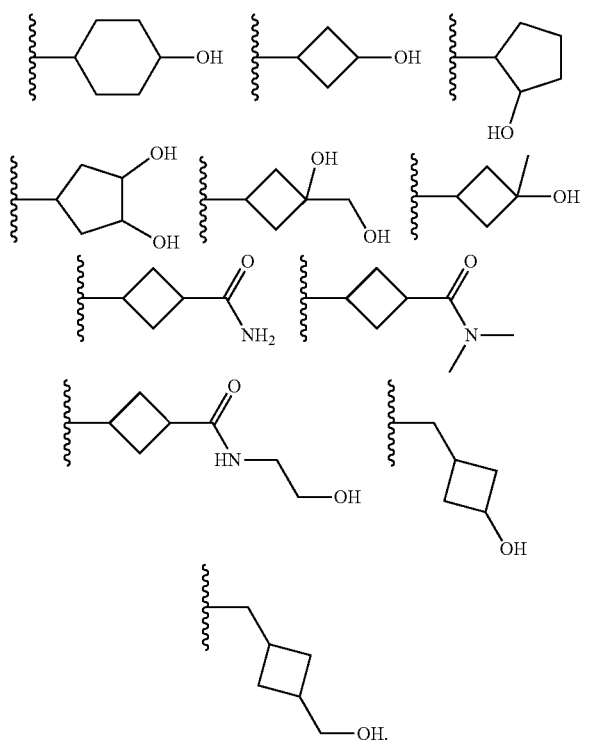

In one embodiment, $R^1$ is hetCyc$^1$, where hetCyc$^1$ is a 4-6 membered heterocyclic ring having a ring heteroatom selected from N, O and S wherein the S is optionally oxidized to $SO_2$, wherein said heterocyclic ring is optionally substituted with a substituent selected from the group consisting of OH, (1-3C alkyl)$C(=O)-$, (1-3C alkyl)$SO_2-$, (1-3C alkyl)$NHC(=O)-$ and $NH_2CH_2C(=O)-$. Non-limiting examples of $R^1$ when represented by hetCyc$^1$ include the structures:

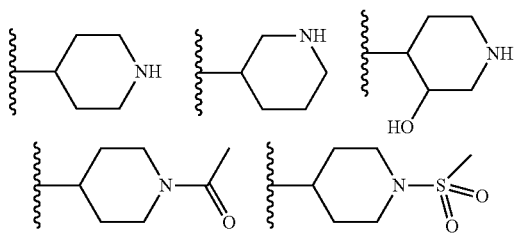

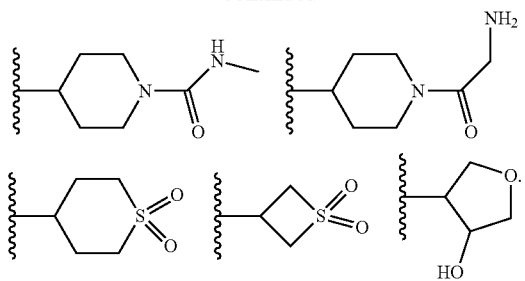

In one embodiment, $R^1$ is hetCyc$^2CH_2-$, where hetCyc$^2$ is a 4-6 membered heterocyclic ring having a ring S atom, wherein the S is oxidized to $SO_2$. A non-limiting example of $R^1$ when represented by hetCyc$^2CH_2-$ includes the structure:

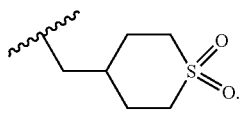

In one embodiment, $R^1$ is $R^aR^bNC(=O)CH_2-$, where $R^a$ and $R^b$ are independently H or (1-3C)alkyl, or $R^a$ and $R^b$ together with the nitrogen atom to which they are attached form a 4-6 membered ring optionally having a ring oxygen atom. Non-limiting examples of $R^1$ when represented by $R^aR^bNC(=O)CH_2-$ include the structures:

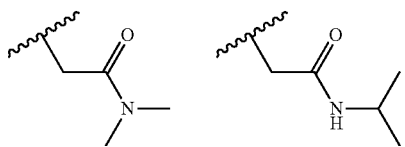

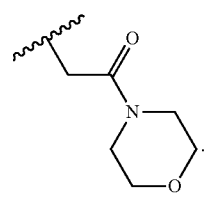

In one embodiment, $R^1$ is hetCyc$^{3a}$(1-3C)alkyl (that is, a 1-3C alkyl as defined herein, where one of the hydrogen atoms is replaced with hetCyc$^{3a}$) or hetCyc$^{3b}$(2-3C)hydroxyalkyl (that is, a 2-3C alkyl as defined herein, where one hydrogen atom is replaced with hydroxy and another hydrogen atom is replaced with hetCyc$^{3b}$), where hetCyc$^{3a}$ and hetCyc$^{3b}$ are independently a 4-6 membered heterocyclic ring having 1-2 ring heteroatoms independently selected from N and O, wherein said heterocyclic ring is optionally substituted with 1-2 substituents independently selected from the group consisting of halogen, OH, (1-4C)alkoxy, $HOCH_2$-(1-3C alkyl)$C(=O)-$ and oxo. Non-limiting examples of $R^1$ when represented by hetCyc$^{3a}$(1-3C)alkyl or hetCyc$^{3b}$(2-3C)hydroxyalkyl include the structures:

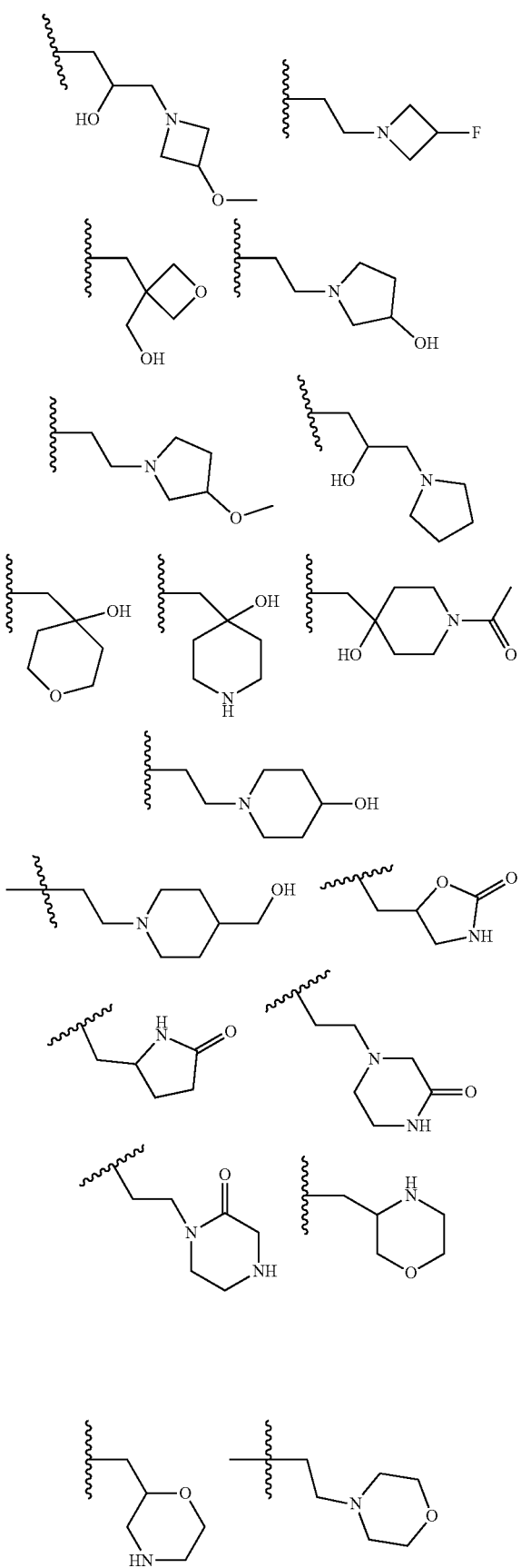

-continued

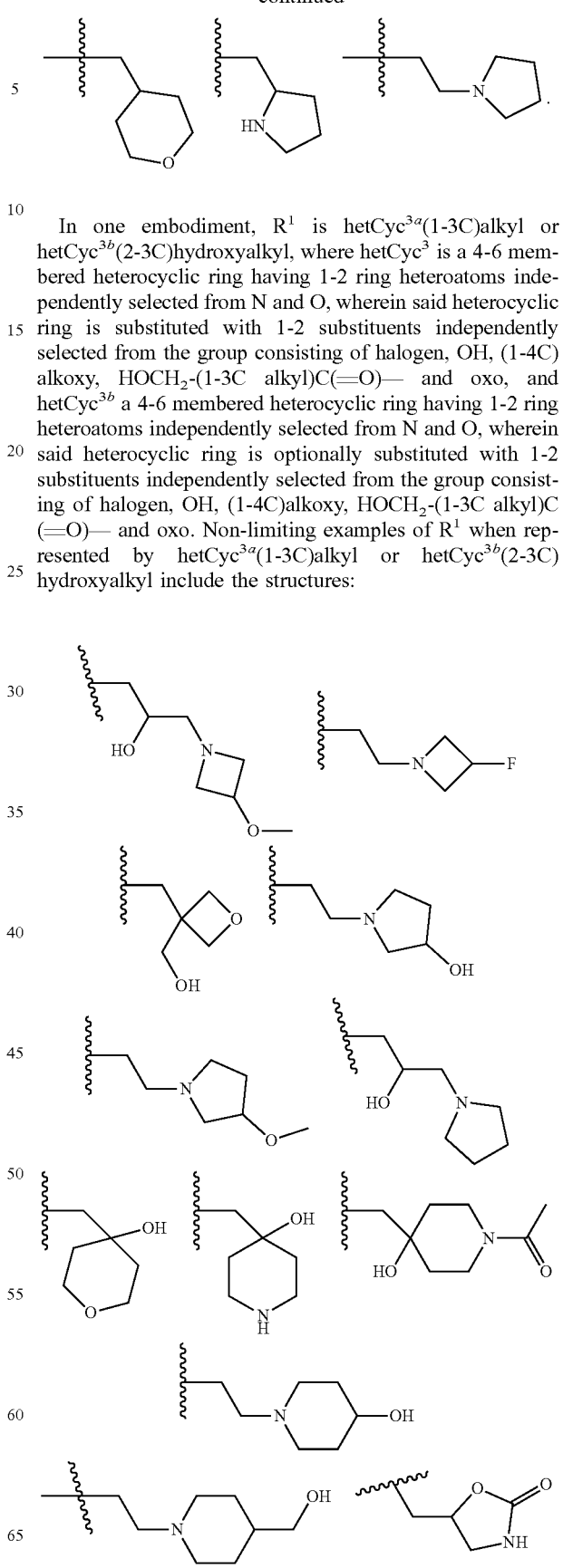

In one embodiment, $R^1$ is hetCyc$^{3a}$(1-3C)alkyl or hetCyc$^{3b}$(2-3C)hydroxyalkyl, where hetCyc$^3$ is a 4-6 membered heterocyclic ring having 1-2 ring heteroatoms independently selected from N and O, wherein said heterocyclic ring is substituted with 1-2 substituents independently selected from the group consisting of halogen, OH, (1-4C)alkoxy, HOCH$_2$-(1-3C alkyl)C(=O)— and oxo, and hetCyc$^{3b}$ a 4-6 membered heterocyclic ring having 1-2 ring heteroatoms independently selected from N and O, wherein said heterocyclic ring is optionally substituted with 1-2 substituents independently selected from the group consisting of halogen, OH, (1-4C)alkoxy, HOCH$_2$-(1-3C alkyl)C(=O)— and oxo. Non-limiting examples of $R^1$ when represented by hetCyc$^{3a}$(1-3C)alkyl or hetCyc$^{3b}$(2-3C)hydroxyalkyl include the structures:

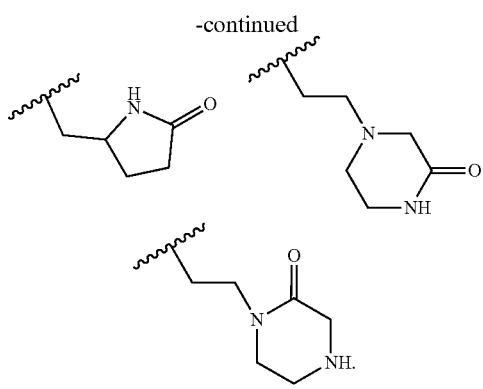

In one embodiment, $R^1$ is $R^cR^dN(2\text{-}3C)$alkyl, that is, a (2-3C)alkyl as defined herein where one of the hydrogen atoms is replaced with a $R^cR^dN$— group, where $R^c$ is H or (1-3C)alkyl; $R^d$ is (1-3C)alkyl, (1-3C alkyl)$SO_2$—, hetCyc$^a$, or (3-6C)cycloalkyl optionally substituted with $HOCH_2$—; and hetCyc$^a$ is a 5-6 membered azacyclic ring optionally substituted with 1-2 substituents independently selected from oxo and (1-3C)alkyl. Non-limiting examples of $R^1$ when represented by $R^cR^dN(2\text{-}3C)$alkyl include the structures:

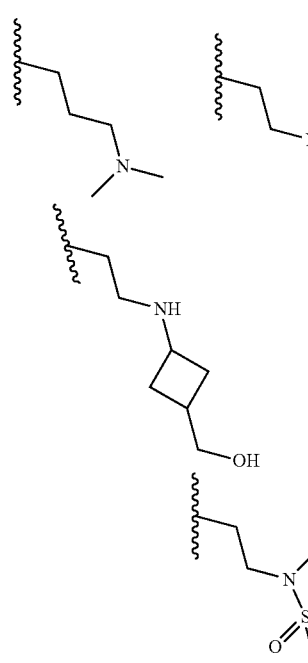

In one embodiment, $R^1$ is (1-3C alkyl)$_2NSO_2(2\text{-}3C)$alkyl, that is, a (2-3C)alkyl as defined herein, wherein one of the hydrogens is replaced with a (1-3C alkyl)$_2NSO_2$— group. A non-limiting example is the structure:

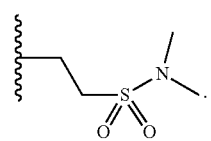 [SMILES: *CCS(=O)(=O)N(C)C]

In one embodiment, $R^1$ is hetCyc$^4$, where hetCyc$^4$ is an azetidinyl ring substituted with $((CH_3)_2N)_2P(=O)$—, Y—C(=O)— or (1-3C)alkylSO$_2$; Y is $R^eR^fN(CH_2)_n$—, hetCyc$^b$CH$_2$—, Cyc$^2$, hydroxy(1-3C)alkyl, (1-3C alkyl)$_2$NC(=O)— or (1-3C)alkyl; n is 0 or 1; $R^e$ and $R^f$ are independently H or (1-3C)alkyl; hetCyc$^b$ is a 4-5 membered azacyclic ring optionally substituted with OH; and Cyc$^2$ is (3-6C)cycloalkyl optionally substituted with OH. Non-limiting examples of $R^1$ when represented by hetCyc$^4$ include the structures:

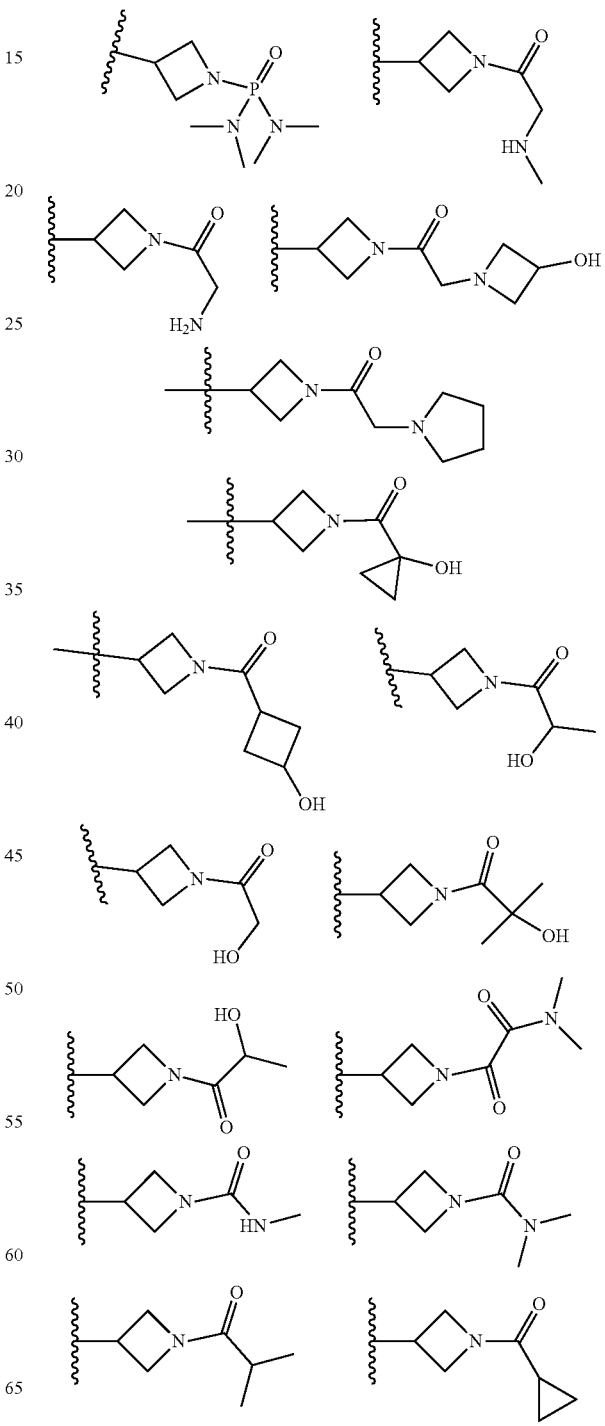

-continued

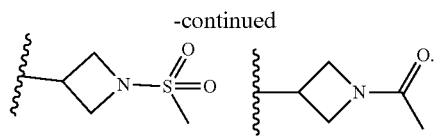

In one embodiment, $R^1$ is hetCyc$^4$, where hetCyc$^4$ is an azetidinyl ring substituted with $((CH_3)_2N)_2P(=O)$— or Y—C(=O)—; Y is $R^eR^fN(CH_2)_n$—, hetCyc$^b$CH$_2$—, Cyc$^2$, hydroxy(1-3C)alkyl or (1-3C alkyl)$_2$NC(=O)—; n is 1; $R^e$ and $R^f$ are independently H or (1-3C)alkyl; hetCyc$^b$ is a 4-5 membered azacyclic ring optionally substituted with OH; and Cyc$^2$ is (3-6C)cycloalkyl substituted with OH. Non-limiting examples of $R^1$ when represented by hetCyc$^4$ include the structures:

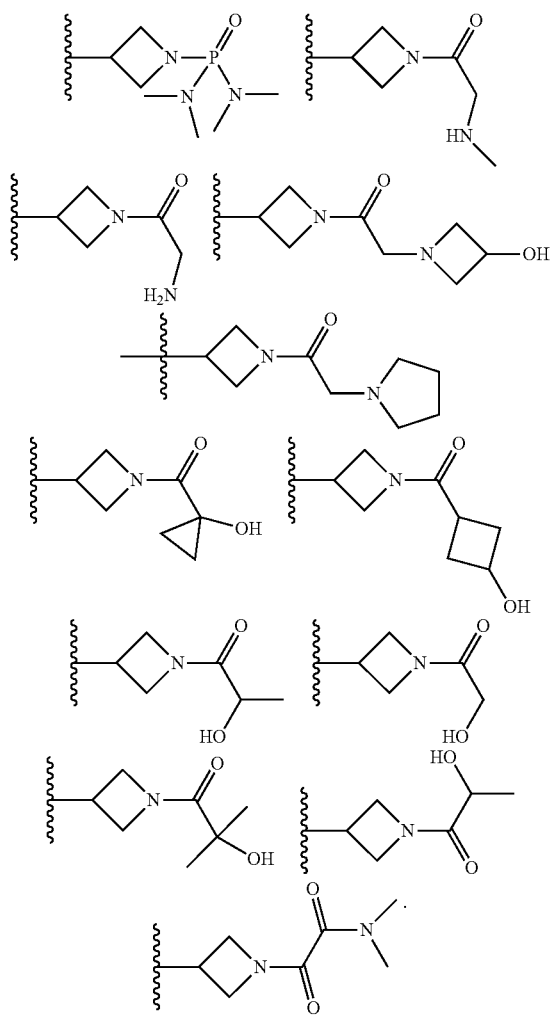

In one embodiment, $R^1$ is (1-6C)alkyl. In one embodiment, $R^1$ is methyl.

In one embodiment, $R^1$ is CH$_3$SO$_2$(1-6C)alkyl. In one embodiment, $R^1$ is CH$_3$SO$_2$CH$_2$CH$_2$— or CH$_3$SO$_2$CH$_2$CH$_2$CH$_2$—.

In one embodiment of General Formula I, $R^1$ is hydroxy (1-6C)alkyl, HOCH$_2$(cyclopropylidine)CH$_2$—, (1-4C alkoxy)(1-6C)hydroxyalkyl, (hydroxy)trifluoro(1-6C)alkyl, dihydroxy(2-6C)alkyl, H$_2$N(3-6C)hydroxyalkyl, (1-3C alkyl)NH(3-6C)hydroxyalkyl, (1-3C alkyl)$_2$N(3-6C)hydroxyalkyl, H$_2$N(1-4C alkoxy)(3-6C)alkyl, Cyc$^1$(CH$_2$)$_m$—, hetCyc$^1$, hetCyc$^2$CH$_2$—, $R^aR^b$NC(=O)CH$_2$—, hetCyc$^{3a}$(1-3C)alkyl, hetCyc$^{3b}$(2-3C)hydroxyalkyl, $R^cR^dN$(2-3C)alkyl, (1-3C alkyl)$_2$NSO$_2$(2-3C)alkyl or hetCyc$^4$;

Cyc$^1$ is a 4-6 membered cycloalkyl substituted with 1-2 substituents independently selected from the group consisting of HO, HOCH$_2$—, (1-3C)alkyl, H$_2$NHC(=O)—, (1-3C alkyl)$_2$NC(=O)—, and HOCH$_2$CH$_2$NHC(=O)—;

m is 0 or 1;

hetCyc$^1$ is a 4-6 membered heterocyclic ring having a ring heteroatom selected from N, O and S wherein the S is optionally oxidized to SO$_2$, wherein said heterocyclic ring is substituted with a substituent selected from the group consisting of OH, (1-3C alkyl)C(=O)—, (1-3C alkyl)SO$_2$—, (1-3C alkyl)NHC(=O)— and H$_2$NCH$_2$C(=O)—;

hetCyc$^2$ is a 4-6 membered heterocyclic ring having a ring S atom, wherein the S is oxidized to SO$_2$;

$R^a$ and $R^b$ are independently H or (1-3C)alkyl, or $R^a$ and $R^b$ together with the nitrogen atom to which they are attached form a 4-6 membered ring optionally having a ring oxygen atom;

hetCyc$^{3a}$ is a 4-6 membered heterocyclic ring having 1-2 ring heteroatoms independently selected from N and O, wherein said heterocyclic ring is substituted with 1-2 substituents independently selected from the group consisting of halogen, OH, (1-4C)alkoxy, HOCH$_2$—, (1-3C alkyl)C(=O)— and oxo;

hetCyc$^{3b}$ is a 4-6 membered heterocyclic ring having 1-2 ring heteroatoms independently selected from N and O, wherein said heterocyclic ring is optionally substituted with 1-2 substituents independently selected from the group consisting of halogen, OH, (1-4C)alkoxy, HOCH$_2$—, (1-3C alkyl)C(=O)— and oxo;

$R^c$ is H or (1-3C)alkyl;

$R^d$ is (1-3C)alkyl, (1-3C alkyl)SO$_2$—, hetCyc$^a$, or (3-6C)cycloalkyl optionally substituted with HOCH$_2$—;

hetCyc$^4$ is azetidinyl substituted with $((CH_3)_2N)_2P(=O)$— or Y—C(=O)—;

Y is $R^eR^fN(CH_2)_n$—, hetCyc$^b$CH$_2$—, Cyc$^2$, hydroxy(1-3C)alkyl or (1-3C alkyl)$_2$NC(=O)—;

n is 0 or 1;

$R^e$ and $R^f$ are independently H or (1-3C)alkyl;

hetCyc$^b$ is a 4-5 membered azacyclic ring optionally substituted with OH; and

Cyc$^2$ is a (3-6C)cycloalkyl optionally substituted with OH.

In one embodiment of General Formula I, $R^1$ is hydroxy (1-6C)alkyl, HOCH$_2$(cyclopropylidine)CH$_2$—, (1-4C alkoxy)(1-6C)hydroxyalkyl, (hydroxy)trifluoro(1-6C)alkyl, dihydroxy(2-6C)alkyl, H$_2$N(3-6C)hydroxyalkyl, (1-3C alkyl)NH(3-6C)hydroxyalkyl, (1-3C alkyl)$_2$N(3-6C)hydroxyalkyl, H$_2$N(1-4C alkoxy)(3-6C)alkyl, Cyc$^1$(CH$_2$)$_m$—, hetCyc$^1$, hetCyc$^2$CH$_2$—, $R^aR^b$NC(=O)CH$_2$—, hetCyc$^{3a}$(1-3C)alkyl, hetCyc$^{3b}$(2-3C)hydroxyalkyl, $R^cR^dN$(2-3C)alkyl, (1-3C alkyl)$_2$NSO$_2$(2-3C)alkyl or hetCyc$^4$;

Cyc$^1$ is a 4-6 membered cycloalkyl substituted with 1-2 substituents independently selected from the group consisting of HO, HOCH$_2$—, H$_2$NHC(=O)—, (1-3C alkyl)$_2$NC(=O)—, and HOCH$_2$CH$_2$NHC(=O)—;

m is 0 or 1;

hetCyc$^1$ is a 4-6 membered heterocyclic ring having a ring heteroatom selected from N, O and S wherein the S is optionally oxidized to SO$_2$, wherein said heterocyclic ring is substituted with a substituent selected from the group consisting of OH, (1-3C alkyl)C(=O)—, (1-3C alkyl)SO$_2$—, (1-3C alkyl)NHC(=O)— and H$_2$NCH$_2$C(=O)—;

hetCyc² is a 4-6 membered heterocyclic ring having a ring S atom, wherein the S is oxidized to SO₂;

R$^a$ and R$^b$ are independently H or (1-3C)alkyl, or

R$^a$ and R$^b$ together with the nitrogen atom to which they are attached form a 4-6 membered ring optionally having a ring oxygen atom;

hetCyc$^{3a}$ is a 4-6 membered heterocyclic ring having 1-2 ring heteroatoms independently selected from N and O, wherein said heterocyclic ring is substituted with 1-2 substituents independently selected from the group consisting of halogen, OH, (1-4C)alkoxy, HOCH₂—, (1-3C alkyl)C(=O)— and oxo;

hetCyc$^{3b}$ is a 4-6 membered heterocyclic ring having 1-2 ring heteroatoms independently selected from N and O, wherein said heterocyclic ring is optionally substituted with 1-2 substituents independently selected from the group consisting of halogen, OH, (1-4C)alkoxy, HOCH₂—, (1-3C alkyl)C(=O)— and oxo;

R$^c$ is H or (1-3C)alkyl;

R$^d$ is (1-3C)alkyl, (1-3C alkyl)SO₂—, hetCyc$^a$, or (3-6C)cycloalkyl optionally substituted with HOCH₂—;

hetCyc⁴ is azetidinyl substituted with ((CH₃)₂N)₂P(=O)— or Y—C(=O)—;

Y is R$^e$R$^f$N(CH₂)$_n$—, hetCyc$^b$CH₂—, Cyc², hydroxy(1-3C)alkyl or (1-3C alkyl)₂NC(=O)—;

n is 0 or 1;

R$^e$ and R$^f$ are independently H or (1-3C)alkyl;

hetCyc$^b$ is a 4-5 membered azacyclic ring optionally substituted with OH; and

Cyc² is a (3-6C)cycloalkyl optionally substituted with OH.

In one embodiment of General Formula I, R¹ is hydroxy(1-6C)alkyl, HOCH₂(cyclopropylidine)CH₂—, (1-4C alkoxy)(1-6C)hydroxyalkyl, (hydroxy)trifluoro(1-6C)alkyl, dihydroxy(2-6C)alkyl, H₂N(3-6C)hydroxyalkyl, (1-3C alkyl)NH(3-6C)hydroxyalkyl, (1-3C alkyl)₂N(3-6C)hydroxyalkyl or H₂N(1-4C alkoxy)(3-6C)alkyl.

In one embodiment of General Formula I, R¹ is dihydroxy(2-6C)alkyl, H₂N(3-6C)hydroxyalkyl, (1-3C alkyl)NH(3-6C)hydroxyalkyl or (1-3C alkyl)₂N(3-6C)hydroxyalkyl.

In one embodiment of General Formula I, R¹ is dihydroxy(2-6C)alkyl.

Reference will now be made to the portion of Formula I having the structure:

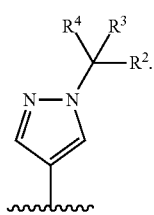

In one embodiment of General Formula I, R² is (1-6C)alkyl, trifluoro(1-6C)alkyl, difluoro(1-6C)alkyl, fluoro(1-6C)alkyl, hydroxy(1-6C)alkyl, (1-6C)alkoxy, (3-6C)cycloalkyl (optionally substituted with one or two halogens), (3-6C)cycloalkylCH₂—, HOC(=O)— or phenyl; R³ is (1-6C)alkyl or (3-6C)cycloalkyl; and R⁴ is hydrogen or (1-6C)alkyl. Non-limiting examples include the structures:

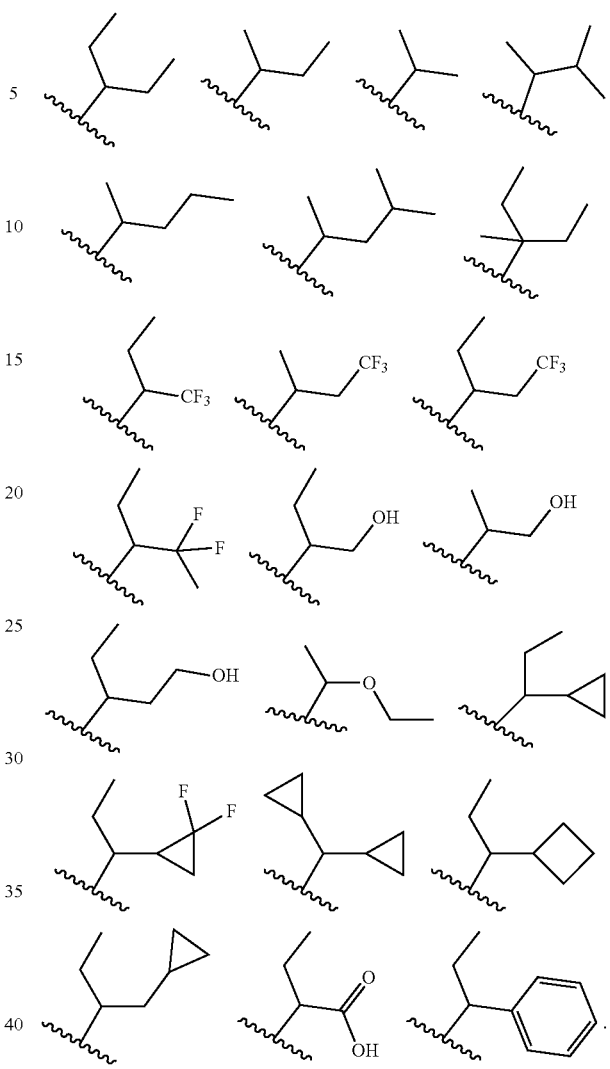

In one embodiment of General Formula I, R² is (1-6C)alkyl; R³ is (1-6C)alkyl; and R⁴ is hydrogen.

In one embodiment of General Formula I, R² and R³ together with the carbon atom to which they are attached form a 3-7 membered cycloalkyl ring optionally substituted by one or two groups independently selected from OH, (1-6C)alkyl and hydroxy(1-6C)alkyl; and R⁴ is hydrogen or (1-6C)alkyl. In one embodiment, R⁴ is hydrogen or methyl. Non-limiting examples include the structures:

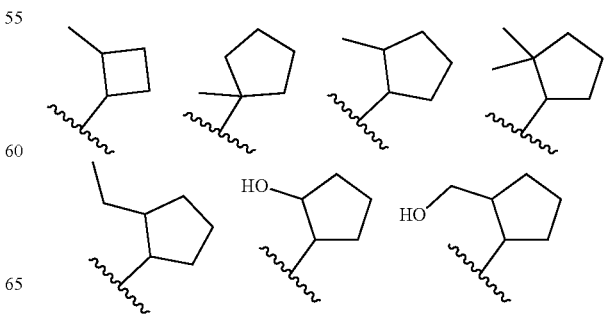

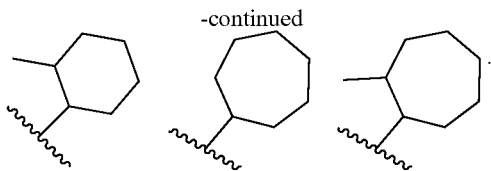

In one embodiment of General Formula I, $R^2$ and $R^3$ together with the carbon atom to which they are attached form a 4-membered saturated azacyclic ring substituted with $SO_2CF_3$; and $R^4$ is hydrogen or (1-6C)alkyl. A non-limiting example is the structure:

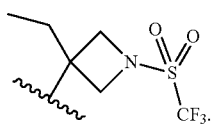

In one embodiment, General Formula I comprises compounds of Formula IA, and stereoisomers and pharmaceutically acceptable salts and solvates thereof, wherein:

$R^1$ is hydroxy(1-6C)alkyl, $HOCH_2$(cyclopropylidine)$CH_2$—, (1-4C alkoxy)(1-6C)hydroxyalkyl, (hydroxy)trifluoro(1-6C)alkyl, dihydroxy(2-6C)alkyl, $H_2N$(3-6C)hydroxyalkyl, (1-3C alkyl)NH(3-6C)hydroxyalkyl, (1-3C alkyl)$_2$N(3-6C)hydroxyalkyl, $H_2N$(1-4C alkoxy)(3-6C)alkyl, $Cyc^1(CH_2)_m$—, $hetCyc^1$, $hetCyc^2CH_2$—, $R^aR^bNC(=O)CH_2$—, $hetCyc^{3a}$(1-3C alkyl)-, $hetCyc^{3b}$(2-3C)hydroxyalkyl, $R^cR^dN$(2-3C)alkyl, (1-3C alkyl)$_2NSO_2$(2-3C)alkyl or $hetCyc^4$;

$Cyc^1$ is a 4-6 membered cycloalkyl substituted with 1-2 substituents independently selected from the group consisting of HO, $HOCH_2$—, (1-3C)alkyl, $H_2NHC(=O)$—, (1-3C alkyl)$_2NC(=O)$—, and $HOCH_2CH_2NHC(=O)$—;

m is 0 or 1;

$hetCyc^1$ is a 4-6 membered heterocyclic ring having a ring heteroatom selected from N, O and S wherein the S is optionally oxidized to $SO_2$, wherein said heterocyclic ring is substituted with a substituent selected from the group consisting of OH, (1-3C alkyl)C(=O)—, (1-3C alkyl)$SO_2$—, (1-3C alkyl)NHC(=O)— and $H_2NCH_2C(=O)$—;

$hetCyc^2$ is a 4-6 membered heterocyclic ring having a ring S atom, wherein the S is oxidized to $SO_2$;

$R^a$ and $R^b$ are independently H or (1-3C)alkyl, or $R^a$ and $R^b$ together with the nitrogen atom to which they are attached form a 4-6 membered ring optionally having a ring oxygen atom;

$hetCyc^{3a}$ is a 4-6 membered heterocyclic ring having 1-2 ring heteroatoms independently selected from N and O, wherein said heterocyclic ring is substituted with 1-2 substituents independently selected from the group consisting of halogen, OH, (1-4C)alkoxy, $HOCH_2$—, (1-3C alkyl)C(=O)— and oxo;

$hetCyc^{3b}$ is a 4-6 membered heterocyclic ring having 1-2 ring heteroatoms independently selected from N and O, wherein said heterocyclic ring is optionally substituted with 1-2 substituents independently selected from the group consisting of halogen, OH, (1-4C)alkoxy, $HOCH_2$—, (1-3C alkyl)C(=O)— and oxo;

$R^c$ is H or (1-3C)alkyl;

$R^d$ is (1-3C)alkyl, (1-3C alkyl)$SO_2$—, $hetCyc^a$, or (3-6C)cycloalkyl optionally substituted with $HOCH_2$—;

$hetCyc^a$ is a 5-6 membered azacyclic ring optionally substituted with 1-2 substituents independently selected from oxo and (1-3C)alkyl;

$hetCyc^4$ is azetidinyl substituted with $((CH_3)_2N)_2P(=O)$— or Y—C(=O)—;

Y is $R^eR^fN(CH_2)_n$—, $hetCyc^bCH_2$—, $Cyc^2$, hydroxy(1-3C)alkyl or (1-3C alkyl)$_2NC(=O)$—;

n is 0 or 1;

$R^e$ and $R^f$ are independently H or (1-3C)alkyl;

$hetCyc^b$ is a 4-5 membered azacyclic ring optionally substituted with OH;

$Cyc^2$ is a (3-6C)cycloalkyl optionally substituted with OH;

$R^2$ is (1-6C)alkyl, trifluoro(1-6C)alkyl, difluoro(1-6C)alkyl, fluoro(1-6C)alkyl, hydroxy(1-6C)alkyl, (1-6C)alkoxy, (3-6C)cycloalkyl (optionally substituted with one or two halogens), (3-6C)cycloalkylCH$_2$—, HOC(=O)— or phenyl, and $R^3$ is (1-6C)alkyl or (3-6C)cycloalkyl, or $R^2$ and $R^3$ together with the carbon atom to which they are attached form a 3-7 membered cycloalkyl ring optionally substituted by one or two groups independently selected from OH, (1-6C)alkyl and hydroxy(1-6C)alkyl, or $R^2$ and $R^3$ together with the carbon atom to which they are attached form a 4-membered saturated azacyclic ring substituted with $SO_2CF_3$; and $R^4$ is hydrogen or (1-6C)alkyl.

In one embodiment of Formula IA, $R^1$ is dihydroxy(2-6C)alkyl.

In one embodiment, General Formula I comprises compounds of Formula IB, and stereoisomers and pharmaceutically acceptable salts and solvates thereof, wherein:

$R^1$ is hydroxy(1-6C)alkyl, $HOCH_2$(cyclopropylidine)$CH_2$—, (1-4C alkoxy)(1-6C)hydroxyalkyl, (hydroxy)trifluoro(1-6C)alkyl, dihydroxy(2-6C)alkyl, $H_2N$(3-6C)hydroxyalkyl, (1-3C alkyl)NH(3-6C)hydroxyalkyl, (1-3C alkyl)$_2$N(3-6C)hydroxyalkyl or $H_2N$(1-4C alkoxy)(3-6C)alkyl;

$R^2$ is (1-6C)alkyl, trifluoro(1-6C)alkyl, difluoro(1-6C)alkyl, fluoro(1-6C)alkyl, hydroxy(1-6C)alkyl, (1-6C)alkoxy, (3-6C)cycloalkyl (optionally substituted with one or two halogens), (3-6C)cycloalkylCH$_2$—, HOC(=O)— or phenyl, and $R^3$ is (1-6C)alkyl or (3-6C)cycloalkyl, or $R^2$ and $R^3$ together with the carbon atom to which they are attached form a 3-7 membered cycloalkyl ring optionally substituted by one or two groups independently selected from OH, (1-6C)alkyl and hydroxy(1-6C)alkyl, or $R^2$ and $R^3$ together with the carbon atom to which they are attached form a 4-membered saturated azacyclic ring substituted with $SO_2CF_3$; and $R^4$ is hydrogen or (1-6C)alkyl.

In one embodiment of Formula IB, $R^1$ is dihydroxy(2-6C)alkyl.

In one embodiment of Formula IB, $R^2$ is (1-6C)alkyl, $R^3$ is (1-6C)alkyl, and $R^4$ is hydrogen.

In one embodiment of Formula IB, $R^1$ is dihydroxy(2-6C)alkyl, $R^2$ is (1-6C)alkyl, $R^3$ is (1-6C)alkyl, and $R^4$ is hydrogen.

In one embodiment, General Formula I comprises compounds of Formula IC, and stereoisomers and pharmaceutically acceptable salts and solvates thereof, wherein:

$R^1$ is hydroxy(1-6C)alkyl, $HOCH_2$(cyclopropylidine)$CH_2$—, (1-4C alkoxy)(1-6C)hydroxyalkyl, (hydroxy)trifluoro(1-6C)alkyl, dihydroxy(2-6C)alkyl, $H_2N$(3-6C)hydroxyalkyl, (1-3C alkyl)NH(3-6C)hydroxyalkyl, (1-3C alkyl)$_2$N(3-6C)hydroxyalkyl or H$_2$N(1-4C alkoxy)(3-6C)alkyl;

$R^2$ is (1-6C)alkyl, trifluoro(1-6C)alkyl, difluoro(1-6C)alkyl, fluoro(1-6C)alkyl, hydroxy(1-6C)alkyl, (1-6C)alkoxy, (3-6C)cycloalkyl (optionally substituted with one or two halogens), (3-6C)cycloalkylCH$_2$—, HOC(=O)— or phenyl;

$R^3$ is (1-6C)alkyl or (3-6C)cycloalkyl; and $R^4$ is hydrogen or (1-6C)alkyl.

In one embodiment of Formula IC, $R^1$ is dihydroxy(2-6C)alkyl.

In one embodiment of Formula IC, $R^2$ is (1-6C)alkyl, $R^3$ is (1-6C)alkyl, and $R^4$ is hydrogen.

In one embodiment of Formula IC, $R^1$ is dihydroxy(2-6C)alkyl, $R^2$ is (1-6C)alkyl, $R^3$ is (1-6C)alkyl, and $R^4$ is hydrogen.

In one embodiment, General Formula I comprises compounds of Formula ID, and stereoisomers and pharmaceutically acceptable salts and solvates thereof, wherein:

$R^1$ is hydroxy(1-6C)alkyl, HOCH$_2$(cyclopropylidine)CH$_2$—, (1-4C alkoxy)(1-6C)hydroxyalkyl, (hydroxy)trifluoro(1-6C)alkyl, dihydroxy(2-6C)alkyl, H$_2$N(3-6C)hydroxyalkyl, (1-3C alkyl)NH(3-6C)hydroxyalkyl, (1-3C alkyl)$_2$N(3-6C)hydroxyalkyl, H$_2$N(1-4C alkoxy)(3-6C)alkyl, Cyc$^1$(CH$_2$)$_m$—, hetCyc$^1$, hetCyc$^2$CH$_2$—, R$^a$R$^b$NC(=O)CH$_2$—, hetCyc$^{3a}$(1-3C alkyl)-, hetCyc$^{3b}$(2-3C)hydroxyalkyl, R$^c$R$^d$N(2-3C)alkyl, (1-3C alkyl)$_2$NSO$_2$(2-3C)alkyl or hetCyc$^4$;

Cyc$^1$ is a 4-6 membered cycloalkyl substituted with 1-2 substituents independently selected from the group consisting of HO, HOCH$_2$—, H$_2$NHC(=O)—, (1-3C alkyl)$_2$NC(=O)— and HOCH$_2$CH$_2$NHC(=O)—;

m is 0 or 1;

hetCyc$^1$ is a 4-6 membered heterocyclic ring having a ring heteroatom selected from N, O and S wherein the S is optionally oxidized to SO$_2$, wherein said heterocyclic ring is substituted with a substituent selected from the group consisting of OH, (1-3C alkyl)C(=O)—, (1-3C alkyl)SO$_2$—, (1-3C alkyl)NHC(=O)— and H$_2$NCH$_2$C(=O)—;

hetCyc$^2$ is a 4-6 membered heterocyclic ring having a ring S atom, wherein the S is oxidized to SO$_2$;

R$^a$ and R$^b$ are independently H or (1-3C)alkyl, or

R$^a$ and R$^b$ together with the nitrogen atom to which they are attached form a 4-6 membered ring optionally having a ring oxygen atom;

hetCyc$^{3a}$ is a 4-6 membered heterocyclic ring having 1-2 ring heteroatoms independently selected from N and O, wherein said heterocyclic ring is substituted with 1-2 substituents independently selected from the group consisting of halogen, OH, (1-4C)alkoxy, HOCH$_2$—, (1-3C alkyl)C(=O)— and oxo;

hetCyc$^{3b}$ is a 4-6 membered heterocyclic ring having 1-2 ring heteroatoms independently selected from N and O, wherein said heterocyclic ring is optionally substituted with 1-2 substituents independently selected from the group consisting of halogen, OH, (1-4C)alkoxy, HOCH$_2$—, (1-3C alkyl)C(=O)— and oxo;

R$^c$ is H or (1-3C)alkyl;

R$^d$ is (1-3C)alkyl, (1-3C alkyl)SO$_2$—, hetCyc$^a$, or (3-6C)cycloalkyl optionally substituted with HOCH$_2$—;

hetCyc$^a$ is a 5-6 membered azacyclic ring optionally substituted with 1-2 substituents independently selected from oxo and (1-3C)alkyl;

hetCyc$^4$ is azetidinyl substituted with ((CH$_3$)$_2$N)$_2$P(=O)— or Y—C(=O)—;

Y is R$^e$R$^f$N(CH$_2$)$_n$—, hetCyc$^b$CH$_2$—, Cyc$^2$, hydroxy(1-3C)alkyl or (1-3C alkyl)$_2$NC(=O)—;

n is 0 or 1;

R$^e$ and R$^f$ are independently H or (1-3C)alkyl;

hetCyc$^b$ is a 4-5 membered azacyclic ring optionally substituted with OH;

Cyc$^2$ is a (3-6C)cycloalkyl optionally substituted with OH;

$R^2$ is (1-6C)alkyl, trifluoro(1-6C)alkyl, difluoro(1-6C)alkyl, fluoro(1-6C)alkyl, hydroxy(1-6C)alkyl, (1-6C)alkoxy, (3-6C)cycloalkyl (optionally substituted with one or two halogens), (3-6C)cycloalkylCH$_2$—, HOC(=O)— or phenyl, and $R^3$ is (1-6C)alkyl or (3-6C)cycloalkyl, or $R^2$ and $R^3$ together with the carbon atom to which they are attached form a 3-7 membered cycloalkyl ring optionally substituted by one or two groups independently selected from OH, (1-6C)alkyl and hydroxy(1-6C)alkyl, or $R^2$ and $R^3$ together with the carbon atom to which they are attached form a 4-membered saturated azacyclic ring substituted with SO$_2$CF$_3$; and $R^4$ is hydrogen or (1-6C)alkyl.

In one embodiment of Formula ID, $R^1$ is dihydroxy(2-6C)alkyl.

In one embodiment of Formula ID, $R^2$ is (1-6C)alkyl, $R^3$ is (1-6C)alkyl, and $R^4$ is hydrogen.

In one embodiment of Formula ID, $R^1$ is dihydroxy(2-6C)alkyl, $R^2$ is (1-6C)alkyl, $R^3$ is (1-6C)alkyl, and $R^4$ is hydrogen.

In one embodiment, General Formula I comprises compounds of Formula IE, and stereoisomers and pharmaceutically acceptable salts and solvates thereof, wherein:

$R^1$ is Cyc$^1$(CH$_2$)$_m$— or (1-6C)alkyl;

Cyc$^1$ is a 4-6 membered cycloalkyl substituted with 1-2 substituents independently selected from the group consisting of (1-3C)alkyl;

m is 0 or 1;

$R^2$ is (1-6C)alkyl, trifluoro(1-6C)alkyl, difluoro(1-6C)alkyl, fluoro(1-6C)alkyl, hydroxy(1-6C)alkyl, (1-6C)alkoxy, (3-6C)cycloalkyl (optionally substituted with one or two halogens), (3-6C)cycloalkylCH$_2$—, HOC(=O)— or phenyl, and $R^3$ is (1-6C)alkyl or (3-6C)cycloalkyl, or $R^2$ and $R^3$ together with the carbon atom to which they are attached form a 3-7 membered cycloalkyl ring optionally substituted with one or two substituents independently selected from OH, (1-6C)alkyl and hydroxy(1-6C)alkyl, or $R^2$ and $R^3$ together with the carbon atom to which they are attached form a 4-membered saturated azacyclic ring substituted with SO$_2$CF$_3$; and $R^4$ is hydrogen or (1-6C)alkyl.

It will be appreciated that certain compounds according to the invention may contain one or more centers of asymmetry and may therefore be prepared and isolated as a mixture of isomers such as a racemic or diastereomeric mixture, or in an enantiomerically or diastereomerically pure form. It is intended that all stereoisomeric forms of the compounds of the invention, including but not limited to, diastereomers, enantiomers and atropisomers, as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

When words are used to describe a substituent, the rightmost-described component of the substituent is the component that has the free valence. To illustrate, (1-4C alkoxy)(1-6C)alkyl refers to an alkyl radical, wherein the radical is on the first carbon atom of (1-6C) alkyl group as shown. An example is 2-methoxyethyl, which can be represented by the structure:

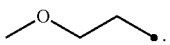

As used herein, the word "a" before a noun represents one or more of the particular noun.

The terms "(1-3C)alkyl", "(2-3C)alkyl", "(1-4C)alkyl", "(1-6C)alkyl", "(2-6C)alkyl" and "(3-6C)alkyl" as used herein refers to saturated linear or branched-chain monovalent hydrocarbon radicals of one to three carbon atoms, two to three carbon atoms, one to four carbon atoms, one to six carbon atoms, two to six carbon atoms, and three to six carbon atoms, respectively. Examples include, but are not limited to, methyl, ethyl, 1-propyl, isopropyl, 1-butyl, isobutyl, sec-butyl, tert-butyl, 2-methyl-2-propyl, pentyl, and hexyl.

The term "(1-6C)alkoxy", as used herein refer to saturated linear or branched-chain monovalent alkoxy radicals of one to six carbon atoms, respectively, wherein the radical is on the oxygen atom. Examples include methoxy, ethoxy, propoxy, isopropoxy, and butoxy.

The terms "trifluoro(1-6C)alkyl", "difluoro(1-6C)alkyl" and "fluoro(1-6C)alkyl" as use herein refer to saturated linear or branched-chain monovalent radicals of one to six carbon atoms, wherein three of the hydrogen atoms are replaced by three, two or one fluorine atoms, respectively. Examples include trifluoromethyl, 2,2,2-trifluoroethyl, 3,3,3-trifluoropropyl, and 2,2-difluoroethyl.

In instances where the term "heterocycle" is used, the term is intended to refer to a saturated heterocyclic ring.

It will also be appreciated that certain compounds of General Formula I may be used as intermediates for the preparation of further compounds of General Formula I.

The compounds of General Formula I include salts thereof. In certain embodiments, the salts are pharmaceutically acceptable salts. In addition, the compounds of General Formula I include other salts of such compounds which are not necessarily pharmaceutically acceptable salts, and which may be useful as intermediates for preparing and/or purifying compounds of Formula I and/or for separating enantiomers of compounds of General Formula I. Particular examples of salts include trifluoroacetic acid salts and hydrochloric acid salts.

The term "pharmaceutically acceptable" indicates that the substance or composition is compatible chemically and/or toxicologically, with the other ingredients comprising a formulation, and/or the mammal being treated therewith.

The term "JAK kinase-associated disease or disorder" as used herein refers to diseases or disorders associated with aberrant JAK kinase activity (including overexpression or mutation of the kinase), and diseases mediated by JAK kinase involved signaling pathways. Non-limiting example of a JAK kinase-associated diseases and disorders include any of the disorders described herein.

The terms "JAK kinase" and "JAK kinases" refer to the four family members of the Janus kinase (JAK) family of non-receptor, intracellular tyrosine kinases, i.e., Tyk2, JAK1, JAK2, and JAK3.

As used herein, the term "inhibitor of JAK kinases" when used in reference to a compound of General Formula I, means that a compound of General Formula I is an inhibitor of one or more of Tyk2, JAK1, JAK2, and/or JAK3.

It will further be appreciated that compounds of General Formula I and their salts may be isolated in the form of solvates, and accordingly any such solvate is included within the scope of the present invention. For example, compounds of General Formula I and their salts can exist in unsolvated as well as solvated forms with pharmaceutically acceptable solvents such as water, ethanol, and the like.

Compounds of General Formula I may also contain unnatural proportions of atomic isotopes at one or more of the atoms that constitute such compounds. That is, an atom, in particular when mentioned in relation to a compound according to General Formula I, comprises all isotopes and isotopic mixtures of that atom, either naturally occurring or synthetically produced, either with natural abundance or in an isotopically enriched form. For example, when hydrogen is mentioned, it is understood to refer to $^{1}H$, $^{2}H$, $^{3}H$ or mixtures thereof; when carbon is mentioned, it is understood to refer to $^{11}C$, $^{12}C$, $^{13}C$, $^{14}C$ or mixtures thereof; when nitrogen is mentioned, it is understood to refer to $^{13}N$, $^{14}N$, $^{15}N$ or mixtures thereof; when oxygen is mentioned, it is understood to refer to $^{14}O$, $^{15}O$, $^{16}O$, $^{17}O$, $^{18}O$ or mixtures thereof; and when fluoro is mentioned, it is understood to refer to $^{18}F$, $^{19}F$ or mixtures thereof. Compounds of General Formula I therefore also include compounds with one or more isotopes of one or more atom, and mixtures thereof, including radioactive compounds, wherein one or more non-radioactive atoms has been replaced by one of its radioactive enriched isotopes. Radiolabeled compounds are useful as therapeutics, research reagents, e.g., assay reagents, and diagnostic agents, e.g., in vivo imaging agents. All isotopic variations of the compounds of General Formula I, whether radioactive or not, are intended to be encompassed within the scope of the present invention.

The compounds of General Formula I also include the compounds of Examples 1-218 described herein, and pharmaceutically acceptable salts and solvates thereof. In one embodiment, the compounds of General Formula I are selected from the group consisting of the free base of the compounds of Examples 1-218, the trifluoroacetic acid salts of the compounds of Examples 1-218, and the hydrochloric acid salts of the compounds of Examples 1-218.

The present invention further provides a process for the preparation of a compound of General Formula I or a pharmaceutically acceptable salt thereof as defined herein which comprises:

(a) reacting a corresponding compound having the formula II:

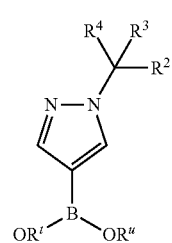

where $R^2$, $R^3$ and $R^4$ is as defined for General Formula I, and $R^t$ and $R^u$ are H or (1-6C)alkyl, or $R^t$ and $R^u$ together with the atoms to which they are connected form a 5-6 membered ring optionally substituted with 1-4 substituents selected from (1-3C alkyl), with a corresponding compound having the formula III

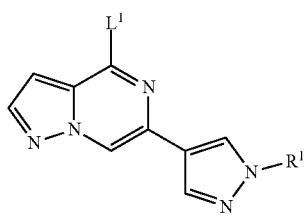

III where $R^1$ is as defined for General Formula I and $L^1$ is halogen, an alkyl sulfonate group, an aryl sulfonate group, or a triflate group, in the presence of a palladium catalyst and a base and optionally in the presence of a ligand; or (b) for a compound of General Formula I where $R^1$ is (1-6C)alkyl, hydroxy(1-6C)alkyl, hetCyc$^1$, hetCyc$^2$CH$_2$—, $R^a R^b$NC(=O)CH$_2$—, hetCyc$^{3a}$(1-3C alkyl)-, $R^c R^d$N(2-3C alkyl)-, (1-3C alkyl)$_2$NSO$_2$(2-3C alkyl)- or CH$_3$SO$_2$(1-6C)alkyl, reacting a corresponding compound having the formula IV

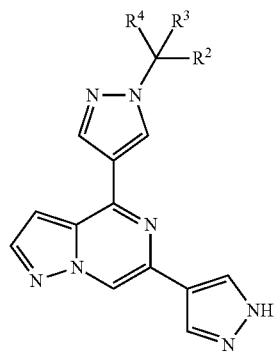

IV where $R^2$, $R^3$ and $R^4$ are as defined for General Formula I, with (1-6C)alkyl-L$^2$, hydroxy(1-6C)alkyl-L$^2$, hetCyc$^1$-L$^2$, hetCyc$^2$CH$_2$-L$^2$, $R^a R^b$NC(=O)CH$_2$-L$^2$, hetCyc$^{3a}$(1-3C alkyl)-L$^2$, $R^c R^d$N(2-3C alkyl)-L$^2$, (1-3C alkyl)$_2$NSO$_2$(2-3C alkyl)-L$^2$ or CH$_3$SO$_2$(1-6C)alkyl-L$^2$ and L$^2$ is halogen, an alkyl sulfonate group or an aryl sulfonate group, in the presence of a base, where hetCyc$^1$, $R^a$, $R^b$, hetCyc$^{3a}$, $R^c$, and $R^d$ are as defined for Formula I; or (c) for a compound of General Formula I where $R^1$ is dihydroxy(2-6C)alkyl, reacting a reacting a corresponding compound having the formula IV

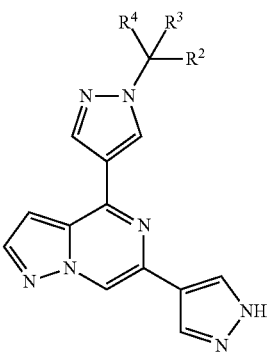

IV where $R^2$, $R^3$ and $R^4$ are as defined for Formula I, with a compound having the formula V, VI or VII

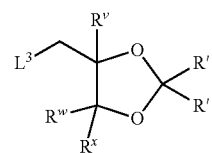

V

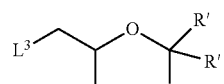

VI

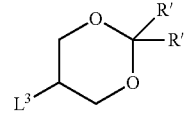

VII where each $R'$ is methyl, $R^v$, $R^w$ and $R^x$ are independently H or methyl, and $L^3$ is a halogen, an alkyl sulfonate group or an aryl sulfonate group, in the presence of a base, followed by treatment with hydrochloric acid; or (d) for a compound of General Formula I where $R^1$ is H$_2$NCH$_2$CH(OH)CH$_2$—, reacting a corresponding compound having the formula VIII

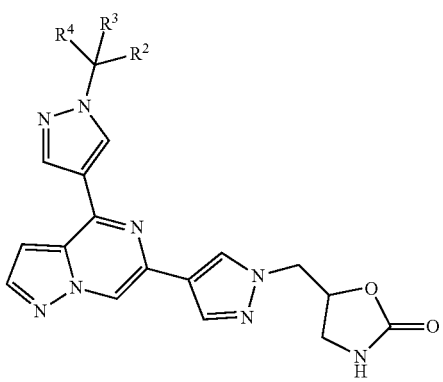

VIII where $R^2$, $R^3$ and $R^4$ are as defined for General Formula I, with a base; or (e) for a compound of General Formula I where $R^1$ is (1-3C alkyl)NH(3-6C)hydroxyalkyl, (1-3C alkyl)$_2$N(3-6C)

hydroxyalkyl, or hetCyc$^{3b}$(2-3C)hydroxyalkyl-, where hetCyc$^{3b}$ is a 4-6 membered heterocyclic ring having a ring nitrogen atom, wherein said heterocyclic ring is optionally substituted with 1-2 substituents independently selected from the group consisting of halogen or (1-4C)alkoxy, reacting a corresponding compound having the formula IX

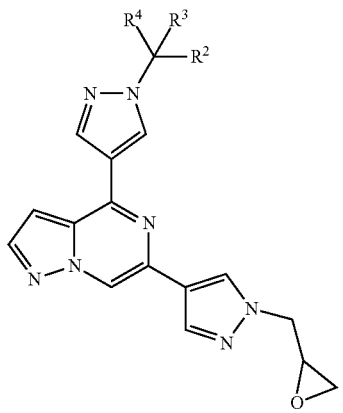

IX where R$^2$, R$^3$ and R$^4$ are as defined for General Formula I, with a reagent having the formula (1-3C alkyl)NH$_2$, (1-3C alkyl)$_2$NH or

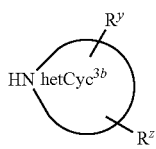

where R$^y$ and R$^z$ are independently selected from the group consisting of halogen or (1-4C)alkoxy and hetCyc$^{3b}$ is a 4-6 membered heterocyclic ring having a ring nitrogen atom, wherein said heterocyclic ring is optionally substituted with 1-2 substituents independently selected from the group consisting of halogen or (1-4C)alkoxy; or (f) for a compound of General Formula I where R$^1$ is hydroxy(1-6C)alkyl, (hydroxy)trifluoro(1-6C)alkyl or (1-4C alkoxy)(1-6C)hydroxyalkyl, reacting a corresponding compound having the formula X

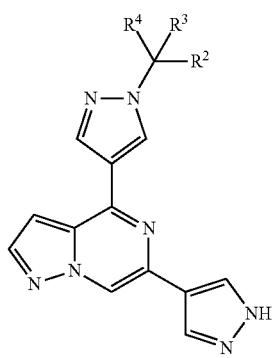

X where R$^2$, R$^3$ and R$^4$ are as defined for General Formula I, with a reagent having the formula

where G is (1-4C)alkyl, trifluoro(1-4C)alkyl or (1-4C alkoxy)(1-4C)alkyl; or (g) for a compound of General Formula I where R$^1$ is

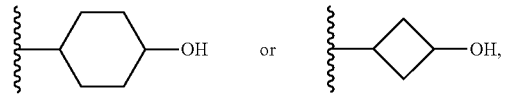

reacting a corresponding compound having the formula XI

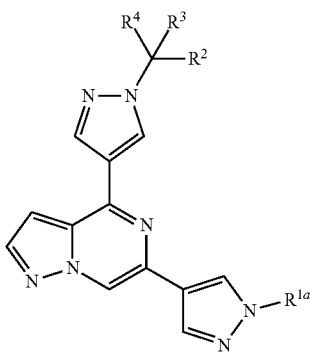

XI where R$^2$, R$^3$ and R$^4$ are as defined for General Formula I and R$^{1a}$ is

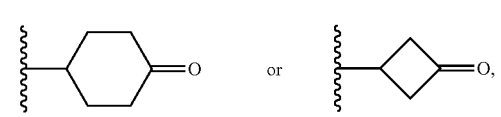

respectively, with a reducing agent; or (h) for a compound of Formula I where R$^1$ is hydroxy(1-6C)alkyl, reacting a corresponding compound wherein the hydroxy(1-6C)alkyl is protected as an alkyl ester with a base; or (i) for a compound of General Formula I where R$^1$ is R$^c$R$^d$N(CH$_2$CH$_2$)— or hetCyc$^{3a}$(CH$_2$CH$_2$)—, where R$^c$, R$^d$, and hetCyc$^{3a}$ are as defined for General Formula I, reacting a corresponding compound having the formula XII

XII

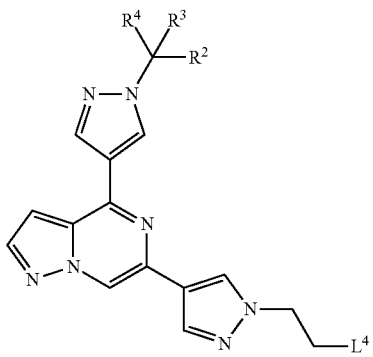

where $R^2$, $R^3$ and $R^4$ are as defined for General Formula I and $L^4$ is a halogen an alkyl sulfonate group or an aryl sulfonate group, with a reagent having the formula $R^cR^dNH_2$ or

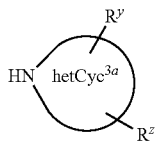

where hetCyc$^{3a}$ is as defined for General Formula I; or (j) for a compound of General Formula I where $R^1$ is $H_2NCH_2CH(OCH_3)CH_2$—, reacting a corresponding compound having the formula XIII

XIII

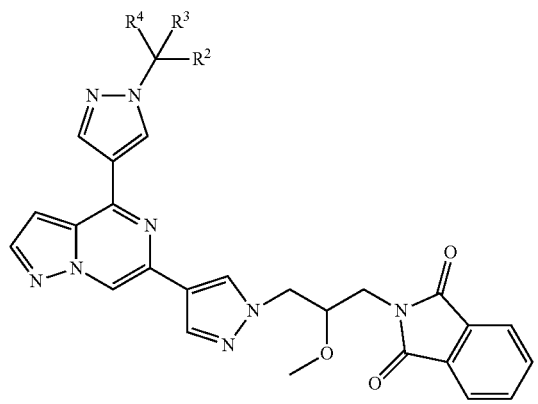

where $R^2$, $R^3$ and $R^4$ are as defined for General Formula I, with hydrazine; or (k) for a compound of Formula I where $R^1$ is

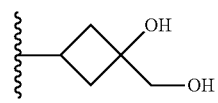

reacting a corresponding compound having the formula XIV

XIV

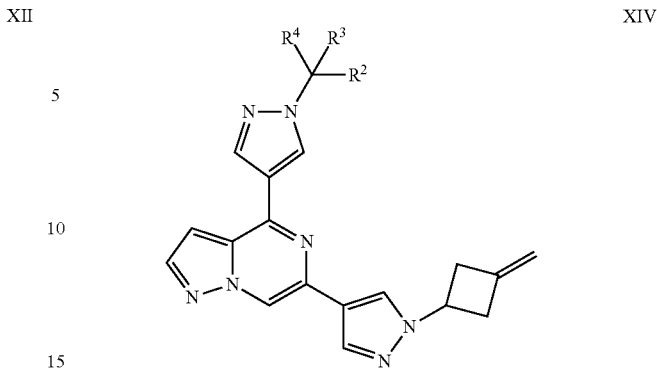

where $R^2$, $R^3$ and $R^4$ are as defined for General Formula I, with an oxidizing agent; or (l) for a compound of General Formula I where $R^1$ is $Cyc^1(CH_2)_m$—, $Cyc^1$ is a 4-6 membered cycloalkyl substituted with $H_2NHC(\!\!=\!\!O)$— or (1-3C alkyl)$_2$NC($\!\!=\!\!O$)—, and m is 0, reacting a corresponding compound of General Formula I where $R^1$ is $Cyc^1(CH_2)_m$—, $Cyc^1$ is a 4-6 membered cycloalkyl substituted with $CH_3C(\!\!=\!\!O)O$— and m is 0 with ammonia or (1-3C alkyl)NH; or (m) for a compound of General Formula I wherein $R^2$ and $R^3$ form a 4-membered azacyclic ring substituted with $SO_2CF_3$, and $R^1$ and $R^4$ are as defined for General Formula I, reacting a compound having the formula XIV

XIV

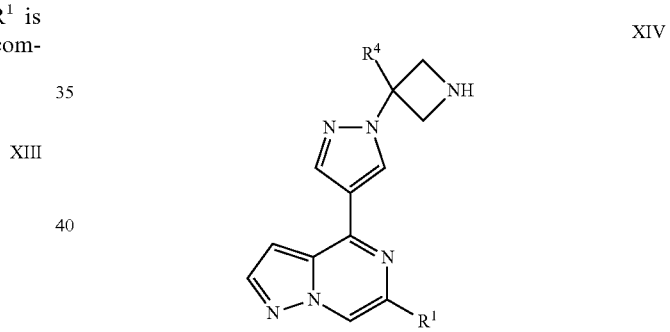

where $R^1$ and $R^4$ are as defined for General Formula I, with trifluoromethanesulfonic anhydride in the presence of a base; and optionally removing any protecting groups and optionally preparing a pharmaceutically acceptable salt thereof.

In the above processes (a), (b), (c), and (i), an example of an alkyl sulfonate includes methyl sulfonate, and an examples of an aryl sulfonate is a 4-toluenesulfonate group (i.e., a tosyl group).

Referring to process (a), suitable palladium catalysts include Pd$_2$(dba)$_3$, Pd(OAc)$_2$, Pd(PPh$_3$)$_2$Cl$_2$, P(Cy)$_3$, PdCl$_2$ (dppf) complex with CH$_2$Cl$_2$, and Pd(PPh$_3$)$_4$. Suitable ligands include XPHOS (dicyclohexylphosphino-2',4',6'-triisopropylbiphenyl), DIPHOS (1,2-Bis(diphenylphosphino) ethane or rac-BINAP (racemic-2,2'-Bis(diphenylphosphino)-1,1'-binaphthyl). The base may be, for example, an alkali metal carbonate, hydroxide, alkoxide or acetate, such as for example cesium carbonate, sodium carbonate, potassium carbonate, sodium hydroxide, sodium tert-butoxide or potassium acetate. Convenient solvents include aprotic solvents such as ethers (for example tetrahydrofuran or p-dioxane), toluene, DMF or DME. The reaction can be conveniently performed at a temperature ranging from ambient temperature to 120° C., for example from 80 to 110° C.

Referring to process (b), the base may be, for example, an alkali metal hydride or carbonate, such as sodium hydride, potassium hydride, sodium carbonate, potassium carbonate or cesium carbonate. Suitable solvents include aprotic solvents such as dimethylacetamide (DMA).

Referring to process (c), the base may be, for example, an alkali metal hydride or carbonate, such as sodium hydride, potassium hydride, sodium carbonate, potassium carbonate or cesium carbonate. Suitable solvents include aprotic solvents such as ethers (for example tetrahydrofuran or p-dioxane), DMF or DME.

Referring to process (d), suitable bases include alkali metal hydroxides such as lithium hydroxide. Suitable solvents include aprotic solvents such as ethers (for example tetrahydrofuran or p-dioxane), toluene or DMF.

Referring to process (g), suitable reducing agents include sodium borohydride, diisobutylaluminum hydride and lithium aluminum hydride.

Referring to process (h), the base may be, for example, an alkali metal hydride or carbonate, such as sodium hydride, potassium hydride, sodium carbonate, potassium carbonate or cesium carbonate.

Referring to process (k), suitable oxidizing agents include N-methylmorpholine-N-oxide in combination with osmium tetraoxide.

Referring to process (m), suitable bases include amine bases, such as diisopropylethylamine (DIEA) or triethylamine. Suitable solvents include neutral solvents such as dichloromethane and dichloroethane. The reaction is conveniently performed at temperatures between 0° C. and ambient temperature.

Amine groups in compounds described in any of the above methods may be protected with any convenient amine protecting group. Examples of amine protecting groups include acyl and alkoxycarbonyl groups, such as t-butoxycarbonyl (Boc), and [2-(trimethylsilyl)ethoxy]methyl (SEM). Likewise, carboxyl groups may be protected with any convenient carboxyl protecting group. Examples of carboxyl protecting groups include (1-6C)alkyl groups, such as methyl, ethyl and t-butyl. Alcohol groups may be protected with any convenient alcohol protecting group. Examples of alcohol protecting groups include benzyl, trityl, silyl ethers, and the like.

The compounds of formulas III, IV, VIII, IX, X, XI, XII, XIII, XIV and XV, which are useful as intermediates for the preparation of compounds of General Formula I, are also provided as further aspects of the invention.

The compounds of General Formula I represent novel inhibitors of one or more JAK kinases. In particular, the compounds are inhibitors of Tyk2, JAK1, JAK2, and/or JAK3, and are useful in the treatment of cytokine or JAK kinase-associated diseases such as autoimmune diseases, inflammatory diseases, rejection of transplanted organs, tissues and cells, and hematologic disorders and malignancies and their co-morbidities.

The ability of compounds of the invention to act as inhibitors of Tyk2 may be demonstrated by the assay described in Example A.

The ability of compounds of the invention to act as inhibitors of JAK1 may be demonstrated by the assay described in Example B.

The ability of compounds of the invention to act as inhibitors of JAK2 may be demonstrated by the assay described in Example C.

The ability of compounds of the invention to act as inhibitors of JAK3 may be demonstrated by the assay described in Example D.

Compounds of General Formula I may be useful in the treatment of JAK kinase-associated diseases and disorders, such as autoimmune diseases and inflammatory diseases. Accordingly, provided herein is a method of treating a JAK kinase-associated disease or disorder in a subject in need thereof, comprising administering to the subject a therapeutically effective amount of a compound of General Formula I (e.g., any of the exemplary compounds described herein), or a pharmaceutically acceptable salt or solvate thereof, or a pharmaceutical composition thereof. Also provided herein is a method of preventing a JAK kinase-associated disease or disorder in a subject in need thereof, comprising administering to the subject a therapeutically effective amount of a compound of General Formula I (e.g., any of the exemplary compounds described herein), or a pharmaceutically acceptable salt or solvate thereof, or a pharmaceutical composition thereof. In one non-limiting embodiment, the autoimmune disease or inflammatory disease is selected from the group:

(i) arthritis, including rheumatoid arthritis, juvenile arthritis, psoriatic arthritis, reactive arthritis, ankylosing spondylitis, osteoarthritis, and seronegative arthopathies;

(ii) intestinal inflammations including Crohn's disease, ulcerative colitis, inflammatory bowel disease, celiac diseases, proctitis, and eosinophilic gastroenteritis;

(iii) airways diseases including asthma and other obstructive airway diseases, including severe refractory asthma, chronic asthma, airway hyper-responsiveness, bronchitis, allergic asthma, and chronic obstruction pulmonary disease;

(iv) allergic reactions including severe allergic reaction (including anaphylaxis);

(v) eye diseases, disorders or conditions including autoimmune diseases of the eye, uveitis including uveitis associated with Behcet's disease, lens-induced uveitis and optic neuritis;

(vi) skin diseases, conditions or disorders including psoriasis, atopic dermatitis, severe dermatitis, eczema, scleroderma, pruritus and other pruritic conditions, alopecia areata and mastocytosis;

(vii) sepsis, systemic inflammatory response syndrome, and neutropenic fever;

(viii) fibrosis, including hepatic fibrosis, idiopathic pulmonary fibrosis, myelofibrosis and scleroderma;

(ix) gout (resolution of tophi);

(x) lupus (also known as systemic lupus erythematosus), including manifestations such as cutaneous lupus, lupus nephritis, neurosychiatric lupus and other manifestations;

(xi) neurodegenerative diseases including demyelinating diseases, such as multiple sclerosis, motor neuron disease, Alzheimer's disease, Parkinson's disease, amyotrophic lateral sclerosis, and ischemic reperfusion injury in stroke;

(xii) diabetes, including Type I diabetes and complications from diabetes, metabolic syndrome and obesity;

(xiii) axial spondyloarthorpathy (axial SpA); and (xiv) Interferon type 1 activation disorders such as systemic lupus erythematosus, Aicardi-Goutieres syndrome, myositis, and periodontitis.

Additional examples of autoimmune diseases and inflammatory diseases include nephropathy, sarcoidosis, pancreatitis, autoimmune thyroiditis, fibromyalgia, atherosclerosis, autoimmune hemolytic anemia, autoimmune atrophic gastritis of pernicious anemia, autoimmune encephalomyelitis, autoimmune orchitis, Goodpasture's disease, autoimmune myocarditis, autoimmune thrombocytopenia, sympathetic ophthalmia, myasthenia gravis, Graves' disease, primary biliary cirrhosis, chronic aggressive hepatitis, membranous glomerulopathy, Sjogren's syndrome, Reiter's syndrome, systemic sclerosis, polyarteritis nodosa, bullous pemphigoid, Cogan's syndrome, Wegener's granulomatosis, cystic fibrosis, mixed connective tissue disease, antiphospholipid syndrome, polymyositis, dermatomyositis, membranous nephritis, primary sclerosing cholangitis, severe chronic urticaria, giant cell arteritis, eosinophilic esophagitis, and eosinophilic gastritis.

In one embodiment, provided herein is a method of treating autoimmune or inflammatory disease in a subject in need thereof, comprising administering to the subject a therapeutically effective amount of a compound of General Formula I (e.g., any of the exemplary compounds described herein), or a pharmaceutically acceptable salt or solvate thereof, or a pharmaceutical composition thereof, wherein the disease or disorder is selected from (i) arthritis, including rheumatoid arthritis, juvenile arthritis, psoriatic arthritis, reactive arthritis, ankylosing spondylitis, osteoarthritis, and seronegative arthopathies; (ii) intestinal inflammations including Crohn's disease, ulcerative colitis, inflammatory bowel disease, celiac diseases, proctitis, and eosinophilic gastroenteritis; (vi) skin diseases, conditions or disorders including psoriasis, atopic dermatitis, severe dermatitis, eczema, scleroderma, pruritus and other pruritic conditions, alopecia areata and mastocytosis; and (x) lupus (also known as systemic lupus erythematosus), including manifestations such as cutaneous lupus, lupus nephritis, neurosychiatric lupus and other manifestations.

In one embodiment, provided herein is a method of treating an autoimmune or inflammatory disease in a subject in need thereof, comprising administering to the subject a therapeutically effective amount of a compound of General Formula I (e.g., any of the exemplary compounds described herein), or a pharmaceutically acceptable salt or solvate thereof, or a pharmaceutical composition thereof, wherein the disease or disorder is selected from lupus, psoriasis, psoriatic arthritis, rheumatoid arthritis, multiple sclerosis and inflammatory bowel diseases.

In one embodiment, provided herein is a method of preventing diseases and disorders in a subject in need thereof, comprising administering to the subject a therapeutically effective amount of a compound of General Formula I (e.g., any of the exemplary compounds described herein), or a pharmaceutically acceptable salt or solvate thereof, or a pharmaceutical composition thereof, wherein the disease or disorder is selected from:

(i) arthritis, including rheumatoid arthritis, juvenile arthritis, psoriatic arthritis, reactive arthritis, ankylosing spondylitis, osteoarthritis, and seronegative arthopathies;

(ii) intestinal inflammations including Crohn's disease, ulcerative colitis, inflammatory bowel disease, celiac diseases, proctitis, and eosinophilic gastroenteritis;

(vi) skin diseases, conditions or disorders including psoriasis, atopic dermatitis, severe dermatitis, eczema, scleroderma, pruritus and other pruritic conditions, alopecia areata and mastocytosis; and (x) lupus (also known as systemic lupus erythematosus), including manifestations such as cutaneous lupus, lupus nephritis, neurosychiatric lupus and other manifestations.

Compounds of General Formula I may also be useful for treating organ, tissue or cell transplant rejections, including bone marrow transplant, and in the treatment of autoimmune and inflammatory diseases and of complications arising therefrom in a subject in need thereof, comprising administering to the subject a therapeutically effective amount of at least one compound of Formula I (e.g., any of the exemplary compounds described herein) or a pharmaceutically acceptable salt or solvate thereof, or a pharmaceutical composition thereof.

Accordingly, provided herein is a method of treating organ, tissue or cell transplant rejection in a subject in need thereof, comprising administering to the subject a therapeutically effective amount of at least one compound of General Formula I (e.g., any of the exemplary compounds described herein) or a pharmaceutically acceptable salt or solvate thereof, or a pharmaceutical composition thereof.

Also provided herein is a method of preventing organ, tissue or cell transplant rejection in a subject in need thereof, comprising administering to the subject a therapeutically effective amount of at least one compound of General Formula I (e.g., any of the exemplary compounds described herein) or a pharmaceutically acceptable salt or solvate thereof, or a pharmaceutical composition thereof.

Compounds of Formula I may also be useful in treating certain malignancies, including solid tumors, skin cancer (e.g., melanoma), and hematological malignancies such as lymphomas and leukemias, and further may be useful in treating the complications thereof, including sequelae of hematologic malignancies (for example, in the treatment of splenomegaly in myelofibrosis), as well as cachexia in patients with solid tumors.

Accordingly, provided herein is a method of treating malignancies in a subject, which comprises administering to said subject a therapeutically effective amount of a compound of Formula I (e.g., any of the exemplary compounds described herein) or a pharmaceutically acceptable salt or solvate thereof, or a pharmaceutical composition thereof. In one embodiment, the malignancies are selected from solid tumors, skin cancer (e.g., melanoma), and hematological malignancies.

In some embodiments, provided herein is a method for treating a subject diagnosed with a JAK kinase-associated disorder (e.g., a JAK kinase-associated disorder as described herein), comprising administering to the subject a therapeutically effective amount of a compound of General Formula I (e.g., any of the exemplary compounds described herein), or a pharmaceutically acceptable salt or solvate thereof, or a pharmaceutical composition thereof.

In some embodiments, the compounds of the present invention are useful for treating a JAK-associated disease (e.g., a JAK kinase-associated disorder as described herein) in combination with one or more additional therapeutic agents or therapies that work by the same or a different mechanism of action.

In some embodiments, the additional therapeutic agent is selected from the group of: cyclosporin A (e.g. Sandimmune® or Neoral®), rapamycin, FK-506 (tacrolimus), leflunomide, deoxyspergualin, mycophenolate (e.g. Cellcept®, azathioprine (e.g. Imuran®), daclizumab (e.g. Zenapax®), OKT3 (e.g. Orthocolone®), AtGam, aspirin, acetaminophen, ibuprofen, naproxen, piroxicam, antiinflammatory steroids (e.g. prednisolone or dexamethasone), methotrexate, statins, anti-TNF agents (e.g., Enbrel® (etanercept) or Humira® (adalimumab)), Orencia® (abatacept), cyclophosphamide, mycophenolic acid, hydroxychloroquine, and metformin.

In some embodiments, the additional therapeutic agent is selected from the group: mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, cytostatic agents anti-androgens, targeted antibodies, HMG-CoA reductase inhibitors, and prenyl-protein transferase inhibitors.

In some embodiments, the additional therapeutic agent or therapy is surgery or radiotherapy, including, e.g., radioiodide therapy, external-beam radiation, and radium 223 therapy.

In some embodiments, provided herein is a method of treating a JAK kinase-associated disease or disorder (e.g., a disease or disorder as described herein) in a subject in need thereof, comprising administering to said subject a compound of General Formula I (e.g., any of the exemplary compounds described herein), or a pharmaceutically acceptable salt or solvate thereof, or a pharmaceutical composition thereof, in combination with at least one additional therapy or therapeutic agent selected from cyclosporin A (e.g. Sandimmune® or Neoral®), rapamycin, FK-506 (tacrolimus), leflunomide, deoxyspergualin, mycophenolate (e.g. Cellcept®, azathioprine (e.g. Imuran®), daclizumab (e.g. Zenapax®), OKT3 (e.g. Orthocolone®), AtGam, aspirin, acetaminophen, ibuprofen, naproxen, piroxicam, antiinflammatory steroids (e.g. prednisolone or dexamethasone), methotrexate, statins, anti-TNF agents (e.g., Enbrel® (etanercept) or Humira® (adalimumab)), Orencia® (abatacept), cyclophosphamide, mycophenolic acid, hydroxychloroquine, metformin, mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, cytostatic agents anti-androgens, targeted antibodies, HMG-CoA reductase inhibitors, prenyl-protein transferase inhibitors, radioiodide therapy, external-beam radiation, and radium 223 therapy, wherein the amount of the compound of General Formula I (e.g., any of the exemplary compounds described herein), or a pharmaceutically acceptable salt or solvate thereof, or pharmaceutical composition thereof, in combination with the additional therapy or therapeutic agent, is effective in treating said JAK kinase-associated disease or disorder. In one embodiment, the JAK kinase-associated disease or disorder is any of the diseases or disorders described hereinabove.

The additional therapeutic agent(s) may be administered as one or more doses with one or more doses of a compound of General Formula I (e.g., any of the exemplary compounds described herein), or a pharmaceutically acceptable salt or solvate thereof, or pharmaceutical composition thereof as part of the same or separate dosage forms, by the same or different routes of administration, and on the same or different administration schedules according to standard pharmaceutical practice known to one skilled in the art.

Also provided herein is (i) a pharmaceutical combination for treating a JAK kinase-associated disease or disorder in a subject in need thereof, which comprises (a) a compound of General Formula I (e.g., any of the exemplary compounds described herein), or a pharmaceutically acceptable salt or solvate thereof, (b) an additional therapeutic agent, and (c) optionally at least one pharmaceutically acceptable carrier, (e.g., for simultaneous, separate or sequential use for the treatment of a JAK kinase-associated disease or disorder), wherein the amounts of the compound of General Formula I, or the pharmaceutically acceptable salt or solvate thereof and of the additional therapeutic agent are together effective in treating said JAK kinase-associated disease or disorder; (ii) a pharmaceutical composition including such a combination; (iii) the use of such a combination for the preparation of a medicament for the treatment of a JAK kinase-associated disease or disorder; and (iv) a commercial package or product including such a combination for simultaneous, separate or sequential use.

The term "pharmaceutical combination" as used herein means a product that results from the mixing or combining of more than one active ingredient, e.g. (a) a compound of General Formula I or a pharmaceutically acceptable salt or solvate thereof and (b) another therapeutic agent, and includes both fixed and non-fixed combinations of the active ingredients. The term "fixed combination" means that the active ingredients, e.g. (a) a compound of General Formula I or a pharmaceutically acceptable salt or solvate thereof and (b) another therapeutic agent, are both administered to a subject simultaneously in the form of a single entity or dosage. The term "non-fixed combination" means that the active ingredients, e.g., (a) a compound of General Formula I or a pharmaceutically acceptable salt or solvate thereof and (b) another agent, are both administered to a subject as separate entities either simultaneously, concurrently or sequentially with no specific time limits, wherein such administration provides therapeutically effective levels of the two compounds in the body of the subject. For a non-fixed combination, the individual active ingredients of the combination may be administered separately at different times during the course of therapy or concurrently in divided or single combination forms.

As used herein, the terms "treat" or "treatment" or "treating" mean an alleviation, in whole or in part, of symptoms associated with a disease or disorder or condition (e.g., a JAK kinase-associated disease or disorder, such as any of the diseases and disorders described herein, including autoimmune diseases, inflammatory diseases, rejection of transplanted organs, tissues and cells, and hematologic disorders and malignancies and their co-morbidities), or slowing, or halting of further progression or worsening of those symptoms.

As used herein, the term "prevent" or "preventing" as used herein means the prevention of the onset, recurrence or spread, in whole or in part, of the disease or disorder or condition (e.g., a JAK kinase-associated disease or disorder, such as any of the diseases and disorders described herein, including autoimmune diseases, inflammatory diseases, rejection of transplanted organs, tissues and cells, and hematologic disorders and malignancies and their co-morbidities), or a symptom thereof.

The terms "effective amount" and "therapeutically effective amount" refer to an amount of compound that, when administered to a subject in need of such treatment, is sufficient to (i) treat a particular disease, condition, or disorder, (ii) attenuate, ameliorate, or eliminate one or more symptoms of the particular disease, condition, or disorder, (iii) delay the onset of one or more symptoms of the particular disease, condition, or disorder, or (iv) prevention of the onset, recurrence or spread, in whole or in part, of the disease or condition described herein. The amount of a compound of General Formula I that will correspond to such an amount will vary depending upon factors such as the particular compound, the disease condition and its severity, and the identity (e.g., weight) of the subject in need of treatment, but can nevertheless be routinely determined by one skilled in the art.

As used herein, the term "subject," "individual," or "patient," used interchangeably, refers to refers to any animal, including mammals. In some embodiments, the subject is a human. In some embodiments, the patient is a human. In some embodiments, the subject has experienced and/or exhibited at least one symptom of the disease or disorder to be treated and/or prevented. In some embodiments, the subject has been identified or diagnosed as having a JAK kinase-associated disease or disorder. In some embodiments, the subject is a pediatric patient (i.e. a patient under the age of 21 years at the time of diagnosis or treatment). The term "pediatric" can be further divided into various subpopulations including: neonates (from birth through the first 28 days of life); infants (29 days of age to less than two years of age); children (two years of age to less than 12 years of age); and adolescents (12 years of age through 21 years of age (up to, but not including, the twenty-second birthday)).

As used herein, the term "mammal" refers to a warm-blooded animal that has or is at risk of developing a disease described herein and includes, but is not limited to, primates (including humans), guinea pigs, dogs, cats, rats, mice and hamsters. In some embodiments, the mammal is a human.

Compounds of General Formula I or pharmaceutically acceptable salts or solvates thereof may be administered by any convenient route, e.g. into the gastrointestinal tract (e.g. rectally or orally), the nose, lungs, musculature or vasculature, or topical (e.g., transdermal, dermal, ophthalmic, and to the mucous membranes including intranasal, vaginal and rectal delivery). Compounds of General Formula I or pharmaceutically acceptable salts or solvates thereof may be administered in any convenient administrative form, e.g. tablets, powders, capsules, solutions, dispersions, suspensions, syrups, sprays, suppositories, gels, emulsions, patches, ointments, creams, etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

A typical formulation is prepared by mixing a compound described herein and a carrier or excipient. Suitable carriers and excipients are well known to those skilled in the art.

The compositions comprising as the active ingredient a compound of General Formula I as provided herein or a pharmaceutically acceptable salt or solvate thereof can be formulated in a unit dosage form, each dosage containing from about 5 to about 1,000 mg (1 g), more usually about 100 mg to about 500 mg, of the active ingredient. The term "unit dosage form" refers to physically discrete units suitable as unitary dosages for administration to the subject in need thereof, each unit containing a predetermined quantity of the active ingredient calculated to produce the desired therapeutic effect, in association with a suitable pharmaceutical excipient.

In some embodiments, the compositions provided herein contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active ingredient may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

Accordingly, provided here in is a pharmaceutical composition, which comprises a compound of General Formula I (e.g., any of the exemplary compounds described herein) or a pharmaceutically acceptable salt or solvate thereof, as defined hereinabove, and a pharmaceutically acceptable carrier. In one embodiment, the pharmaceutical composition is formulated for oral administration. In one embodiment, the pharmaceutical composition is formulated as a tablet or capsule.

Also provided herein is a compound of General Formula I or a pharmaceutically acceptable salt or solvate thereof, or a pharmaceutical composition thereof, for use in therapy. In one embodiment, provided herein is a compound of General Formula I or a pharmaceutically acceptable salt or solvate thereof, for use in the treatment of cytokine or JAK kinase-associated diseases in a subject.

In one embodiment, provided herein is a compound of General Formula I or a pharmaceutically acceptable salt or solvate thereof, or a pharmaceutical composition thereof, for use in the treatment of autoimmune diseases and inflammatory diseases in a subject.

In one embodiment, provided herein is a compound of General Formula I or a pharmaceutically acceptable salt or solvate thereof, or a pharmaceutical composition thereof, for use in the prevention of autoimmune diseases and inflammatory diseases in a subject.

In one embodiment, provided herein is a compound of General Formula I or a pharmaceutically acceptable salt or solvate thereof, or a pharmaceutical composition thereof, for use in the treatment of transplant rejection in a subject.

In one embodiment, provided herein is a compound of General Formula I or a pharmaceutically acceptable salt or solvate thereof, or a pharmaceutical composition thereof, for use in the prevention of transplant rejection in a subject.

In one embodiment, provided herein is a compound of General Formula I or a pharmaceutically acceptable salt or solvate thereof, or a pharmaceutical composition thereof, for use in the treatment of hematologic disorders and malignancies in a subject.

According to a further aspect, provided herein is the use of a compound of General Formula I or a pharmaceutically acceptable salt or solvate thereof, or a pharmaceutical composition thereof, in the treatment of cytokine or JAK kinase-associated diseases in a subject.

In one embodiment, provided herein is the use of a compound of Formula I or a pharmaceutically acceptable salt or solvate thereof, or a pharmaceutical composition thereof, in the treatment of autoimmune diseases and inflammatory diseases.

In one embodiment, the invention provides the use of a compound of General Formula I or a pharmaceutically acceptable salt or solvate thereof, or a pharmaceutical composition thereof, in the treatment of organ, tissue or cell transplant rejection in a subject.

In one embodiment, provided herein is the use of a compound of General Formula I or a pharmaceutically acceptable salt or solvate thereof, or a pharmaceutical composition thereof, in the treatment of malignancies in a subject.

Also provided herein is method for inhibiting JAK kinase activity in a cell, the method comprising contacting the cell with a compound of Formula I or pharmaceutically acceptable salt or solvate thereof, or a pharmaceutical composition thereof. In one embodiment, the cell is a mammalian cell. In one embodiment, the contacting occurs in vitro. In one embodiment, the contacting occurs in vivo.

As used herein, the term "contacting" refers to the bringing together of indicated moieties in an in vitro system or an in vivo system. For example, "contacting" a JAK kinase with a compound provided herein includes the administration of a compound provided herein to an individual or patient, such as a human, having a JAK kinase, as well as, for example, introducing a compound provided herein into a sample containing a cellular or purified preparation containing the JAK kinase.

Provided herein are pharmaceutical kits useful, for example, in the treatment of JAK kinase-associated diseases or disorders, which include one or more containers containing a pharmaceutical composition comprising a therapeutically effective amount of a compound of General Formula I or a pharmaceutically acceptable salt or solvate thereof, provided herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

One skilled in the art will recognize that both in vivo and in vitro trials using suitable, known and generally accepted cell and/or animal models are predictive of the ability of a of General Formula I or a pharmaceutically acceptable salt or solvate thereof, or a pharmaceutical composition thereof, to treat or prevent a given disease or disorder.

One skilled in the art will further recognize that human clinical trials with a compound of General Formula I or a pharmaceutically acceptable salt or solvate thereof, or a pharmaceutical composition thereof, including first-in-human, dose ranging and efficacy trials, in healthy patients and/or those suffering from a given disorder, may be completed according to methods well known in the clinical and medical arts.

EXAMPLES

The following examples illustrate the invention. In the examples described below, unless otherwise indicated all temperatures are set forth in degrees Celsius. Reagents were purchased from commercial suppliers and were used without further purification unless otherwise indicated.

General Enzyme Inhibition Assay Method

The assays described in Examples A, B, C and D for the determination of Tyk2, JAK1, JAK2 and JAK3 kinase activity, respectively, utilized the Omnia® Kinase fluorescence peptide substrate-based technology (Invitrogen). The specific components of the assay mixture are described in Examples A, B, C and D. In these assays, $Mg^{2+}$ is chelated upon phosphorylation of the Omnia peptide by the kinase to form a bridge between the chelation-enhanced fluorophore Sox and the phosphate, resulting in an increase in fluorescence emission at 485 nM when excited at 360 nM. The reactions were therefore read at excitation 360 nm and emission was measured at 485 nm every 50 seconds for 45 minutes using a PerkinElmer EnVision Multilabel Plate Reader.

The final buffer conditions for Tyk2, JAK1, JAK2, and JAK3 assays were as follows: 25 mM HEPES, pH 7.4, 10 mM $MgCl_2$, 0.01% Triton X-100 and 1 mM DTT.

$IC_{50}$ Determinations

Compounds were prepared at 50× the final concentration in DMSO by conducting 3-fold serial dilutions from a 500-μM intermediate dilution to give a 10-point dosing curve having a high dose of 10 μM. Two-μL aliquots of these were transferred to a fresh plate for a ten-fold intermediate dilution with assay buffer. Five-μL aliquots of the diluted compounds were then transferred to 20-μL of assay mixtures described in Examples A, B, C and D for a final concentration of DMSO of 2%. A standard or reference compound was typically included on each assay plate to validate that plate. For each plate, percent of control (POC) values were calculated for each well according to the following equation:

$$POC = \frac{\text{Sample} - \overline{X}_{min}}{\overline{X}_{max} - \overline{X}_{min}} \times 100,$$

where $\overline{X}_{max}$=Average Uninhibited Controls
$\overline{X}_{min}$=Average Background
$IC_{50}$'s were estimated from the POC's using a standard 4-parameter logistic model:

$$Y = A + \frac{B-A}{1+\left(\frac{C}{X}\right)^D},$$

where A=Minimum Y (Bottom Asymptote)
B=Maximum Y (Top Asymptote)
C=$EC_{50}$
D=Slope Factor
X=Compound Concentration (nM)
Y=POC
The $IC_{50}$ is defined as the concentration of inhibitor at which the POC equals 50 for the fitted curve.

Example A

Tyk2 Inhibition Assay

Compounds of Formula I were screened for their ability to inhibit Tyk2 using the general enzyme inhibition assay method, in which the assay mixture contained 1 mM ATP, 8 µM Omnia® Y12 peptide (Catalog # IVGN KPZ3121C; Invitrogen Corporation, Carlsbad, Calif.) and 1 nM Tyk2 in a total volume of 25 µL. Human Tyk2 kinase domain, comprising amino acids 886 to 1187 with 10 additional histidine residues (histidine tag) on the carboxy terminus, was expressed and purified from bacculovirus in-house at Array BioPharma Inc. (Boulder, Colo.). The histidine tag was cleaved after purification using standard conditions.

Example B

JAK1 Inhibition Assay

Compounds of Formula I were screened for their ability to inhibit JAK1 using the general enzyme inhibition assay method, in which the assay mixture contained 1 mM ATP, 8 µM Omnia® Y12 peptide (Catalog # IVGN KPZ3121C; Invitrogen Corporation, Carlsbad, Calif.) and 12.5 nM JAK1 in a total volume of 25 µL. JAK1 was purchased from Invitrogen Corporation, Carlsbad, Calif. (catalog # IVGN PV4775).

Example C

JAK2 Inhibition Assay

Compounds of Formula I were screened for their ability to inhibit JAK2 using the general enzyme inhibition assay method, in which the assay mixture contained 1 mM ATP, 10 µM Omnia® Y7 peptide (Catalog # IVGN KNZ3071C, Invitrogen Corporation, Carlsbad, Calif.) and 4 nM JAK2 in a total volume of 25 µL. JAK2 was purchased from Invitrogen Corporation, Carlsbad, Calif. (catalog # IVGN PV4288).

Example D

JAK3 Inhibition Assay

Compounds of Formula I were screened for their ability to inhibit JAK3 using the general enzyme inhibition assay method, in which the assay mixture contained 1 mM ATP, 10 µM Omnia® Y7 peptide (Catalog # IVGN KNZ3071C, Invitrogen Corporation, Carlsbad, Calif.) and 2 nM JAK3 in a total volume of 25 µL. JAK3 was purchased from Invitrogen Corporation, Carlsbad, Calif. (catalog # IVGN PV4080).

Table 1 provides averaged $IC_{50}$ ranges for compounds described in the Examples when tested in the assays described in Examples A, B, C and D. For each $IC_{50}$ value shown in Table 1, "A" represents an $IC_{50}$ value of less than 10 nM, "B" represents an $IC_{50}$ value of greater than 10 nM and less than 100 nM, "C" represents an $IC_{50}$ value of greater than 100 nM and less than 1000 nM, and "D" represents an $IC_{50}$ value of greater than 1000 nM and less than or equal to 10,000 nM.

TABLE 1

| Ex. # | TYK2 Enzyme $IC_{50}$ 1 mM ATP | JAK1 Enzyme $IC_{50}$ 1 mM ATP | JAK2 Enzyme $IC_{50}$ 1 mM ATP | JAK3 Enzyme $IC_{50}$ 1 mM ATP |
|---|---|---|---|---|
| 1 | D | D | D | D |
| 2 | C | D | C | D |
| 3 | B | D | B | D |
| 4 | B | C | B | D |
| 5 | B | C | C | D |
| 6 | B | B | B | D |
| 7 | B | D | B | D |
| 8 | B | B | B | D |
| 9 | B | C | B | D |
| 10 | B | D | B | D |
| 11 | B | D | B | D |
| 12 | C | D | C | D |
| 13 | B | C | A | D |
| 14 | B | B | B | D |
| 15 | B | B | B | D |
| 16 | B | B | B | D |
| 17 | B | C | B | D |
| 18 | B | B | B | D |
| 19 | D | D | D | D |
| 20 | B | B | B | D |
| 21 | C | D | B | D |
| 22 | B | C | B | D |
| 23 | B | C | B | D |
| 24 | B | C | B | D |
| 25 | B | C | B | D |
| 26 | C | D | C | D |
| 27 | B | D | B | D |
| 28 | B | D | B | D |
| 29 | B | C | B | D |
| 30 | B | C | B | D |
| 31 | B | C | A | D |
| 32 | A | B | A | D |
| 33 | A | C | A | D |
| 34 | B | B | A | D |
| 35 | B | C | B | D |
| 36 | A | C | A | D |
| 37 | B | C | A | D |
| 38 | B | C | B | D |
| 39 | B | B | B | D |
| 40 | B | C | B | D |
| 41 | B | C | B | D |
| 42 | B | D | B | D |
| 43 | B | D | B | D |
| 44 | B | D | D | D |
| 45 | D | D | D | D |
| 46 | N/T | N/T | N/T | N/T |
| 47 | D | D | D | D |
| 48 | A | B | A | D |
| 49 | C | D | D | D |
| 50 | D | D | C | C |
| 51 | C | D | D | D |
| 52 | B | C | B | D |
| 53 | C | D | C | D |
| 54 | B | C | B | D |
| 55 | B | C | C | D |
| 56 | B | D | B | D |
| 57 | B | C | B | D |
| 58 | B | C | B | D |
| 59 | B | C | B | D |
| 60 | B | D | B | D |
| 61 | B | C | B | D |
| 62 | B | C | B | D |
| 63 | B | C | B | D |
| 64 | B | C | B | D |
| 65 | B | C | B | D |
| 66 | B | B | B | C |
| 67 | C | C | B | C |
| 68 | B | C | B | D |
| 69 | C | D | C | D |
| 70 | B | C | B | D |
| 71 | C | D | C | D |
| 72 | C | C | C | D |
| 73 | B | D | B | D |
| 74 | B | D | C | D |
| 75 | C | D | C | D |
| 76 | C | D | C | D |
| 77 | C | D | C | D |
| 78 | C | D | C | D |
| 79 | B | B | B | D |
| 80 | C | D | C | D |

TABLE 1-continued

| Ex. # | TYK2 Enzyme IC$_{50}$ 1 mM ATP | JAK1 Enzyme IC$_{50}$ 1 mM ATP | JAK2 Enzyme IC$_{50}$ 1 mM ATP | JAK3 Enzyme IC$_{50}$ 1 mM ATP |
|---|---|---|---|---|
| 81 | B | C | B | D |
| 82 | C | C | B | D |
| 83 | B | D | B | D |
| 84 | B | B | B | D |
| 85 | C | D | A | D |
| 86 | A | C | B | D |
| 87 | C | D | C | D |
| 88 | C | D | C | D |
| 89 | B | C | B | D |
| Peak A | | | | |
| 90 | B | C | B | D |
| Peak B | | | | |
| 91 | B | C | B | D |
| Peak A | | | | |
| 92 | B | C | B | D |
| Peak B | | | | |
| 93 | B | D | C | D |
| Peak A | | | | |
| 94 | B | C | B | D |
| Peak B | | | | |
| 95 | D | D | D | N/T |
| Peak A | | | | |
| 96 | D | D | C | D |
| Peak B | | | | |
| 97 | B | C | C | D |
| 98 | B | D | B | D |
| 99 | B | D | B | D |
| 100 | B | D | B | D |
| 101 | B | D | B | D |
| 102 | C | D | B | D |
| 103 | B | D | B | D |
| 104 | B | D | B | D |
| 105 | C | D | C | D |
| 106 | C | D | C | D |
| 107 | B | C | B | D |
| 108 | B | C | B | D |
| 109 | C | D | D | D |
| 110 | B | C | B | D |
| 111 | B | C | B | D |
| 112 | C | D | C | D |
| 113 | B | D | C | D |
| 114 | B | C | B | D |
| 115 | B | C | B | D |
| 116 | B | D | B | D |
| 117 | C | C | C | D |
| 118 | B | B | A | D |
| 119 | A | C | B | D |
| 120 | B | C | B | D |
| 121 | B | C | B | D |
| 122 | B | B | B | D |
| 123 | B | C | B | D |
| 124 | B | C | B | D |
| 125 | B | D | C | D |
| 126 | B | C | B | D |
| 127 | C | D | C | D |
| 128 | C | D | C | D |
| 129 | B | C | B | D |
| 130 | B | D | B | D |
| 131 | B | C | B | D |
| 132 | B | C | B | D |
| Peak A | | | | |
| 133 | B | B | A | D |
| Peak B | | | | |
| 134 | B | B | B | D |
| 135 | B | D | B | D |
| 136 | B | C | B | D |
| 137 | B | C | B | D |
| 138 | B | D | B | D |
| 139 | B | C | C | D |
| 140 | B | D | B | D |
| 141 | B | D | B | D |
| 142 | B | D | B | D |
| 143 | C | D | B | D |
| 144 | B | C | B | D |
| 145 | C | C | B | D |
| 146 | B | D | B | D |
| 147 | B | D | B | D |
| 148 | C | D | C | D |
| Peak A | | | | |
| 149 | B | D | B | D |
| Peak B | | | | |
| 150 | B | D | B | D |
| Peak A | | | | |
| 151 | B | C | B | D |
| Peak B | | | | |
| 152 | B | D | B | D |
| Peak B | | | | |
| 153 | B | C | B | D |
| Peak A | | | | |
| 154 | B | C | B | D |
| Peak B | | | | |
| 155 | B | C | B | D |
| Peak A | | | | |
| 156 | B | C | B | D |
| Peak B | | | | |
| 157 | B | C | B | D |
| Peak A | | | | |
| 158 | B | B | B | D |
| Peak B | | | | |
| 159 | B | C | B | D |
| Peak A | | | | |
| 160 | B | D | B | D |
| Peak B | | | | |
| 161 | B | C | B | D |
| 162 | A | C | B | D |
| 163 | B | C | A | D |
| Peak A | | | | |
| 164 | C | D | C | D |
| Peak B | | | | |
| 165 | B | C | B | D |
| 166 | B | C | B | D |
| 167 | B | C | B | D |
| 168 | B | D | B | D |
| 169 | C | D | C | D |
| 170 | B | C | B | D |
| 171 | B | C | B | D |
| 172 | B | B | B | D |
| 173 | B | C | B | D |
| 174 | B. | C | B | D |
| 175 | C | D | B | D |
| 176 | A | C | C | D |
| 177 | A | C | B | D |
| 178 | B | D | B | D |
| 179 | B | D | B | D |
| 180 | C | D | C | D |
| 181 | B | C | B | D |
| 182 | B | C | B | D |
| 183 | B | D | B | D |
| 184 | C | D | C | D |
| 185 | C | C | C | D |
| 186 | B | D | B | D |
| 187 | B | C | B | D |
| 188 | B | D | B | D |
| 189 | | | | |
| Peak A | | | | |
| 190 | C | D | C | D |
| Peak B | | | | |
| 191 | B | B | B | D |
| 192 | B | B | B | D |
| 193 | C | D | C | D |
| 194 | C | D | C | D |
| Peak A | | | | |
| 195 | C | D | C | D |
| Peak B | | | | |
| 196 | C | D | C | D |
| Peak A | | | | |
| 197 | B | C | B | D |
| Peak B | | | | |
| 198 | C | D | C | D |
| Peak A | | | | |
| 199 | C | D | C | D |

TABLE 1-continued

| Ex. # | TYK2 Enzyme IC$_{50}$ 1 mM ATP | JAK1 Enzyme IC$_{50}$ 1 mM ATP | JAK2 Enzyme IC$_{50}$ 1 mM ATP | JAK3 Enzyme IC$_{50}$ 1 mM ATP |
|---|---|---|---|---|
| Peak B 200 | B | C | B | D |
| Peak A 201 | B | D | B | D |
| Peak B 202 | B | C | B | D |
| Peak A 203 | B | C | B | D |
| Peak B 204 | C | D | C | D |
| Peak A 205 | B | C | B | D |
| Peak A 206 | C | D | C | D |
| Peak B 207 | B | C | A | C |
| Peak A 208 | C | D | B | D |
| Peak B 209 | B | C | B | D |
| Peak A 210 | C | D | C | D |
| Peak B 211 | B | C | B | D |
| Peak A 212 | C | D | C | D |
| Peak B 213 | B | C | B | D |
| Peak B 214 | B | C | C | D |
| Peak A 215 | B | C | B | D |
| Peak B 216 | C | D | C | D |
| 217 | C | D | C | D |
| 218 | B | C | B | D |

N/T = Not tested in the assays described in Examples A, B, C and D but found to be active when tested in alternative Tyk2, JAK1, JAK2 and JAK3 enzyme assay protocols.

Preparation of Synthetic Intermediates

Preparation 1

4-chloro-6-(1-methyl-1H-pyrazol-4-yl)pyrazolo[1,5-a]pyrazine hydrochloride

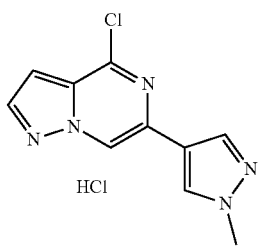 [SMILES: Cn1cc(-c2cn3nccc3c(Cl)n2)cn1 ; Cl]

Step A:

In 250 mL of acetonitrile was dissolved 2-chloro-1-(1-methyl-1H-pyrazol-4-yl)ethanone (18.3 g, 115 mmol) and diethyl 1H-pyrazole-3,5-dicarboxylate (24.5 g, 115 mmol) before finely ground K$_2$CO$_3$ (31.9 g, 231 mmol) was added in one portion. The reaction mixture was stirred at ambient temperature overnight. The reaction mixture was filtered and the cake was washed with acetonitrile (100 mL). The filtrate was concentrated in vacuo to a thick oil. The oil was dissolved in EtOAc (80 mL), and heptane (200 mL) was added slowly with stirring. The resultant solids were stirred for 2 hours, then filtered and washed with heptane. The solids were dried in a vacuum oven to afford diethyl 1-(2-(1-methyl-1H-pyrazol-4-yl)-2-oxoethyl)-1H-pyrazole-3,5-dicarboxylate (26.4 g, 77.4 mmol, 67.1% yield).

Step B:

In 320 mL of acetic acid were combined diethyl 1-(2-(1-methyl-1H-pyrazol-4-yl)-2-oxoethyl)-1H-pyrazole-3,5-dicarboxylate (8.0 g, 23.9 mmol) and NH$_4$OAc (55.3 g, 718 mmol) in a 500 mL glass pressure vessel. The vessel was sealed and the reaction mixture was heated to 120° C. overnight, followed by heating at 160° C. for 48 hours. The reaction mixture was cooled to ambient temperature and then poured into a 2 L flask. Water (960 mL) was slowly added and the mixture was stirred with cooling for 2 hours. The fine pink suspension that resulted after stirring overnight was collected by vacuum filtration. The solids were collected and dried in a vacuum oven to afford a 2:1 mixture of ethyl 4-hydroxy-6-(1-methyl-1H-pyrazol-4-yl)pyrazolo[1,5-a]pyrazine-2-carboxylate (5.45 g, 6.26 mmol, 26.2% yield) and 4-hydroxy-6-(1-methyl-1H-pyrazol-4-yl)pyrazolo[1,5-a]pyrazine-2-carboxylic acid (5.45 g, 13.9 mmol, 58.0% yield).

Step C:

Crude ethyl 4-hydroxy-6-(1-methyl-1H-pyrazol-4-yl)pyrazolo[1,5-a]pyrazine-2-carboxylate (10.00 g, 34.81 mmol) was charged to a 500 mL flask equipped with mechanical stirring, a thermocouple, and a reflux condenser equipped with a nitrogen balloon. 6 N HCl (100 mL) was added and the reaction mixture was heated to 65° C. for 32 hours. The reaction mixture was cooled to ambient temperature overnight and water (100 mL) was added. The reaction mixture was stirred for 1 hour and then filtered. The resulting solids were rinsed with water and dried in the vacuum oven overnight to afford 6-(1-methyl-1H-pyrazol-4-yl)-4-oxo-4,5-dihydropyrazolo[1,5-a]pyrazine-2-carboxylic acid (8.8 g, 33.95 mmol, 97.5% yield).

Step D:

6-(1-Methyl-1H-pyrazol-4-yl)-4-oxo-4,5-dihydropyrazolo[1,5-a]pyrazine-2-carboxylic acid (10.0 g, 38.6 mmol) was added to a 500 mL flask equipped with mechanical stirring, a thermocouple, a reflux condenser and static nitrogen pressure. Cu(OAc)$_2$ (3.5 g, 19.3 mmol), 1,10-phenanthroline (3.5 g, 19.3 mmol) and N-methylpyrrolidone (100 mL) were added. The reaction mixture was heated to 165° C. overnight. The reaction mixture was cooled to ambient temperature, and 3 M HCl (200 mL) was added to afford a slurry, which was stirred overnight. The product was collected by vacuum filtration, rinsed with water, and dried in the vacuum oven overnight to afford 6-(1-methyl-1H-pyrazol-4-yl)pyrazolo[1,5-a]pyrazin-4(5H)-one (8.0 g, 37.2 mmol, 96.4% yield).

Step E:

To a 100 mL 3-neck flask fitted with a magnetic stir bar, internal temperature probe, and reflux condenser was added 6-(1-methyl-1H-pyrazol-4-yl)pyrazolo[1,5-a]pyrazin-4(5H)-one (5.0 g, 23.2 mmol), followed by phosphoryl trichloride (34.6 mL, 371 mmol). The reaction mixture was heated to 80° C. under nitrogen for 7 hours. The reaction mixture was cooled to 50° C., then charged with 40 mL of acetonitrile and cooled to ambient temperature. The resulting solids were filtered, washed with 20 mL of acetonitrile and dried in a vacuum oven to afford 2.65 g of 4-chloro-6-(1-methyl-1H-pyrazol-4-yl)pyrazolo[1,5-a]pyrazine hydrochloride. The filtrates were diluted with 80 mL of methyl tert-butyl ether and the reaction mixture was stirred at ambient temperature overnight. The resultant solids were filtered and dried to afford an additional 2.97 g of product. The total yield of 4-chloro-6-(1-methyl-1H-pyrazol-4-yl)pyrazolo[1,5-a]pyrazine hydrochloride was 4.55 g (16.8 mmol, 72.5% yield).

Preparation 2

4-chloro-6-(1-(4-methoxybenzyl)-1H-pyrazol-4-yl)pyrazolo[1,5-a]pyrazine hydrochloride

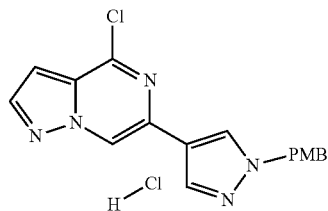

Step A:
4-Iodo-1H-pyrazole (5.0 g, 25.8 mmol) was dissolved in DMF (50 mL), and K$_2$CO$_3$ (4.27 g, 30.9 mmol) was added followed by 1-(chloromethyl)-4-methoxybenzene (3.86 mL, 28.4 mmol). The reaction mixture was stirred at ambient temperature overnight. The reaction mixture was then poured into water and extracted with Et$_2$O, washed with brine, dried over sodium sulfate, filtered and concentrated to afford 4-iodo-1-(4-methoxybenzyl)-1H-pyrazole (8.3 g, 26.4 mmol, 103% yield).

Step B:
4-Iodo-1-(4-methoxybenzyl)-1H-pyrazole (8.1 g, 26 mmol) was dissolved in THF (50 mL) and cooled in an ice bath. Isopropylmagnesium chloride (2.9 M, 8.9 mL, 26 mmol) was added slowly. The reaction mixture was stirred for 10 minutes, and then 2-chloro-N-methoxy-N-methylacetamide (3.5 g, 26 mmol) dissolved in THF (15 mL) was added slowly by syringe. The reaction mixture was warmed to ambient temperature and stirred for 1 hour. The reaction mixture was partitioned between EtOAc and 1N HCl, and the organic layer was dried over sodium sulfate, filtered and concentrated to afford crude 2-chloro-1-(1-(4-methoxybenzyl)-1H-pyrazol-4-yl)ethanone (7.1 g, 27 mmol, 104% yield) as an amber oil that slowly solidified.

Step C:
Crude 2-chloro-1-(1-(4-methoxybenzyl)-1H-pyrazol-4-yl)ethanone (7.1 g, 21 mmol) was dissolved in acetonitrile (100 mL). Diethyl 1H-pyrazole-3,5-dicarboxylate (4.6 g, 21 mmol) was added, followed by K$_2$CO$_3$ (5.9 g, 43 mmol), and the reaction mixture was stirred at 45° C. for 1 hour. The reaction mixture was cooled to ambient temperature, diluted with EtOAc, filtered and concentrated. The residue was purified over silica gel to afford diethyl 1-(2-(1-(4-methoxybenzyl)-1H-pyrazol-4-yl)-2-oxoethyl)-1H-pyrazole-3,5-dicarboxylate (8.7 g, 20 mmol, 92% yield) as a white solid.

Step D:
Diethyl 1-(2-(1-(4-methoxybenzyl)-1H-pyrazol-4-yl)-2-oxoethyl)-1H-pyrazole-3,5-dicarboxylate (8.2 g, 18.6 mmol) was dissolved in HOAc (100 mL) and NH$_4$OAc (43.1 g, 559 mmol) was added. The reaction mixture heated in a sealed tube at 120° C. for 48 hours. The reaction mixture was cooled to ambient temperature, poured into water (200 mL), filtered and dried to afford ethyl 4-hydroxy-6-(1-(4-methoxybenzyl)-1H-pyrazol-4-yl)pyrazolo[1,5-a]pyrazine-2-carboxylate (5.65 g, 14.4 mmol, 77.1% yield) as a white solid.

Step E:
Ethyl 4-hydroxy-6-(1-(4-methoxybenzyl)-1H-pyrazol-4-yl)pyrazolo[1,5-a]pyrazine-2-carboxylate (5.4 g, 14 mmol) was suspended in THF (60 mL), and 1M lithium hydroxide (30 mL, 30 mmol) was added. The reaction mixture was heated to 50° C. for 30 minutes. The reaction mixture was quenched with slow addition of 1M HCl (35 mL) with vigorous stirring. Additional water (10 mL) was added to aid in stirring. The mixture was stirred vigorously at 50° C. for 15 minutes, then cooled and filtered. The isolated solids were washed with water and dried in vacuum oven to afford 4-hydroxy-6-(1-(4-methoxybenzyl)-1H-pyrazol-4-yl)pyrazolo[1,5-a]pyrazine-2-carboxylic acid (4.6 g, 13 mmol, 92% yield) as a white solid.

Step F:
4-Hydroxy-6-(1-(4-methoxybenzyl)-1H-pyrazol-4-yl)pyrazolo[1,5-a]pyrazine-2-carboxylic acid (4.6 g, 13 mmol) was charged to a 25 mL flask and 1,10-phenanthroline (1.00 g, 5.5 mmol) and diacetoxycopper (1.0 g, 5.5 mmol) were added. The reaction mixture was diluted with N-methylpyrrolidone (12 mL) and then heated to 165° C. under nitrogen for 6 hours. The reaction mixture was cooled to ambient temperature overnight, transferred to a flask with 1N HCl (20 mL) and stirred at 50° C. for 45 minutes. The reaction mixture was then filtered, and the isolated solids were washed with water and dried in vacuum oven to afford 4.7 g of a dark brown solid. The dried solid was suspended in 1N HCl (60 mL), and N-methylpyrrolidone (10 mL) was added to aid in wetting. The mixture was stirred at 65° C. for 1 hour. The mixture was filtered and the isolated solids were washed with water until the resulting filtrate was colorless. The isolated solids were dried in vacuum oven to afford 6-(1-(4-methoxybenzyl)-1H-pyrazol-4-yl)pyrazolo[1,5-a]pyrazin-4-ol (3.7 g, 12 mmol, 91% yield) as a brown solid.

Step G:
6-(1-(4-Methoxybenzyl)-1H-pyrazol-4-yl)pyrazolo[1,5-a]pyrazin-4-ol (3.7 g, 11.5 mmol) was suspended in phosphoryl trichloride (10.6 mL, 115 mmol) and heated to 80° C. under nitrogen for 3 hours. The reaction mixture was cooled to ambient temperature and poured into methyl tert-butyl ether (80 mL) with vigorous stirring. The mixture was stirred for 10 minutes and then filtered. The isolated solids were washed with methyl tert-butyl ether and dried in vacuum oven to afford 2.7 g of the desired product as a tan solid. After sitting for 2 days, the filtrate had solids as well. These were filtered and dried to afford an additional 1.2 g of 4-chloro-6-(1-(4-methoxybenzyl)-1H-pyrazol-4-yl)pyrazolo[1,5-a]pyrazine hydrochloride (Total yield: 3.9 g, 10.4 mmol, 90.0% yield).

Preparation 3

4-chloro-6-(1H-pyrazol-4-yl)pyrazolo[1,5-a]pyrazine

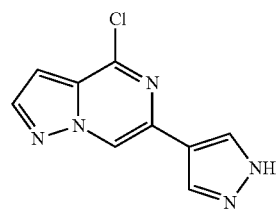 [SMILES: Clc1nc(-c2cn[nH]c2)cn2nccc12]

To a 150 mL glass bomb were added 4-chloro-6-(1-(4-methoxybenzyl)-1H-pyrazol-4-yl)pyrazolo[1,5-a]pyrazine (10.0 g, 29.4 mmol), anisole (16.0 mL, 147 mmol), 2,2,2-trifluoroacetic acid (45.3 mL, 589 mmol), and trifluoromethanesulfonic acid (5.26 mL, 58.9 mmol) were combined and then sealed and heated to 75° C. for 4 hours. The reaction mixture was diluted with CH$_3$CN and concentrated under reduced pressure. The resulting warm oil was immediately quenched with saturated sodium bicarbonate and extracted with EtOAc. The combined organic layers were dried over MgSO$_4$, filtered, and concentrated under reduced pressure. The residue taken up in 100 mL of CH$_2$Cl$_2$ and sonicated for 2 hour, stirred for 1 hour, and sonicated and then stirred intermittently over the next 30 min to create a fine suspension. The solid was collected by vacuum filtration and dried to afford 4-chloro-6-(1H-pyrazol-4-yl)pyrazolo[1,5-a]pyrazine (6.99 g, 28.6 mmol, 97.3% yield).

Preparation 4

1-(pentan-3-yl)-4-(4,4,5,5-tetramethyl-1,3,2-dioxaborolan-2-yl)-1H-pyrazole

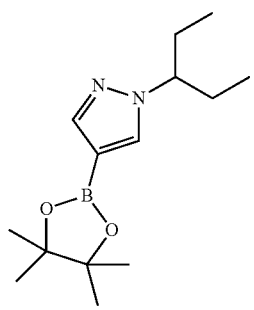 [SMILES: CCC(CC)n1cc(B2OC(C)(C)C(C)(C)O2)cn1]

4-(4,4,5,5-tetramethyl-1,3,2-dioxaborolan-2-yl)-1H-pyrazole (4.0 g, 20.61 mmol), 3-bromopentane (5.121 mL, 41.23 mmol) and Cs$_2$CO$_3$ (8.060 g, 24.74 mmol) were suspended in DMF (8 mL) and sealed in a glass pressure vessel and heated to 100° C. overnight. After cooling to ambient temperature, the cap was removed slowly [pressure release], partitioned between water (20 mL) and EtOAc (100 mL), washed with water and brine, dried over sodium sulfate, filtered and concentrated. The residue was purified over silica gel (15% EtOAc in hexanes) to afford 1-(pentan-3-yl)-4-(4,4,5,5-tetramethyl-1,3,2-dioxaborolan-2-yl)-1H-pyrazole (3.8 g, 14.38 mmol, 69.78% yield) as a clear colorless oil.

Preparation 5

(S)-1-(4-methylpentan-2-yl)-4-(4,4,5,5-tetramethyl-1,3,2-dioxaborolan-2-yl)-1H-pyrazole

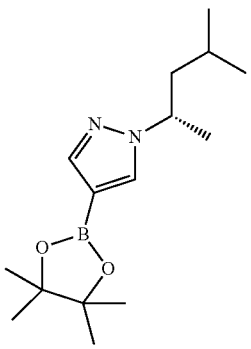 [SMILES: CC(C)C[C@H](C)n1cc(B2OC(C)(C)C(C)(C)O2)cn1]

Step A:
A solution of (R)-4-methylpentan-2-ol (3.74 mL, 29.4 mmol) in anhydrous CH$_2$Cl$_2$ (30 mL) at 0° C. was treated with diisopropylethylamine (10.3 mL, 7.59 mmol) followed by the dropwise addition of mesyl chloride (2.5 mL, 32.3 mmol). The mixture was stirred for 2 hours and partitioned between saturated aqueous NaHCO$_3$ (50 mL) and CH$_2$Cl$_2$ (50 mL) and the aqueous layer was extracted with CH$_2$Cl$_2$ (2×30 mL). The combined organic phases were washed with brine (20 mL), dried over Na$_2$SO$_4$, filtered and concentrated to afford (R)-4-methylpentan-2-yl methanesulfonate as a brown oil that was used directly in the next reaction without purification.

Step B:
To a solution of 4-(4,4,5,5-tetramethyl-1,3,2-dioxaborolan-2-yl)-1H-pyrazole (3.59 g, 18.5 mmol) in anhydrous DMA (10 mL) was added (R)-4-methylpentan-2-yl methanesulfonate (5.0 g, 27.7 mmol) followed by cesium carbonate (12.0 g, 37.0 mmol). The mixture was stirred in a sealed vessel at 80° C. overnight. The mixture was partitioned between water (100 mL) and EtOAc (50 mL) and the aqueous layer extracted with EtOAc (2×50 mL). The combined organic phases were washed with water (5×30 mL) and brine (30 mL) then dried over Na$_2$SO$_4$, filtered and concentrated to afford a brown oil. The oil was purified over silica gel (9:1 hexane:EtOAc) to afford (S)-1-(4-methylpentan-2-yl)-4-(4,4,5,5-tetramethyl-1,3,2-dioxaborolan-2-yl)-1H-pyrazole (3.21 g, 62.4% yield) as a pale yellow oil.

The following compounds were synthesized using the procedure described in Preparation 3 or 4.

| Preparation | Structure | Name |
|---|---|---|
| 6 | 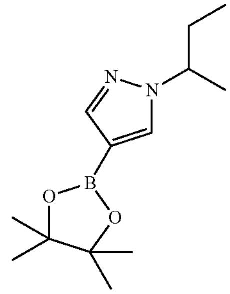 [SMILES: CCC(C)n1cc(B2OC(C)(C)C(C)(C)O2)cn1] | 1-(sec-butyl)-4-(4,4,5,5-tetramethyl-1,3,2-dioxaborolan-2-yl)-1H-pyrazole |

-continued

| Preparation | Structure | Name |
|---|---|---|
| 7 | 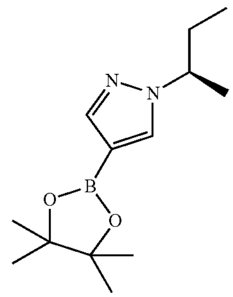 [SMILES: CC[C@@H](C)n1cc(B2OC(C)(C)C(C)(C)O2)cn1] | (R)-1-(sec-butyl)-4-(4,4,5,5-tetramethyl-1,3,2-dioxaborolan-2-yl)-1H-pyrazole |
| 8 | 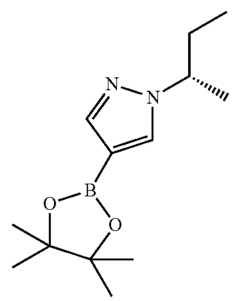 [SMILES: CC[C@H](C)n1cc(B2OC(C)(C)C(C)(C)O2)cn1] | (S)-1-(sec-butyl)-4-(4,4,5,5-tetramethyl-1,3,2-dioxaborolan-2-yl)-1H-pyrazole |
| 9 | 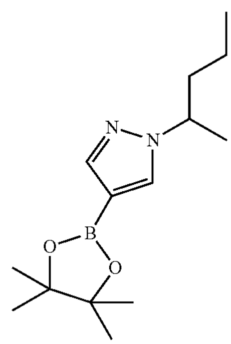 [SMILES: CCCC(C)n1cc(B2OC(C)(C)C(C)(C)O2)cn1] | 1-(pentan-2-yl)-4-(4,4,5,5-tetramethyl-1,3,2-dioxaborolan-2-yl)-1H-pyrazole |
| 10 | 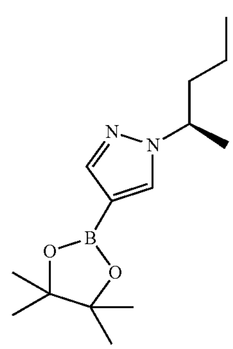 [SMILES: CCC[C@@H](C)n1cc(B2OC(C)(C)C(C)(C)O2)cn1] | (R)-1-(pentan-2-yl)-4-(4,4,5,5-tetramethyl-1,3,2-dioxaborolan-2-yl)-1H-pyrazole |

-continued

| Preparation | Structure | Name |
|---|---|---|
| 11 | 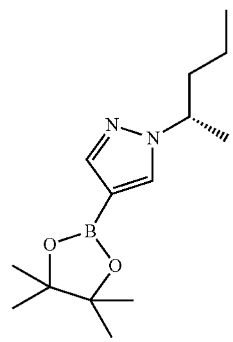 [SMILES: CCC[C@H](C)n1cc(B2OC(C)(C)C(C)(C)O2)cn1] | (S)-1-(pentan-2-yl)-4-(4,4,5,5-tetramethyl-1,3,2-dioxaborolan-2-yl)-1H-pyrazole |
| 12 | 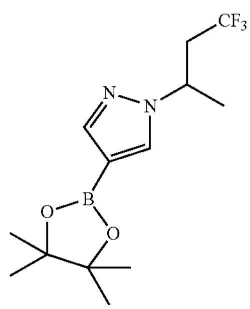 [SMILES: CC(CC(F)(F)F)n1cc(B2OC(C)(C)C(C)(C)O2)cn1] | 4-(4,4,5,5-tetramethyl-1,3,2-dioxaborolan-2-yl)-1-(4,4,4-trifluorobutan-2-yl)-1H-pyrazole |
| 13 | 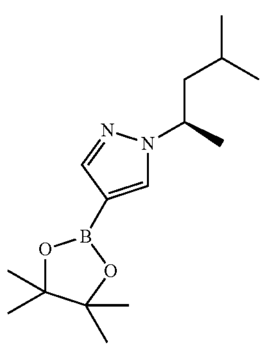 [SMILES: CC(C)C[C@@H](C)n1cc(B2OC(C)(C)C(C)(C)O2)cn1] | (R)-1-(4-methylpentan-2-yl)-4-(4,4,5,5-tetramethyl-1,3,2-dioxaborolan-2-yl)-1H-pyrazole |
| 14 | 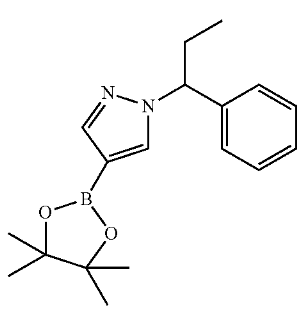 [SMILES: CCC(c1ccccc1)n1cc(B2OC(C)(C)C(C)(C)O2)cn1] | 1-(1-phenylpropyl)-4-(4,4,5,5-tetramethyl-1,3,2-dioxaborolan-2-yl)-1H-pyrazole |
| 15 | 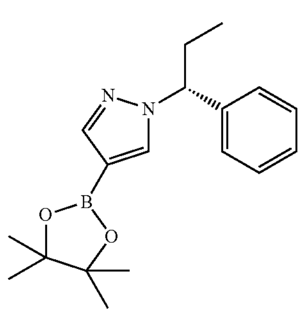 | (R)-1-(1-phenylpropyl)-4-(4,4,5,5-tetramethyl-1,3,2-dioxaborolan-2-yl)-1H-pyrazole |

-continued

| Preparation | Structure | Name |
|---|---|---|
| 16 | 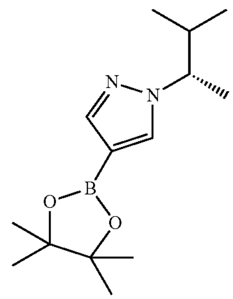 [SMILES: CC(C)[C@H](C)n1cc(B2OC(C)(C)C(C)(C)O2)cn1] | (S)-1-(3-methylbutan-2-yl)-4-(4,4,5,5-tetramethyl-1,3,2-dioxaborolan-2-yl)-1H-pyrazole |
| 17 | 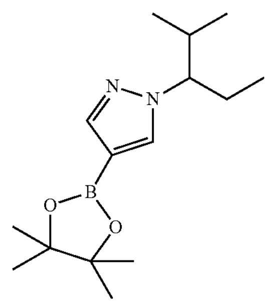 [SMILES: CCC(C(C)C)n1cc(B2OC(C)(C)C(C)(C)O2)cn1] | 1-(2-methylpentan-3-yl)-4-(4,4,5,5-tetramethyl-1,3,2-dioxaborolan-2-yl)-1H-pyrazole |
| 18 | 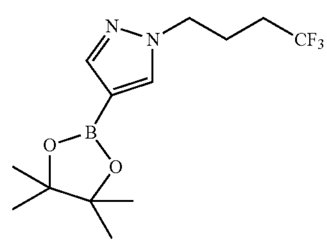 [SMILES: CC1(C)OB(c2cnn(CCCC(F)(F)F)c2)OC1(C)C] | 4-(4,4,5,5-tetramethyl-1,3,2-dioxaborolan-2-yl)-1-(4,4,4-trifluorobutyl)-1H-pyrazole |
| 19 | 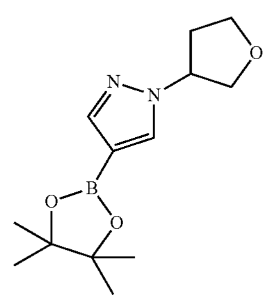 [SMILES: CC1(C)OB(c2cnn(C3CCOC3)c2)OC1(C)C] | 1-(tetrahydrofuran-3-yl)-4-(4,4,5,5-tetramethyl-1,3,2-dioxaborolan-2-yl)-1H-pyrazole |
| 20 | 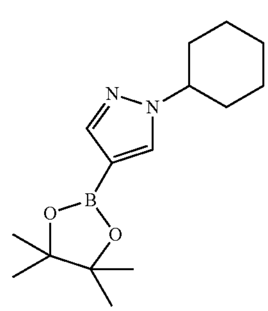 [SMILES: CC1(C)OB(c2cnn(C3CCCCC3)c2)OC1(C)C] | 1-cyclohexyl-4-(4,4,5,5-tetramethyl-1,3,2-dioxaborolan-2-yl)-1H-pyrazole |

-continued

| Preparation | Structure | Name |
|---|---|---|
| 21 | 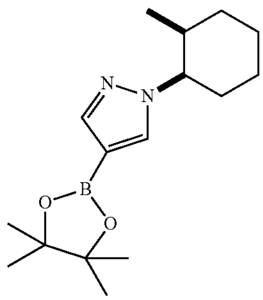 | 1-(cis-2-methylcyclohexyl)-4-(4,4,5,5-tetramethyl-1,3,2-dioxaborolan-2-yl)-1H-pyrazole |
| 22 | 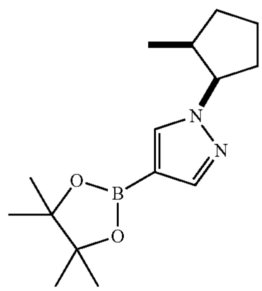 [SMILES: C[C@H]1CCC[C@H]1n1cc(B2OC(C)(C)C(C)(C)O2)cn1] | 1-(cis-2-methylcyclopentyl)-4-(4,4,5,5-tetramethyl-1,3,2-dioxaborolan-2-yl)-1H-pyrazole |
| 23 | 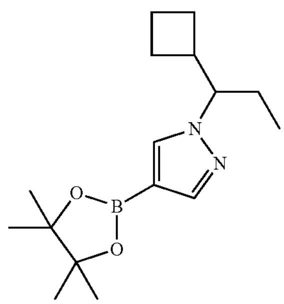 [SMILES: CCC(C1CCC1)n1cc(B2OC(C)(C)C(C)(C)O2)cn1] | 1-(1-cyclobutylpropyl)-4-(4,4,5,5-tetramethyl-1,3,2-dioxaborolan-2-yl)-1H-pyrazole |
| 24 | 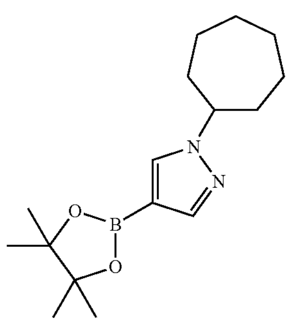 [SMILES: CC1(C)OB(c2cnn(C3CCCCCC3)c2)OC1(C)C] | 1-cycloheptyl-4-(4,4,5,5-tetramethyl-1,3,2-dioxaborolan-2-yl)-1H-pyrazole |
| 25 | 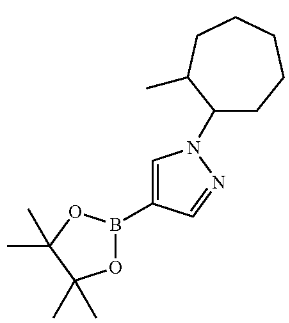 [SMILES: CC1CCCCCC1n1cc(B2OC(C)(C)C(C)(C)O2)cn1] | 1-(2-methylcycloheptyl)-4-(4,4,5,5-tetramethyl-1,3,2-dioxaborolan-2-yl)-1H-pyrazole |

-continued

| Preparation | Structure | Name |
|---|---|---|
| 26 | 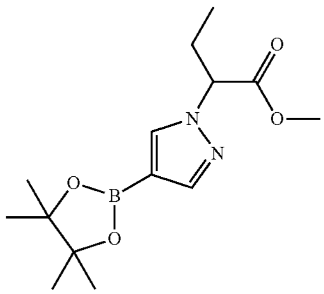 | methyl 2-(4-(4,4,5,5-tetramethyl-1,3,2-dioxaborolan-2-yl)-1H-pyrazol-1-yl)butanoate |
| 27 | 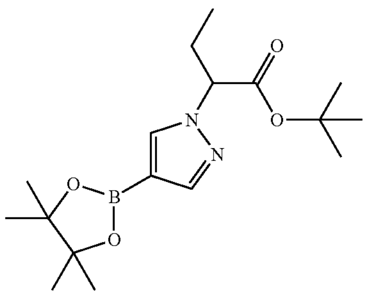 [SMILES: CCC(C(=O)OC(C)(C)C)n1cc(B2OC(C)(C)C(C)(C)O2)cn1] | tert-butyl 2-(4-(4,4,5,5-tetramethyl-1,3,2-dioxaborolan-2-yl)-1H-pyrazol-1-yl)butanoate |
| 28 | 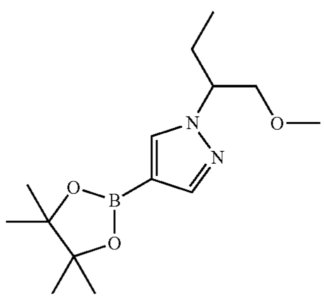 | 1-(1-methoxybutan-2-yl)-4-(4,4,5,5-tetramethyl-1,3,2-dioxaborolan-2-yl)-1H-pyrazole |
| 29 | 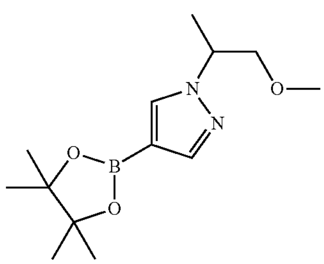 | 1-(1-methoxypropan-2-yl)-4-(4,4,5,5-tetramethyl-1,3,2-dioxaborolan-2-yl)-1H-pyrazole |
| 30 | 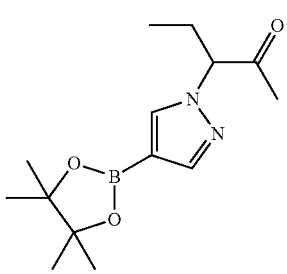 [SMILES: CCC(C(C)=O)n1cc(B2OC(C)(C)C(C)(C)O2)cn1] | 3-(4-(4,4,5,5-tetramethyl-1,3,2-dioxaborolan-2-yl)-1H-pyrazol-1-yl)pentan-2-one |

-continued

| Preparation | Structure | Name |
|---|---|---|
| 31 | 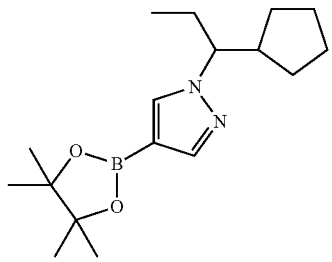 [SMILES: CCC(C1CCCC1)n1cc(B2OC(C)(C)C(C)(C)O2)cn1] | 1-(1-cyclopentylpropyl)-4-(4,4,5,5-tetramethyl-1,3,2-dioxaborolan-2-yl)-1H-pyrazole |
| 32 | 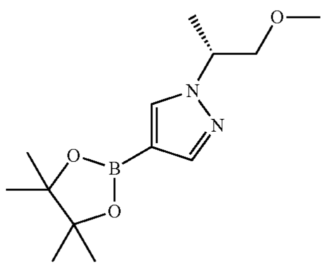 | (R)-1-(1-methoxypropan-2-yl)-4-(4,4,5,5-tetramethyl-1,3,2-dioxaborolan-2-yl)-1H-pyrazole |
| 33 | 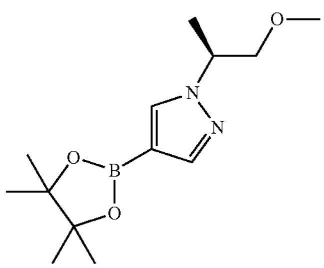 | (S)-1-(1-methoxypropan-2-yl)-4-(4,4,5,5-tetramethyl-1,3,2-dioxaborolan-2-yl)-1H-pyrazole |
| 34 | 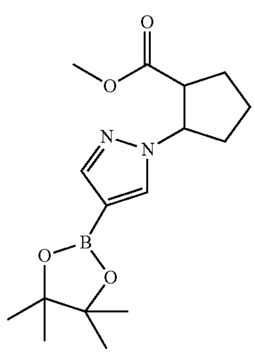 [SMILES: COC(=O)C1CCCC1n1cc(B2OC(C)(C)C(C)(C)O2)cn1] | methyl 2-(4-(4,4,5,5-tetramethyl-1,3,2-dioxaborolan-2-yl)-1H-pyrazol-1-yl)cyclopentanecarboxylate |
| 35 | 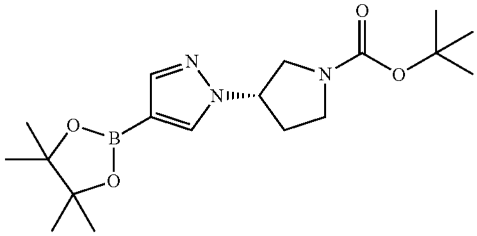 [SMILES: CC(C)(C)OC(=O)N1CC[C@H](n2cc(B3OC(C)(C)C(C)(C)O3)cn2)C1] | (S)-tert-butyl 3-(4-(4,4,5,5-tetramethyl-1,3,2-dioxaborolan-2-yl)-1H-pyrazol-1-yl)pyrrolidine-1-carboxylate |

| Preparation | Structure | Name |
|---|---|---|
| 36 | 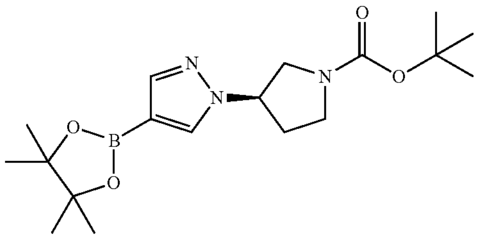 [SMILES: CC(C)(C)OC(=O)N1CC[C@@H](n2cc(B3OC(C)(C)C(C)(C)O3)cn2)C1] | (R)-tert-butyl 3-(4-(4,4,5,5-tetramethyl-1,3,2-dioxaborolan-2-yl)-1H-pyrazol-1-yl)pyrrolidine-1-carboxylate |

Preparation 37

1-(trans-2-methylcyclohexyl)-4-(4,4,5,5-tetramethyl-1,3,2-dioxaborolan-2-yl)-1H-pyrazole

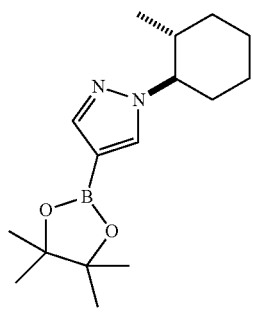

Step A:

2-Methylcyclohexanone (5.41 mL, 44.6 mmol) and tert-butyl hydrazinecarboxylate (6.19 g, 46.8 mmol) were dissolved in EtOH (50 mL) and stirred at ambient temperature overnight. The reaction mixture was concentrated and suspended in 1:1 water:acetic acid (30 mL). NaCNBH$_3$ (2.94 g, 46.8 mmol) was added in portions and the reaction mixture was stirred at room temperature for 3 hours. The mixture was slowly poured into EtOAc (120 mL) and 2M K$_2$CO$_3$ (40 mL). The organic layer was separated, washed with brine, dried over sodium sulfate, filtered and concentrated. The residue was purified over silica gel (10% EtOAc in hexanes) to afford tert-butyl 2-(cis-2-methylcyclohexyl)hydrazinecarboxylate (3.0 g) (having the higher R$_f$), and tert-butyl 2-(trans-2-methylcyclohexyl)hydrazinecarboxylate (4.1 g, 18.0 mmol, 40.3% yield) (having the lower R$_f$).

Step B:

tert-Butyl 2-(trans-2-methylcyclohexyl)hydrazinecarboxylate (4.1 g, 18.0 mmol) was dissolved in EtOH (25 mL).

Hydrogen chloride (10 M, 3.59 mL, 35.9 mmol) was added and the reaction mixture was heated to 75° C. for 10 minutes. 1,1,3,3-Tetramethoxypropane (2.96 mL, 18.0 mmol) was added and the reaction mixture was heated for 2 hours. The reaction mixture was cooled to room temperature, concentrated, partitioned between EtOAc and saturated aqueous NaHCO$_3$, dried over sodium sulfate, filtered and concentrated. The residue was purified over silica gel (20% EtOAc in hexanes) to afford 1-(trans-2-methylcyclohexyl)-1H-pyrazole (1.5 g, 9.13 mmol, 50.9% yield).

Step C:

1-(Trans-2-methylcyclohexyl)-1H-pyrazole (1.5 g, 9.1 mmol) was dissolved in CH$_2$Cl$_2$ (30 mL) and 1-bromopyrrolidine-2,5-dione (2.0 g, 11 mmol) was added. The reaction mixture was stirred at room temperature for 3.5 hours. The reaction mixture was partitioned between CH$_2$Cl$_2$ and water, washed with brine, dried over sodium sulfate, filtered and concentrated. The residue was purified over silica gel (10% EtOAc in hexanes) to afford 4-bromo-1-(trans-2-methylcyclohexyl)-1H-pyrazole (2.0 g, 8.2 mmol, 90% yield) as a clear colorless oil.

Step D:

4-Bromo-1-(trans-2-methylcyclohexyl)-1H-pyrazole (2.0 g, 8.23 mmol) was dissolved in dioxane (80 mL) and treated with 4,4,4',4',5,5,5',5'-octamethyl-2,2'-bi(1,3,2-dioxaborolane) (2.30 g, 9.05 mmol) and potassium acetate (2.42 g, 24.7 mmol). Argon was bubbled through the reaction mixture for 1 minute. PdCl$_2$(dppf)*CH$_2$Cl$_2$ (0.672 g, 0.823 mmol) was added and Argon was bubbled through the reaction mixture for 1 minute. The reaction mixture was sealed and heated to 95° C. overnight. The reaction mixture was diluted with EtOAc, filtered through Celite® and concentrated. The residue was purified over silica gel (5 to 10% EtOAc in hex) to afford 1-(trans-2-methylcyclohexyl)-4-(4,4,5,5-tetramethyl-1,3,2-dioxaborolan-2-yl)-1H-pyrazole (1.35 g, 4.65 mmol, 56.6% yield) as a white solid.

The following compounds were synthesized according to the procedure described in Preparation 37.

| Preparation | Structure | Name |
|---|---|---|
| 38 | 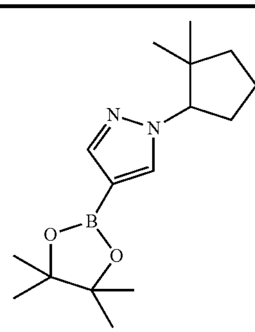 | 1-(2,2-dimethylcyclopentyl)-4-(4,4,5,5-tetramethyl-1,3,2-dioxaborolan-2-yl)-1H-pyrazole |

-continued

| Preparation | Structure | Name |
|---|---|---|
| 39 | 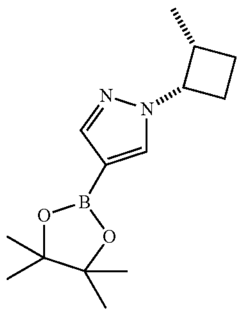 | 1-(cis-2-methylcyclobutyl)-4-(4,4,5,5-tetramethyl-1,3,2-dioxaborolan-2-yl)-1H-pyrazole |
| 40 | 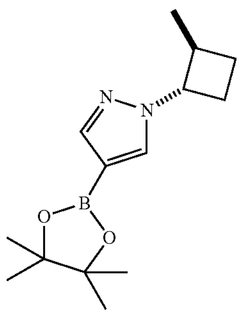 | 1-(trans-2-methylcyclobutyl)-4-(4,4,5,5-tetramethyl-1,3,2-dioxaborolan-2-yl)-1H-pyrazole |
| 41 | 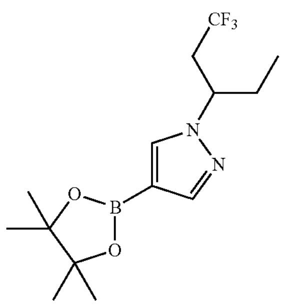 [SMILES: CCC(CC(F)(F)F)n1cc(B2OC(C)(C)C(C)(C)O2)cn1] | 4-(4,4,5,5-tetramethyl-1,3,2-dioxaborolan-2-yl)-1-(1,1,1-trifluoropentan-3-yl)-1H-pyrazole |

Preparation 42

1-(1-cyclopropylpropyl)-4-(4,4,5,5-tetramethyl-1,3,2-dioxaborolan-2-yl)-1H-pyrazole Step A:

Ethylmagnesium chloride (8.20 mL, 16.4 mmol) was added to 50 mL of THF, followed by cooling to 0° C. Cyclopropanecarbaldehyde (1.00 g, 14.3 mmol) in 10 mL of THF was added dropwise to the Grignard solution over 10 minutes. The reaction mixture was stirred at 0° C. for 1 hour, then quenched with NH₄Cl. The reaction mixture was back extracted with Et₂O, dried over Magnesium sulfate, and concentrated in vacuo (19° C. bath temp), affording the desired adduct 1-cyclopropylpropan-1-ol (0.998 g, 9.96 mmol, 69.8% yield) as a light tan oil.

Step B:

A round bottom flask equipped with a stir bar and nitrogen inlet was charged with 4-iodo-1H-pyrazole (0.50 g, 2.58 mmol) and 25 mL of dry CH₂Cl₂. To this was added 1-cyclopropylpropan-1-ol (0.31 g, 3.09 mmol) and resin-bound triphenylphosphine (1.36 g, 3.09 mmol, 2.27 mmol/g). The mixture was stirred at room temperature for 10 minutes and then chilled to 0° C. Diisopropyl azodicarboxylate (0.607 mL, 3.09 mmol) was added by syringe and the mixture was allowed to stir at 0° C. for 10 minutes, then allowed to warm to room temperature for 3 hours. The reaction mixture was filtered and the filtrate concentrated under reduced pressure. The resulting material was passed through a 40 g Redi Sep column, eluting with 15% ethyl acetate:Hexane to afford 1-(1-cyclopropylpropyl)-4-iodo-1H-pyrazole (0.140 g, 0.507 mmol) as an oil.

Step C:

A round bottom flask equipped with a stir bar and nitrogen inlet was charged with 1-(1-cyclopropylpropyl)-4-iodo-1H-pyrazole (0.140 g, 0.507 mmol), dry THF (5 mL), and 2-isopropoxy-4,4,5,5-tetramethyl-1,3,2-dioxaborolane (0.283 g, 1.52 mmol). The reaction mixture was chilled to 0° C. and isopropylmagnesium lithium chloride (1.06 mL, 1.01 mmol, 0.96 M) was added by syringe. The mixture was stirred for 1 hour, quenched with saturated ammonium chloride solution and allowed to warm to room temperature. Water was added and the mixture was extracted with EtOAc. The combined organic extracts were dried over sodium sulfate and concentrated under reduced pressure to afford 1-(1-cyclopropylpropyl)-4-(4,4,5,5-tetramethyl-1,3,2-dioxaborolan-2-yl)-1H-pyrazole (0.120 mg, 85.7% yield) as an oil.

The following compounds were synthesized according to the procedure described for Preparation 42.

| Preparation | Structure | Name |
|---|---|---|
| 43 | 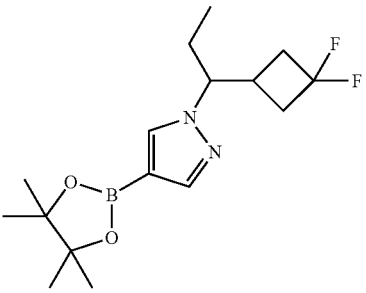 [SMILES: CCC(C1CC(F)(F)C1)n1cc(B2OC(C)(C)C(C)(C)O2)cn1] | 1-(1-(3,3-difluorocyclobutyl)propyl)-4-(4,4,5,5-tetramethyl-1,3,2-dioxaborolan-2-yl)-1H-pyrazole |
| 43 | 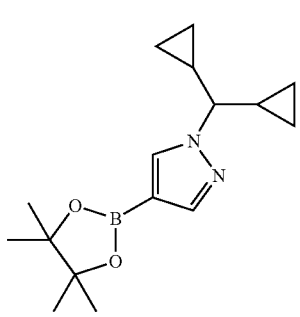 [SMILES: CC1(C)OB(c2cnn(C(C3CC3)C3CC3)c2)OC1(C)C] | 1-(dicyclopropylmethyl)-4-(4,4,5,5-tetramethyl-1,3,2-dioxaborolan-2-yl)-1H-pyrazole |

Preparation 45

1-(1-cyclopropylbutan-2-yl)-4-(4,4,5,5-tetramethyl-1,3,2-dioxaborolan-2-yl)-1H-pyrazole

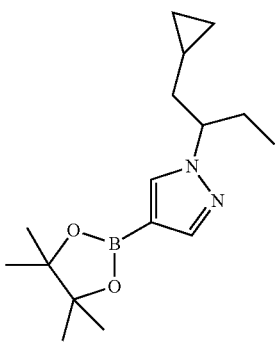 [SMILES: CCC(CC1CC1)n1cc(B2OC(C)(C)C(C)(C)O2)cn1]

Step A:

A round bottom flask equipped with a stir bar and nitrogen inlet was charged with 2-cyclopropylacetic acid (3.00 g, 30.0 mmol) and 120 mL of dry $CH_2Cl_2$. The reaction mixture was chilled to 0° C. and to this was added N,O-dimethylhydroxylamine hydrochloride (3.51 g, 36.0 mmol), EDCI (6.89 g, 36.0 mmol), HOBt (4.86 g, 36.0 mmol), and diisopropylethylamine (3.87 g, 36.0 mmol). The reaction mixture was allowed to warm to room temperature overnight, then diluted with $CH_2Cl_2$, washed with 10% aqueous $K_2CO_2$, dried over sodium sulfate and concentrated under reduced pressure to give 3.77 g of 2-cyclopropyl-N-methoxy-N-methylacetamide as an oil.

Step B:

A round bottom flask containing 2-cyclopropyl-N-methoxy-N-methylacetamide (3.7 g, 26 mmol) and 130 mL of $Et_2O$ was chilled to −78° C. To this was added ethylmagnesium bromide (78 mL, 78 mmol, 1M in THF) and the reaction mixture was stirred at −78° C. for 20 minutes, then allowed to warm to room temperature and quenched by the slow addition of 1M aq. HCl. The mixture was diluted with water and extracted with EtOAc. The combined organic extracts were dried over sodium sulfate and concentrated under reduced pressure to give 1 g of 1-cyclopropylbutan-2-one as an oil.

Step C:

A round bottom flask containing 1-cyclopropylbutan-2-one (1.0 g, 8.92 mmol) was charged with 90 mL of methanol and chilled to 0° C. To this was added sodium borohydride (0.675 g, 17.8 mmol) and the mixture was stirred at 0° C. for 10 minutes, then allowed to warm to room temperature. The mixture was concentrated under reduced pressure and quenched with saturated ammonium chloride solution. Water was added and the mixture was extracted with EtOAc, dried over sodium sulfate and concentrated under reduced pressure to give 543 mg of -cyclopropylbutan-2-ol as an oil.

Steps D and E:

Following the procedures described in Preparation 42, Steps B and C, 1-cyclopropylbutan-2-ol was converted to 1-(1-cyclopropylbutan-2-yl)-4-(4,4,5,5-tetramethyl-1,3,2-dioxaborolan-2-yl)-1H-pyrazole.

The following compound was synthesized following the procedure described in Preparation 45.

| Preparation | Structure | Name |
|---|---|---|
| 46 | 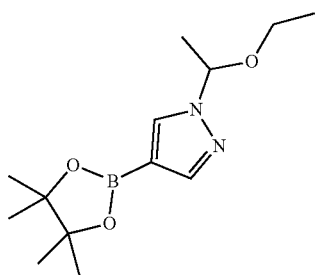 [SMILES: CCOC(C)n1cc(B2OC(C)(C)C(C)(C)O2)cn1] | 1-(1-(2,2-difluorocyclopropyl)propyl)-4-(4,4,5,5-tetramethyl-1,3,2-dioxaborolan-2-yl)-1H-pyrazole |

Preparation 47

1-(1-ethoxyethyl)-4-(4,4,5,5-tetramethyl-1,3,2-dioxaborolan-2-yl)-1H-pyrazole

Step A:

4-Iodo-1H-pyrazole (5.0 g, 25.8 mmol) was suspended in toluene (50 mL) and ethoxyethene (3.70 mL, 38.7 mmol) was added. To the suspension was added HCl [4M in dioxane] (0.161 mL, 0.644 mmol) and the reaction mixture was heated to 35° C. for 1 hour. The reaction mixture was quenched with solid $NaHCO_3$ and stirred for 1 hour. The reaction mixture was filtered and concentrated. The residue was purified by Kugelrohr distillation to afford 1-(1-ethoxyethyl)-4-iodo-1H-pyrazole (7.1 g, 26.7 mmol, 104% yield) as a pale yellow oil.

Step B:

In 15 mL of DMSO were combined 1-(1-ethoxyethyl)-4-iodo-1H-pyrazole (4.0 g, 15 mmol), bis(pinacolato)diboron (5.7 g, 23 mmol), KOAc (4.4 g, 45 mmol), and PdCl$_2$(dppf)-CH$_2$Cl$_2$ adduct (0.61 g, 0.75 mmol). The reaction mixture was stirred and sparged with argon for 10 minutes, and the flask was then sealed and the reaction mixture was heated to 70° C. overnight. To the reaction mixture was added 200 mL of 1:1 saturated sodium bicarbonate:water and the mixture was extracted with EtOAc. The combined organic layers were washed with 150 mL of brine. The combined aqueous washes were back extracted with EtOAc (300 mL). The combined organic layers were dried over MgSO$_4$, filtered and concentrated. The residue was purified over silica gel (20% EtOAc in hexanes) to afford 1-(1-ethoxyethyl)-4-(4,4,5,5-tetramethyl-1,3,2-dioxaborolan-2-yl)-1H-pyrazole (2.9 g, 11 mmol, 72% yield).

Preparation 48 methyl 3-(4-(4,4,5,5-tetramethyl-1,3,2-dioxaborolan-2-yl)-1H-pyrazol-1-yl)pentanoate

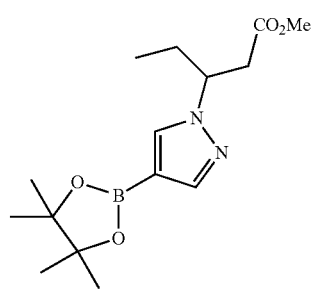 [SMILES: CCC(CC(=O)OC)n1cc(B2OC(C)(C)C(C)(C)O2)cn1]

To a solution of 4-(4,4,5,5-tetramethyl-1,3,2-dioxaborolan-2-yl)-1H-pyrazole (4 g, 21 mmol) in CH$_3$CN (30 mL) was added 2,3,4,6,7,8,9,10-octahydropyrimido[1,2-a]azepine (0.31 g, 2.1 mmol) and (E)-methyl pent-2-enoate (3.3 g, 29 mmol) and the reaction mixture was stirred overnight at 60° C. The reaction mixture was concentrated in vacuo and residue was partitioned between water and EtOAc. The combined organic layers were washed with water, brine, dried over MgSO$_4$, filtered and concentrated in vacuo. The residue was purified over silica gel (20% EtOAc in CH$_2$Cl$_2$) to afford methyl 3-(4-(4,4,5,5-tetramethyl-1,3,2-dioxaborolan-2-yl)-1H-pyrazol-1-yl)pentanoate.

The following compound was synthesized using the procedure described in Preparation 48.

| Preparation | Structure | Name |
|---|---|---|
| 49 | 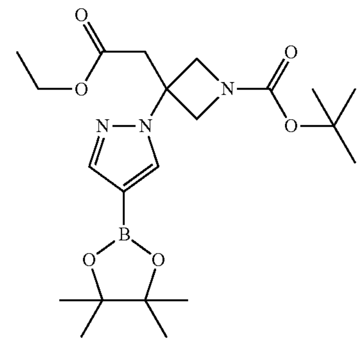 [SMILES: CCOC(=O)CC1(n2cc(B3OC(C)(C)C(C)(C)O3)cn2)CN(C(=O)OC(C)(C)C)C1] | tert-butyl 3-(2-ethoxy-2-oxoethyl)-3-(4-(4,4,5,5-tetramethyl-1,3,2-dioxaborolan-2-yl)-1H-pyrazol-1-yl)azetidine-1-carboxylate |

Preparation 50 tert-butyl 2-(4-(4,4,5,5-tetramethyl-1,3,2-dioxaborolan-2-yl)-1H-pyrazol-1-yl)propanoate To a solution of 4-(4,4,5,5-tetramethyl-1,3,2-dioxaborolan-2-yl)-1H-pyrazole (1.0 g, 5.2 mmol) in DMF (25 mL) was added sodium hydride (0.33 g, 8.2 mmol) in small portions under a stream of nitrogen. tert-Butyl 2-bromopropanoate (2.2 g, 10 mmol) was added and the reaction mixture was stirred at room temperature overnight. The reaction mixture was poured into water and the aqueous layer was extracted with EtOAc. The combined organic extracts were washed with water, brine, dried over MgSO$_4$ and concentrated in vacuo. The residue was purified over silica gel (0 to 30% EtOAc in CH$_2$Cl$_2$) to afford tert-butyl 2-(4-(4,4,5,5-tetramethyl-1,3,2-dioxaborolan-2-yl)-1H-pyrazol-1-yl)propanoate (0.30 g, 17.6% yield).

Preparation 51

6-(1-methyl-1H-pyrazol-4-yl)-4-(1H-pyrazol-4-yl)pyrazolo[1,5-a]pyrazine

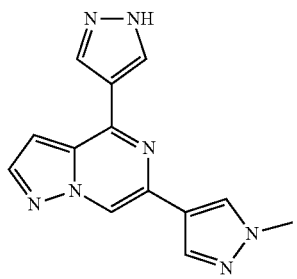 [SMILES: Cn1cc(-c2cn3nccc3c(-c3cn[nH]c3)n2)cn1]

In 30 mL of THF were combined 4-chloro-6-(1-methyl-1H-pyrazol-4-yl)pyrazolo[1,5-a]pyrazine hydrochloride (2.10 g, 7.77 mmol), tert-butyl 4-(4,4,5,5-tetramethyl-1,3,2-dioxaborolan-2-yl)-H-pyrazole-1-carboxylate (2.74 g, 9.33 mmol), XPHOS (0.741 g, 1.55 mmol), and Pd$_2$(dba)$_3$ (0.356 g, 0.389 mmol). The reaction mixture was sparged with argon for 1 minute before 2 M aqueous K$_2$CO$_3$ (15.5 mL, 31.1 mmol) was added by syringe. The sparging was continued for 5 minutes before the reaction mixture was sealed and heated to 80° C. over the weekend. To the reaction mixture was added 100 mL of EtOAc and 20 mL of water and the layers were separated. The aqueous layer was washed with EtOAc and the combined organic extracts were dried over MgSO$_4$, filtered, and concentrated. The residue was diluted with CH$_2$Cl$_2$ and stirred for 5 minutes, filtered and dried to 6-(1-methyl-1H-pyrazol-4-yl)-4-(1H-pyrazol-4-yl)pyrazolo[1,5-a]pyrazine (1.37 g, 4.91 mmol, 63.1% yield).

The following compound was synthesized according to the procedure described in Preparation 51

Step A:

Methyl (S)-(−)-2,2-dimethyl-1,3-dioxolane-4-carboxylate (4.6 mL, 32 mmol) was dissolved in THF (125 mL) and cooled in an ice bath. Methylmagnesium bromide (23 mL, 70 mmol) was added slowly and the reaction mixture was stirred at room temperature for 30 minutes. Saturated aqueous NH$_4$Cl was added carefully. The reaction mixture was extracted with EtOAc, dried over sodium sulfate, filtered and concentrated to afford (S)-2-(2,2-dimethyl-1,3-dioxolan-4-yl)propan-2-ol (4.2 g, 26 mmol, 82% yield).

Step B:

Anhydrous 4-methylbenzenesulfonic acid (0.226 g, 1.31 mmol) was partially dissolved in CH$_2$Cl$_2$ (50 mL), and (S)-2-(2,2-dimethyl-1,3-dioxolan-4-yl)propan-2-ol (4.2 g, 26.2 mmol) was added. After 1 hour at room temperature, prop-1-en-2-yl acetate (3.32 mL, 30.1 mmol) was added and the reaction mixture was stirred at room temperature overnight. The reaction mixture was quenched with aqueous NaHCO$_3$ and stirred for 1 hour. The mixture was partitioned, and the organic layer was dried over sodium sulfate and concentrated. The resulting oil was purified over silica gel (10% EtOAc in hexanes) to afford (S)-(2,2,5,5-tetramethyl-1,3-dioxolan-4-yl)methyl acetate (4.0 g, 19.8 mmol, 75.4% yield) as a clear, colorless oil.

Step C:

(S)-(2,2,5,5-tetramethyl-1,3-dioxolan-4-yl)methyl acetate (4.0 g, 20 mmol) was dissolved in THF (60 mL) and cooled in an ice bath. LiAlH$_4$ (9.9 mL, 9.9 mmol) [1M in THF] was added slowly and the reaction mixture was stirred at 0° C. for 30 minutes. Sodium sulfate decahydrate was added and the reaction mixture was stirred vigorously for 20 minutes at room temperature. The resultant suspension was filtered through Celite® and concentrated to afford crude (S)-(2,2,5,5-tetramethyl-1,3-dioxolan-4-yl)methanol (3.3 g, 21 mmol, 104% yield) as a clear, colorless oil.

Step D:

(S)-(2,2,5,5-tetramethyl-1,3-dioxolan-4-yl)methanol (3.3 g, 20.6 mmol) was dissolved in CH$_2$Cl$_2$ (100 mL) and

| Preparation | Structure | Name |
| --- | --- | --- |
| 52 | 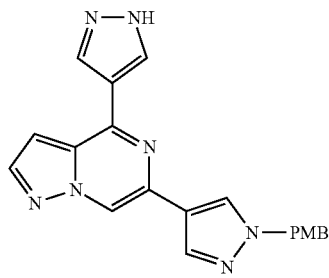 | 6-(1-(4-methoxybenzyl)-1H-pyrazol-4-yl)-4-(1-(1,1,1-trifluorobutan-2-yl)-1H-pyrazol-4-yl)pyrazolo[1,5-a]pyrazine |

Preparation 53

(S)-(2,2,5,5-tetramethyl-1,3-dioxolan-4-yl)methyl methanesulfonate

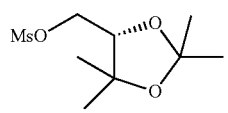

cooled in ice bath. Triethylamine (4.31 mL, 30.9 mmol) was added, followed by methanesulfonyl chloride (1.75 mL, 22.7 mmol). The ice bath was removed and the reaction mixture was warmed to room temperature. After 45 minutes, the reaction mixture was partitioned between water and CH$_2$Cl$_2$. The combined organic extracts were dried over sodium sulfate, filtered and concentrated. The residue was purified over silica gel (30% EtOAc in hexanes) to afford (S)-(2,2,5,5-tetramethyl-1,3-dioxolan-4-yl)methyl methanesulfonate (3.6 g, 15.1 mmol, 73.3% yield) as a clear, colorless oil.

The following compound was synthesized according to the procedure described in Preparation 53.

| Preparation | Structure | Name |
|---|---|---|
| 54 | 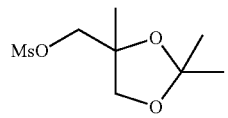 | (R)-(2,2,5,5-tetramethyl-1,3-dioxolan-4-yl)methyl methanesulfonate |

Preparation 55

((4R,5R)-2,2,5-trimethyl-1,3-dioxolan-4-yl)methyl methanesulfonate

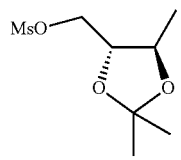

Step A:

(4S,5R)-Methyl 2,2,5-trimethyl-1,3-dioxolane-4-carboxylate (5.0 g, 29 mmol) was dissolved in THF (100 mL) and cooled in an ice bath. LiAlH$_4$ (14 mL, 14 mmol) was added slowly and stirred for 30 min in ice bath. Sodium sulfate decahydrate added carefully and stirred for 20 minutes at room temperature. The mixture was filtered through Celite® and concentrated to afford ((4R,5R)-2,2,5-trimethyl-1,3-dioxolan-4-yl)methanol (4.2 g, 29 mmol, 100% yield) as a clear, colorless oil.

Step B:

((4R,5R)-2,2,5-Trimethyl-1,3-dioxolan-4-yl)methanol (4.2 g, 28.7 mmol) was dissolved in CH$_2$Cl$_2$ (100 mL) and cooled in an ice bath. Triethylamine (6.01 mL, 43.1 mmol) was added, followed by methanesulfonyl chloride (2.45 mL, 31.6 mmol). The ice bath was removed and the reaction mixture was warmed to room temperature. After 45 min, the reaction mixture was partitioned between water and CH$_2$Cl$_2$, and combined organic extracts were dried over sodium sulfate, filtered and concentrated. The residue was purified over silica gel (30% EtOAc in hexanes) to afford ((4R,5R)-2,2,5-trimethyl-1,3-dioxolan-4-yl)methyl methanesulfonate (4.8 g, 21.4 mmol, 74.5% yield) as a clear, colorless oil.

The following compound was synthesized according to the procedure described in Preparation 55.

| Preparation | Structure | Name |
|---|---|---|
| 56 | TsO— (structure) | ((4S,5S)-2,2,5-trimethyl-1,3-dioxolan-4-yl)methyl 4-methylbenzenesulfonate |

Preparation 57

(2,2,4-trimethyl-1,3-dioxolan-4-yl)methyl methanesulfonate

Step A:

Osmium(VIII) oxide (2.0 mL, 0.327 mmol) was added to a solution of 4-methylmorpholine 4-oxide (8.44 g, 72.1 mmol), water (10 mL), acetone (7.5 mL) and tBuOH (6.7 mL). tert-Butyl methacrylate (5.71 mL, 35.2 mmol) in acetone (10 mL) was added dropwise and the reaction mixture was stirred at room temperature over the weekend. The reaction mixture was quenched with dilute aqueous NaHSO$_3$. The phases were separated, and the organic layer was dried over sodium sulfate and concentrated to afford crude tert-butyl 2,3-dihydroxy-2-methylpropanoate (6.2 g, 35.2 mmol, 100% yield) which was taken forward without further purification.

Step B:

Crude tert-butyl 2,3-dihydroxy-2-methylpropanoate (6.2 g, 35.2 mmol) was dissolved in 2,2-dimethoxypropane (43.2 mL, 352 mmol) and 4-methylbenzenesulfonic acid (0.909 g, 5.28 mmol) was added and the reaction mixture was stirred at room temperature overnight. The reaction mixture was quenched with saturated aqueous NaHCO$_3$ and diluted with EtOAc. The organic layer was separated, dried over sodium sulfate, filtered and concentrated to afford tert-butyl 2,2,4-trimethyl-1,3-dioxolane-4-carboxylate (5.3 g, 24.5 mmol, 69.6% yield) as a clear, colorless oil Step C:

Tert-butyl 2,2,4-trimethyl-1,3-dioxolane-4-carboxylate (5.3 g, 25 mmol) was dissolved in THF (100 mL) and cooled in an ice bath. LiAlH$_4$ (15 mL, 15 mmol) was added slowly and stirred in an ice bath for 30 min. Sodium sulfate decahydrate was added cautiously, and the reaction mixture was warmed to room temperature, stirred for 20 min, filtered through Celite® and concentrated to afford (2,2,4-trimethyl-1,3-dioxolan-4-yl)methanol (3.1 g, 21 mmol, 87% yield) as a clear, colorless oil.

Step D:

(2,2,4-Trimethyl-1,3-dioxolan-4-yl)methanol (3.11 g, 21.3 mmol) was dissolved in CH$_2$Cl$_2$ (100 mL) and cooled in ice bath. Triethylamine (3.85 mL, 27.7 mmol) was added, followed by methanesulfonyl chloride (1.81 mL, 23.4 mmol). The ice bath was removed and the reaction mixture was stirred for 30 min. The reaction mixture was partitioned between CH$_2$Cl$_2$ and water, and the combined organic extracts were dried over sodium sulfate, filtered and concentrated. The residue was purified over silica gel (50% EtOAc in hexanes) to afford (2,2,4-trimethyl-1,3-dioxolan-4-yl)methyl methanesulfonate (4.0 g, 17.8 mmol, 83.8% yield) as a clear, colorless oil.

Preparation 58

(2,2-dimethyl-1,3-dioxan-5-yl)methyl methanesulfonate

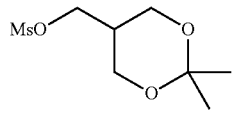

(2,2-Dimethyl-1,3-dioxan-5-yl)methanol (1.0 g, 6.84 mmol) was dissolved in $CH_2Cl_2$ (30 mL) and cooled in ice bath. Triethylamine (1.14 mL, 8.21 mmol) was added, followed by methanesulfonyl chloride (0.586 mL, 7.52 mmol) and the reaction mixture was warmed to room temperature. The reaction mixture was washed with 0.1 N HCl, saturated aqueous $NaHCO_3$, and the combined organic extracts were dried over sodium sulfate, filtered and concentrated to afford (2,2-dimethyl-1,3-dioxan-5-yl)methyl methanesulfonate (1.5 g, 6.69 mmol, 97.8% yield) as a clear colorless oil.

The following compounds were synthesized using the procedure described in Preparation 58.

| Preparation | Structure | Name |
|---|---|---|
| 59 | 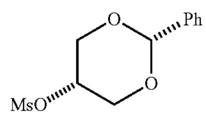 [SMILES: CS(=O)(=O)O[C@H]1CO[C@@H](c2ccccc2)OC1] | cis-2-phenyl-1,3-dioxan-5-yl methanesulfonate |
| 60 | 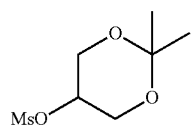 | 2,2-dimethyl-1,3-dioxan-5-yl methanesulfonate |
| 61 | 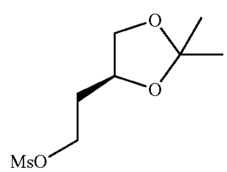 | (S)-2-(2,2-dimethyl-1,3-dioxolan-4-yl)ethyl ethanesulfonate |
| 62 | 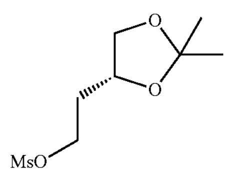 | (R)-2-(2,2-dimethyl-1,3-dioxolan-4-yl)ethyl methanesulfonate |
| 63 | 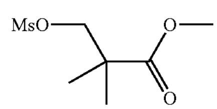 | methyl 2,2-dimethyl-3-((methylsulfonyl)oxy)propanoate |
| 64 | 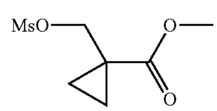 | ethyl 1-(((methylsulfonyl)oxy)methyl)cyclopropanecarboxylate |
| 65 | 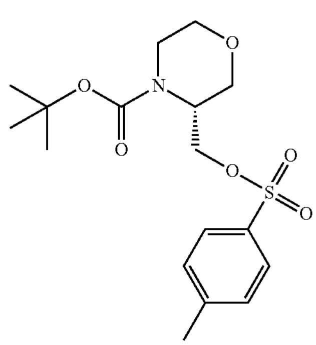 [SMILES: Cc1ccc(S(=O)(=O)OC[C@H]2COCCN2C(=O)OC(C)(C)C)cc1] | (R)-tert-butyl 3-((tosyloxy)methyl)morpholine-4-carboxylate |

| Preparation | Structure | Name |
|---|---|---|
| 66 | 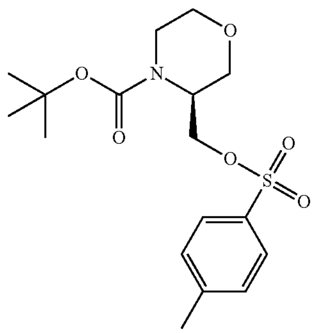 [SMILES: Cc1ccc(S(=O)(=O)OC[C@@H]2COCCN2C(=O)OC(C)(C)C)cc1] | (S)-tert-butyl 3-((tosyloxy)methyl)morpholine-4-carboxylate |
| 67 | 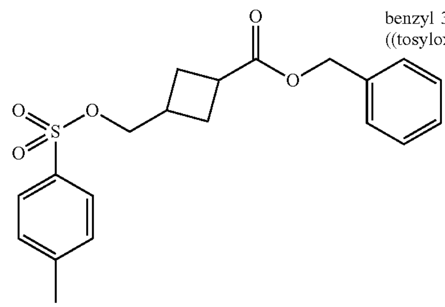 | benzyl 3-((tosyloxy)methyl)cyclobutanecarboxylate |
| 68 | 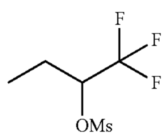 | 1,1,1-trifluorobutan-2-yl methanesulfonate |

Preparation 69

1-((R)-1,4-dioxaspiro[4.5]decan-2-yl)ethyl methanesulfonate

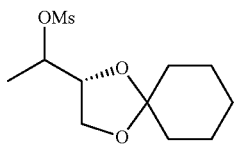 [SMILES: CC(OS(C)(=O)=O)[C@H]1COC2(CCCCC2)O1]

Step A:

A solution of (R)-1,4-dioxaspiro[4.5]decane-2-carbaldehyde (1.0 g, 5.9 mmol) in THF (30 mL) was cooled to 0° C. and methylmagnesium bromide (4.2 mL, 5.9 mmol) was added dropwise. The reaction mixture was stirred for 1 hour, quenched with water and extracted with CH$_2$Cl$_2$. The combined organic layers were washed with brine, dried over MgSO$_4$, filtered and concentrated in vacuo to provide 1-((R)-1,4-dioxaspiro[4.5]decan-2-yl)ethyl methanesulfonate. The material was used in the next step without purification.

Step B:

A solution of 1-((R)-1,4-dioxaspiro[4.5]decan-2-yl)ethanol (0.90 g, 4.83 mmol) in CH$_2$Cl$_2$ (30 mL) was cooled to 0° C. and N-ethyl-N-isopropylpropan-2-amine (1.30 mL, 7.25 mmol) added. DMAP (1 chip) was added, followed by dropwise addition of methanesulfonyl chloride (0.420 mL, 5.32 mmol). The reaction mixture as stirred for 3 hours. The reaction mixture was quenched with water and the layers were separated. The combined organic layers were washed with brine, dried over MgSO$_4$ and concentrated in vacuo to afford 1-((R)-1,4-dioxaspiro[4.5]decan-2-yl)ethyl methanesulfonate.

The following compound was synthesized using the procedure described in Preparation 69.

| Preparation | Structure | Name |
|---|---|---|
| 70 | 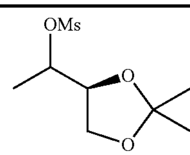 | 1-((S)-2,2-dimethyl-1,3-dioxolan-4-yl)ethyl methanesulfonate |

Preparation 71

2-(N-methylmethylsulfonamido)ethyl methanesulfonate

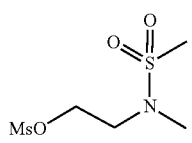

2-(Methylamino)ethanol (2.1 mL, 26.6 mmol) was dissolved in CH₂Cl₂ (200 mL) and the flask was placed in a water bath. Triethylamine (9.3 mL, 66.6 mmol) was added, followed by slow addition of methanesulfonyl chloride (4.6 mL, 58.6 mmol). After 1 hour, the reaction mixture was washed with 0.1 M HCl and saturated aqueous NaHCO₃. The combined organic layers were dried over sodium sulfate, filtered and concentrated to afford 2-(N-methylmethylsulfonamido)ethyl methanesulfonate (5.2 g, 22.48 mmol, 84.43% yield) as an oil.

Preparation 72

(1,1-dioxidotetrahydro-2H-thiopyran-4-yl)methyl methanesulfonate

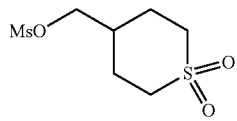

Step A:

Methyl tetrahydrothiopyran-4-carboxylate (1.0 g, 6.2 mmol) was dissolved in CH₂Cl₂ (50 mL) and cooled in an ice bath. 3-Chlorobenzoperoxoic acid (3.4 g, 14 mmol) was added in portions and the reaction mixture was allowed to warm to room temperature overnight. The reaction mixture was diluted with CH₂Cl₂ and washed with saturated aqueous NaHCO₃, and the combined organic extracts were dried over sodium sulfate, filtered and concentrated to afford methyl tetrahydro-2H-thiopyran-4-carboxylate 1,1-dioxide (1.1 g, 5.7 mmol, 92% yield) as a white solid.

Step B:

Methyl tetrahydro-2H-thiopyran-4-carboxylate 1,1-dioxide (1.1 g, 5.7 mmol) was dissolved in THF (50 mL) and cooled in ice bath. LiAlH₄ (3.4 mL, 3.4 mmol) was added slowly and the reaction mixture was allowed to stir in ice bath for 30 minutes. Sodium sulfate decahydrate was added in portions. The reaction mixture was allowed to warm to room temperature and then filtered through Celite® and concentrated to afford 4-(hydroxymethyl)tetrahydro-2H-thiopyran 1,1-dioxide (0.96 g, 5.8 mmol, 102% yield) as a white solid.

Step C:

4-(Hydroxymethyl)tetrahydro-2H-thiopyran 1,1-dioxide (0.90 g, 5.480 mmol) was dissolved in CH₂Cl₂ (25 mL) and cooled in ice bath. Triethylamine (1.146 mL, 8.221 mmol) was added, followed by methanesulfonyl chloride (0.5111 mL, 6.576 mmol) and ice bath removed. After 1 hour the reaction mixture was diluted with CH₂Cl₂ and washed with 0.1 M HCl, saturated aqueous NaHCO₃ and brine, dried over sodium sulfate, filtered and concentrated to afford (1,1-dioxidotetrahydro-2H-thiopyran-4-yl)methyl methanesulfonate (1.04 g, 4.292 mmol, 78.32% yield) as a white solid.

Preparation 73 cis-3-(tosyloxy)cyclobutyl pivalate

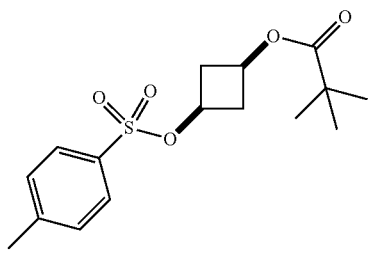

Step A:

To a solution of 3-oxocyclobutyl pivalate (1.0 g, 5.88 mmol) in EtOH (7.34 mL, 5.88 mmol) at 0° C. was carefully added NaBH₄ (0.333 g, 8.81 mmol). The reaction mixture was stirred for 60 minutes and then slowly quenched with a saturated aqueous NH₄Cl solution (20 mL). The reaction mixture was extracted with CH₂Cl₂ (3×15 mL). The combined extracts were washed with brine, dried over Na₂SO₄, filtered and concentrated to afford cis-3-hydroxycyclobutyl pivalate as a light yellow oil.

Step B:

To a solution of cis-3-hydroxycyclobutyl pivalate (0.830 g, 4.82 mmol) in pyridine (12.0 mL, 4.82 mmol) at 0° C. was added p-toluenesulfonyl chloride (1.84 g, 9.64 mmol). The reaction mixture was stirred for 18 hours as the ice bath warmed to ambient temperature over 2 hours. The mixture was concentrated, diluted with water and extracted with EtOAc. The combined extracts were washed with brine, dried over Na₂SO₄, filtered and concentrated. The residual yellow oil was dissolved in minimal EtOAc (5 mL) and the mixture was diluted with hexanes (90 mL) and cooled to −2° C. in a freezer for 3 hours. The resulting solid was isolated by vacuum filtration and the solid was washed with hexanes and dried in vacuo providing cis-3-(tosyloxy)cyclobutyl pivalate (600 mg, 38% yield) as an off-white solid.

Preparation 74

4-(1-(pentan-3-yl)-1H-pyrazol-4-yl)-6-(1H-pyrazol-4-yl)pyrazolo[1,5-a]pyrazine

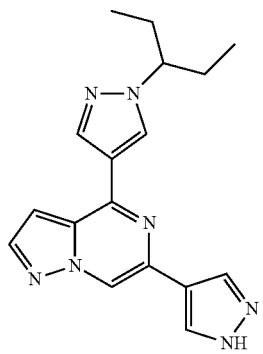 [SMILES: CCC(CC)n1cc(-c2nc(-c3cn[nH]c3)cn3nccc23)cn1]

To 6-(1-(4-methoxybenzyl)-1H-pyrazol-4-yl)-4-(1-(pentan-3-yl)-1H-pyrazol-4-yl)pyrazolo[1,5-a]pyrazine (0.80 g, 1.8 mmol) was added TFA (4.1 g, 36 mmol) and the reaction mixture was stirred for 4 hours at 70° C. The TFA was removed by concentration in vacuo. The residue was slurried in water and the aqueous layer was basified by addition of 1M NaOH. The aqueous layer was extracted with EtOAc. The combined organic extracts were washed with brine, dried over MgSO$_4$, filtered and concentrated in vacuo. The residue was purified over silica gel (0 to 10% MeOH in CH$_2$Cl$_2$) to afford 4-(1-(pentan-3-yl)-1H-pyrazol-4-yl)-6-(1H-pyrazol-4-yl)pyrazolo[1,5-a]pyrazine (0.4 g, 1.2 mmol, 69% yield) as a solid. Mass spectrum (apci) m/z=322.1 (M+H). $^1$H NMR (d$_6$-DMSO) δ 13.04 (s, 1H), 9.01 (s, 1H), 8.75 (s, 1H), 8.41 (m, 2H), 8.20 (m, 1H), 8.16 (d, J=2.5 Hz, 1H), 7.36 (m, 1H), 4.14 (m, 1H), 1.97-1.80 (m, 4H), 0.75 (t, J=7.4 Hz, 6H).

The following compounds were prepared according to the procedure described for Preparation 74.

| Preparation | Structure | Name | Data |
| --- | --- | --- | --- |
| 75 | 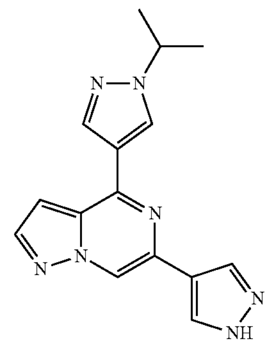 [SMILES: CC(C)n1cc(-c2nc(-c3cn[nH]c3)cn3nccc23)cn1] | 4-(1-isopropyl-1H-pyrazol-4-yl)-6-(1H-pyrazol-4-yl)pyrazolo[1,5-a]pyrazine | Mass spectrum (apci) m/z = 294.1 (M + H) |
| 76 | 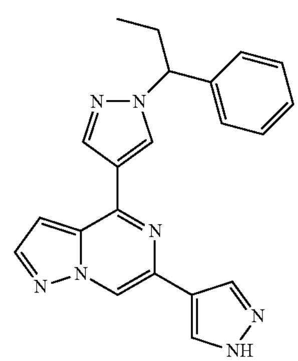 [SMILES: CCC(c1ccccc1)n1cc(-c2nc(-c3cn[nH]c3)cn3nccc23)cn1] | 4-(1-(1-phenylpropyl)-1H-pyrazol-4-yl)-6-(1H-pyrazol-4-yl)pyrazolo[1,5-a]pyrazine | Mass spectrum (apci) m/z = 370.2 (M + H) |
| 77 | 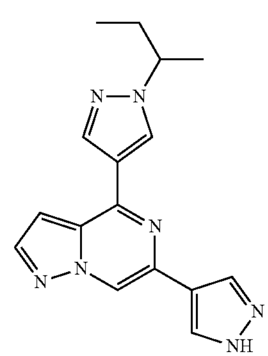 [SMILES: CCC(C)n1cc(-c2nc(-c3cn[nH]c3)cn3nccc23)cn1] | 4-(1-(sec-butyl)-1H-pyrazol-4-yl)-6-(1H-pyrazol-4-yl)pyrazolo[1,5-a]pyrazine | Mass spectrum (apci) m/z = 308.1 (M + H) |

| Preparation | Structure | Name | Data |
|---|---|---|---|
| 78 | 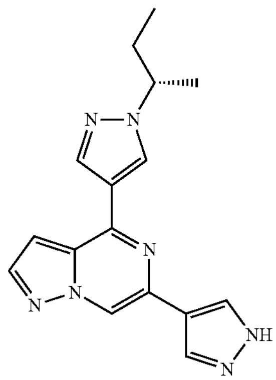 [SMILES: CC[C@H](C)n1cc(-c2nc(-c3cn[nH]c3)cn3nccc23)cn1] | (S)-4-(1-(sec-butyl)-1H-pyrazol-4-yl)-6-(1H-pyrazol-4-yl)pyrazolo[1,5-a]pyrazine | Mass spectrum (apci) m/z = 308.1 (M + H) |
| 79 | 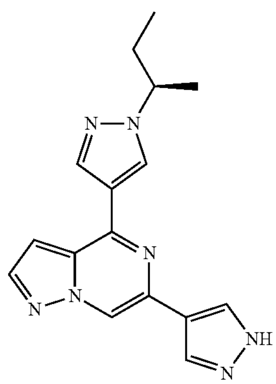 [SMILES: CC[C@@H](C)n1cc(-c2nc(-c3cn[nH]c3)cn3nccc23)cn1] | (R)-4-(1-(sec-butyl)-1H-pyrazol-4-yl)-6-(1H-pyrazol-4-yl)pyrazolo[1,5-a]pyrazine | Mass spectrum (apci) m/z = 308.1 (M + H) |
| 80 | 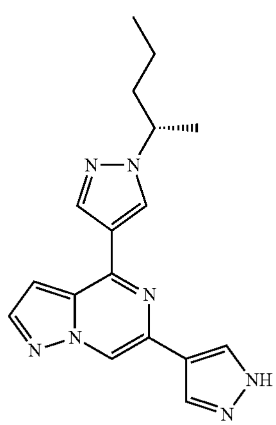 [SMILES: CCC[C@H](C)n1cc(-c2nc(-c3cn[nH]c3)cn3nccc23)cn1] | (S)-4-(1-(pentan-2-yl)-1H-pyrazol-4-yl)-6-(1H-pyrazol-4-yl)pyrazolo[1,5-a]pyrazine | Mass spectrum (apci) m/z = 322.1 (M + H) |
| 81 | 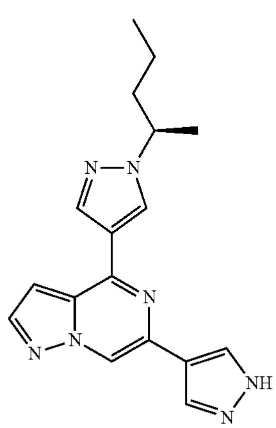 [SMILES: CCC[C@@H](C)n1cc(-c2nc(-c3cn[nH]c3)cn3nccc23)cn1] | (R)-4-(1-(pentan-2-yl)-1H-pyrazol-4-yl)-6-(1H-pyrazol-4-yl)pyrazolo[1,5-a]pyrazine | Mass spectrum (apci) m/z = 322.1 (M + H) |

| Preparation | Structure | Name | Data |
| --- | --- | --- | --- |
| 82 | 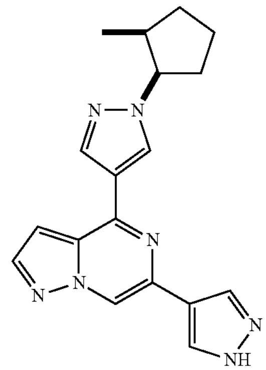 | 4-(1-(cis-2-methylcyclopentyl)-1H-pyrazol-4-yl)-6-(1H-pyrazol-4-yl)pyrazolo[1,5-a]pyrazine | Mass spectrum (apci) m/z = 334.1 (M + H) |
| 83 | 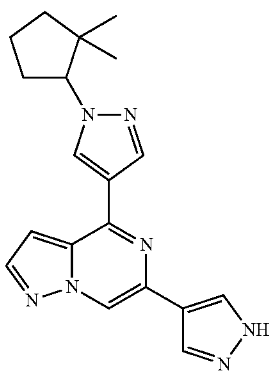 [SMILES: CC1(C)CCCC1n1cc(-c2nc(-c3cn[nH]c3)cn3nccc23)cn1] | 4-(1-(2,2-dimethylcyclopentyl)-1H-pyrazol-4-yl)-6-(1H-pyrazol-4-yl)pyrazolo[1,5-a]pyrazine | Mass spectrum (apci) m/z = 348.2 (M + H) |

The following compounds were prepared according to the procedure described for Example 1 below.

| Preparation | Structure | Name | Data |
| --- | --- | --- | --- |
| 84 | 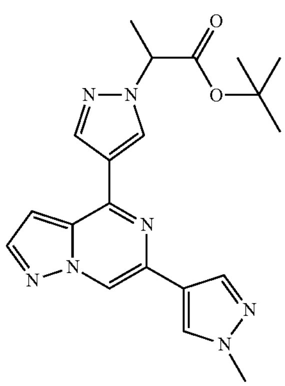 [SMILES: CC(C(=O)OC(C)(C)C)n1cc(-c2nc(-c3cnn(C)c3)cn3nccc23)cn1] | tert-butyl 2-(4-(6-(1-methyl-1H-pyrazol-4-yl)pyrazolo[1,5-a]pyrazin-4-yl)-1H-pyrazol-1-yl)propanoate | Mass spectrum (apci) m/z = 394.1 (M + H) |

-continued
| Preparation | Structure | Name | Data |
|---|---|---|---|
| 85 | 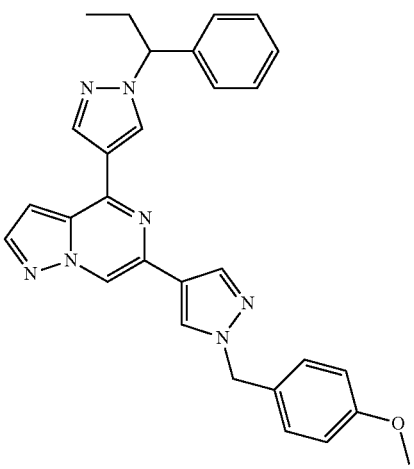 [SMILES: CCC(c1ccccc1)n1cc(-c2nc(-c3cnn(Cc4ccc(OC)cc4)c3)cn3nccc23)cn1] | 6-(1-(4-methoxybenzyl)-1H-pyrazol-4-yl)-4-(1-(1-phenylpropyl)-1H-pyrazol-4-yl)pyrazolo[1,5-a]pyrazine | Mass spectrum (apci) m/z = 490.2 (M + H) |
| 86 | 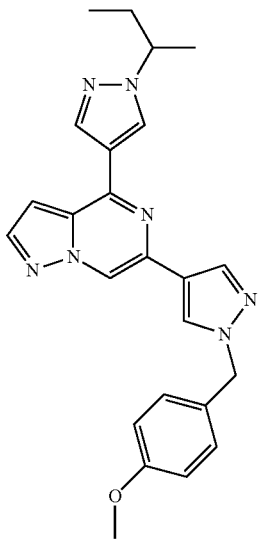 [SMILES: CCC(C)n1cc(-c2nc(-c3cnn(Cc4ccc(OC)cc4)c3)cn3nccc23)cn1] | 4-(1-(sec-butyl)-1H-pyrazol-4-yl)-6-(1-(4-methoxybenzyl)-1H-pyrazol-4-yl)pyrazolo[1,5-a]pyrazine | Mass spectrum (apci) m/z 428.2 (M + H) |
| 87 | 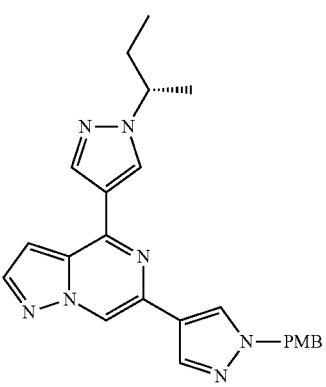 | (S)-4-(1-(sec-butyl)-1H-pyrazol-4-yl)-6-(1-(4-methoxybenzyl)-1H-pyrazol-4-yl)pyrazolo[1,5-a]pyrazine | Mass spectrum (apci) m/z = 428.2 (M + H) |

-continued

| Preparation | Structure | Name | Data |
|---|---|---|---|
| 88 | 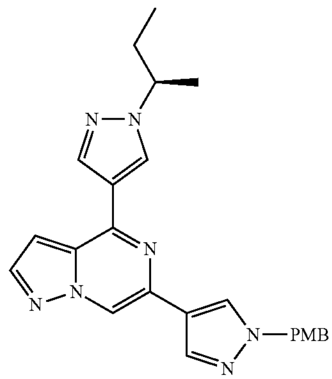 | (R)-4-(1-(sec-butyl)-1H-pyrazol-4-yl)-6-(1-(4-methoxybenzyl)-1H-pyrazol-4-yl)pyrazolo[1,5-a]pyrazine | Mass spectrum (apci) m/z = 428.2 (M + H) |
| 89 | 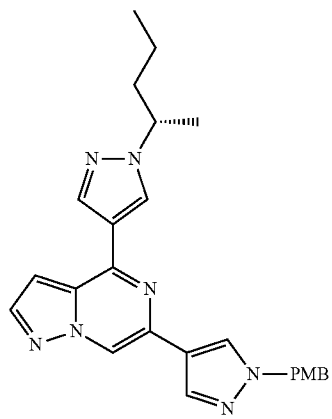 | (S)-6-(1-(4-methoxybenzyl)-1H-pyrazol-4-yl)-4-(1-(pentan-2-yl)-1H-pyrazol-4-yl)pyrazolo[1,5-a]pyrazine | Mass spectrum (apci) m/z = 442.2 (M + H) |
| 90 | 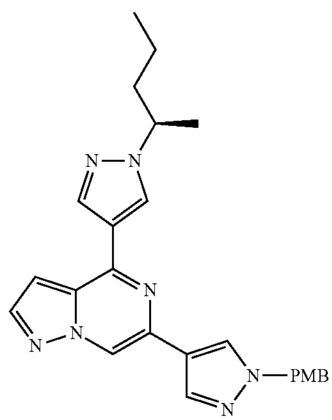 | (R)-6-(1-(4-methoxybenzyl)-1H-pyrazol-4-yl)-4-(1-(pentan-2-yl)-1H-pyrazol-4-yl)pyrazolo[1,5-a]pyrazine | Mass spectrum (apci) m/z = 442.2 (M + H) |

-continued
| Preparation | Structure | Name | Data |
|---|---|---|---|
| 91 | 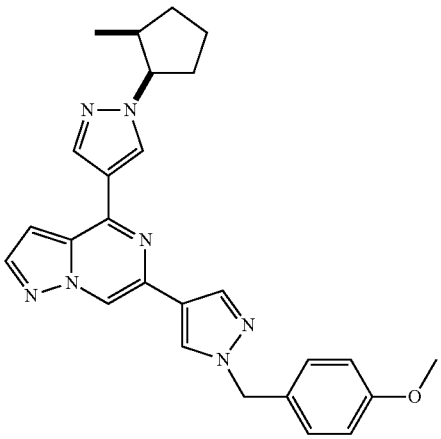 | 6-(1-(4-methoxybenzyl)-1H-pyrazol-4-yl)-4-(1-(cis-2-methylcyclopentyl)-1H-pyrazol-4-yl)pyrazolo[1,5-a]pyrazine | Mass spectrum (apci) m/z = 454.2 (M + H) |
| 92 | 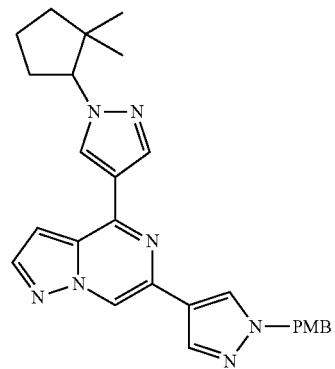 | 4-(1-(2,2-dimethylcyclopentyl)-1H-pyrazol-4-yl)-6-(1-(4-methoxybenzyl)-1H-pyrazol-4-yl)pyrazolo[1,5-a]pyrazine | Mass spectrum (apci) m/z = 468.2 (M + H) |

-continued

| Preparation | Structure | Name | Data |
|---|---|---|---|
| 93 | 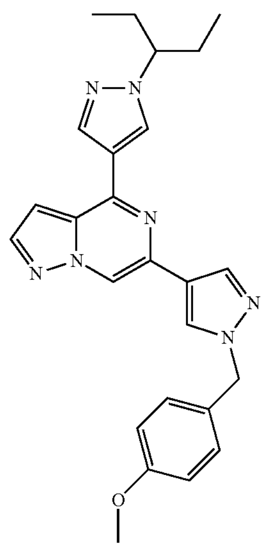 [SMILES: CCC(CC)n1cc(-c2nc(-c3cnn(Cc4ccc(OC)cc4)c3)cn3nccc23)cn1] | 6-(1-(4-methoxybenzyl)-1H-pyrazol-4-yl)-4-(1-(pentan-3-yl)-1H-pyrazol-4-yl)pyrazolo[1,5-a]pyrazine | Mass spectrum (apci) m/z = 442.2 (M + H) |
| 94 | 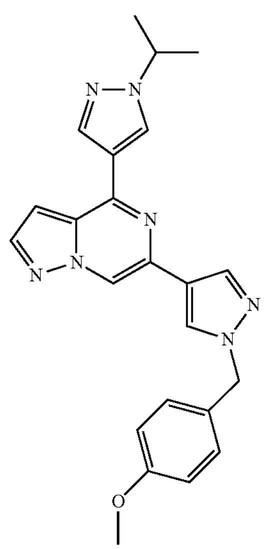 [SMILES: COc1ccc(Cn2cc(-c3cn4nccc4c(-c4cnn(C(C)C)c4)n3)cn2)cc1] | 4-(1-isopropyl-1H-pyrazol-4-yl)-6-(1-(4-methoxybenzyl)-1H-pyrazol-4-yl)pyrazolo[1,5-a]pyrazine | Mass spectrum (apci) m/z = 414.2 (M + H) |

The following compounds were prepared according to Example 31 below.

| Preparation | Structure | Name | Data |
|---|---|---|---|
| 95 | 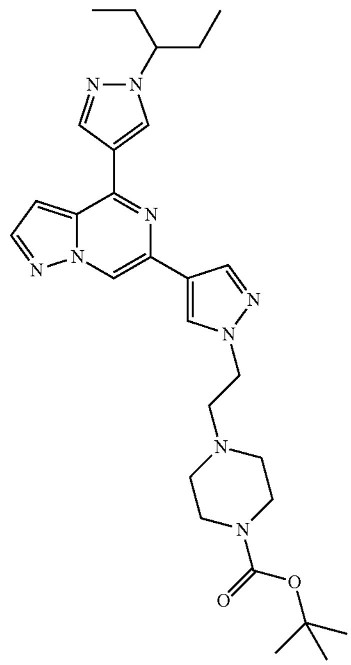 [SMILES: CCC(CC)n1cc(-c2nc(-c3cnn(CCN4CCN(C(=O)OC(C)(C)C)CC4)c3)cn3nccc23)cn1] | tert-butyl 4-(2-(4-(4-(1-(pentan-3-yl)-1H-pyrazol-4-yl)pyrazolo[1,5-a]pyrazin-6-yl)-1H-pyrazol-1-yl)ethyl)piperazine-1-carboxylate | Mass spectrum (apci) m/z = 534.3 (M + H) |
| 96 | 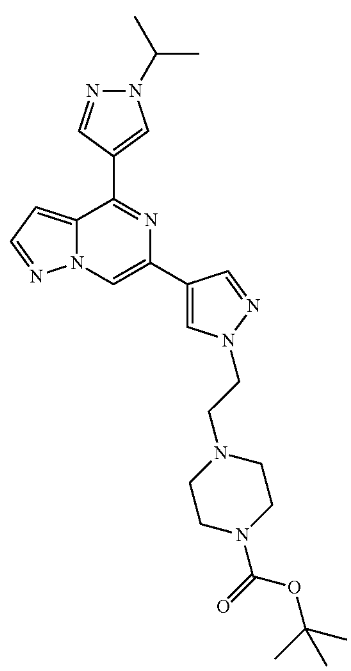 [SMILES: CC(C)n1cc(-c2nc(-c3cnn(CCN4CCN(C(=O)OC(C)(C)C)CC4)c3)cn3nccc23)cn1] | tert-butyl 4-(2-(4-(4-(1-isopropyl-1H-pyrazol-4-yl)pyrazolo[1,5-a]pyrazin-6-yl)-1H-pyrazol-1-yl)ethyl)piperazine-1-carboxylate | Mass spectrum (apci) m/z = 506.3 (M + H) |

SYNTHETIC EXAMPLES

Example 1

4-(1-(1-ethoxyethyl)-1H-pyrazol-4-yl)-6-(1-methyl-1H-pyrazol-4-yl)pyrazolo[1,5-a]pyrazine

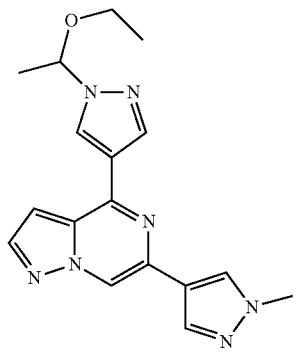 [SMILES: CCOC(C)n1cc(-c2nc(-c3cnn(C)c3)cn3nccc23)cn1]

4-Chloro-6-(1-methyl-1H-pyrazol-4-yl)pyrazolo[1,5-a]pyrazine hydrochloride (0.750 g, 2.78 mmol), 1-(1-ethoxyethyl)-4-(4,4,5,5-tetramethyl-1,3,2-dioxaborolan-2-yl)-1H-pyrazole (0.887 g, 3.33 mmol), dicyclohexyl(2',4',6'-triisopropyl-[1,1'-biphenyl]-2-yl)phosphine (0.397 g, 0.833 mmol), and $Pd_2dba_3$ (0.127 g, 0.139 mmol) were combined in 30 mL of dioxane. The reaction mixture was sparged with argon for 5 minutes before potassium carbonate (4.16 mL, 8.33 mmol) was added with stirring. The sparging was continued for another 2 minutes before the reaction vessel was sealed and then heated to 75° C. overnight. The reaction mixture was diluted with 200 mL of EtOAc and washed with 20 mL of brine. The organic layer was dried over $MgSO_4$, filtered, and removed under reduced pressure. The residue was purified over silica (80% EtOAc in Hexanes) to afford 4-(1-(1-ethoxyethyl)-1H-pyrazol-4-yl)-6-(1-methyl-1H-pyrazol-4-yl)pyrazolo[1,5-a]pyrazine (0.340 g, 0.957 mmol, 34.5% yield). Mass spectrum (apci) m/z=338.1 (M+H). $^1$H NMR ($d_6$-DMSO) δ 9.01 (d, J=1.0 Hz, 1H), 8.87 (s, 1H), 8.43 (s, 1H), 8.37 (s, 1H), 8.18 (d, J=2.4 Hz, 1H), 8.14 (d, J=0.9 Hz, 1H), 7.40 (dd, J=2.5, 1.0 Hz, 1H), 5.69 (q, J=6.1 Hz, 1H), 3.91 (s, 3H), 3.55-3.46 (m, 1H), 3.33-3.24 (m, 1H), 1.72 (d, J=6.1 Hz, 3H), 1.07 (t, J=7.0 Hz, 3H).

Example 2

4-(1-cycloheptyl-1H-pyrazol-4-yl)-6-(1-methyl-1H-pyrazol-4-yl)pyrazolo[1,5-a]pyrazine

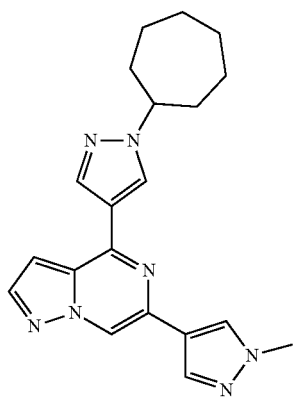 [SMILES: Cn1cc(-c2cn3nccc3c(-c3cnn(C4CCCCCC4)c3)n2)cn1]

4-Chloro-6-(1-methyl-1H-pyrazol-4-yl)pyrazolo[1,5-a]pyrazine hydrochloride (30 mg, 0.11 mmol) and 1-cycloheptyl-4-(4,4,5,5-tetramethyl-1,3,2-dioxaborolan-2-yl)-1H-pyrazole (64 mg, 0.22 mmol) were dissolved in $K_2CO_3$ (167 μL, 0.33 mmol) and THF (1 mL). $Pd_2dba_3$ (2.5 mg, 0.0028 mmol) and dicyclohexyl(2',4',6'-triisopropyl-[1,1'-biphenyl]-2-yl)phosphine (5.3 mg, 0.011 mmol) were added. The vial was sealed and heated to 70° C. overnight. The reaction mixture was cooled to room temperature, diluted with EtOAc, decanted, concentrated and purified over silica gel (80% EtOAc in hexanes) to afford 4-(1-cycloheptyl-1H-pyrazol-4-yl)-6-(1-methyl-1H-pyrazol-4-yl)pyrazolo[1,5-a]pyrazine (33 mg, 0.091 mmol, 82% yield) as a tan waxy solid. Mass spectrum (apci) m/z=362.2 (M+H). H NMR ($CDCl_3$) δ 8.44 (s, 1H), 8.21 (s, 1H), 8.19 (s, 1H), 8.02 (m, 1H), 7.94 (s, 2H), 6.93 (m, 1H), 4.47-4.38 (m, 1H), 3.99 (s, 3H), 2.29-2.20 (m, 2H), 2.12-2.00 (m, 2H), 1.92-1.82 (m, 2H), 1.76-1.55 (m, 6H).

Example 3

4-(2-(4-(4-(1-(pentan-3-yl)-1H-pyrazol-4-yl)pyrazolo[1,5-a]pyrazin-6-yl)-1H-pyrazol-1-yl)ethyl)morpholine

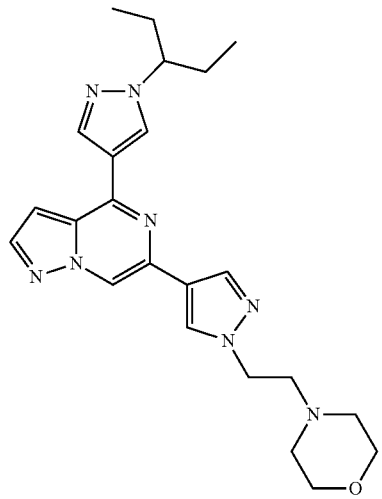 [SMILES: CCC(CC)n1cc(-c2nc(-c3cnn(CCN4CCOCC4)c3)cn3nccc23)cn1]

To a solution of 4-(1-(pentan-3-yl)-1H-pyrazol-4-yl)-6-(1H-pyrazol-4-yl)pyrazolo[1,5-a]pyrazine (0.042 g, 0.131 mmol) in 1 mL of DMA was added 4-(2-chloroethyl)morpholine hydrochloride (0.0486 g, 0.261 mmol) and cesium carbonate (0.170 g, 0.523 mmol) and reaction mixture was stirred overnight at 70° C. The reaction mixture was purified by reverse phase chromatography (C18, 0-50% $CH_3CN$/water) to afford 4-(2-(4-(4-(1-(pentan-3-yl)-1H-pyrazol-4-yl)pyrazolo[1,5-a]pyrazin-6-yl)-1H-pyrazol-1-yl)ethyl)morpholine (0.0222 g, 0.0511 mmol, 39.1% yield). Mass spectrum (apci) m/z=435.2 (M+H). $^1$H NMR ($CDCl_3$) δ 8.46 (d, J=0.8 Hz, 1H), 8.27 (s, 1H), 8.17 (s, 1H), 8.06 (s, 1H), 8.03 (d, J=2.3 Hz, 1H), 7.97 (s, 1H), 6.95 (dd, J=2.3, 0.8 Hz, 1H), 4.32 (t, J=6.7 Hz, 2H), 4.07-3.99 (m, 1H), 3.72 (m, 4H), 2.89 (t, J=6.7 Hz, 2H), 2.53 (m, 4H), 2.06-1.85 (m, 4H), 0.86 (t, J=7.4 Hz, 3H).

The following compounds were prepared according to the procedure described for Example 3.

| Example | Structure | Name | Data |
|---|---|---|---|
| 4 | 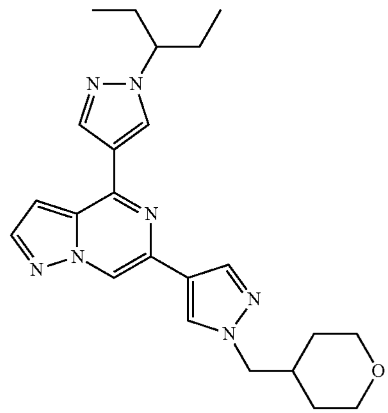 [SMILES: CCC(CC)n1cc(-c2nc(-c3cnn(CC4CCOCC4)c3)cn3nccc23)cn1] | 4-(1-(pentan-3-yl)-1H-pyrazol-4-yl)-6-(1-((tetrahydro-2H-pyran-4-yl)methyl)-1H-pyrazol-4-yl)pyrazolo[1,5-a]pyrazine | Mass spectrum (apci) m/z = 420.2 (M + H) |
| 5 | 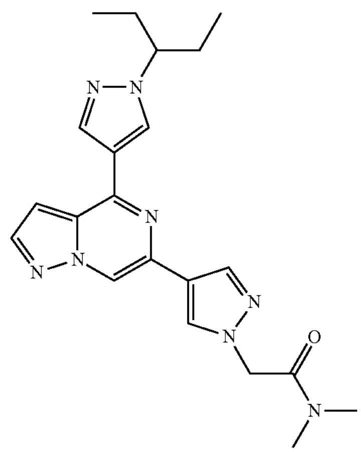 [SMILES: CCC(CC)n1cc(-c2nc(-c3cnn(CC(=O)N(C)C)c3)cn3nccc23)cn1] | N,N-dimethyl-2-(4-(4-(1-(pentan-3-yl)-1H-pyrazol-4-yl)pyrazolo[1,5-a]pyrazin-6-yl)-1H-pyrazol-1-yl)acetamide | Mass spectrum (apci) m/z = 407.2 (M + H) |
| 6 | 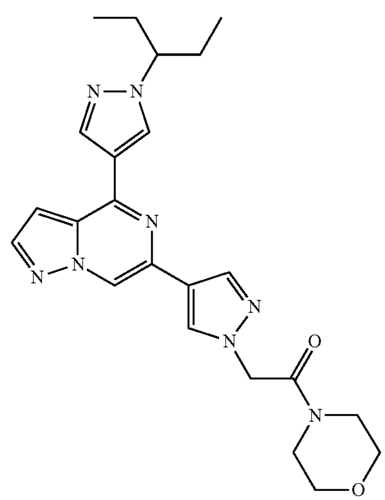 [SMILES: CCC(CC)n1cc(-c2nc(-c3cnn(CC(=O)N4CCOCC4)c3)cn3nccc23)cn1] | 1-morpholino-2-(4-(4-(1-(pentan-3-yl)-1H-pyrazol-4-yl)pyrazolo[1,5-a]pyrazin-6-yl)-1H-pyrazol-1-yl)ethanone | Mass spectrum (apci) m/z = 449.2 (M + H) |

| Example | Structure | Name | Data |
|---|---|---|---|
| 7 | 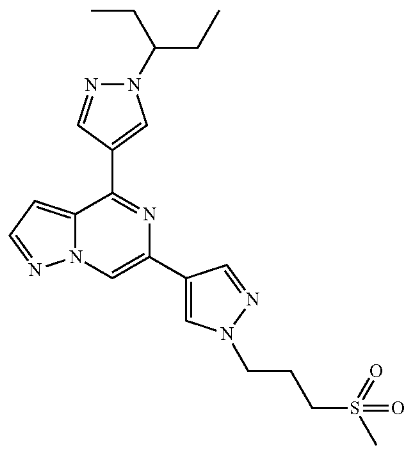 [SMILES: CCC(CC)n1cc(-c2nc(-c3cnn(CCCS(C)(=O)=O)c3)cn3nccc23)cn1] | 6-(1-(3-(methylsulfonyl)propyl)-1H-pyrazol-4-yl)-4-(1-(pentan-3-yl)-1H-pyrazol-4-yl)pyrazolo[1,5-a]pyrazine | Mass spectrum (apci) m/z = 442.2 (M + H) |
| 8 | 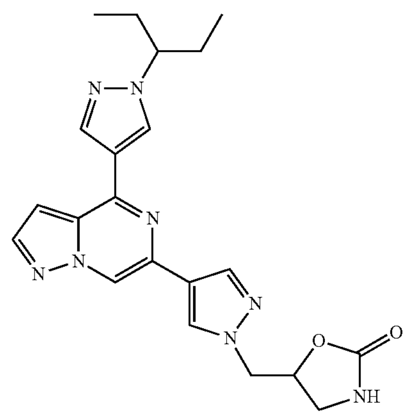 [SMILES: CCC(CC)n1cc(-c2nc(-c3cnn(CC4CNC(=O)O4)c3)cn3nccc23)cn1] | 5-((4-(4-(1-(pentan-3-yl)-1H-pyrazol-4-yl)pyrazolo[1,5-a]pyrazin-6-yl)-1H-pyrazol-1-yl)methyl)oxazolidin-2-one | Mass spectrum (apci) m/z = 421.2 (M + H) |
| 9 | 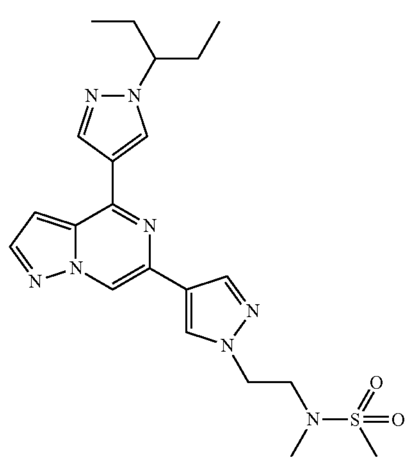 [SMILES: CCC(CC)n1cc(-c2nc(-c3cnn(CCN(C)S(C)(=O)=O)c3)cn3nccc23)cn1] | N-methyl-N-(2-(4-(4-(1-(pentan-3-yl)-1H-pyrazol-4-yl)pyrazolo[1,5-a]pyrazin-6-yl)-1H-pyrazol-1-yl)ethyl)methanesulfonamide | Mass spectrum (apci) m/z = 457.2 (M + H) |

| Example | Structure | Name | Data |
|---------|-----------|------|------|
| 10 | 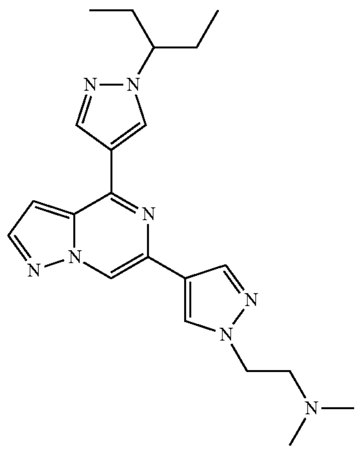 [SMILES: CCC(CC)n1cc(-c2nc(-c3cnn(CCN(C)C)c3)cn3nccc23)cn1] | N,N-dimethyl-2-(4-(4-(1-(pentan-3-yl)-1H-pyrazol-4-yl)pyrazolo[1,5-a]pyrazin-6-yl)-1H-pyrazol-1-yl)ethanamine | Mass spectrum (apci) m/z = 393.2 (M + H) |
| 11 | 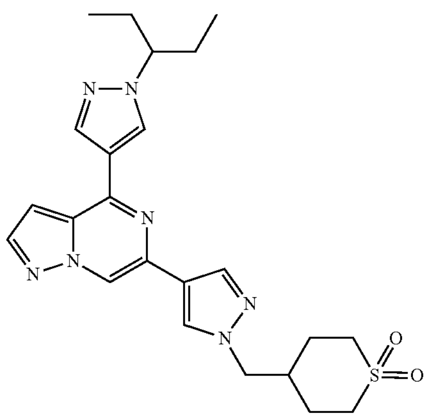 [SMILES: CCC(CC)n1cc(-c2nc(-c3cnn(CC4CCS(=O)(=O)CC4)c3)cn3nccc23)cn1] | 4-((4-(4-(1-(pentan-3-yl)-1H-pyrazol-4-yl)pyrazolo[1,5-a]pyrazin-6-yl)-1H-pyrazol-1-yl)methyl)tetrahydro-2H-thiopyran 1,1-dioxide | Mass spectrum (apci) m/z = 468.2 (M + H) |
| 12 | 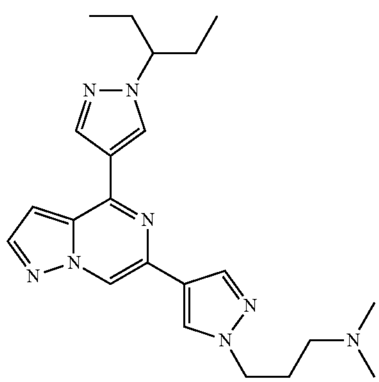 [SMILES: CCC(CC)n1cc(-c2nc(-c3cnn(CCCN(C)C)c3)cn3nccc23)cn1] | N,N-dimethyl-3-(4-(4-(1-(pentan-3-yl)-1H-pyrazol-4-yl)pyrazolo[1,5-a]pyrazin-6-yl)-1H-pyrazol-1-yl)propan-1-amine | Mass spectrum (apci) m/z = 407.3 (M + H) |

-continued

| Example | Structure | Name | Data |
|---|---|---|---|
| 13 | 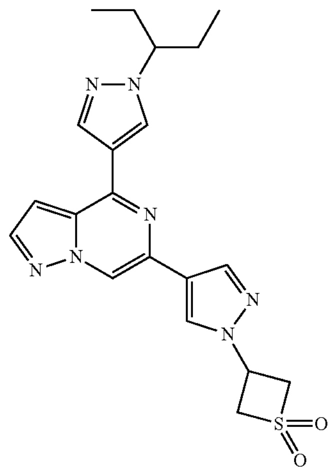 [SMILES: CCC(CC)n1cc(-c2nc(-c3cnn(C4CS(=O)(=O)C4)c3)cn3nccc23)cn1] | 3-(4-(4-(1-(pentan-3-yl)-1H-pyrazol-4-yl)pyrazolo[1,5-a]pyrazin-6-yl)-1H-pyrazol-1-yl)thietane 1,1-dioxide | Mass spectrum (apci) m/z = 426.2 (M + H) |
| 14 | 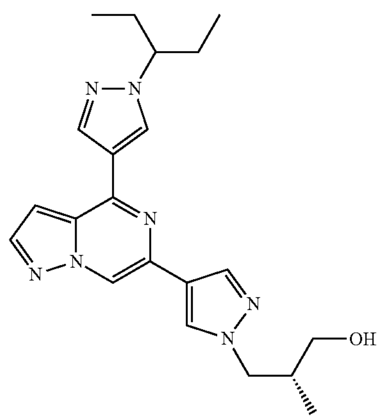 [SMILES: CCC(CC)n1cc(-c2nc(-c3cnn(C[C@@H](C)CO)c3)cn3nccc23)cn1] | (R)-2-methyl-3-(4-(4-(1-(pentan-3-yl)-1H-pyrazol-4-yl)pyrazolo[1,5-a]pyrazin-6-yl)-1H-pyrazol-1-yl)propan-1-ol | Mass spectrum (apci) m/z = 394.9 (M + H) |
| 15 | 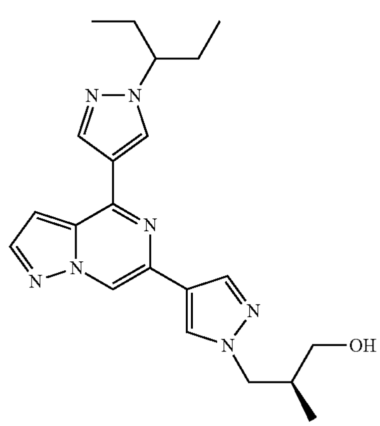 [SMILES: CCC(CC)n1cc(-c2nc(-c3cnn(C[C@H](C)CO)c3)cn3nccc23)cn1] | (S)-2-methyl-3-(4-(4-(1-(pentan-3-yl)-1H-pyrazol-4-yl)pyrazolo[1,5-a]pyrazin-6-yl)-1H-pyrazol-1-yl)propan-1-ol | Mass spectrum (apci) m/z = 394.2 (M + H) |

-continued

| Example | Structure | Name | Data |
|---|---|---|---|
| 16 | 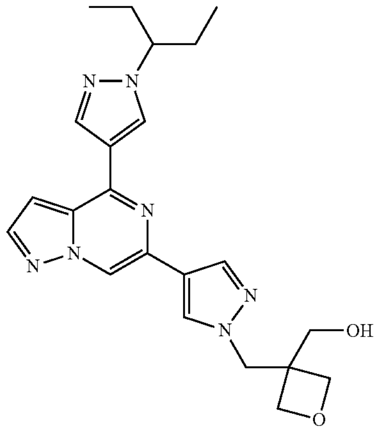 [SMILES: CCC(CC)n1cc(-c2nc(-c3cnn(CC4(CO)COC4)c3)cn3nccc23)cn1] | (3-((4-(4-(1-(pentan-3-yl)-1H-pyrazol-4-yl)pyrazolo[1,5-a]pyrazin-6-yl)-1H-pyrazol-1-yl)methyl)oxetan-3-yl)methanol | Mass spectrum (apci) m/z = 422.2 (M + H) |
| 17 | 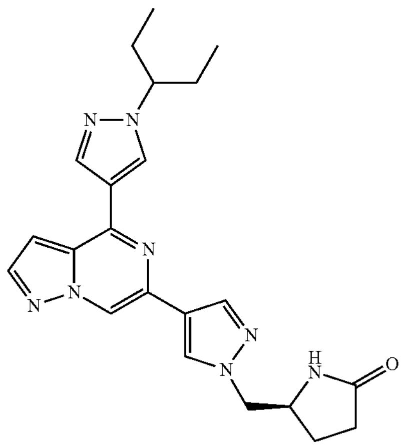 [SMILES: CCC(CC)n1cc(-c2nc(-c3cnn(C[C@@H]4CCC(=O)N4)c3)cn3nccc23)cn1] | (S)-5-((4-(4-(1-(pentan-3-yl)-1H-pyrazol-4-yl)pyrazolo[1,5-a]pyrazin-6-yl)-1H-pyrazol-1-yl)methyl)pyrrolidin-2-one | Mass spectrum (apci) m/z = 419.2 (M + H) |
| 18 | 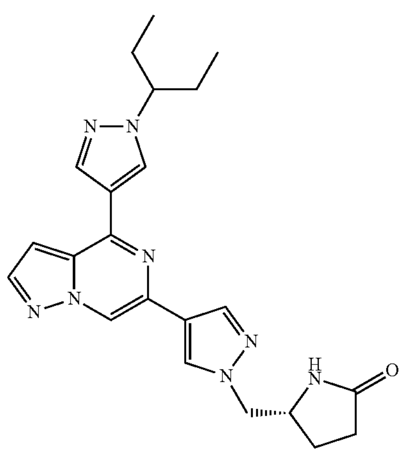 [SMILES: CCC(CC)n1cc(-c2nc(-c3cnn(C[C@H]4CCC(=O)N4)c3)cn3nccc23)cn1] | (R)-5-((4-(4-(1-(pentan-3-yl)-1H-pyrazol-4-yl)pyrazolo[1,5-a]pyrazin-6-yl)-1H-pyrazol-1-yl)methyl)pyrrolidin-2-one | Mass spectrum (apci) m/z = 419.2 (M + H) |

-continued

| Example | Structure | Name | Data |
|---|---|---|---|
| 19 | 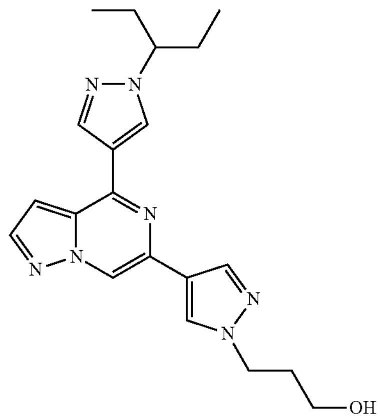 [SMILES: CCC(CC)n1cc(-c2nc(-c3cnn(CCCO)c3)cn3nccc23)cn1] | 3-(4-(4-(1-(pentan-3-yl)-1H-pyrazol-4-yl)pyrazolo[1,5-a]pyrazin-6-yl)-1H-pyrazol-1-yl)propan-1-ol | Mass spectrum (apci) m/z = 380.2 (M + H) |
| 20 | 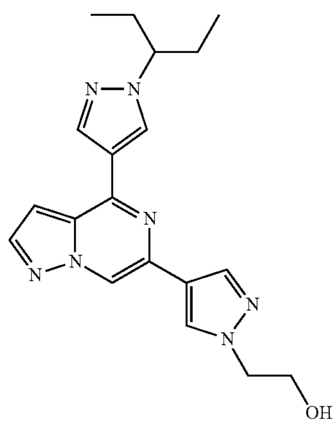 [SMILES: CCC(CC)n1cc(-c2nc(-c3cnn(CCO)c3)cn3nccc23)cn1] | 2-(4-(4-(1-(pentan-3-yl)-1H-pyrazol-4-yl)pyrazolo[1,5-a]pyrazin-6-yl)-1H-pyrazol-1-yl)ethanol | Mass spectrum (apci) m/z = 366.1 (M + H) |
| 21 | 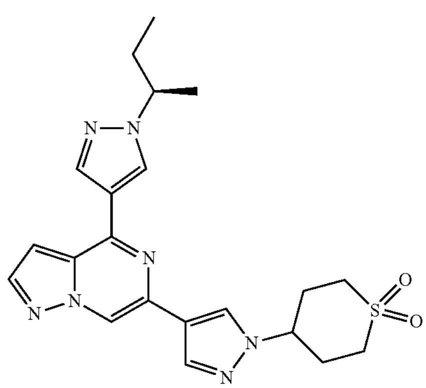 [SMILES: CC[C@@H](C)n1cc(-c2nc(-c3cnn(C4CCS(=O)(=O)CC4)c3)cn3nccc23)cn1] | (R)-4-(4-(4-(1-(sec-butyl)-1H-pyrazol-4-yl)pyrazolo[1,5-a]pyrazin-6-yl)-1H-pyrazol-1-yl)tetrahydro-2H-thiopyran 1,1-dioxide | Mass spectrum (apci) m/z = 440.2 (M + H) |

Example 22

6-(1-(2-(methyl sulfonyl)ethyl)-1H-pyrazol-4-yl)-4-(1-(pentan-3-yl)-1H-pyrazol-4-yl)pyrazolo[1,5-a]pyrazine

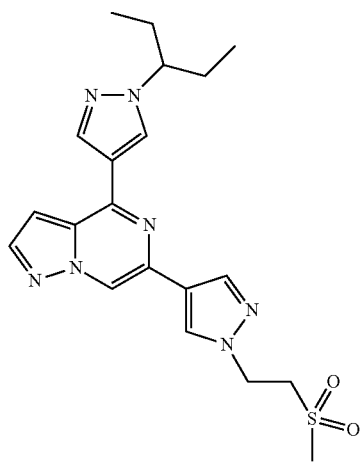 [SMILES: CCC(CC)n1cc(-c2nc(-c3cnn(CCS(C)(=O)=O)c3)cn3nccc23)cn1]

To a solution of 4-(1-(pentan-3-yl)-1H-pyrazol-4-yl)-6-(1H-pyrazol-4-yl)pyrazolo[1,5-a]pyrazine (0.042 g, 0.131 mmol) in 1 mL of CH$_3$CN was added (methylsulfonyl)ethene (0.00139 g, 0.0131 mmol) and 2,3,4,6,7,8,9,10-octahydropyrimido[1,2-a]azepine (0.00 mmol) and the reaction mixture was stirred overnight at 70° C. The reaction mixture was purified by reverse phase chromatography (C18, 0-50% CH$_3$CN/water) to afford 6-(1-(2-(methylsulfonyl)ethyl)-1H-pyrazol-4-yl)-4-(1-(pentan-3-yl)-1H-pyrazol-4-yl)pyrazolo[1,5-a]pyrazine (0.0397 g, 0.0929 mmol, 71.1% yield). Mass spectrum (apci) m/z=428.2 (M+H). $^1$H NMR (CDCl$_3$) δ 8.48 (s, 1H), 8.26 (s, 1 h), 8.19 (s, 1H), 8.14 (s, 1H), 8.04 (m, 2H), 6.97 (dd, J=2.4, 0.8 Hz, 1H), 4.70 (t, J=6.1 Hz, 2H), 4.04 (m, 1H), 3.73 (t, J=6.1 Hz, 2H), 2.61 (s, 3H), 2.07-1.85 (m, 4H), 0.86 (t, J=7.2 Hz, 6H).

The following compounds were prepared according to the procedure described for Example 57.

| Example | Structure | Name | Data |
|---|---|---|---|
| 23 | 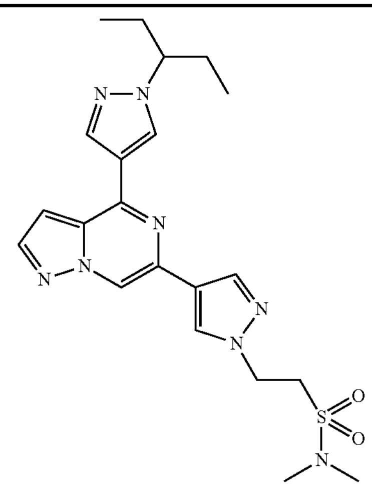 | N,N-dimethyl-2-(4-(4-(1-(pentan-3-yl)-1H-pyrazol-4-yl)pyrazolo[1,5-a]pyrazin-6-yl)-1H-pyrazol-1-yl)ethanesulfonamide | Mass spectrum (apci) m/z = 457.2 (M + H) |
| 24 | 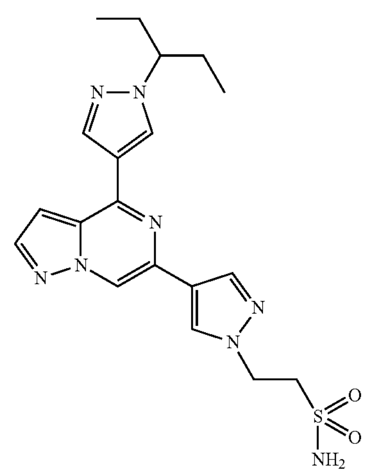 [SMILES: CCC(CC)n1cc(-c2nc(-c3cnn(CCS(N)(=O)=O)c3)cn3nccc23)cn1] | 2-(4-(4-(1-(pentan-3-yl)-1H-pyrazol-4-yl)pyrazolo[1,5-a]pyrazin-6-yl)-1H-pyrazol-1-yl)ethanesulfonamide | Mass spectrum (apci) m/z = 429.1 (M + H) |

Example 25

4-(1-(pentan-3-yl)-1H-pyrazol-4-yl)-6-(1-(piperidin-4-yl)-1H-pyrazol-4-yl)pyrazolo[1,5-a]pyrazine hydrochloride

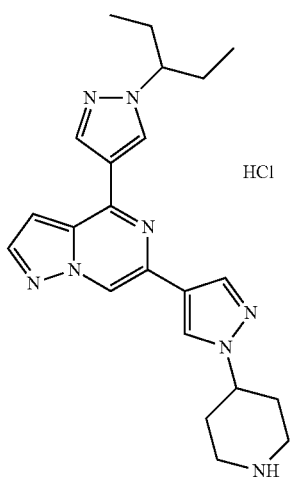 [SMILES: CCC(CC)n1cc(-c2nc(-c3cnn(C4CCNCC4)c3)cn3nccc23)cn1 ; Cl]

Step A:
To a solution of 4-(1-(pentan-3-yl)-1H-pyrazol-4-yl)-6-(1H-pyrazol-4-yl)pyrazolo[1,5-a]pyrazine (0.080 g, 0.25 mmol) in 1 mL of DMA was added tert-butyl 4-((methylsulfonyl)oxy)piperidine-1-carboxylate (0.21 g, 0.75 mmol) and cesium carbonate (0.32 g, 1.00 mmol) and the reaction mixture was stirred overnight at 70° C. The reaction mixture was purified over silica gel (20 to 100% EtOAc in $CH_2Cl_2$) to afford tert-butyl 4-(4-(4-(1-(pentan-3-yl)-1H-pyrazol-4-yl)pyrazolo[1,5-a]pyrazin-6-yl)-1H-pyrazol-1-yl)piperidine-1-carboxylate (0.065 g, 0.13 mmol, 52% yield).

Step B:
To a solution of tert-butyl 4-(4-(4-(1-(pentan-3-yl)-1H-pyrazol-4-yl)pyrazolo[1,5-a]pyrazin-6-yl)-1H-pyrazol-1-yl)piperidine-1-carboxylate (0.060 g, 0.119 mmol) in isopropyl alcohol (1 mL) was added hydrogen chloride (0.00434 g, 0.119 mmol) (1 mL of a 5 M solution in isopropyl alcohol) and the reaction mixture was stirred overnight. The reaction mixture was concentrated in vacuo to afford 4-(1-(pentan-3-yl)-1H-pyrazol-4-yl)-6-(1-(piperidin-4-yl)-1H-pyrazol-4-yl)pyrazolo[1,5-a]pyrazine hydrochloride (39.8 mg, 83% yield). Mass spectrum (apci) m/z=405.2 (M+H). $^1$H NMR ($d_6$-DMSO) δ 9.04 (s, 1H), 8.98 (br s, 1H), 8.74 (s, 1H), 8.73 (br s, 1H), 8.44 (s, 1H), 8.40 (s, 1H), 8.22 (s, 1H), 8.18 (d, J=2.3 Hz, 1H), 7.38 (dd, J=2.3, 0.8 Hz, 1H), 4.57 (m, 1H), 4.14 (m, 1H), 3.43 (m, 2H), 3.11 (m, 2H), 2.35-2.15 (m, 4H), 1.88 (m, 4H), 0.75 (t, J=7.2 Hz, 6H).

The following compounds were prepared according to the procedure described for Example 61.

| Example | Structure | Name | Data |
|---|---|---|---|
| 26 | 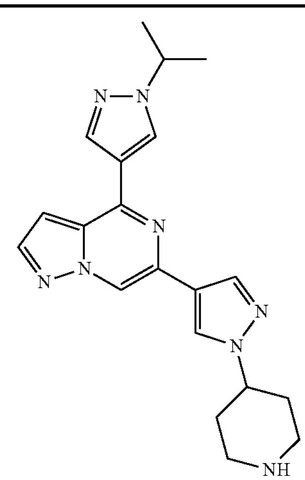 | 4-(1-isopropyl-1H-pyrazol-4-yl)-6-(1-(piperidin-4-yl)-1H-pyrazol-4-yl)pyrazolo[1,5-a]pyrazine | Mass spectrum (apci) m/z = 377.2 (M + H) |
| 27 | 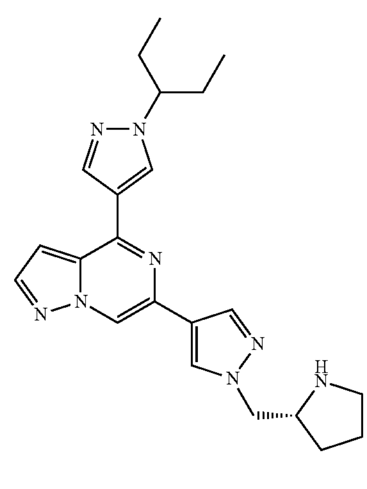 [SMILES: CCC(CC)n1cc(-c2nc(-c3cnn(C[C@H]4CCCN4)c3)cn3nccc23)cn1] | (R)-4-(1-(pentan-3-yl)-1H-pyrazol-4-yl)-6-(1-(pyrrolidin-2-ylmethyl)-1H-pyrazol-4-yl)pyrazolo[1,5-a]pyrazine | Mass spectrum (apci) m/z = 405.2 (M + H) |

| Example | Structure | Name | Data |
|---|---|---|---|
| 28 | 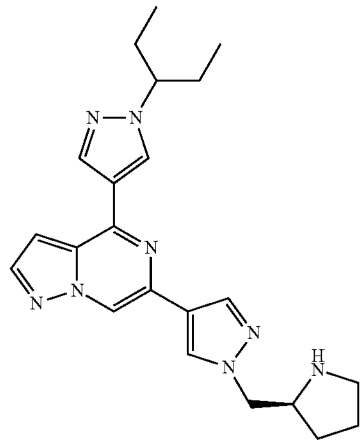 [SMILES: CCC(CC)n1cc(-c2nc(-c3cnn(C[C@@H]4CCCN4)c3)cn3nccc23)cn1] | (S)-4-(1-(pentan-3-yl)-1H-pyrazol-4-yl)-6-(1-(pyrrolidin-2-ylmethyl)-1H-pyrazol-4-yl)pyrazolo[1,5-a]pyrazine | Mass spectrum (apci) m/z = 405.2 (M + H) |
| 29 | 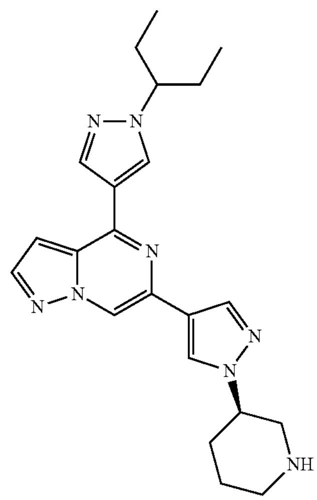 [SMILES: CCC(CC)n1cc(-c2nc(-c3cnn([C@@H]4CCCNC4)c3)cn3nccc23)cn1] | (R)-4-(1-(pentan-3-yl)-1H-pyrazol-4-yl)-6-(1-(piperidin-3-yl)-1H-pyrazol-4-yl)pyrazolo[1,5-a]pyrazine | Mass spectrum (apci) m/z = 405.2 (M + H) |
| 30 | 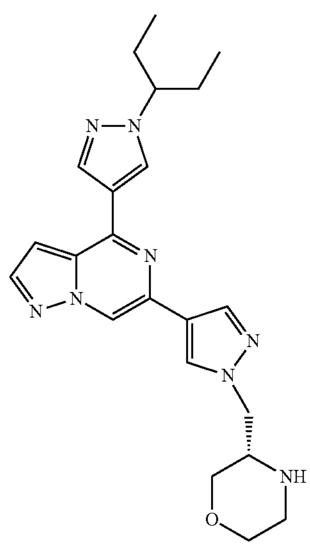 [SMILES: CCC(CC)n1cc(-c2nc(-c3cnn(C[C@H]4COCCN4)c3)cn3nccc23)cn1] | (S)-3-((4-(4-(1-(pentan-3-yl)-1H-pyrazol-4-yl)pyrazolo[1,5-a]pyrazin-6-yl)-1H-pyrazol-1-yl)methyl)morpholine | Mass spectrum (apci) m/z = 421.2 (M + H) |

Example 31

1-(4-(4-(4-(1-(pentan-3-yl)-1H-pyrazol-4-yl)pyrazolo[1,5-a]pyrazin-6-yl)-1H-pyrazol-1-yl)piperidin-1-yl)ethanone

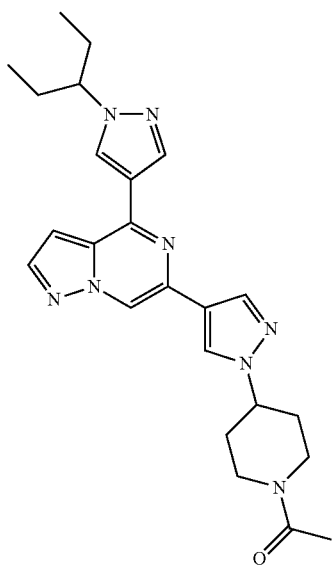 [SMILES: CCC(CC)n1cc(-c2nc(-c3cnn(C4CCN(C(C)=O)CC4)c3)cn3nccc23)cn1]

4-(1-(Pentan-3-yl)-1H-pyrazol-4-yl)-6-(1-(piperidin-4-yl)-1H-pyrazol-4-yl)pyrazolo[1,5-a]pyrazine hydrochloride salt (20 mg, 0.04 mmol) was stirred in CH$_2$Cl$_2$ (1 mL) and cooled in an ice bath. Triethylamine (23 μL, 0.16 mmol) was added, followed by acetic anhydride (5.9 μL, 0.06 mmol). The reaction mixture was stirred in an ice bath for 15 minutes and then quenched with water. The layers were separated, and the organic layer was dried, filtered and concentrated. The residue was purified over silica gel to afford 1-(4-(4-(4-(1-(pentan-3-yl)-1H-pyrazol-4-yl)pyrazolo[1,5-a]pyrazin-6-yl)-1H-pyrazol-1-yl)piperidin-1-yl)ethanone (9 mg, 48% yield). Mass spectrum (apci) m/z=447.3 (M+H). $^1$H NMR (d$_6$-DMSO) δ 8.98 (d, J=0.8 Hz, 1H), 8.73 (s, 1H), 8.46 (s, 1H), 8.41 (s, 1H), 8.16 (m, 2H), 7.36 (dd, J=2.3, 0.8 Hz, 1H), 4.50 (m, 2H), 4.13 (m, 1H), 3.95 (m, 1H), 3.24 (m, 1H), 2.75 (td, J=12.9, 2.3 Hz, 1H), 2.10 (m, 2H), 2.06 (s, 3H), 2.00-1.75 (m, 6H), 0.75 (t, J=7.4 Hz, 6H).

The following compounds were prepared according to the procedure described for Example 31, using the appropriate anhydride, alkyl sulfonate or aryl sulfonate.

| Example | Structure | Name | Data |
|---|---|---|---|
| 32 | 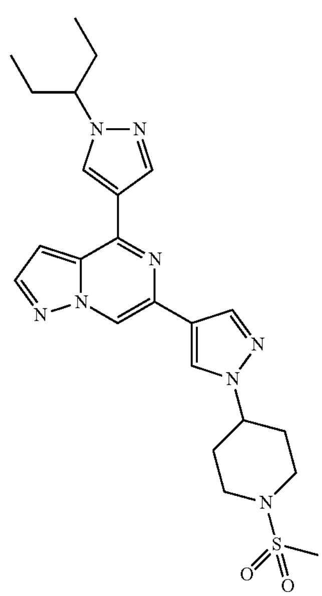 [SMILES: CCC(CC)n1cc(-c2nc(-c3cnn(C4CCN(S(C)(=O)=O)CC4)c3)cn3nccc23)cn1] | 6-(1-(1-(methylsulfonyl)piperidin-4-yl)-1H-pyrazol-4-yl)-4-(1-(pentan-3-yL)-1H-pyrazol-4-yl)pyrazolo[1,5-a]pyrazine | Mass spectrum (apci) m/z = 483.2 (M + H) |

| Example | Structure | Name | Data |
|---|---|---|---|
| 33 | 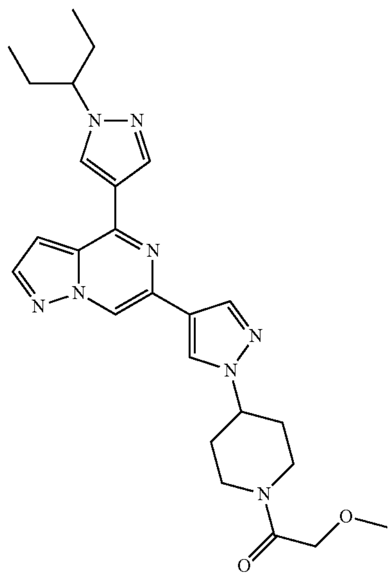 [SMILES: CCC(CC)n1cc(-c2nc(-c3cnn(C4CCN(C(=O)COC)CC4)c3)cn3nccc23)cn1] | 2-methoxy-1-(4-(4-(4-(1-(pentan-3-yl)-1H-pyrazol-4-yl)pyrazolo[1,5-a]pyrazin-6-yl)-1H-pyrazol-1-yl)piperidin-1-yl)ethanone | Mass spectrum (apci) m/z = 477.2 (M + H) |
| 34 | 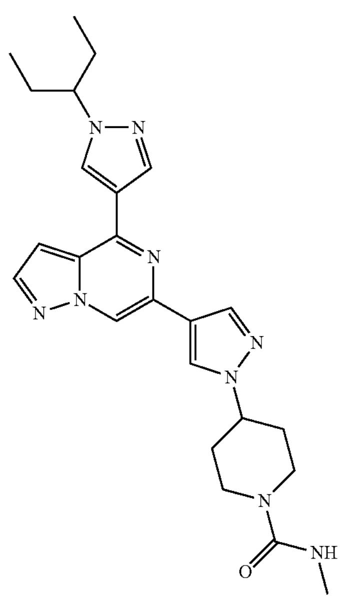 [SMILES: CCC(CC)n1cc(-c2nc(-c3cnn(C4CCN(C(=O)NC)CC4)c3)cn3nccc23)cn1] | N-methyl-4-(4-(4-(1-(pentan-3-yl)-1H-pyrazol-4-yl)pyrazolo[1,5-a]pyrazin-6-yl)-1H-pyrazol-1-yl)piperidine-1-carboxamide | Mass spectrum (apci) m/z = 462.3 (M + H) |

| Example | Structure | Name | Data |
|---|---|---|---|
| 35 | 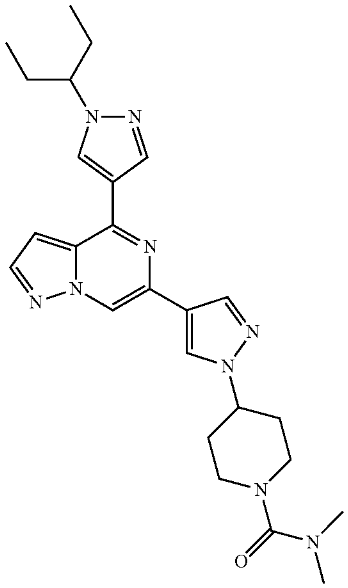 [SMILES: CCC(CC)n1cc(-c2nc(-c3cnn(C4CCN(C(=O)N(C)C)CC4)c3)cn3nccc23)cn1] | N,N-dimethyl-4-(4-(4-(1-(pentan-3-yl)-1H-pyrazol-4-yl)pyrazolo[1,5-a]pyrazin-6-yl)-1H-pyrazol-1-yl)piperidine-1-carboxamide | Mass spectrum (apci) m/z = 476.3 (M + H) |

Example 36

2-amino-1-(4-(4-(4-(1-(pentan-3-yl)-1H-pyrazol-4-yl)pyrazolo[1,5-a]pyrazin-6-yl)-1H-pyrazol-1-yl)piperidin-1-yl)ethanone

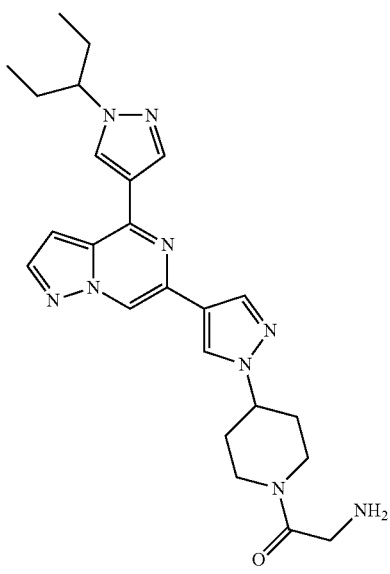 [SMILES: CCC(CC)n1cc(-c2nc(-c3cnn(C4CCN(C(=O)CN)CC4)c3)cn3nccc23)cn1]

Step A:

4-(1-(Pentan-3-yl)-1H-pyrazol-4-yl)-6-(1-(piperidin-4-yl)-1H-pyrazol-4-yl)pyrazolo[1,5-a]pyrazine dihydrochloride salt (30 mg, 0.063 mmol) was stirred in CH$_2$Cl$_2$ (1 mL) and Et$_3$N (52 µL, 0.38 mmol) was added, followed by 2,5-dioxopyrrolidin-1-yl 2-((tert-butoxycarbonyl)amino)acetate (34 mg, 0.13 mmol). The reaction mixture was stirred at room temperature for 1 hour. Water (0.1 mL) was added and the reaction mixture was concentrated. The residue was purified by reverse phase chromatography (5-95% CH$_3$CN in water) to afford tert-butyl (2-oxo-2-(4-(4-(4-(1-(pentan-3-yl)-1H-pyrazol-4-yl)pyrazolo[1,5-a]pyrazin-6-yl)-1H-pyrazol-1-yl)piperidin-1-yl)ethyl)carbamate (25 mg, 71% yield).

Step B:

tert-Butyl (2-oxo-2-(4-(4-(4-(1-(pentan-3-yl)-1H-pyrazol-4-yl)pyrazolo[1,5-a]pyrazin-6-yl)-1H-pyrazol-1-yl)piperidin-1-yl)ethyl)carbamate (24 mg, 0.042 mmol) was dissolved in CH$_2$Cl$_2$ (2 mL) and 5.5 M HCl in isopropyl alcohol (155 µL, 0.85 mmol) was added. The reaction mixture was stirred at room temperature for 3 hours. The solvent was evaporated to afford 2-amino-1-(4-(4-(4-(1-(pentan-3-yl)-1H-pyrazol-4-yl)pyrazolo[1,5-a]pyrazin-6-yl)-1H-pyrazol-1-yl)piperidin-1-yl)ethanone (21.5 mg, 94% yield). Mass spectrum (apci) m/z=462.2 (M+H). $^1$H NMR (d$_6$-DMSO) δ 9.00 (d, J=0.8 Hz, 1H), 8.74 (s, 1H), 8.45 (s, 1H), 8.40 (s, 1H), 8.18 (s, 1H), 8.17 (d, J=2.5 Hz, 1H), 8.12 (m, 2H), 7.37 (dd, J=2.5, 1.0 Hz, 1H), 4.56 (tt, J=11.1, 4.1 Hz, 1H), 4.49 (m, 1H), 4.14 (m, 1H), 3.95 (m, 4H), 3.26 (m, 1H), 2.93 (m, 1H), 2.15 (m, 2H), 2.01 (m, 1H), 1.97-1.80 (m, 4H), 0.75 (t, J=7.2 Hz, 6H).

Example 37

6-(1-(1-(methylsulfonyl)azetidin-3-yl)-1H-pyrazol-4-yl)-4-(1-(pentan-3-yl)-1H-pyrazol-4-yl)pyrazolo[1,5-a]pyrazine

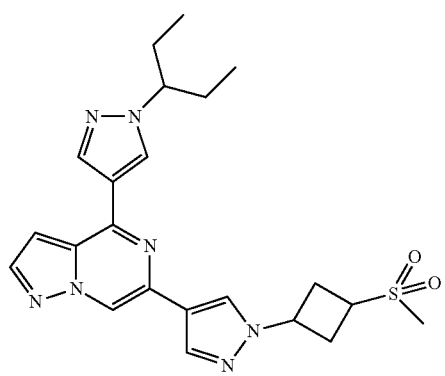 [SMILES: CCC(CC)n1cc(-c2nc(-c3cnn(C4CC(S(C)(=O)=O)C4)c3)cn3nccc23)cn1]

Step A:

4-(1-(Pentan-3-yl)-1H-pyrazol-4-yl)-6-(1H-pyrazol-4-yl)pyrazolo[1,5-a]pyrazine (0.50 g, 1.6 mmol) was dissolved in DMF (8 mL). tert-Butyl 3-((methylsulfonyl)oxy)azetidine-1-carboxylate (0.39 g, 1.6 mmol) and $Cs_2CO_3$ (1.01 g, 3.1 mmol) were added and the reaction mixture was heated to 70° C. overnight. The reaction mixture was poured into water (100 mL) and extracted with EtOAc. The combined organic extracts were washed with water, dried over sodium sulfate, filtered and concentrated. The residue was purified over silica gel (10-80% EtOAc in hexanes) to afford tert-butyl 3-(4-(4-(1-(pentan-3-yl)-H-pyrazol-4-yl)pyrazolo[1,5-a]pyrazin-6-yl)-1H-pyrazol-1-yl)azetidine-1-carboxylate (0.55 g, 74% yield).

Step B:

tert-Butyl 3-(4-(4-(1-(pentan-3-yl)-1H-pyrazol-4-yl)pyrazolo[1,5-a]pyrazin-6-yl)-1H-pyrazol-1-yl)azetidine-1-carboxylate (0.5 g, 1.1 mmol) was dissolved in $CH_2Cl_2$. TFA (10 mL) was added and the reaction mixture was stirred at room temperature for 3 hours. The reaction mixture was concentrated, partitioned between saturated aqueous $NaHCO_3$ and 5% isopropyl alcohol in $CHCl_3$. The organic layer was dried over sodium sulfate, filtered and concentrated to afford 6-(1-(azetidin-3-yl)-1H-pyrazol-4-yl)-4-(1-(pentan-3-yl)-1H-pyrazol-4-yl)pyrazolo[1,5-a]pyrazine (380 mg, 96% yield) as a tan solid. Mass spectrum (apci) m/z=377.2 (M+H).

Step C:

6-(1-(Azetidin-3-yl)-1H-pyrazol-4-yl)-4-(1-(pentan-3-yl)-1H-pyrazol-4-yl)pyrazolo[1,5-a]pyrazine (30 mg, 0.0797 mmol) was dissolved in THF (0.5 mL) and triethylamine (13.3 μL, 0.0956 mmol) was added, followed by methanesulfonyl chloride (6.83 μL, 0.0877 mmol), and the reaction mixture was stirred for 15 minutes. The reaction mixture was diluted with water and extracted with DCM and then with EtOAc. The combined organic extracts were dried, filtered and concentrated. The residue was purified over silica gel (90% EtOAc in hexane) to afford 6-(1-(1-(methylsulfonyl)azetidin-3-yl)-1H-pyrazol-4-yl)-4-(1-(pentan-3-yl)-1H-pyrazol-4-yl)pyrazolo[1,5-a]pyrazine (25 mg, 0.0550 mmol, 69.0% yield) as a pale yellow solid. Mass spectrum (apci) m/z=455.2 (M+H). $^1$H NMR ($CDCl_3$) δ 8.47 (d, J=1.0 Hz, 1H), 8.27 (s, 1H), 8.17 (s, 1H), 8.10 (s, 1H), 8.04 (m, 2H), 6.97 (dd, J=2.3, 1.0 Hz, 1H), 5.17 (m, 2H), 4.53-4.40 (m, 4H), 4.03 (m, 1H), 3.06 (m, 1H), 2.05-1.85 (m, 4H), 0.86 (t, J=7.4 Hz, 6H).

The following compounds were prepared according to the procedure described for Example 80.

| Example | Structure | Name | Data |
|---|---|---|---|
| 38 | 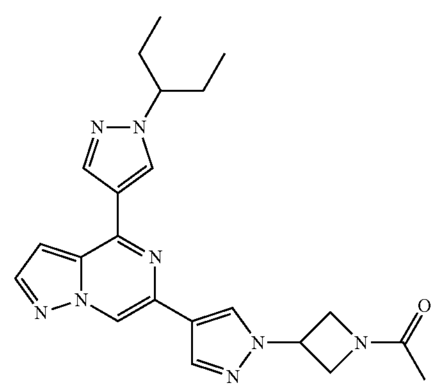 [SMILES: CCC(CC)n1cc(-c2nc(-c3cnn(C4CN(C(C)=O)C4)c3)cn3nccc23)cn1] | 1-(3-(4-(4-(1-(pentan-3-yl)-1H-pyrazol-4-yl)pyrazolo[1,5-a]pyrazin-6-yl)-1H-pyrazol-1-yl)azetidin-1-yl)ethanone | Mass spectrum (apci) m/z = 419.2 (M + H) |

-continued

| Example | Structure | Name | Data |
|---|---|---|---|
| 39 | 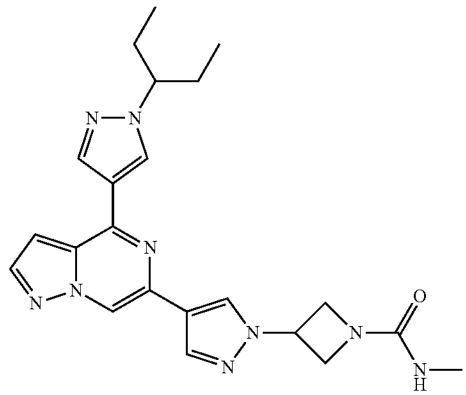 [SMILES: CCC(CC)n1cc(-c2nc(-c3cnn(C4CN(C(=O)NC)C4)c3)cn3nccc23)cn1] | N-methyl-3-(4-(4-(1-(pentan-3-yl)-1H-pyrazol-4-yl)pyrazolo[1,5-a]pyrazin-6-yl)-1H-pyrazol-1-yl)azetidine-1-carboxamide | Mass spectrum (apci) m/z = 434.2 (M + H) |
| 40 | 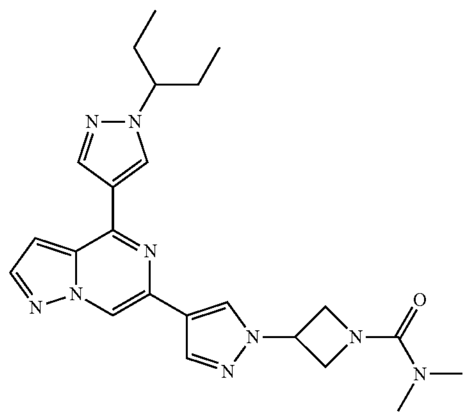 | N,N-dimethyl-3-(4-(4-(1-(pentan-3-yl)-1H-pyrazol-4-yl)pyrazolo[1,5-a]pyrazin-6-yl)-1H-pyrazol-1-yl)azetidine-1-carboxamide | Mass spectrum (apci) m/z = 448.2 (M + H) |
| 41 | 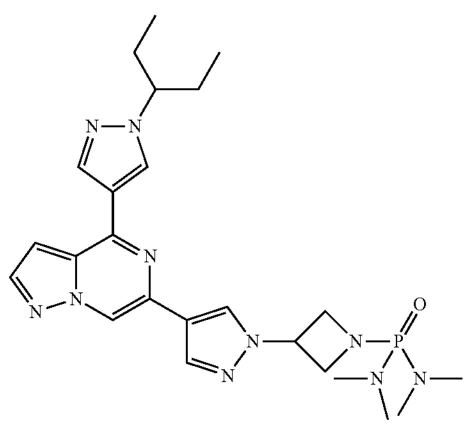 [SMILES: CCC(CC)n1cc(-c2nc(-c3cnn(C4CN(P(=O)(N(C)C)N(C)C)C4)c3)cn3nccc23)cn1] | Bis-N,N-dimethyl-P-(3-(4-(4-(1-(pentan-3-yl)-1H-pyrazol-4-yl)pyrazolo[1,5-a]pyrazin-6-yl)-1H-pyrazol-1-yl)azetidin-1-yl)phosphonic amide | Mass spectrum (apci) m/z = 511.2 (M + H) |

| Example | Structure | Name | Data |
|---|---|---|---|
| 42 | 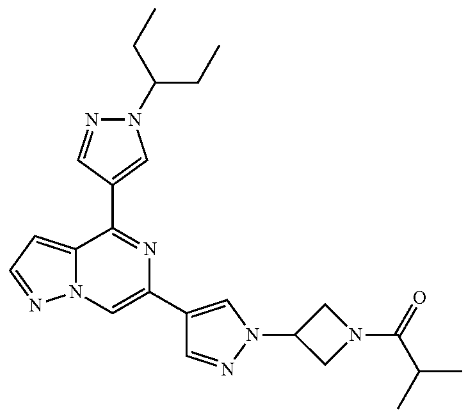 [SMILES: CCC(CC)n1cc(-c2nc(-c3cnn(C4CN(C(=O)C(C)C)C4)c3)cn3nccc23)cn1] | 2-methyl-1-(3-(4-(4-(1-(pentan-3-yl)-1H-pyrazol-4-yl)pyrazolo[1,5-a]pyrazin-6-yl)-1H-pyrazol-1-yl)azetidin-1-yl)propan-1-one | Mass spectrum (apci) m/z = 447.3 (M + H) |
| 43 | 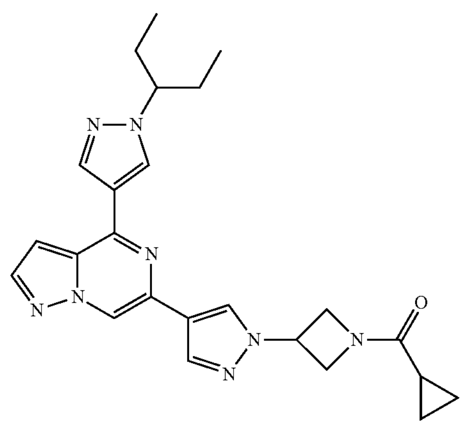 [SMILES: CCC(CC)n1cc(-c2nc(-c3cnn(C4CN(C(=O)C5CC5)C4)c3)cn3nccc23)cn1] | cyclopropyl(3-(4-(4-(1-(pentan-3-yl)-1H-pyrazol-4-yl)pyrazolo[1,5-a]pyrazin-6-yl)-1H-pyrazol-1-yl)azetidin-1-yl)methanone | Mass spectrum (apci) m/z = 445.2 (M + H) |

Example 44

2-(4-(6-(1-methyl-1H-pyrazol-4-yl)pyrazolo[1,5-a]pyrazin-4-yl)-1H-pyrazol-1-yl)butanoic acid

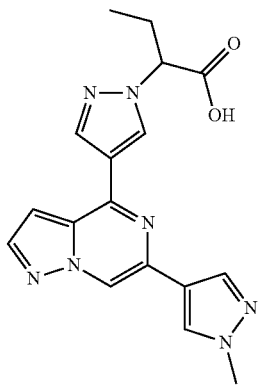 [SMILES: CCC(C(=O)O)n1cc(-c2nc(-c3cnn(C)c3)cn3nccc23)cn1]

To a solution of tert-butyl 2-(4-(6-(1-methyl-1H-pyrazol-4-yl)pyrazolo[1,5-a]pyrazin-4-yl)-1H-pyrazol-1-yl)butanoate (0.20 g, 0.49 mmol) in THF (5 mL) was added lithium hydroxide (2.5 mL, 4.9 mmol) and the reaction mixture was stirred overnight at room temperature. The reaction mixture was concentrated to remove the THF, and the aqueous layer was acidified with HCl (1 M). The aqueous layer was extracted into EtOAc, and the organic layer was washed with brine, dried over MgSO$_4$ and concentrated in vacuo to afford 2-(4-(6-(1-methyl-1H-pyrazol-4-yl)pyrazolo[1,5-a]pyrazin-4-yl)-1H-pyrazol-1-yl)butanoic acid (0.140 g, 82% yield). Mass spectrum (apci) m/z=350.1 (M−H). $^1$H NMR (d$_6$-DMSO) δ 13.16 (s, 1H), 8.96 (d, J=0.8 Hz, 1H), 8.75 (s, 1H), 8.37 (s, 1H), 8.32 (s, 1H), 8.14 (d, J=2.4 Hz, 1H), 8.09 (s, 1H), 7.32 (dd, J=2.4, 0.8 Hz, 1H), 5.02 (dd, J=9.6, 5.7 Hz, 1H), 3.88 (s, 3H), 2.30-2.15 (m, 2H), 0.81 (t, J=7.2 Hz, 3H).

Example 45

2-(4-(6-(1-methyl-1H-pyrazol-4-yl)pyrazolo[1,5-a]pyrazin-4-yl)-H-pyrazol-1-yl)butan-1-ol

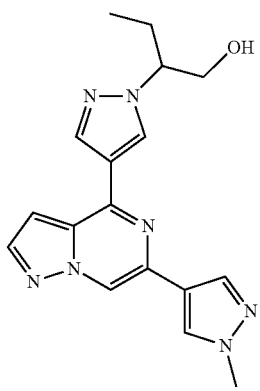 [SMILES: CCC(CO)n1cc(-c2nc(-c3cnn(C)c3)cn3nccc23)cn1]

To a solution of tert-butyl 2-(4-(6-(1-methyl-1H-pyrazol-4-yl)pyrazolo[1,5-a]pyrazin-4-yl)-1H-pyrazol-1-yl)butanoate (0.05 g, 0.12 mmol) in isopropyl alcohol (1 mL) was added NaBH$_4$ (0.014 g, 0.37 mmol) and the reaction mixture was stirred at room temperature for 5 hours. The reaction mixture was poured into water and extracted into EtOAc. The organic layer was washed with brine, dried over MgSO$_4$ and concentrated in vacuo. The residue was purified over silica gel (0-10% MeOH in CH$_2$Cl$_2$) to afford 2-(4-(6-(1-methyl-1H-pyrazol-4-yl)pyrazolo[1,5-a]pyrazin-4-yl)-1H-pyrazol-1-yl)butan-1-ol (0.013 g, 0.039 mmol, 31% yield). Mass spectrum (apci) m/z=338.1 (M+H). $^1$H NMR (d$_6$-DMSO) δ 8.39 (d, J=1.0 Hz, 1H), 8.23 (s, 1H), 8.22 (s, 1H), 8.00 (d, J=2.3 Hz, 1H), 7.90 (m, 2H), 6.89 (dd, J=2.4, 1.0 Hz, 1H), 4.24 (m, 1H), 4.10-3.98 (m, 2H), 3.97 (s, 3H), 2.12-1.90 (m, 2H), 0.95 (t, J=7.4 Hz, 3H).

The following compounds were prepared according to the procedure described for Example 45.

| Example | Structure | Name | Data |
|---|---|---|---|
| 46 | 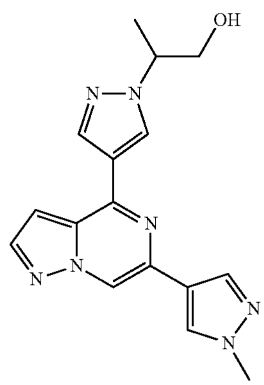 [SMILES: CC(CO)n1cc(-c2nc(-c3cnn(C)c3)cn3nccc23)cn1] | 2-(4-(6-(1-methyl-1H-pyrazol-4-yl)pyrazolo[1,5-a]pyrazin-4-yl)-1H-pyrazol-1-yl)propan-1-ol | Mass spectrum (apci) m/z = 324.1 (M + H) |
| 47 | 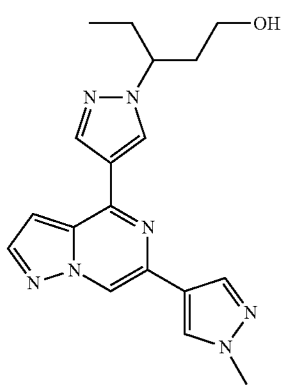 [SMILES: CCC(CCO)n1cc(-c2nc(-c3cnn(C)c3)cn3nccc23)cn1] | 3-(4-(6-(1-methyl-1H-pyrazol-4-yl)pyrazolo[1,5-a]pyrazin-4-yl)-1H-pyrazol-1-yl)pentan-1-ol | Mass spectrum (apci) m/z = 352.1 (M + H) |

Example 48

4-(1-(3-ethyl-1-((trifluoromethyl)sulfonyl)azetidin-3-yl)-1H-pyrazol-4-yl)-6-(1-methyl-1H-pyrazol-4-yl)pyrazolo[1,5-a]pyrazine

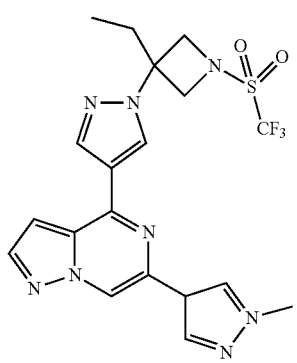

Step A:

4-Chloro-6-(1-methyl-1H-pyrazol-4-yl)pyrazolo[1,5-a]pyrazine hydrochloride (1.0 g, 3.7 mmol), tert-butyl 3-(2-ethoxy-2-oxoethyl)-3-(4-(4,4,5,5-tetramethyl-1,3,2-dioxaborolan-2-yl)-1H-pyrazol-1-yl)azetidine-1-carboxylate (2.01 g, 4.6 mmol), 2-dicyclohexylphosphino-2',4',6'-triisopropylbiphenyl (XPHOS) (353 mg, 0.74 mmol) and Pd$_2$(dba)$_3$ (170 mg, 0.19 mmol) were combined in THF (15 mL) and treated with K$_2$CO$_3$ (7.4 mL, 2.0 M, 14.8 mmol). The reaction vessel was sealed, placed into an 80° C. oil bath and stirred overnight. The reaction mixture was filtered through GF/F paper with EtOAc and washed with water. The filtrate layers were separated and the aqueous layer was extracted with EtOAc (2×50 mL). The combined organic phases were washed with brine (50 mL), dried over Na$_2$SO$_4$, filtered and concentrated. The residue was purified over silica gel (20% acetone/CH$_2$Cl$_2$) to afford tert-butyl 3-(2-ethoxy-2-oxoethyl)-3-(4-(6-(1-methyl-1H-pyrazol-4-yl)pyrazolo[1,5-a]pyrazin-4-yl)-1H-pyrazol-1-yl)azetidine-1-carboxylate (1.47 g, 78.3% yield) as a beige solid.

Step B:

A solution of tert-butyl 3-(2-ethoxy-2-oxoethyl)-3-(4-(6-(1-methyl-1H-pyrazol-4-yl)pyrazolo[1,5-a]pyrazin-4-yl)-1H-pyrazol-1-yl)azetidine-1-carboxylate (1.47 g, 2.9 mmol) in CH$_2$Cl$_2$ (20 mL) was treated with 5-6 N HCl/isopropyl alcohol (10 mL). The reaction mixture was allowed to stir at room temperature overnight. The reaction mixture was concentrated and dried in vacuo to afford ethyl 2-(3-(4-(6-(1-methyl-1H-pyrazol-4-yl)pyrazolo[1,5-a]pyrazin-4-yl)-1H-pyrazol-1-yl)azetidin-3-yl)acetate dihydrochloride (1.56 g, 112% yield) as a yellow solid.

Step C:

To a suspension of ethyl 2-(3-(4-(6-(1-methyl-1H-pyrazol-4-yl)pyrazolo[1,5-a]pyrazin-4-yl)-1H-pyrazol-1-yl)azetidin-3-yl)acetate dihydrochloride (1.39 g, 2.9 mmol) in CH$_2$Cl$_2$ (50 mL) was added triethylamine (2.02 mL, 14.5 mmol) and the resulting solution cooled to 0° C. and treated dropwise with trifluoromethanesulfonyl chloride (340 µL, 3.19 mmol). The reaction mixture was stirred 0° C. for 2 hours. The reaction mixture was treated with trifluoromethanesulfonyl chloride (200 µL) and stirred for an additional 30 minutes. The reaction mixture was partitioned between saturated aqueous NaHCO$_3$ (50 mL) and CH$_2$Cl$_2$ (50 mL) and the aqueous layer was extracted with CH$_2$Cl$_2$. The combined organic phases were washed with brine (20 mL), dried over Na$_2$SO$_4$, filtered and concentrated to afford ethyl 2-(3-(4-(6-(1-methyl-1H-pyrazol-4-yl)pyrazolo[1,5-a]pyrazin-4-yl)-1H-pyrazol-1-yl)-1-((trifluoromethyl)sulfonyl)azetidin-3-yl)acetate (1.54 g, 98.6% yield) as a beige foam.

Step D:

To a solution of ethyl 2-(3-(4-(6-(1-methyl-1H-pyrazol-4-yl)pyrazolo[1,5-a]pyrazin-4-yl)-1H-pyrazol-1-yl)-1-((trifluoromethyl)sulfonyl)azetidin-3-yl)acetate (1.0 g, 1.86 mmol) in THF (50 mL) at 0° C. was added LiAlH$_4$ (1.11 mL, 1.0 M, 1.11 mmol) dropwise over 3 minutes. After 1 hour, 0.5 mL of LiAlH$_4$ was added and the reaction mixture was stirred for 10 minutes. The reaction mixture was quenched with sodium sulfate decahydrate, stirred at room temperature for 30 minutes and then filtered through GF/F paper and concentrated. The residue was purified over silica gel (2.5% MeOH in CH$_2$Cl$_2$) to afford 2-(3-(4-(6-(1-methyl-1H-pyrazol-4-yl)pyrazolo[1,5-a]pyrazin-4-yl)-1H-pyrazol-1-yl)-1-((trifluoromethyl)sulfonyl)azetidin-3-yl)ethanol (394 mg, 42.7% yield) as a white solid.

Step E:

2-(3-(4-(6-(1-Methyl-1H-pyrazol-4-yl)pyrazolo[1,5-a]pyrazin-4-yl)-1H-pyrazol-1-yl)-1-((trifluoromethyl)sulfonyl)azetidin-3-yl)ethanol (50 mg, 0.10 mmol) and perbromomethane (67 mg, 0.20 mmol) were dissolved in CH$_2$Cl$_2$ (1 mL). Triphenylphosphine (53 mg, 0.20 mmol) was added and the reaction mixture was stirred at room temperature for 1 hour. The reaction mixture was purified directly over silica gel (70% EtOAc in hexanes) to afford crude 4-(1-(3-(2-bromoethyl)-1-((trifluoromethyl)sulfonyl)azetidin-3-yl)-1H-pyrazol-4-yl)-6-(1-methyl-1H-pyrazol-4-yl)pyrazolo[1,5-a]pyrazine (81 mg, 0.14 mmol, 144% yield) with some P(O)Ph$_3$.

Step F:

4-(1-(3-(2-Bromoethyl)-1-((trifluoromethyl)sulfonyl)azetidin-3-yl)-1H-pyrazol-4-yl)-6-(1-methyl-1H-pyrazol-4-yl)pyrazolo[1,5-a]pyrazine (56 mg, 0.10 mmol) was dissolved in THF (1 mL) and potassium 2-methylpropan-2-olate (200 µL, 0.20 mmol) was added. The reaction mixture was stirred at room temperature for 15 minutes. The reaction mixture was quenched with aqueous NH$_4$OAc. The organic layer was separated, dried over sodium sulfate, filtered and concentrated. The residue was purified over silica gel (80% EtOAc in hexanes), followed by reverse phase chromatography (C18, 10-95% CH$_3$CN in water) to afford 6-(1-methyl-1H-pyrazol-4-yl)-4-(1-(1-((trifluoromethyl)sulfonyl)-3-vinylazetidin-3-yl)-1H-pyrazol-4-yl)pyrazolo[1,5-a]pyrazine (18 mg, 0.038 mmol, 38% yield) as a white foam.

Step G:

6-(1-Methyl-1H-pyrazol-4-yl)-4-(1-(1-((trifluoromethyl)sulfonyl)-3-vinylazetidin-3-yl)-1H-pyrazol-4-yl)pyrazolo[1,5-a]pyrazine (18 mg, 0.0376 mmol) was dissolved in MeOH/EtOAc (2:1) and 10% Pd/C was added and stirred under a hydrogen atmosphere for 1 hour. The reaction mixture was filtered through Celite® and concentrated to afford 4-(1-(3-ethyl-1-((trifluoromethyl)sulfonyl)azetidin-3-yl)-1H-pyrazol-4-yl)-6-(1-methyl-1H-pyrazol-4-yl)pyrazolo[1,5-a]pyrazine (14.8 mg, 0.0308 mmol, 81.9% yield) as a tan solid. Mass spectrum (apci) m/z=481.1 (M+H). $^1$H NMR (CDCl$_3$) δ 8.48 (d, J=1.0 Hz, 1H), 8.31 (s, 1H), 8.21 (s, 1H), 8.05 (d, J=2.3 Hz, 1H), 7.95 (s, 1H), 7.93 (s, 1H), 6.93 (dd, J=2.3, 1.0 Hz, 1H), 4.86 (d, J=8.6 Hz, 2H), 4.38 (d, J=8.6 Hz, 2H), 4.00 (s, 3H), 2.36 (q, J=7.2 Hz, 3H).

Example 49

6-(1-methyl-1H-pyrazol-4-yl)-4-(1-(1-methylcyclopentyl)-1H-pyrazol-4-yl)pyrazolo[1,5-a]pyrazine

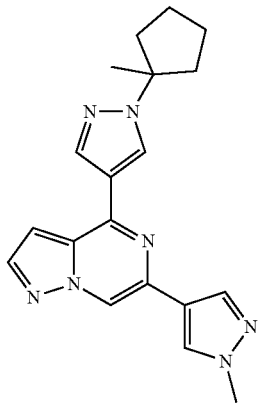 [SMILES: Cn1cc(-c2cn3nccc3c(-c3cnn(C4(C)CCCC4)c3)n2)cn1]

6-(1-Methyl-1H-pyrazol-4-yl)-4-(1H-pyrazol-4-yl)pyrazolo[1,5-a]pyrazine (0.100 g, 0.377 mmol) and methylenecyclopentane (0.992 mL, 9.42 mmol) were combined in 3 mL of TFA. The reaction mixture began to reflux upon addition. The reaction mixture was concentrated and the residue was partitioned between EtOAc (50 mL) and 1 M NaOH (20 mL). The organic layer was washed with water and brine, dried over MgSO$_4$, filtered and concentrated. The residue was purified over silica gel (10% acetone in CH$_2$Cl$_2$) to afford 6-(1-methyl-1H-pyrazol-4-yl)-4-(1-(1-methylcyclopentyl)-1H-pyrazol-4-yl)pyrazolo[1,5-a]pyrazine (0.068 g, 0.194 mmol, 51.4% yield). Mass spectrum (apci) m/z=348.2 (M+H). $^1$H NMR (CDCl$_3$) δ 8.44 (d, J=0.8 Hz, 1H), 8.28 (s, 1H), 8.23 (s, 1H), 8.02 (d, J=2.3 Hz, 1H), 7.94 (s, 2H), 6.93 (dd, J=2.3, 0.8 Hz, 1H), 3.98 (s, 3H), 2.47 (m, 2H), 1.99 (m, 2H), 1.84 (m, 4H), 1.68 (s, 3H).

The following compound was prepared according to the procedure described for Example 49.

Example 51

(2-(4-(6-(1-methyl-1H-pyrazol-4-yl)pyrazolo[1,5-a]pyrazin-4-yl)-1H-pyrazol-1-yl)cyclopentyl)methanol

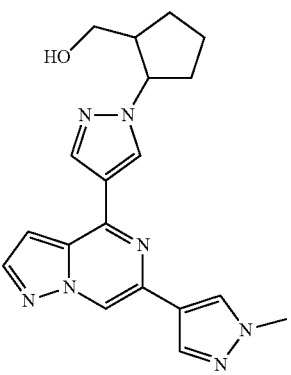 [SMILES: Cn1cc(-c2cn3nccc3c(-c3cnn(C4CCCC4CO)c3)n2)cn1]

Step A:

A solution of 4-chloro-6-(1-methyl-1H-pyrazol-4-yl)pyrazolo[1,5-a]pyrazine hydrochloride (0.565 g, 2.09 mmol), methyl 2-(4-(4,4,5,5-tetramethyl-1,3,2-dioxaborolan-2-yl)-1H-pyrazol-1-yl)cyclopentanecarboxylate (0.670 g, 2.09 mmol), and K$_2$CO$_3$ (4.18 mL, 8.37 mmol) in dioxane 50 mL was degassed with nitrogen for 5 minutes. Pd$_2$(dba)$_3$ (0.192 g, 0.209 mmol) and dicyclohexyl(2',4',6'-triisopropyl-[1,1'-biphenyl]-2-yl)phosphine (0.200 g, 0.418 mmol) were added and the reaction mixture was degassed for 5 minutes and then heated to 80° C. overnight. The reaction mixture was partitioned between water (50 mL) and EtOAc (100 mL). The organic layer was washed with brine, dried over MgSO$_4$ and concentrated. The residue was purified by reverse phase chromatography (C18, 5 to 95% CH$_3$CN in water) to afford methyl 2-(4-(6-(1-methyl-1H-pyrazol-4-yl)pyrazolo[1,5-a]pyrazin-4-yl)-1H-pyrazol-1-yl)cyclopentanecarboxylate (0.40 g, 48.8% yield).

Step B:

Methyl 2-(4-(6-(1-methyl-1H-pyrazol-4-yl)pyrazolo[1,5-a]pyrazin-4-yl)-1H-pyrazol-1-yl)cyclopentanecarboxylate (0.150 g, 0.38 mmol) and 4 mL of THF were combined and cooled to −40° C. LiAlH$_4$ (0.38 mL, 0.38 mmol) was added slowly and the reaction mixture was stirred for 1 hour. To the

| Example | Structure | Name | Data |
|---|---|---|---|
| 50 | 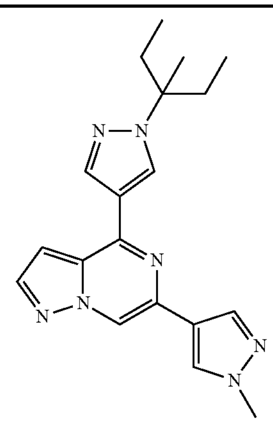 | 6-(1-methyl-1H-pyrazol-4-yl)-4-(1-(3-methylpentan-3-yl)-1H-pyrazol-4-yl)pyrazolo[1,5-a]pyrazine | Mass spectrum (apci) m/z = 350.2 (M + H). |

137 cold reaction mixture was added excess sodium sulfate decahydrate and the reaction mixture was stirred and allowed to warm to room temperature. After 1 hour the reaction mixture was diluted with EtOAc (50 mL), filtered through a nylon membrane and concentrated to afford (2-(4-(6-(1-methyl-1H-pyrazol-4-yl)pyrazolo[1,5-a]pyrazin-4-yl)-1H-pyrazol-1-yl)cyclopentyl)methanol (0.118 g, 0.299 mmol, 78% yield). Mass spectrum (apci) m/z=364.1 (M+H). $^1$H NMR (CDCl$_3$) δ (1:1 mix of diastereomers) 8.41 (d, J=1.0 Hz, 1H), 8.25 (s, 1H), 8.21 (s, 1H), 7.99 (d, J=2.5 Hz, 1H), 7.91 (m, 2H), 6.90 (dd, J=2.5, 1.0 Hz, 1H), 4.57 (q, J=8.0 Hz, 1H), 4.41 (q, J=8.2 Hz, 0.5H), 4.10 (m, 0.5H), 3.96 (s, 3H), 3.73 (m, 1H), 3.65 (m, 1H), 2.54 (m, 1H), 2.42-2.20 (m, 2H), 2.14-1.45 (m, 5H).

Example 52

6-(1-methyl-1H-pyrazol-4-yl)-4-(1-(2-methylcycloheptyl)-1H-pyrazol-4-yl)pyrazolo[1,5-a]pyrazine

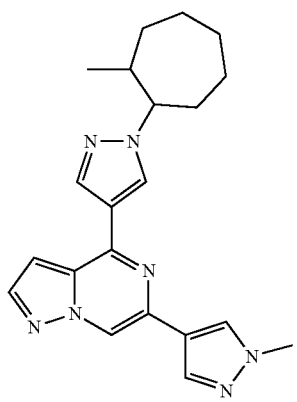 [SMILES: CC1CCCCCC1n1cc(-c2nc(-c3cnn(C)c3)cn3nccc23)cn1]

A solution of 6-(1-methyl-1H-pyrazol-4-yl)-4-(1H-pyrazol-4-yl)pyrazolo[1,5-a]pyrazine (50 mg, 0.19 mmol) and 2-methylcycloheptyl methanesulfonate (58 mg, 0.28 mmol) in DMA (2 mL) was treated with cesium carbonate (123 mg, 0.38 mmol) and then stirred at 80° C. in a sealed tube for 24 hours. The reaction mixture was partitioned between water (30 mL) and EtOAc (20 mL) and the aqueous layer was extracted with EtOAc. The combined organic phases were washed with water and brine, then dried over Na$_2$SO$_4$, filtered and concentrated. The residue was purified over silica gel (10% acetone/CH$_2$Cl$_2$) to afford 6-(1-methyl-1H-pyrazol-4-yl)-4-(1-(2-methylcycloheptyl)-1H-pyrazol-4-yl)pyrazolo[1,5-a]pyrazine (0.035 g, 49% yield). Mass spectrum (apci) m/z=376.2 (M+H). $^1$H NMR (CDCl$_3$) δ (1:1 mixture of diastereomers) 8.44 (m, 1H), 8.22 (s, 1H), 8.17 (d, J=2.2 Hz, 1H), 8.02 (dd, J=2.3, 1.2 Hz, 1H), 7.94 (s, 2H), 6.93 (m, 1H), 4.55 (dt, J=10.2, 5.3 Hz, 0.5H), 3.99 (s, 3H), 3.93 (td, J=10.0, 3.7 Hz, 0.5H), 2.45-2.20 (m, 3H), 1.95-1.40 (m, 9H), 1.25 (d, J=5.5 Hz, 1.5H), 0.80 (d, J=6.6 Hz, 1.5H), 0.74 (d, J=7.0 Hz, 1.5H).

138

Example 53

2-(4-(6-(1-methyl-1H-pyrazol-4-yl)pyrazolo[1,5-a]pyrazin-4-yl)-1H-pyrazol-1-yl)cyclopentanol

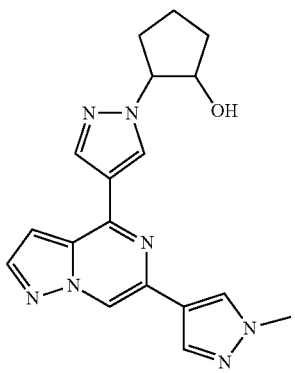 [SMILES: Cn1cc(-c2cn3nccc3c(-c3cnn(C4CCCC4O)c3)n2)cn1]

Step A:

In 1 mL of acetonitrile were combined 6-(1-methyl-1H-pyrazol-4-yl)-4-(1H-pyrazol-4-yl)pyrazolo[1,5-a]pyrazine (0.025 g, 0.0942 mmol), 2-chlorocyclopentanone (0.0168 g, 0.141 mmol), and 1,8-diazabicyclo[5.4.0]undec-7-ene (0.0281 mL, 0.188 mmol) at room temperature. The reaction mixture was sealed under nitrogen and heated to 80° C. overnight. The reaction mixture was concentrated and purified over silica gel (20% acetone in CH$_2$Cl$_2$) to 2-(4-(6-(1-methyl-1H-pyrazol-4-yl)pyrazolo[1,5-a]pyrazin-4-yl)-1H-pyrazol-1-yl)cyclopentanone (14 mg, 38% yield).

Step B:

In 1 mL of MeOH were combined 2-(4-(6-(1-methyl-1H-pyrazol-4-yl)pyrazolo[1,5-a]pyrazin-4-yl)-1H-pyrazol-1-yl)cyclopentanone (0.012 g, 0.035 mmol) and NaBH$_4$ (0.0039 g, 0.10 mmol) at 0° C. The reaction mixture was allowed to warm to room temperature and stirred for 3 hours. The reaction mixture was quenched with 3 drops of 50% NaOH in water. After 20 minutes the reaction mixture was quenched with 3 drops of TFA and purified by reverse phase chromatography (C18, 5 to 95% CH$_3$CN in water with 0.1% TFA) to afford 2-(4-(6-(1-methyl-1H-pyrazol-4-yl)pyrazolo[1,5-a]pyrazin-4-yl)-1H-pyrazol-1-yl)cyclopentanol (20 mg, 166% yield) as a mixture of diastereomers. Mass spectrum (apci) m/z=350.2 (M+H). $^1$H NMR (CDCl$_3$) δ 8.46 (m, 1H), 8.25 (m, 2H), 8.03 (d, J=2.5 Hz, 1H), 7.94 (m, 2H), 6.92 (m, 1H), 5.49 (m, 0.5H), 4.92 (m, 1H), 4.45 (m, 0.5H), 3.99 (m, 4H), 2.83 (m, 0.5H), 2.51-1.85 (m, 4.5H), 1.40-1.20 (m, 2H).

Example 54

(R)-3-(4-(4-(1-(pentan-3-yl)-1H-pyrazol-4-yl)pyrazolo[1,5-a]pyrazin-6-yl)-1H-pyrazol-1-yl)propane-1,2-diol

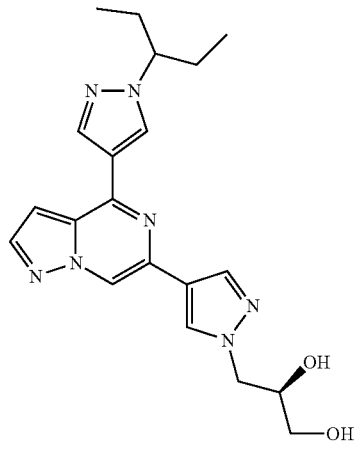 [SMILES: CCC(CC)n1cc(-c2nc(-c3cnn(C[C@@H](O)CO)c3)cn3nccc23)cn1]

Step A:

To a solution of 4-(1-(pentan-3-yl)-1H-pyrazol-4-yl)-6-(1H-pyrazol-4-yl)pyrazolo[1,5-a]pyrazine (0.56 g, 1.7 mmol) in DMF (3 mL) under nitrogen was added $Cs_2CO_3$ (1.1 g, 3.5 mmol) followed by (S)-4-(chloromethyl)-2,2-dimethyl-1,3-dioxolane (0.52 g, 3.5 mmol) and the reaction mixture was heated to 80° C. overnight. The reaction mixture was diluted with EtOAc and washed with water, brine, dried over $MgSO_4$ and concentrated in vacuo. The resulting material was purified over silica gel (0-70% EtOAc/$CH_2Cl_2$) to afford (R)-6-(1-((2,2-dimethyl-1,3-dioxolan-4-yl)methyl)-1H-pyrazol-4-yl)-4-(1-(pentan-3-yl)-1H-pyrazol-4-yl)pyrazolo[1,5-a]pyrazine.

Step B:

To (R)-6-(1-((2,2-dimethyl-1,3-dioxolan-4-yl)methyl)-1H-pyrazol-4-yl)-4-(1-(pentan-3-yl)-1H-pyrazol-4-yl)pyrazolo[1,5-a]pyrazine (0.4 g, 0.92 mmol) in isopropyl alcohol (10 mL) was added 4 drops of 12M HCl and the reaction mixture was heated to 55° C. for 2 hours. The reaction mixture was concentrated in vacuo and the residue was taken up in water. The water was made basic using 1N NaOH and the aqueous layer was extracted with EtOAc. The organic layer was washed with brine, dried over $MgSO_4$, filtered and concentrated in vacuo. The residue was purified over silica gel (0-10% MeOH/$CH_2Cl_2$) to afford (R)-3-(4-(4-(1-(pentan-3-yl)-1H-pyrazol-4-yl)pyrazolo[1,5-a]pyrazin-6-yl)-1H-pyrazol-1-yl)propane-1,2-diol (0.25 g, 0.63 mmol, 69% yield). Mass spectrum (apci) m/z=396.2 (M+H). $^1$H NMR ($d_6$-DMSO) δ 9.01 (d, J=1.0 Hz, 1H), 8.74 (s, 1H), 8.40 (s, 1H), 8.36 (s, 1H), 8.17 (m, 2H), 7.37 (dd, J=2.5, 1.0 Hz, 1H), 5.05 (d, J=5.3 Hz, 1H), 4.78 (t, J=5.9 Hz, 1H), 4.30 (dd, J=13.7, 3.9 Hz, 1H), 4.15 (m, 1H), 4.06 (dd, J=13.7, 7.8 Hz, 1H), 3.90 (m, 1H), 3.46-3.34 (m, 2H), 2.00-1.79 (m, 4H), 0.76 (t, J=7.4 Hz, 6H).

Example 55

(S)-3-(4-(4-(1-(pentan-3-yl)-1H-pyrazol-4-yl)pyrazolo[1,5-a]pyrazin-6-yl)-1H-pyrazol-1-yl)propane-1,2-diol

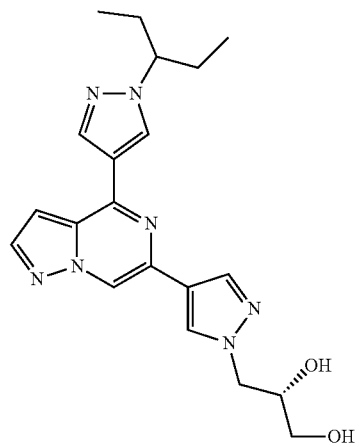 [SMILES: CCC(CC)n1cc(-c2nc(-c3cnn(C[C@H](O)CO)c3)cn3nccc23)cn1]

Step A:

To a solution of 4-(1-(pentan-3-yl)-1H-pyrazol-4-yl)-6-(1H-pyrazol-4-yl)pyrazolo[1,5-a]pyrazine (0.5 g, 2 mmol) in DMF (5 mL) was added (R)-4-(chloromethyl)-2,2-dimethyl-1,3-dioxolane (0.5 g, 3 mmol) and $Cs_2CO_3$ (1 g, 3 mmol) and the reaction mixture was heated to 70° C. overnight. The reaction mixture was poured into water and extracted into EtOAc. The combined organic phases were washed with brine, dried over $MgSO_4$ and concentrated in vacuo. The residue was purified over silica gel (0-70% EtOAc in hexanes) to afford (S)-6-(1-((2,2-dimethyl-1,3-dioxolan-4-yl)methyl)-1H-pyrazol-4-yl)-4-(1-(pentan-3-yl)-1H-pyrazol-4-yl)pyrazolo[1,5-a]pyrazine (0.4 g, 0.9 mmol, 59% yield).

Step B:

To a solution of (S)-6-(1-((2,2-dimethyl-1,3-dioxolan-4-yl)methyl)-1H-pyrazol-4-yl)-4-(1-(pentan-3-yl)-1H-pyrazol-4-yl)pyrazolo[1,5-a]pyrazine (0.4 g, 0.918 mmol) in isopropyl alcohol (10 mL) was added 4 drops of HCl and the reaction mixture was heated to 60° C. for 2 hours. The reaction mixture was concentrated and the residue was partitioned between EtOAc and 1N NaOH. The combined organic phases were separated, washed with brine, dried over $MgSO_4$ and concentrated in vacuo. The residue was purified over silica gel (1-10% MeOH in $CH_2Cl_2$) to afford a solid, which was triturated with methyl tert-butyl ether to afford (S)-3-(4-(4-(1-(pentan-3-yl)-1H-pyrazol-4-yl)pyrazolo[1,5-a]pyrazin-6-yl)-1H-pyrazol-1-yl)propane-1,2-diol (0.118 g, 0.298 mmol, 32.5% yield). Mass spectrum (apci) m/z=396.2 (M+H). $^1$H NMR ($d_6$-DMSO) δ 9.01 (d, J=0.8 Hz, 1H), 8.74 (s, 1H), 8.40 (s, 1H), 8.36 (s, 1H), 8.17 (m, 2H), 7.37 (dd, J=2.5, 1.0 Hz, 1H), 5.05 (d, J=5.3 Hz, 1H), 4.78 (t, J=5.7 Hz, 1H), 4.30 (dd, J=13.7, 3.9 Hz, 1H), 4.15 (m, 1H), 4.06 (dd, J=13.7, 7.8 Hz, 1H), 3.90 (m, 1H), 3.46-3.34 (m, 2H), 2.00-1.79 (m, 4H), 0.76 (t, J=7.4 Hz, 6H).

The following compounds were prepared according to the procedure described for Example 55.

| Example | Structure | Name | Data |
|---|---|---|---|
| 56 | 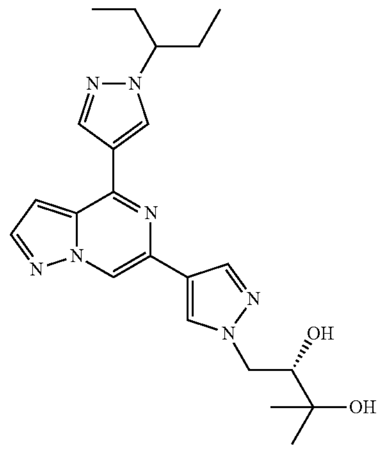 [SMILES: CCC(CC)n1cc(-c2nc(-c3cnn(C[C@H](O)C(C)(C)O)c3)cn3nccc23)cn1] | (S)-3-methyl-1-(4-(4-(1-(pentan-3-yl)-1H-pyrazol-4-yl)pyrazolo[1,5-a]pyrazin-6-yl)-1H-pyrazol-1-yl)butane-2,3-diol | Mass spectrum (apci) m/z = 424.2 (M + H) |
| 57 | 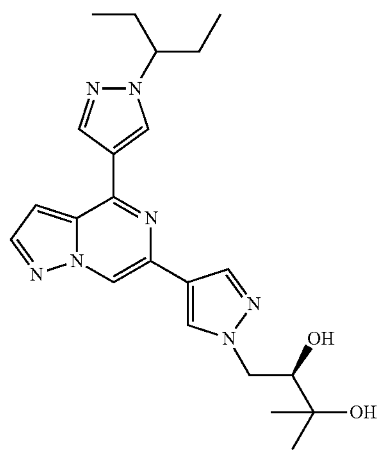 [SMILES: CCC(CC)n1cc(-c2nc(-c3cnn(C[C@@H](O)C(C)(C)O)c3)cn3nccc23)cn1] | (R)-3-methyl-1-(4-(4-(1-(pentan-3-yl)-1H-pyrazol-4-yl)pyrazolo[1,5-a]pyrazin-6-yl)-1H-pyrazol-1-yl)butane-2,3-diol | Mass spectrum (apci) m/z = 424.2 (M + H) |
| 58 | 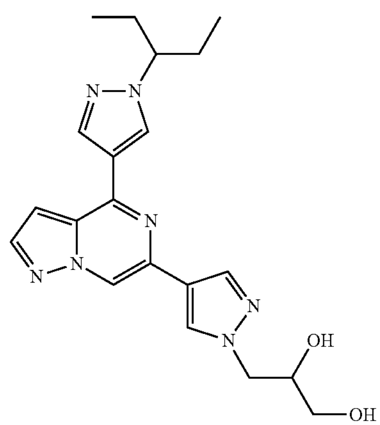 [SMILES: CCC(CC)n1cc(-c2nc(-c3cnn(CC(O)CO)c3)cn3nccc23)cn1] | 3-(4-(4-(1-(pentan-3-yl)-1H-pyrazol-4-yl)pyrazolo[1,5-a]pyrazin-6-yl)-1H-pyrazol-1-yl)propane-1,2-diol | Mass spectrum (apci) m/z = 396.2 (M + H) |

-continued

| Example | Structure | Name | Data |
|---|---|---|---|
| 59 | 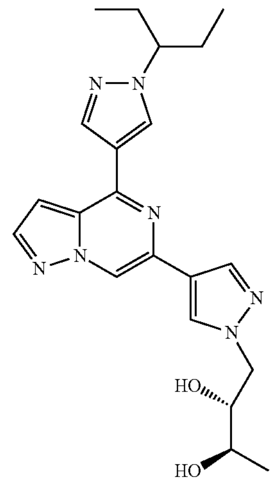 [SMILES: CCC(CC)n1cc(-c2nc(-c3cnn(C[C@@H](O)[C@@H](C)O)c3)cn3nccc23)cn1] | (2R,3R)-1-(4-(4-(1-(pentan-3-yl)-1H-pyrazol-4-yl)pyrazolo[1,5-a]pyrazin-6-yl)-1H-pyrazol-1-yl)butane-2,3-diol | Mass spectrum (apci) m/z = 410.2 (M + H) |
| 60 | 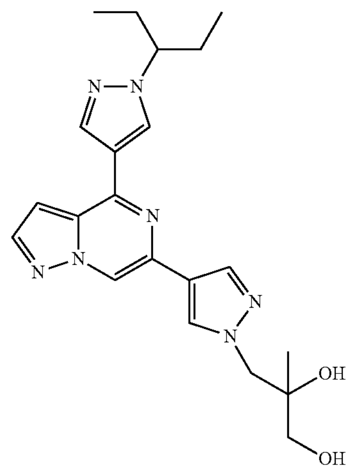 [SMILES: CCC(CC)n1cc(-c2nc(-c3cnn(CC(C)(O)CO)c3)cn3nccc23)cn1] | 2-methyl-3-(4-(4-(1-(pentan-3-yl)-1H-pyrazol-4-yl)pyrazolo[1,5-a]pyrazin-6-yl)-1H-pyrazol-1-yl)propane-1,2-diol | Mass spectrum (apci) m/z = 410.2 (M + H) |
| 61 | 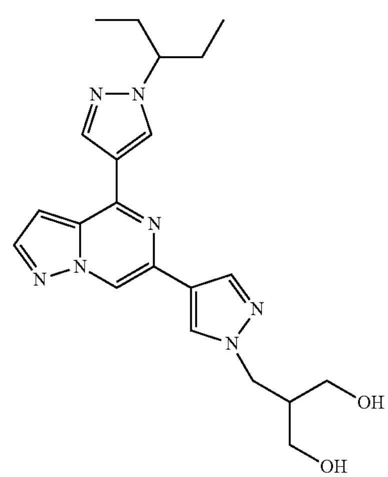 [SMILES: CCC(CC)n1cc(-c2nc(-c3cnn(CC(CO)CO)c3)cn3nccc23)cn1] | 2-((4-(4-(1-(pentan-3-yl)-1H-pyrazol-4-yl)pyrazolo[1,5-a]pyrazin-6-yl)-1H-pyrazol-1-yl)methyl)propane-1,3-diol | Mass spectrum (apci) m/z = 410.2 (M + H) |

-continued
| Example | Structure | Name | Data |
|---|---|---|---|
| 62 | 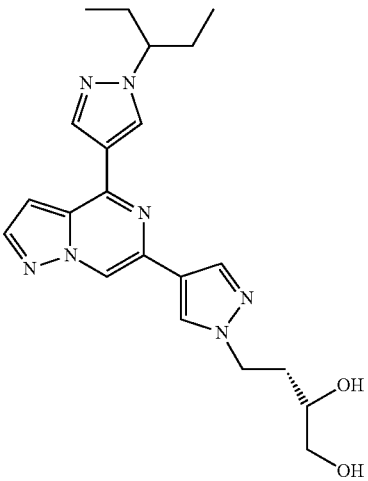 | (S)-4-(4-(4-(1-(pentan-3-yl)-1H-pyrazol-4-yl)pyrazolo[1,5-a]pyrazin-6-yl)-1H-pyrazol-1-yl)butane-1,2-diol | Mass spectrum (apci) m/z = 410.2 (M + H) |
| 63 | 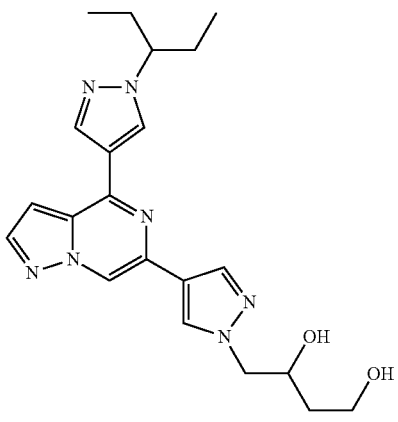 [SMILES: CCC(CC)n1cc(-c2nc(-c3cnn(CC(O)CCO)c3)cn3nccc23)cn1] | 4-(4-(4-(1-(pentan-3-yl)-1H-pyrazol-4-yl)pyrazolo[1,5-a]pyrazin-6-yl)-1H-pyrazol-1-yl)butane-1,3-diol | Mass spectrum (apci) m/z = 410.2 (M + H) |
| 64 | 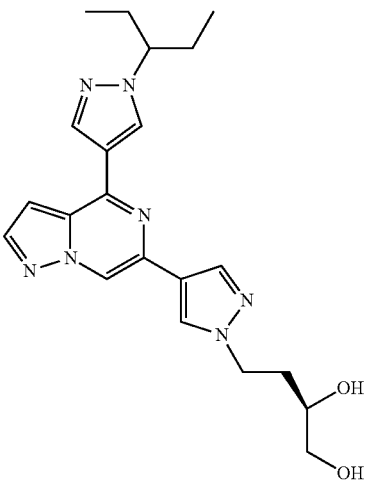 [SMILES: CCC(CC)n1cc(-c2nc(-c3cnn(CC[C@@H](O)CO)c3)cn3nccc23)cn1] | (R)-4-(4-(4-(1-(pentan-3-yl)-1H-pyrazol-4-yl)pyrazolo[1,5-a]pyrazin-6-yl)-1H-pyrazol-1-yl)butane-1,2-diol | Mass spectrum (apci) m/z = 410.2 (M + H) |

-continued

| Example | Structure | Name | Data |
| --- | --- | --- | --- |
| 65 | 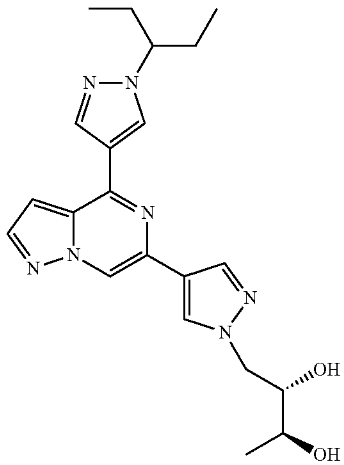 [SMILES: CCC(CC)n1cc(-c2nc(-c3cnn(C[C@H](O)[C@H](C)O)c3)cn3nccc23)cn1] | (2S,3S)-1-(4-(4-(1-(pentan-3-yl)-1H-pyrazol-4-yl)pyrazolo[1,5-a]pyrazin-6-yl)-1H-pyrazol-1-yl)butane-2,3-diol | Mass spectrum (apci) m/z = 410.2 (M + H) |
| 66 | 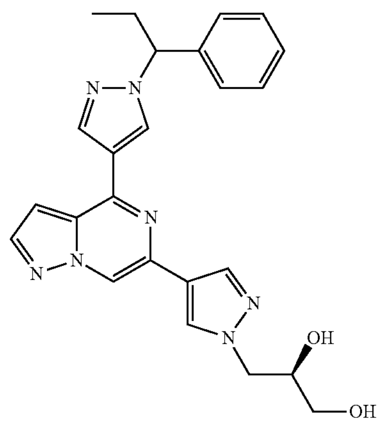 [SMILES: CCC(c1ccccc1)n1cc(-c2nc(-c3cnn(C[C@@H](O)CO)c3)cn3nccc23)cn1] | (2R)-3-(4-(4-(1-(1-phenylpropyl)-1H-pyrazol-4-yl)pyrazolo[1,5-a]pyrazin-6-yl)-1H-pyrazol-1-yl)propane-1,2-diol | Mass spectrum (apci) m/z = 444.2 (M + H) |
| 67 | 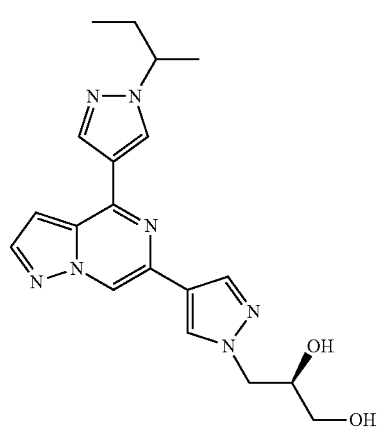 [SMILES: CCC(C)n1cc(-c2nc(-c3cnn(C[C@@H](O)CO)c3)cn3nccc23)cn1] | (2R)-3-(4-(4-(1-(sec-butyl)-1H-pyrazol-4-yl)pyrazolo[1,5-a]pyrazin-6-yl)-1H-pyrazol-1-yl)propane-1,2-diol | Mass spectrum (apci) m/z = 382.2 (M + H) |

-continued

| Example | Structure | Name | Data |
|---|---|---|---|
| 68 | 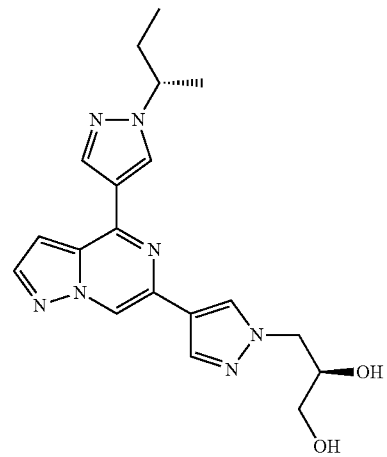 [SMILES: CC[C@H](C)n1cc(-c2nc(-c3cnn(C[C@@H](O)CO)c3)cn3nccc23)cn1] | (R)-3-(4-(4-(1-((S)-sec-butyl)-1H-pyrazol-4-yl)pyrazolo[1,5-a]pyrazin-6-yl)-1H-pyrazol-1-yl)propane-1,2-diol | Mass spectrum (apci) m/z = 382.2 (M + H) |
| 69 | 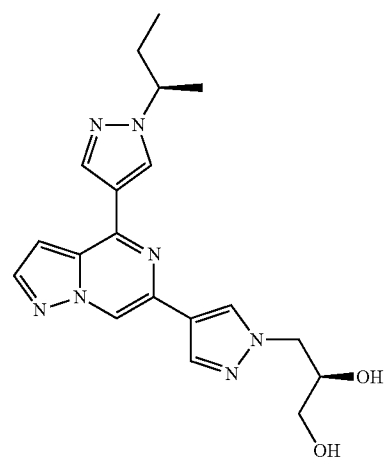 [SMILES: CC[C@@H](C)n1cc(-c2nc(-c3cnn(C[C@@H](O)CO)c3)cn3nccc23)cn1] | (R)-3-(4-(4-(1-((R)-sec-butyl)-1H-pyrazol-4-yl)pyrazolo[1,5-a]pyrazin-6-yl)-1H-pyrazol-1-yl)propane-1,2-diol | Mass spectrum (apci) m/z = 382.2 (M + H) |
| 70 | 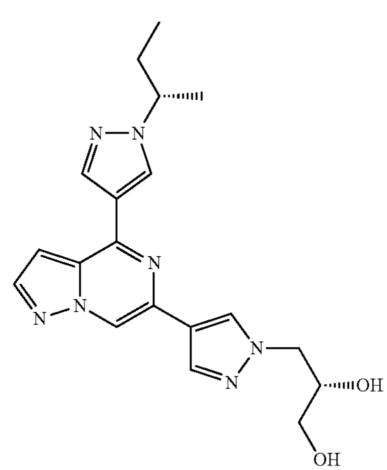 [SMILES: CC[C@H](C)n1cc(-c2nc(-c3cnn(C[C@H](O)CO)c3)cn3nccc23)cn1] | (S)-3-(4-(4-(1-((S)-sec-butyl)-1H-pyrazol-4-yl)pyrazolo[1,5-a]pyrazin-6-yl)-1H-pyrazol-1-yl)propane-1,2-diol hydrochloride | Mass spectrum (apci) m/z = 382.2 (M + H) |

-continued

| Example | Structure | Name | Data |
|---|---|---|---|
| 71 | 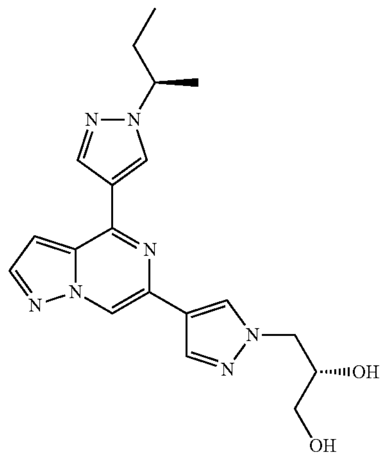 [SMILES: CC[C@@H](C)n1cc(-c2nc(-c3cnn(C[C@H](O)CO)c3)cn3nccc23)cn1] | (S)-3-(4-(4-(1-((R)-sec-butyl)-1H-pyrazol-4-yl)pyrazolo[1,5-a]pyrazin-6-yl)-1H-pyrazol-1-yl)propane-1,2-diol | Mass spectrum (apci) m/z = 382.2 (M + H) |
| 72 | 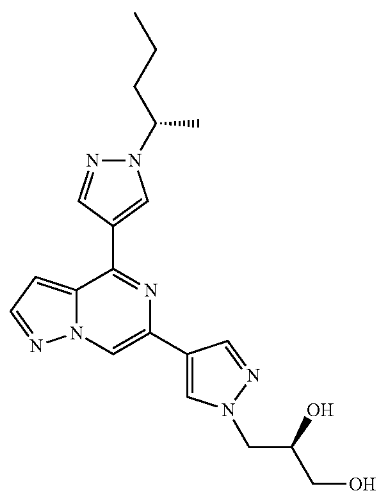 [SMILES: CCC[C@H](C)n1cc(-c2nc(-c3cnn(C[C@@H](O)CO)c3)cn3nccc23)cn1] | (R)-3-(4-(4-(1-((S)-pentan-2-yl)-1H-pyrazol-4-yl)pyrazolo[1,5-a]pyrazin-6-yl)-1H-pyrazol-1-yl)propane-1,2-diol | Mass spectrum (apci) m/z = 396.2 (M + H) |
| 73 | 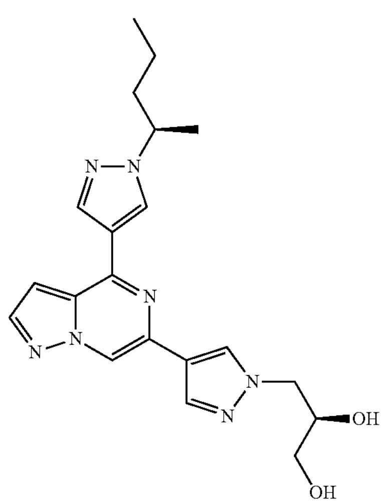 [SMILES: CCC[C@@H](C)n1cc(-c2nc(-c3cnn(C[C@@H](O)CO)c3)cn3nccc23)cn1] | (R)-3-(4-(4-(1-((R)-pentan-2-yl)-1H-pyrazol-4-yl)pyrazolo[1,5-a]pyrazin-6-yl)-1H-pyrazol-1-yl)propane-1,2-diol | Mass spectrum (apci) m/z = 396.2 (M + H) |

| Example | Structure | Name | Data |
|---|---|---|---|
| 74 | 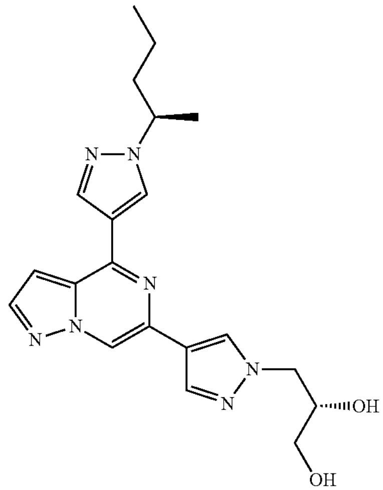 [SMILES: CCC[C@@H](C)n1cc(-c2nc(-c3cnn(C[C@H](O)CO)c3)cn3nccc23)cn1] | (S)-3-(4-(4-(1-((R)-pentan-2-yl)-1H-pyrazol-4-yl)pyrazolo[1,5-a]pyrazin-6-yl)-1H-pyrazol-1-yl)propane-1,2-diol | Mass spectrum (apci) m/z = 396.2 (M + H) |
| 75 | 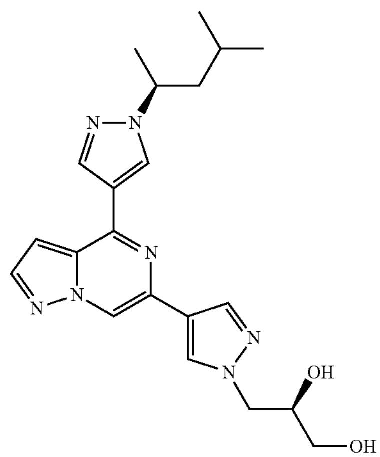 [SMILES: CC(C)C[C@H](C)n1cc(-c2nc(-c3cnn(C[C@@H](O)CO)c3)cn3nccc23)cn1] | (R)-3-(4-(4-(1-((S)-4-methylpentan-2-yl)-1H-pyrazol-4-yl)pyrazolo[1,5-a]pyrazin-6-yl)-1H-pyrazol-1-yl)propane-1,2-diol | Mass spectrum (apci) m/z = 410.2 (M + H) |
| 76 | 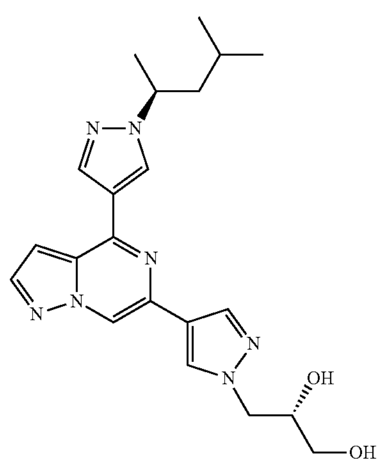 [SMILES: CC(C)C[C@H](C)n1cc(-c2nc(-c3cnn(C[C@H](O)CO)c3)cn3nccc23)cn1] | (S)-3-(4-(4-(1-((S)-4-methylpentan-2-yl)-1H-pyrazol-4-yl)pyrazolo[1,5-a]pyrazin-6-yl)-1H-pyrazol-1-yl)propane-1,2-diol | Mass spectrum (apci) m/z = 410.2 (M + H) |

-continued

| Example | Structure | Name | Data |
|---|---|---|---|
| 77 | 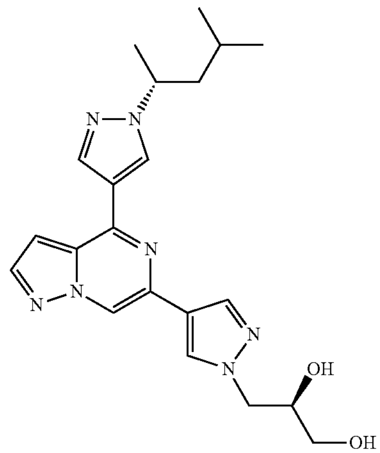 [SMILES: CC(C)C[C@@H](C)n1cc(-c2nc(-c3cnn(C[C@@H](O)CO)c3)cn3nccc23)cn1] | (R)-3-(4-(4-(1-((R)-4-methylpentan-2-yl)-1H-pyrazol-4-yl)pyrazolo[1,5-a]pyrazin-6-yl)-1H-pyrazol-1-yl)propane-1,2-diol | Mass spectrum (apci) m/z = 410.2 (M + H) |
| 78 | 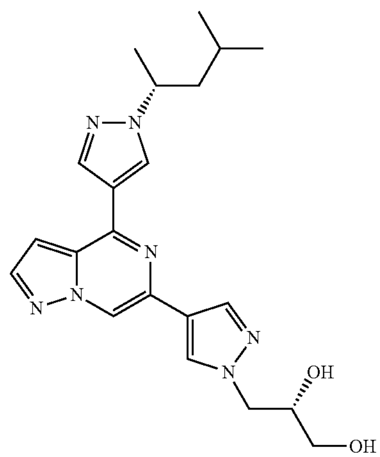 [SMILES: CC(C)C[C@@H](C)n1cc(-c2nc(-c3cnn(C[C@H](O)CO)c3)cn3nccc23)cn1] | (S)-3-(4-(4-(1-((R)-4-methylpentan-2-yl)-1H-pyrazol-4-yl)pyrazolo[1,5-a]pyrazin-6-yl)-1H-pyrazol-1-yl)propane-1,2-diol | Mass spectrum (apci) m/z = 410.2 (M + H) |
| 79 | 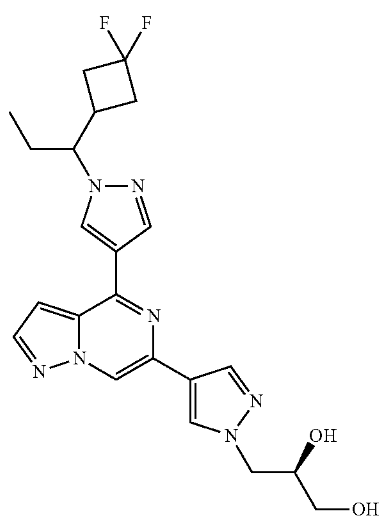 [SMILES: CCC(C1CC(F)(F)C1)n1cc(-c2nc(-c3cnn(C[C@@H](O)CO)c3)cn3nccc23)cn1] | (2R)-3-(4-(4-(1-(1-(3,3-difluorocyclobutyl)propyl)-1H-pyrazol-4-yl)pyrazolo[1,5-a]pyrazin-6-yl)-1H-pyrazol-1-yl)propane-1,2-diol | Mass spectrum (apci) m/z = 458.2 (M + H) |

| Example | Structure | Name | Data |
| --- | --- | --- | --- |
| 80 | 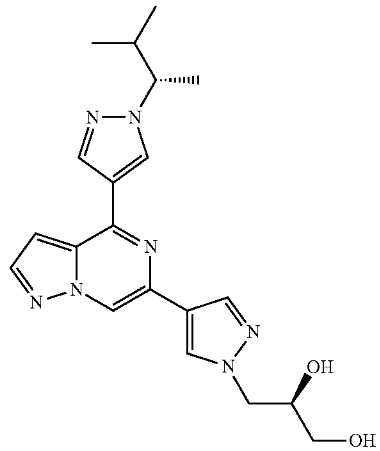 [SMILES: CC(C)[C@H](C)n1cc(-c2nc(-c3cnn(C[C@@H](O)CO)c3)cn3nccc23)cn1] | (R)-3-(4-(4-(1-((S)-3-methylbutan-2-yl)-1H-pyrazol-4-yl)pyrazolo[1,5-a]pyrazin-6-yl)-1H-pyrazol-1-yl)propane-1,2-diol | Mass spectrum (apci) m/z = 396.2 (M + H) |

Example 81

2-(4-(4-(1-(pentan-3-yl)-1H-pyrazol-4-yl)pyrazolo[1,5-a]pyrazin-6-yl)-1H-pyrazol-1-yl)propane-1,3-diol

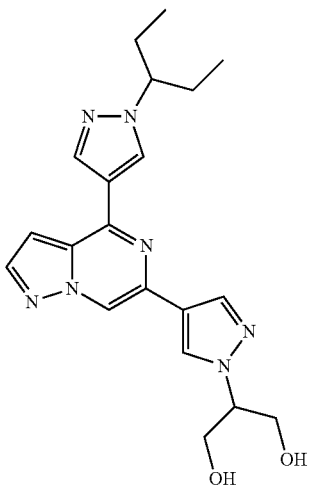 [SMILES: CCC(CC)n1cc(-c2nc(-c3cnn(C(CO)CO)c3)cn3nccc23)cn1]

To a solution of 4-(1-(pentan-3-yl)-1H-pyrazol-4-yl)-6-(1H-pyrazol-4-yl)pyrazolo[1,5-a]pyrazine (200 mg, 0.62 mmol) in DMF (2 mL) was added $Cs_2CO_3$ (1.0 g, 3.1 mmol) and 2,2-dimethyl-1,3-dioxan-5-yl methanesulfonate (262 mg, 1.2 mmol) and the reaction mixture was heated to 80° C. overnight. The reaction mixture was poured into water and extracted with EtOAc. The organic layer was washed with brine, dried over $MgSO_4$, filtered and concentrated. The residue was purified over silica gel (0-100% EtOAc in $CH_2Cl_2$) to afford 6-(1-(2,2-dimethyl-1,3-dioxan-5-yl)-1H-pyrazol-4-yl)-4-(1-(pentan-3-yl)-1H-pyrazol-4-yl)pyrazolo[1,5-a]pyrazine (0.2 g, 0.46 mmol, 74% yield).

To a solution of 6-(1-(2,2-dimethyl-1,3-dioxan-5-yl)-1H-pyrazol-4-yl)-4-(1-(pentan-3-yl)-1H-pyrazol-4-yl)pyrazolo[1,5-a]pyrazine (0.18 g, 0.41 mmol) in isopropyl alcohol (10 mL) was added 2 drops of 12M HCl and the reaction mixture was heated to 80° C. for 1 hour. The reaction was concentrated in vacuo and the material partitioned between saturated aqueous $NaHCO_3$ and EtOAc. The organic layer was washed with brine, dried over $MgSO_4$ and concentrated in vacuo. The residue was purified over silica gel (0-10% MeOH in $CH_2Cl_2$) to afford 2-(4-(4-(1-(pentan-3-yl)-1H-pyrazol-4-yl)pyrazolo[1,5-a]pyrazin-6-yl)-1H-pyrazol-1-yl)propane-1,3-diol (0.13 g, 0.33 mmol, 80% yield). Mass spectrum (apci) m/z=396.2 (M+H). $^1$H NMR ($d_6$-DMSO) δ 8.99 (d, J=1.0 Hz, 1H), 8.73 (s, 1H), 8.40 (s, 1H), 8.37 (s, 1H), 8.16 (m, 2H), 7.36 (dd, J=2.5, 1.0 Hz, 1H), 4.93 (t, J=5.5 Hz, 2H), 4.30 (pentet, J=6.5 Hz, 1H), 4.15 (m, 1H), 3.79 (m, 4H), 1.99-1.79 (m, 4H), 0.75 (t, J=7.4 Hz, 6H).

Example 82

(S)-2-(4-(4-(1-(pentan-2-yl)-1H-pyrazol-4-yl)pyrazolo[1,5-a]pyrazin-6-yl)-1H-pyrazol-1-yl)propane-1,3-diol

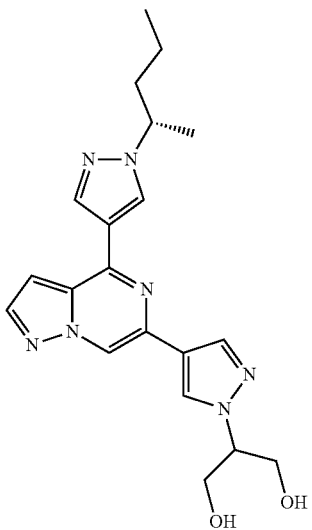 [SMILES: CCC[C@H](C)n1cc(-c2nc(-c3cnn(C(CO)CO)c3)cn3nccc23)cn1]

Step A:

To a slurry of (S)-4-(1-(pentan-2-yl)-1H-pyrazol-4-yl)-6-(1H-pyrazol-4-yl)pyrazolo[1,5-a]pyrazine (0.10 g, 0.31 mmol) in DMF (0.5 mL) was added 2-phenyl-1,3-dioxan-5-yl methanesulfonate (0.16 g, 0.62 mmol) and Cs$_2$CO$_3$ (0.20 g, 0.62 mmol) and the reaction mixture was heated to 70° C. overnight. The reaction mixture was partitioned between EtOAc and water. The combined organic phases were separated and washed with brine, dried over MgSO$_4$ and concentrated in vacuo. The crude material was purified over silica gel (0-100% EtOAc/CH$_2$Cl$_2$) to afford (S)-4-(1-(pentan-2-yl)-1H-pyrazol-4-yl)-6-(1-(2-phenyl-1,3-dioxan-5-yl)-1H-pyrazol-4-yl)pyrazolo[1,5-a]pyrazine (0.10 g, 0.21 mmol, 66% yield).

Step B:

To a solution of (S)-4-(1-(pentan-2-yl)-1H-pyrazol-4-yl)-6-(1-(2-phenyl-1,3-dioxan-5-yl)-1H-pyrazol-4-yl)pyrazolo[1,5-a]pyrazine (0.10 g, 0.21 mmol) in isopropyl alcohol (10 mL) were added 2 drops of HCl and the reaction mixture was heated to 60° C. for 2 hours. The reaction mixture was concentrated in vacuo and the residue was partitioned between EtOAc and 0.1N NaOH. The combined organic phases were washed with brine, dried over MgSO$_4$ and concentrated in vacuo. The crude material was purified over silica gel (0-10% MeOH/CH$_2$Cl$_2$) to afford (S)-2-(4-(4-(1-(pentan-2-yl)-1H-pyrazol-4-yl)pyrazolo[1,5-a]pyrazin-6-yl)-1H-pyrazol-1-yl)propane-1,3-diol (0.009 g, 0.023 mmol, 11% yield). Mass spectrum (apci) m/z=396.2 (M+H). $^1$H NMR (CDCl$_3$) δ 8.41 (d, J=1.0 Hz, 1H), 8.20 (s, 2H), 8.12 (s, 1H), 8.01 (d, J=2.5 Hz, 1H), 7.96 (s, 1H), 6.94 (dd, J=2.3, 0.8 Hz, 1H), 4.48-4.36 (m, 2H), 4.17-4.11 (m, 4H), 1.99 (m, 1H), 1.79 (m, 1H), 1.59 (d, J=6.8 Hz, 3H), 1.37-1.18 (m, 2H), 0.93 (t, J=7.2 Hz, 3H).

The following compounds were prepared according to the procedure described for Example 82.

| Example | Structure | Name | Data |
|---|---|---|---|
| 83 | 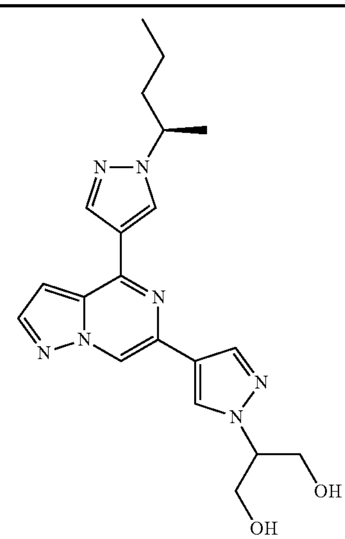 | (R)-2-(4-(4-(1-(pentan-2-yl)-1H-pyrazol-4-yl)pyrazolo[1,5-a]pyrazin-6-yl)-1H-pyrazol-1-yl)propane-1,3-diol | Mass spectrum (apci) m/z = 396.2 (M + H) |
| 84 | 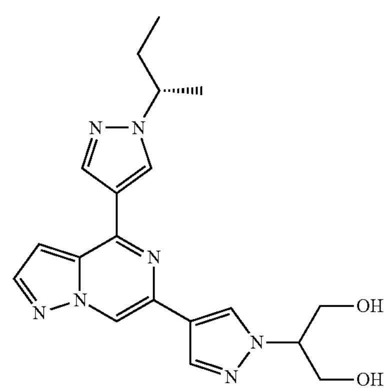 [SMILES: CC[C@H](C)n1cc(-c2nc(-c3cnn(C(CO)CO)c3)cn3nccc23)cn1] | (S)-2-(4-(4-(1-(sec-butyl)-1H-pyrazol-4-yl)pyrazolo[1,5-a]pyrazin-6-yl)-1H-pyrazol-1-yl)propane-1,3-diol | Mass spectrum (apci) m/z = 382.2 (M + H) |

| Example | Structure | Name | Data |
|---|---|---|---|
| 85 | 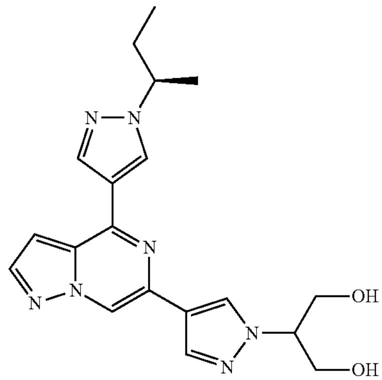 [SMILES: CC[C@@H](C)n1cc(-c2nc(-c3cnn(C(CO)CO)c3)cn3nccc23)cn1] | (R)-2-(4-(4-(1-(sec-butyl)-1H-pyrazol-4-yl)pyrazolo[1,5-a]pyrazin-6-yl)-1H-pyrazol-1-yl)propane-1,3-diol | Mass spectrum (apci) m/z = 382.2 (M + H) |
| 86 | 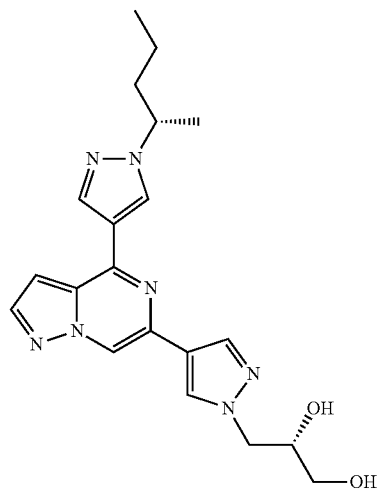 [SMILES: CCC[C@H](C)n1cc(-c2nc(-c3cnn(C[C@H](O)CO)c3)cn3nccc23)cn1] | (S)-3-(4-(4-(1-((S)-pentan-2-yl)-1H-pyrazol-4-yl)pyrazolo[1,5-a]pyrazin-6-yl)-1H-pyrazol-1-yl)propane-1,2-diol | Mass spectrum (apci) m/z = 396.2 (M + H) |
| 87 | 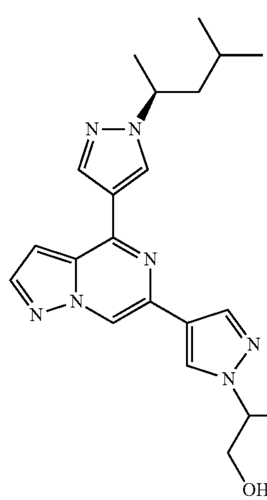 | (S)-2-(4-(4-(1-(4-methylpentan-2-yl)-1H-pyrazol-4-yl)pyrazolo[1,5-a]pyrazin-6-yl)-1H-pyrazol-1-yl)propane-1,3-diol | Mass spectrum (apci) m/z = 410.2 (M + H) |

| Example | Structure | Name | Data |
|---|---|---|---|
| 88 | 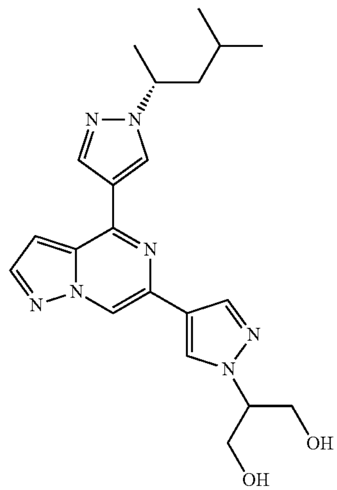 [SMILES: CC(C)C[C@@H](C)n1cc(-c2nc(-c3cnn(C(CO)CO)c3)cn3nccc23)cn1] | (R)-2-(4-(4-(1-(4-methylpentan-2-yl)-1H-pyrazol-4-yl)pyrazolo[1,5-a]pyrazin-6-yl)-1H-pyrazol-1-yl)propane-1,3-diol | Mass spectrum (apci) m/z = 410.2 (M + H) |

Example 89

(2S,3S)-3-(4-(4-(1-(pentan-3-yl)-1H-pyrazol-4-yl)pyrazolo[1,5-a]pyrazin-6-yl)-1H-pyrazol-1-yl)butane-1,2-diol

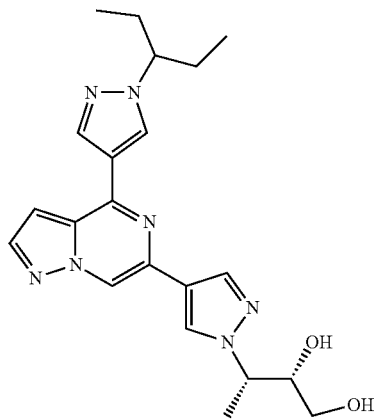 [SMILES: CCC(CC)n1cc(-c2nc(-c3cnn([C@@H](C)[C@H](O)CO)c3)cn3nccc23)cn1]

Step A:

To 4-(1-(pentan-3-yl)-1H-pyrazol-4-yl)-6-(1H-pyrazol-4-yl)pyrazolo[1,5-a]pyrazine (0.2 g, 0.6 mmol) was added Cs$_2$CO$_3$ (0.4 g, 1 mmol) followed by the addition of 8 mL of DMF. To the reaction mixture was added 1-((R)-1,4-dioxaspiro[4.5]decan-2-yl)ethyl methanesulfonate (0.3 g, 1 mmol) and the reaction mixture was stirred under N$_2$ at 80° C. overnight. The reaction mixture was cooled and diluted with water (750 mL). The aqueous layer was extracted twice with methyl tert-butyl ether. The combined methyl tert-butyl ether layers were back extracted with water and brine, dried over MgSO$_4$ and concentrated in vacuo The crude material was purified over silica gel (20-70% EtOAc in CH$_2$Cl$_2$) to afford 2 products. The higher eluting spot (Peak A) was 6-(1-((R)-1-((S)-1,4-dioxaspiro[4.5]decan-2-yl)ethyl)-1H-pyrazol-4-yl)-4-(1-(pentan-3-yl)-1H-pyrazol-4-yl)pyrazolo[1,5-a]pyrazine (0.040 g, 0.082 mmol) and the lower eluting spot (Peak B) was 6-(1-(1-((S)-1,4-dioxaspiro[4.5]decan-2-yl)ethyl)-1H-pyrazol-4-yl)-4-(1-(pentan-3-yl)-1H-pyrazol-4-yl)pyrazolo[1,5-a]pyrazine (0.1 g, 0.2 mmol, 33% yield).

Step B:

To a solution of 6-(1-((S)-1-((S)-1,4-dioxaspiro[4.5]decan-2-yl)ethyl)-1H-pyrazol-4-yl)-4-(1-(pentan-3-yl)-1H-pyrazol-4-yl)pyrazolo[1,5-a]pyrazine (0.07 g, 0.14 mmol) in isopropyl alcohol (50 mL) was added 1 drop of concentrated HCl and the reaction mixture was heated to 60° C. for 2 hours. The reaction mixture was concentrated in vacuo and the resulting material was partitioned between 1N NaOH and EtOAc. The layers were separated and the aqueous layer was extracted with EtOAc. The combined organic layers were washed with brine and dried over MgSO$_4$ and concentrated in vacuo. The residue was purified over silica gel (0-10% MeOH in CH$_2$C2) to afford (2S,3S)-3-(4-(4-(1-(pentan-3-yl)-1H-pyrazol-4-yl)pyrazolo[1,5-a]pyrazin-6-yl)-1H-pyrazol-1-yl)butane-1,2-diol (isolated "Peak A") (0.030 g, 0.073 mmol, 51% yield). Mass spectrum (apci) m/z=410.2 (M+H). $^1$H NMR (CDCl$_3$) δ 8.43 (d, J=0.8 Hz, 1H), 8.24 (s, 1H), 8.17 (s, 1H), 8.07 (s, 1H), 8.01 (d, J=2.3, Hz, 1H), 7.91 (s, 1H), 6.93 (dd, J=2.3, 0.8 Hz, 1H), 4.58 (m, 1H), 4.02 (septet, J=4.5 Hz, 1H), 3.95 (q, J=5.1 Hz, 1H), 3.59 (dd, J=11.5, 5.6 Hz, 1H), 3.52 (dd, J=11.3, 5.3 Hz, 1H), 2.05-1.84 (m, 4H), 1.65 (d, J=7.0 Hz, 3H), 0.85 (t, J=7.4 Hz, 6H).

The following compounds were prepared according to the procedure described for Example 89.

| Example | Structure | Name | Data |
|---|---|---|---|
| 90 | (isolated "Peak B") | (2S,3R)-3-(4-(4-(1-(pentan-3-yl)-1H-pyrazol-4-yl)pyrazolo[1,5-a]pyrazin-6-yl)-1H-pyrazol-1-yl)butane-1,2-diol | Mass spectrum (apci) m/z = 410.2 (M + H) |
| 91 | (isolated "Peak A") | (2R,3S)-3-(4-(4-(1-(pentan-3-yl)-1H-pyrazol-4-yl)pyrazolo[1,5-a]pyrazin-6-yl)-1H-pyrazol-1-yl)butane-1,2-diol | Mass spectrum (apci) m/z = 410.2 (M + H) |
| 92 | (isolated "Peak B") | (2R,3R)-3-(4-(4-(1-(pentan-3-yl)-1H-pyrazol-4-yl)pyrazolo[1,5-a]pyrazin-6-yl)-1H-pyrazol-1-yl)butane-1,2-diol | Mass spectrum (apci) m/z = 410.2 (M + H) |

Examples 93 and 94

(R)-3-(4-(4-(1-((1R,2S)-2-methylcyclopentyl)-H-pyrazol-4-yl)pyrazolo[1,5-a]pyrazin-6-yl)-1H-pyrazol-1-yl)propane-1,2-diol and (R)-3-(4-(4-(1-((1S,2R)-2-methylcyclopentyl)-1H-pyrazol-4-yl)pyrazolo[1,5-a]pyrazin-6-yl)-1H-pyrazol-1-yl)propane-1,2-diol

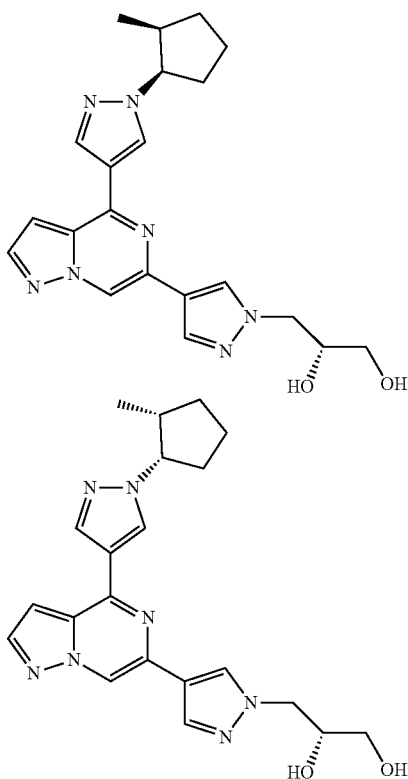

Step A:

A round bottom flask equipped with a stir bar was charged with 4-(1-(cis-2-methylcyclopentyl)-1H-pyrazol-4-yl)-6-(1H-pyrazol-4-yl)pyrazolo[1,5-a]pyrazine (0.057 g, 0.171 mmol) and 2 mL of DMA. To this was added (S)-4-(chloromethyl)-2,2-dimethyl-1,3-dioxolane (0.034 g, 0.222 mmol) and cesium carbonate (0.11 g, 0.342 mmol). The reaction mixture was heated to 70° C. After about 2.5 hours, another 0.5 equivalents of (S)-4-(chloromethyl)-2,2-dimethyl-1,3-dioxolane was added. After another 5 hours, the reaction mixture was allowed to cool to room temperature and diluted with water. The reaction mixture was extracted with EtOAc, and the combined organic extracts were washed with brine, dried over sodium sulfate and concentrated under reduced pressure. The crude material was purified by preparative TLC (2×0.5 mm plates, 1:1 ethyl acetate:Hexane, developed two times) to afford 6-(1-(((R)-2,2-dimethyl-1,3-dioxolan-4-yl)methyl)-1H-pyrazol-4-yl)-4-(1-((1R,2S)-2-methylcyclopentyl)-1H-pyrazol-4-yl)pyrazolo[1,5-a]pyrazine (17 mg, 22% yield).

Step B:

A microwave pressure tube containing 6-(1-(((R)-2,2-dimethyl-1,3-dioxolan-4-yl)methyl)-1H-pyrazol-4-yl)-4-(1-(cis-2-methylcyclopentyl)-1H-pyrazol-4-yl)pyrazolo[1,5-a]pyrazine (0.017 g, 0.038 mmol) was charged with 1 mL of isopropyl alcohol and a couple of drops of concentrated HCl. The tube was sealed and warmed to 60° C. for 2.5 hours. The reaction mixture was concentrated under reduced pressure and the crude material was purified by chiral chromatography (Chiral Tech IA 4.6 mm×450 mm, 5 micron, 15% EtOH in hexanes, 1 mL/min) to afford the title compounds as isolated diastereomers. Peak A: retention time=11.3 min; Mass spectrum (apci) m/z=408.2 (M+H). Peak B: retention time=13.7 min; Mass spectrum (apci) m/z=408.2 (M+H).

Examples 95 and 96

(R)-3-(4-(4-(1-((S)-2,2-dimethylcyclopentyl)-1H-pyrazol-4-yl)pyrazolo[1,5-a]pyrazin-6-yl)-1H-pyrazol-1-yl)propane-1,2-diol and (R)-3-(4-(4-(1-((R)-2,2-dimethylcyclopentyl)-1H-pyrazol-4-yl)pyrazolo[1,5-a]pyrazin-6-yl)-1H-pyrazol-1-yl)propane-1,2-diol

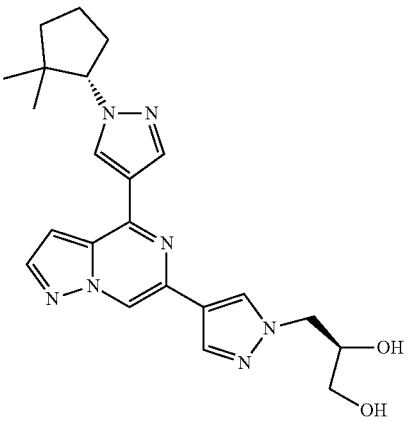

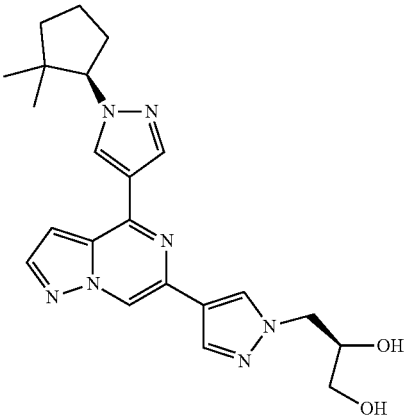

Step A:

A suspension of 4-(1-(2,2-dimethylcyclopentyl)-1H-pyrazol-4-yl)-6-(1H-pyrazol-4-yl)pyrazolo[1,5-a]pyrazine (123 mg, 0.354 mmol), (S)-(−)-4-(Chloromethyl)-2,2-dimethyl-1,3-dioxolane (53.2 μL, 0.389 mmol), Cs$_2$CO$_3$ (231 mg, 0.708 mmol) in DMF (1770 μL, 0.354 mmol) was heated at 60° C. overnight. The mixture was partitioned between EtOAc and water. The aqueous layer was extracted with EtOAc. The combined organic layers were dried over sodium sulfate and concentrated. The residue was purified by reverse phase chromatography (5 to 95% CH$_3$CN in water) to afford 6-(1-(((R)-2,2-dimethyl-1,3-dioxolan-4-yl)methyl)-1H-pyrazol-4-yl)-4-(1-(2,2-dimethylcyclopentyl)-1H-pyrazol-4-yl)pyrazolo[1,5-a]pyrazine (88 mg, 54% yield).

Step B:

To a solution of 6-(1-(((R)-2,2-dimethyl-1,3-dioxolan-4-yl)methyl)-1H-pyrazol-4-yl)-4-(1-(2,2-dimethylcyclopentyl)-1H-pyrazol-4-yl)pyrazolo[1,5-a]pyrazine (88 mg, 0.19 mmol) in methanol was added 3 drops of concentrated HCl and the reaction mixture was heated at 80° C. overnight. The reaction mixture was concentrated and purified by chiral chromatography (Chiral Tech IA column, 4.6 mm×250 mm, 5 micron, 30% EtOH in hexanes, 1 mL/min) to afford 2 diastereomers. The stereochemistry was arbitrarily assigned. Peak A: retention time=24.6 min; Mass spectrum (apci) m/z=422.2; (M+H). $^1$H NMR (CDCl$_3$) δ 8.43 (s, 1H), 8.21 (s, 1H), 8.15 (s, 1H), 8.02 (m, 2H), 7.98 (s, 1H), 6.92 (dd, J=2.3, 0.8 Hz, 1H), 4.34 (m, 3H), 4.17 (br s, 1H), 3.70 (m, 3H), 2.64 (br s, 1H), 2.50-2.31 (m, 2H), 2.07-1.95 (m, 1H), 1.90-1.75 (m, 2H), 1.70-1.57 (m, 2H), 1.17 (s, 3H), 0.73 (s, 3H). Peak B: retention time=27.6 min; Mass spectrum (apci) m/z=422.3 (M+H); $^1$H NMR (CDCl$_3$) δ 8.44 (s, 1H), 8.22 (s, 1H), 8.15 (s, 1H), 8.03 (m, 2H), 7.99 (s, 1H), 6.93 (dd, J=2.3, 0.8 Hz, 1H), 4.34 (m, 3H), 4.17 (br s, 1H), 3.68 (br s, 2H), 3.57 (br s, 1H), 2.54-2.30 (m, 3H), 2.07-1.95 (m, 1H), 1.90-1.75 (m, 2H), 1.67-1.57 (m, 2H), 1.17 (s, 3H), 0.73 (s, 3H).

Example 97

N-isopropyl-2-(4-(4-(1-(pentan-3-yl)-1H-pyrazol-4-yl)pyrazolo[1,5-a]pyrazin-6-yl)-1H-pyrazol-1-yl)acetamide

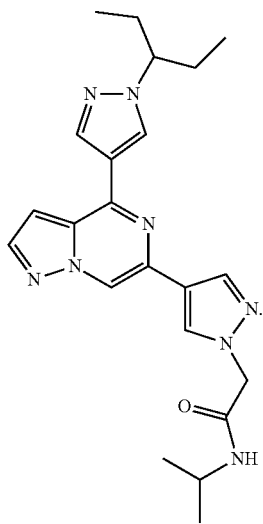 [SMILES: CCC(CC)n1cc(-c2nc(-c3cnn(CC(=O)NC(C)C)c3)cn3nccc23)cn1]

Step A:

To a solution of 4-(1-(pentan-3-yl)-1H-pyrazol-4-yl)-6-(1H-pyrazol-4-yl)pyrazolo[1,5-a]pyrazine (0.060 g, 0.187 mmol) in 0.5 mL of DMA was added cesium carbonate (0.243 g, 0.747 mmol) and methyl 2-bromoacetate (0.0344 mL, 0.373 mmol) and the reaction mixture was stirred for 4 hours at 70° C. The reaction mixture was purified by reverse phase chromatography (C18; 0 to 50% CH$_3$CN in water) to afford methyl 2-(4-(4-(1-(pentan-3-yl)-1H-pyrazol-4-yl)pyrazolo[1,5-a]pyrazin-6-yl)-1H-pyrazol-1-yl)acetate (65 mg, 88% yield).

Step B:

To a solution of methyl 2-(4-(4-(1-(pentan-3-yl)-1H-pyrazol-4-yl)pyrazolo[1,5-a]pyrazin-6-yl)-1H-pyrazol-1-yl)acetate (0.0650 g, 0.165 mmol) in THF (2 mL) was added 1M lithium hydroxide (0.661 mL, 0.661 mmol) and the reaction mixture was stirred for 4 hours at room temperature. The combined organic phases were concentrated in vacuo and the aqueous layer was acidified to pH 1 using (HCl, 1N). The aqueous layer was extracted with EtOAc and the combined organic extracts were washed with brine, dried over MgSO$_4$ and concentrated in vacuo to afford 2-(4-(4-(1-(pentan-3-yl)-1H-pyrazol-4-yl)pyrazolo[1,5-a]pyrazin-6-yl)-H-pyrazol-1-yl)acetic acid (40 mg, 64% yield).

Step C:

To a solution of 2-(4-(4-(1-(pentan-3-yl)-1H-pyrazol-4-yl)pyrazolo[1,5-a]pyrazin-6-yl)-1H-pyrazol-1-yl)acetic acid (0.04 g, 0.105 mmol) in DMA (0.5 mL) was added propan-2-amine (0.0249 g, 0.422 mmol) and Hunig's Base (0.0184 mL, 0.105 mmol) followed by 2,4,6-tripropyl-1,3,5,2,4,6-trioxatriphosphinane 2,4,6-trioxide (0.134 g, 0.211 mmol), and the reaction mixture was stirred at room temperature for 1 hour. The reaction mixture was purified by reverse phase chromatography (C18, 0-60% CH$_3$CN/water) to afford N-isopropyl-2-(4-(4-(1-(pentan-3-yl)-1H-pyrazol-4-yl)pyrazolo[1,5-a]pyrazin-6-yl)-1H-pyrazol-1-yl)acetamide (0.0198 g, 0.0471 mmol, 44.7% yield). Mass spectrum (apci) m/z=421.2 (M+H). $^1$H NMR (CDCl$_3$) δ 8.49 (d, J=0.8 Hz, 1H), 8.27 (s, 1H), 8.25 (s, 1H), 8.09 (s, 1H), 8.08 (s, 1H), 8.06 (d, J=2.5 Hz, 1H), 7.00 (dd, J=2.5, 0.8 Hz, 1H), 6.14 (d, J=7.4 Hz, 1H), 4.85 (s, 2H), 4.13-4.00 (m, 2H), 2.07-1.86 (m, 4H), 1.13 (d, J=6.7 Hz, 3H), 0.86 (t, J=7.4 Hz, 6H).

Example 98

1-amino-3-(4-(4-(1-(pentan-3-yl)-1H-pyrazol-4-yl)pyrazolo[1,5-a]pyrazin-6-yl)-1H-pyrazol-1-yl)propan-2-ol

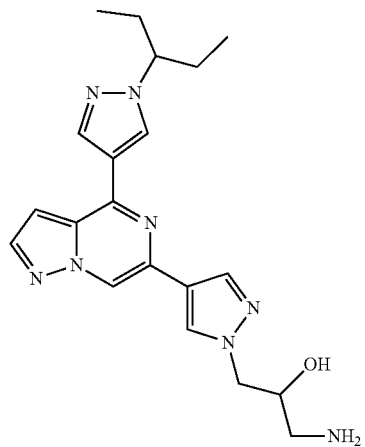 [SMILES: CCC(CC)n1cc(-c2nc(-c3cnn(CC(O)CN)c3)cn3nccc23)cn1]

To 5-((4-(4-(1-(pentan-3-yl)-1H-pyrazol-4-yl)pyrazolo[1,5-a]pyrazin-6-yl)-1H-pyrazol-1-yl)methyl)oxazolidin-2-one (0.04 g, 0.10 mmol) was added a mixture of 1:1 dioxanes/1M LiOH and the reaction mixture was stirred at 70° C. for 4 hours. The reaction mixture was concentrated in vacuo and the material purified by reverse phase chromatography (C18, 5-75% CH₃CN/water) to afford 1-amino-3-(4-(4-(1-(pentan-3-yl)-1H-pyrazol-4-yl)pyrazolo[1,5-a]pyrazin-6-yl)-1H-pyrazol-1-yl)propan-2-ol (0.005 g, 0.01 mmol, 13% yield). Mass spectrum (apci) m/z=395.3 (M+H). ¹H NMR (CDCl₃) δ 8.45 (d, J=0.8 Hz, 1H), 8.25 (s, 1H), 8.17 (s, 1H), 8.06 (s, 1H), 8.02 (d, J=2.3 Hz, 1H), 7.97 (s, 1H), 6.94 (dd, J=2.3, 1.0 Hz, 1H), 4.32 (dd, J=13.9, 3.7 Hz, 1H), 4.23 (dd, J=13.9, 6.7 Hz, 1H), 4.02 (m, 2H), 2.89 (dd, J=12.7, 4.1 Hz, 1H), 2.72 (dd, J=12.7, 7.0 Hz, 1H), 2.06-1.85 (m, 4H), 0.86 (t, J=7.2 Hz, 6H).

Example 99

(R)-1-(dimethylamino)-3-(4-(4-(1-(pentan-3-yl)-1H-pyrazol-4-yl)pyrazolo[1,5-a]pyrazin-6-yl)-1H-pyrazol-1-yl)propan-2-ol

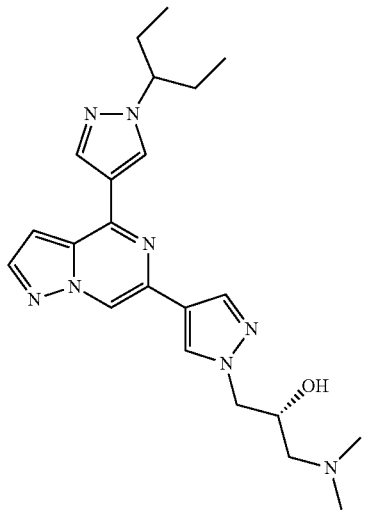 [SMILES: CCC(CC)n1cc(-c2nc(-c3cnn(C[C@H](O)CN(C)C)c3)cn3nccc23)cn1]

Step A:

4-(1-(Pentan-3-yl)-1H-pyrazol-4-yl)-6-(1H-pyrazol-4-yl)pyrazolo[1,5-a]pyrazine (300 mg, 0.933 mmol), (S)-2-(chloromethyl)oxirane (864 mg, 9.3 mmol) and Cs₂CO₃ (912 mg, 2.80 mmol) were placed in DMF (2 mL) and stirred for 3 hours. Water was added and the reaction mixture was extracted with EtOAc. The combined organic layers were washed with water. The organic layer was concentrated to give crude (S)-6-(1-(oxiran-2-ylmethyl)-1H-pyrazol-4-yl)-4-(1-(pentan-3-yl)-1H-pyrazol-4-yl)pyrazolo[1,5-a]pyrazine which was used in the next step without further purification.

Step B:

(R)-6-(1-(oxiran-2-ylmethyl)-1H-pyrazol-4-yl)-4-(1-(pentan-3-yl)-1H-pyrazol-4-yl)pyrazolo[1,5-a]pyrazine (30 mg, 0.0795 mmol) was placed in THF (1 mL). 2.0M Dimethylamine (397 μL, 0.795 mmol) was added and the reaction vessel was sealed and heated to 50° C. for 18 hours. The reaction mixture was concentrated and the residue was purified over silica gel (2-20% MeOH in CH₂Cl₂) to afford (R)-1-(dimethylamino)-3-(4-(4-(1-(pentan-3-yl)-1H-pyrazol-4-yl)pyrazolo[1,5-a]pyrazin-6-yl)-1H-pyrazol-1-yl)propan-2-ol (18.1 mg, 0.0428 mmol, 53.9% yield). Mass spectrum (apci) m/z=423.3 (M+H). ¹H NMR (d₆-DMSO) δ 8.99 (d, J=0.8 Hz, 1H), 8.73 (s, 1H), 8.38 (s, 1H), 8.34 (s, 1H), 8.16 (d, J=2.3 Hz, 1H), 8.15 (s, 1H), 7.36 (dd, J=2.5, 1.0 Hz, 1H), 4.96 (m, 1H), 4.27 (dd, J=13.1, 2.9 Hz, 1H), 4.14 (m, 1H), 4.08-3.95 (m, 2H), 2.28 (t, J=5.7 Hz, 2H), 2.21 (s, 6H), 1.97-1.80 (m, 4H), 0.75 (t, J=7.2 Hz, 6H).

The following compounds were prepared according to the procedure described for Example 99.

| Example | Structure | Name | Data |
|---|---|---|---|
| 100 | 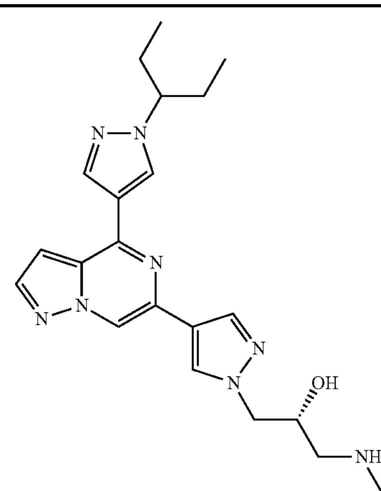 | (R)-1-(methylamino)-3-(4-(4-(1-(pentan-3-yl)-1H-pyrazol-4-yl)pyrazolo[1,5-a]pyrazin-6-yl)-1H-pyrazol-1-yl)propan-2-ol | Mass spectrum (apci) m/z = 409.2 (M + H) |

| Example | Structure | Name | Data |
|---|---|---|---|
| 101 | 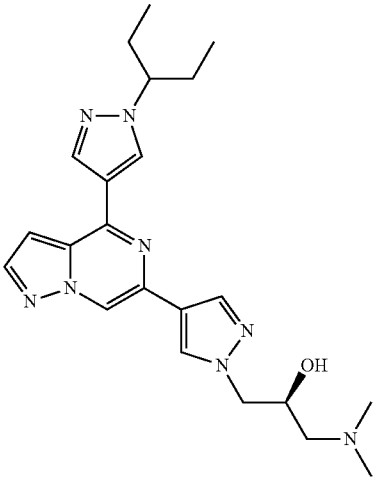 [SMILES: CCC(CC)n1cc(-c2nc(-c3cnn(C[C@@H](O)CN(C)C)c3)cn3nccc23)cn1] | (S)-1-(dimethylamino)-3-(4-(4-(1-(pentan-3-yl)-1H-pyrazol-4-yl)pyrazolo[1,5-a]pyrazin-6-yl)-1H-pyrazol-1-yl)propan-2-ol | Mass spectrum (apci) m/z = 423.3 (M + H) |
| 102 | 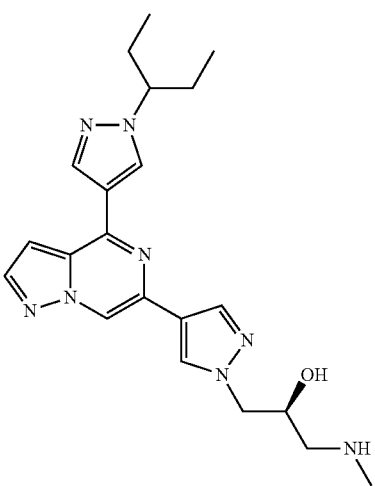 [SMILES: CCC(CC)n1cc(-c2nc(-c3cnn(C[C@@H](O)CNC)c3)cn3nccc23)cn1] | (S)-1-(methylamino)-3-(4-(4-(1-(pentan-3-yl)-1H-pyrazol-4-yl)pyrazolo[1,5-a]pyrazin-6-yl)-1H-pyrazol-1-yl)propan-2-ol | Mass spectrum (apci) m/z = 409.2 (M + H) |
| 103 | 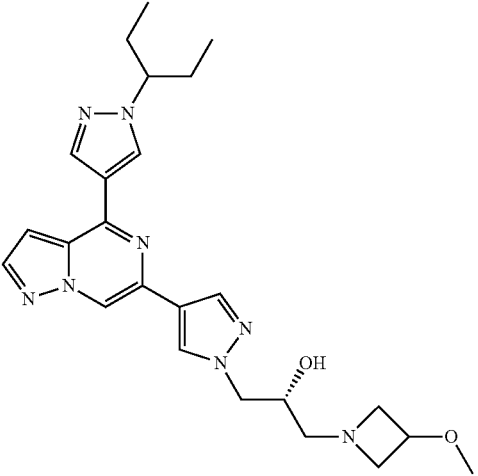 [SMILES: CCC(CC)n1cc(-c2nc(-c3cnn(C[C@H](O)CN4CC(OC)C4)c3)cn3nccc23)cn1] | (R)-1-(3-methoxyazetidin-1-yl)-3-(4-(4-(1-(pentan-3-yl)-1H-pyrazol-4-yl)pyrazolo[1,5-a]pyrazin-6-yl)-1H-pyrazol-1-yl)propan-2-ol | Mass spectrum (apci) m/z = 465.3 (M + H) |

-continued

| Example | Structure | Name | Data |
|---|---|---|---|
| 104 | 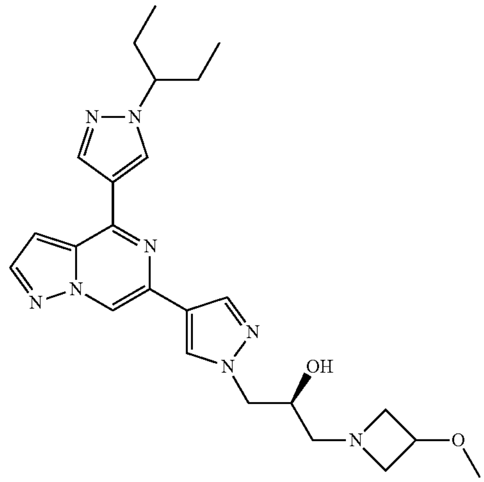 [SMILES: CCC(CC)n1cc(-c2nc(-c3cnn(C[C@@H](O)CN4CC(OC)C4)c3)cn3nccc23)cn1] | (S)-1-(3-methoxyazetidin-1-yl)-3-(4-(4-(1-(pentan-3-yl)-1H-pyrazol-4-yl)pyrazolo[1,5-a]pyrazin-6-yl)-1H-pyrazol-1-yl)propan-2-ol | Mass spectrum (apci) m/z = 465.3 (M + H) |
| 105 | 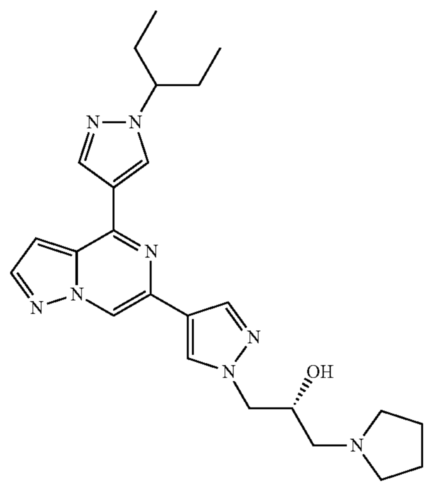 [SMILES: CCC(CC)n1cc(-c2nc(-c3cnn(C[C@H](O)CN4CCCC4)c3)cn3nccc23)cn1] | (R)-1-(4-(4-(1-(pentan-3-yl)-1H-pyrazol-4-yl)pyrazolo[1,5-a]pyrazin-6-yl)-1H-pyrazol-1-yl)-3-(pyrrolidin-1-yl)propan-2-ol | Mass spectrum (apci) m/z = 449.3 (M + H) |
| 106 | 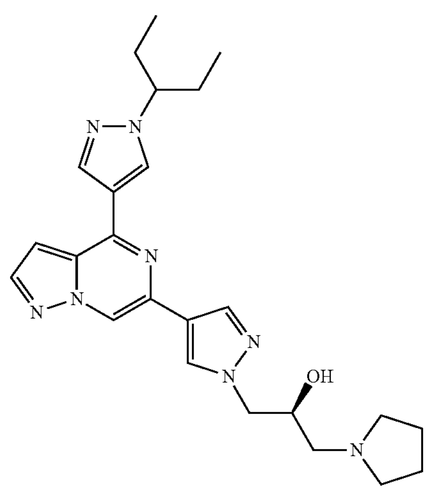 [SMILES: CCC(CC)n1cc(-c2nc(-c3cnn(C[C@@H](O)CN4CCCC4)c3)cn3nccc23)cn1] | (S)-1-(4-(4-(1-(pentan-3-yl)-1H-pyrazol-4-yl)pyrazolo[1,5-a]pyrazin-6-yl)-1H-pyrazol-1-yl)-3-(pyrrolidin-1-yl)propan-2-ol | Mass spectrum (apci) m/z = 449.3 (M + H) |

Example 107

(R)-1-methoxy-3-(4-(4-(1-(pentan-3-yl)-1H-pyrazol-4-yl)pyrazolo[1,5-a]pyrazin-6-yl)-1H-pyrazol-1-yl)propan-2-ol

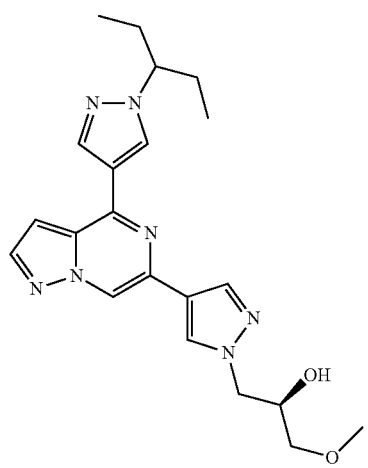 [SMILES: CCC(CC)n1cc(-c2nc(-c3cnn(C[C@@H](O)COC)c3)cn3nccc23)cn1]

4-(1-(Pentan-3-yl)-1H-pyrazol-4-yl)-6-(1H-pyrazol-4-yl)pyrazolo[1,5-a]pyrazine (40 mg, 0.124 mmol) was dissolved in DMF (0.5 mL) and 60% sodium hydride (5.97 mg, 0.149 mmol) was added, followed by (R)-2-(methoxymethyl)oxirane (14.5 µL, 0.162 mmol). The reaction mixture was heated to 50° C. overnight. The reaction was cooled to ambient temperature, diluted with water (3 mL) and extracted with EtOAc. The organic layer was dried over Na$_2$SO$_4$, filtered and concentrated. The residue was purified over silica gel (2% MeOH in EtOAc) to afford (R)-1-methoxy-3-(4-(4-(1-(pentan-3-yl)-1H-pyrazol-4-yl)pyrazolo[1,5-a]pyrazin-6-yl)-1H-pyrazol-1-yl)propan-2-ol (29.5 mg, 0.0720 mmol, 57.9% yield). Mass spectrum (apci) m/z=410.2 (M+H). $^1$H NMR (CDCl$_3$) δ 8.45 (m, 1H), 8.26 (s, 1H), 8.17 (s, 1H), 8.03 (m, 2H), 7.99 (s, 1H), 6.95 (dd, J=2.5, 1.0 Hz, 1H), 4.37 (dd, J=13.5, 3.1 Hz, 1H), 4.31-4.20 (m, 2H), 4.03 (m, 1H), 3.45-3.55 (m, 5H), 2.06-1.85 (m, 4H), 0.86 (t, J=7.2 Hz, 6H).

The following compounds were prepared according to the procedure described for Example 107.

| Example | Structure | Name | Data |
|---|---|---|---|
| 108 | 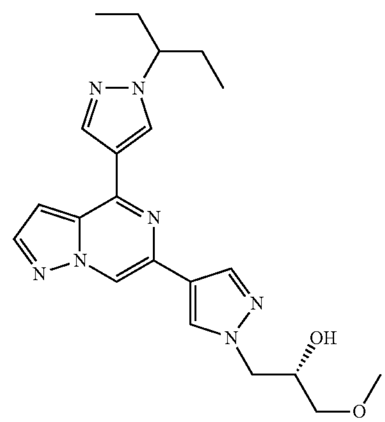 [SMILES: CCC(CC)n1cc(-c2nc(-c3cnn(C[C@H](O)COC)c3)cn3nccc23)cn1] | (S)-1-methoxy-3-(4-(4-(1-(pentan-3-yl)-1H-pyrazol-4-yl)pyrazolo[1,5-a]pyrazin-6-yl)-1H-pyrazol-1-yl)propan-2-ol | Mass spectrum (apci) m/z = 410.2 (M + H) |
| 109 | 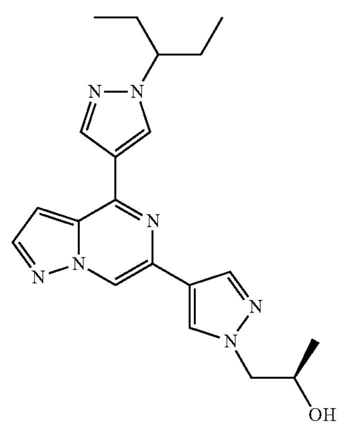 [SMILES: CCC(CC)n1cc(-c2nc(-c3cnn(C[C@@H](C)O)c3)cn3nccc23)cn1] | (R)-1-(4-(4-(1-(pentan-3-yl)-1H-pyrazol-4-yl)pyrazolo[1,5-a]pyrazin-6-yl)-1H-pyrazol-1-yl)propan-2-ol | Mass spectrum (apci) m/z = 380.2 (M + H) |

-continued

| Example | Structure | Name | Data |
|---|---|---|---|
| 110 | 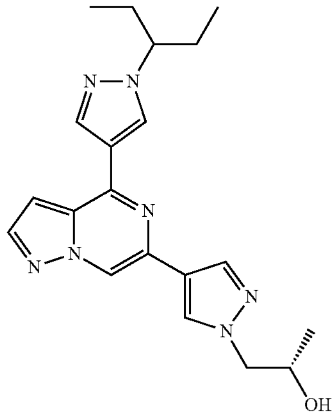 [SMILES: CCC(CC)n1cc(-c2nc(-c3cnn(C[C@H](C)O)c3)cn3nccc23)cn1] | (S)-1-(4-(4-(1-(pentan-3-yl)-1H-pyrazol-4-yl)pyrazolo[1,5-a]pyrazin-6-yl)-1H-pyrazol-1-yl)propan-2-ol | Mass spectrum (apci) m/z = 380.2 (M + H) |
| 111 | 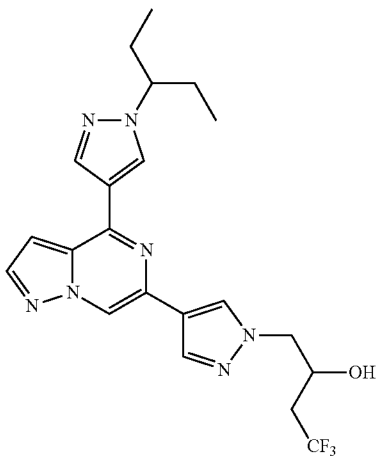 [SMILES: CCC(CC)n1cc(-c2nc(-c3cnn(CC(O)CC(F)(F)F)c3)cn3nccc23)cn1] | 4,4,4-trifluoro-1-(4-(4-(1-(pentan-3-yl)-1H-pyrazol-4-yl)pyrazolo[1,5-a]pyrazin-6-yl)-1H-pyrazol-1-yl)butan-2-ol | Mass spectrum (apci) m/z = 448.2 (M + H) |
| 112 | 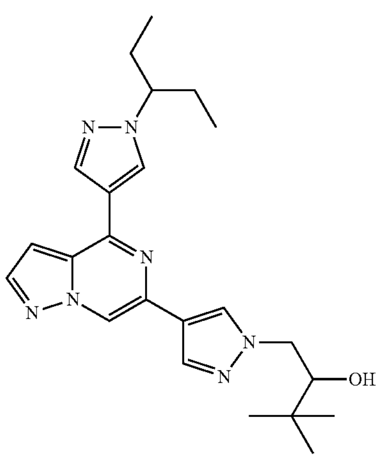 [SMILES: CCC(CC)n1cc(-c2nc(-c3cnn(CC(O)C(C)(C)C)c3)cn3nccc23)cn1] | 3,3-dimethyl-1-(4-(4-(1-(pentan-3-yl)-1H-pyrazol-4-yl)pyrazolo[1,5-a]pyrazin-6-yl)-1H-pyrazol-1-yl)butan-2-ol | Mass spectrum (apci) m/z = 422.3 (M + H) |

| Example | Structure | Name | Data |
| --- | --- | --- | --- |
| 113 | 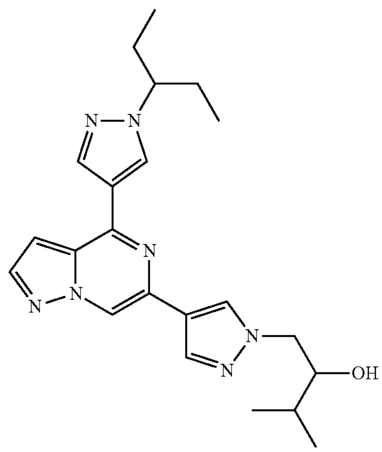 [SMILES: CCC(CC)n1cc(-c2nc(-c3cnn(CC(O)C(C)C)c3)cn3nccc23)cn1] | 3-methyl-1-(4-(4-(1-(pentan-3-yl)-1H-pyrazol-4-yl)pyrazolo[1,5-a]pyrazin-6-yl)-1H-pyrazol-1-yl)butan-2-ol | Mass spectrum (apci) m/z = 408.3 (M + H) |
| 114 | 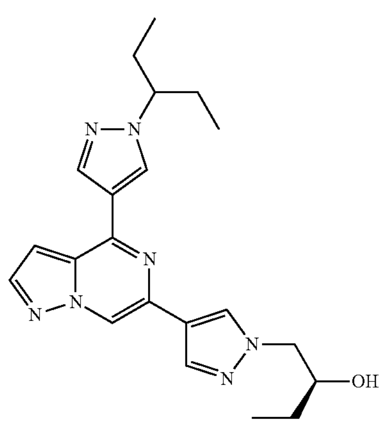 [SMILES: CCC(CC)n1cc(-c2nc(-c3cnn(C[C@@H](O)CC)c3)cn3nccc23)cn1] | (S)-1-(4-(4-(1-(pentan-3-yl)-1H-pyrazol-4-yl)pyrazolo[1,5-a]pyrazin-6-yl)-1H-pyrazol-1-yl)butan-2-ol | Mass spectrum (apci) m/z = 394.2 (M + H) |

-continued

| Example | Structure | Name | Data |
|---------|-----------|------|------|
| 115 | 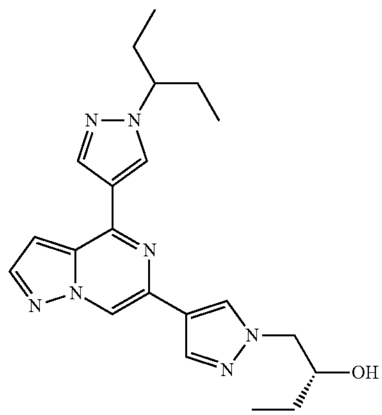 [SMILES: CCC(CC)n1cc(-c2nc(-c3cnn(C[C@H](O)CC)c3)cn3nccc23)cn1] | (R)-1-(4-(4-(1-(pentan-3-yl)-1H-pyrazol-4-yl)pyrazolo[1,5-a]pyrazin-6-yl)-1H-pyrazol-1-yl)butan-2-ol | Mass spectrum (apci) m/z = 394.2 (M + H) |
| 116 | 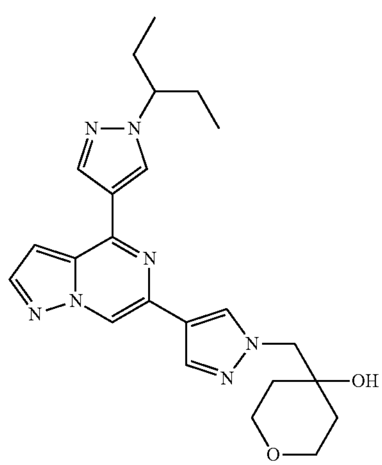 [SMILES: CCC(CC)n1cc(-c2nc(-c3cnn(CC4(O)CCOCC4)c3)cn3nccc23)cn1] | 4-((4-(4-(1-(pentan-3-yl)-1H-pyrazol-4-yl)pyrazolo[1,5-a]pyrazin-6-yl)-1H-pyrazol-1-yl)methyl)tetrahydro-2H-pyran-4-ol | Mass spectrum (apci) m/z = 436.2 (M + H) |

Example 117

2-methyl-1-(4-(4-(1-(pentan-3-yl)-1H-pyrazol-4-yl)pyrazolo[1,5-a]pyrazin-6-yl)-1H-pyrazol-1-yl)propan-2-ol

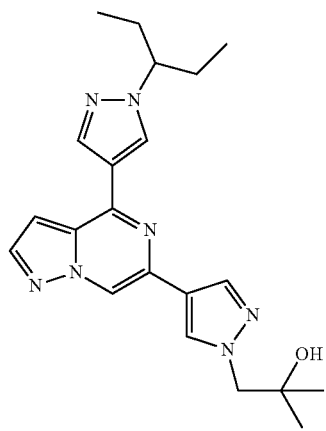 [SMILES: CCC(CC)n1cc(-c2nc(-c3cnn(CC(C)(C)O)c3)cn3nccc23)cn1]

To a slurry of 4-(1-(pentan-3-yl)-1H-pyrazol-4-yl)-6-(1H-pyrazol-4-yl)pyrazolo[1,5-a]pyrazine (0.050 g, 0.16 mmol) in DMF (0.5 mL) was added Cs$_2$CO$_3$ (0.10 g, 0.31 mmol) and 2,2-dimethyloxirane (0.022 g, 0.31 mmol) and the reaction mixture was heated to 70° C. overnight. The reaction mixture was partitioned between EtOAc and water. The combined organic phases were separated and washed with brine, dried over MgSO$_4$ and concentrated in vacuo. The material was purified over silica gel (0-10% MeOH/CH$_2$Cl$_2$) to afford 2-methyl-1-(4-(4-(1-(pentan-3-yl)-1H-pyrazol-4-yl)pyrazolo[1,5-a]pyrazin-6-yl)-1H-pyrazol-1-yl)propan-2-ol (0.011 g, 0.028 mmol, 18% yield). Mass spectrum (apci) m/z=394.2 (M+H). $^1$H NMR (CDCl$_3$) δ 8.47 (d J=1.0 Hz, 1H), 8.27 (s, 1H), 8.20 (s, 1H), 8.04 (d, J=2.5 Hz, 1H), 8.03 (s, 1H), 8.02 (s, 1H), 6.96 (dd, J=2.5, 1.0 Hz, 1H), 4.16 (s, 2H), 4.03 (m, 1H), 2.05-1.85 (m, 4H), 1.24 (s, 6H), 0.86 (t, J=7.4 Hz, 6H).

Example 118 trans-4-(4-(4-(1-(pentan-3-yl)-1H-pyrazol-4-yl)pyrazolo[1,5-a]pyrazin-6-yl)-1H-pyrazol-1-yl)cyclohexanol

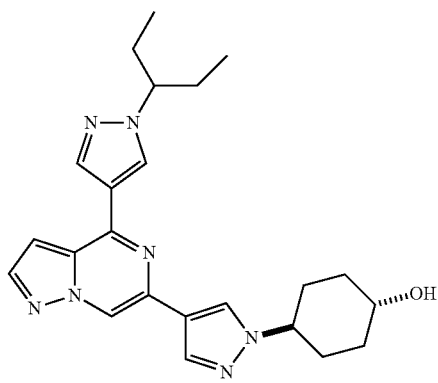

Step A:

To a solution of 4-(1-(pentan-3-yl)-1H-pyrazol-4-yl)-6-(1H-pyrazol-4-yl)pyrazolo[1,5-a]pyrazine (0.100 g, 0.311 mmol) and 1,4-dioxaspiro[4.5]dec-8-yl 4-methylbenzenesulfonate (0.194 g, 0.622 mmol) in DMF (1.56 mL, 0.311 mmol) was added Cs$_2$CO$_3$ (0.203 g, 0.622 mmol) and the mixture was stirred at 80° C. for 6 hours. The reaction mixture was cooled to ambient temperature and then diluted with water (15 mL) and stirred for 10 minutes. The reaction mixture was extracted with EtOAc and the combined organic extracts were washed with brine, dried over Na$_2$SO$_4$, filtered and concentrated. The residue was purified over silica gel (70% EtOAc/hexanes) to afford 6-(1-(1,4-dioxaspiro[4.5]decan-8-yl)-1H-pyrazol-4-yl)-4-(1-(pentan-3-yl)-1H-pyrazol-4-yl)pyrazolo[1,5-a]pyrazine (120 mg, 83% yield) as a white foam.

Step B:

A solution of 6-(1-(1,4-dioxaspiro[4.5]decan-8-yl)-1H-pyrazol-4-yl)-4-(1-(pentan-3-yl)-1H-pyrazol-4-yl)pyrazolo[1,5-a]pyrazine (0.114 g, 0.247 mmol) in acetone (1.23 mL, 0.247 mmol) and HCl (0.823 mL, 2.47 mmol, 3.0 M) was stirred at ambient temperature for 4 hours. The reaction mixture was treated with 3N NaOH (0.8 mL) and diluted with EtOAc (10 mL) and the layers were separated. The reaction mixture was extracted with EtOAc and the combined organic extracts were dried over Na$_2$SO$_4$, filtered and concentrated. The residue was purified over silica gel (70% EtOAc/hexanes) to afford 4-(4-(4-(1-(pentan-3-yl)-1H-pyrazol-4-yl)pyrazolo[1,5-a]pyrazin-6-yl)-1H-pyrazol-1-yl)cyclohexanone (94 mg, 91% yield) as a white foam.

Step C:

A round bottom flask equipped with a stir bar and nitrogen inlet was charged with 4-(4-(4-(1-(pentan-3-yl)-1H-pyrazol-4-yl)pyrazolo[1,5-a]pyrazin-6-yl)-1H-pyrazol-1-yl)cyclohexanone (0.090 g, 0.22 mmol) and MeOH (2.2 mL, 0.22 mmol). The reaction mixture was chilled to 0° C. and NaBH$_4$ (0.016 g, 0.43 mmol) was added in one portion. The reaction mixture was allowed to warm to room temperature over 1.5 hours. The reaction mixture was diluted with a saturated aqueous ammonium chloride solution, and extracted with EtOAc. The combined extracts were dried over Na$_2$SO$_4$, filtered and concentrated. The residue was purified over silica gel (5% MeOH/CH$_2$Cl$_2$) to afford trans-4-(4-(4-(1-(pentan-3-yl)-1H-pyrazol-4-yl)pyrazolo[1,5-a]pyrazin-6-yl)-1H-pyrazol-1-yl)cyclohexanol (38 mg, 42% yield) as a white foam. Mass spectrum (apci) m/z=420.2 (M+H). $^1$H NMR (CDCl$_3$) δ 8.45 (s, 1H), 8.27 (s, 1H), 8.17 (s, 1H), 8.03 (s, J=1.7 Hz, 1H), 8.00 (s, 1H), 7.95 (s, 1H), 6.95 (m, 1H), 4.21 (tt, J=11.5, 3.7 Hz, 1H), 4.03 (m, 1H), 3.79 (m, 1H), 2.27 (m, 2H), 2.17 (m, 2H), 2.06-1.85 (m, 6H), 1.54 (m, 2H), 0.86 (t, J=7.4 Hz, 6H).

The following compounds were prepared according to the procedure described for Example 118.

| Example | Structure | Name | Data |
|---|---|---|---|
| 119 | 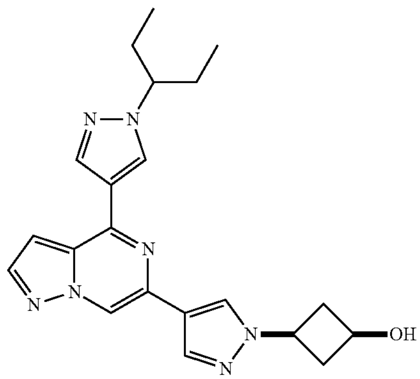 | cis-3-(4-(4-(1-(pentan-3-yl)-1H-pyrazol-4-yl)pyrazolo[1,5-a]pyrazin-6-yl)-1H-pyrazol-1-yl)cyclobutanol | Mass spectrum (apci) m/z = 392.2 (M + H) |
| 120 | 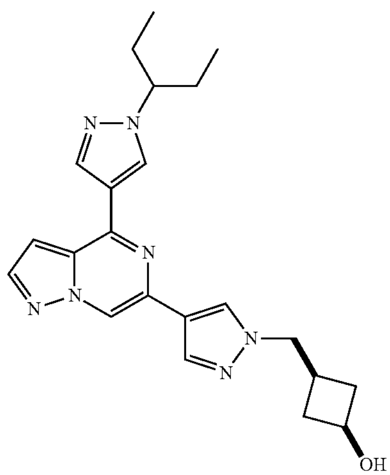 | (1s,3s)-3-((4-(4-(1-(pentan-3-yl)-1H-pyrazol-4-yl)pyrazolo[1,5-a]pyrazin-6-yl)-1H-pyrazol-1-yl)methyl)cyclobutanol | Mass spectrum (apci) m/z = 406.2 (M + H) |

Example 121 cis-4-(4-(4-(1-(pentan-3-yl)-1H-pyrazol-4-yl)pyrazolo[1,5-a]pyrazin-6-yl)-1H-pyrazol-1-yl)cyclohexanol

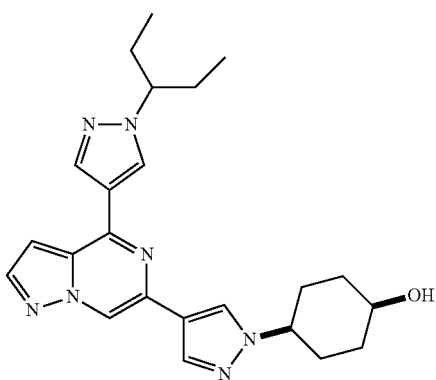

To a vial containing trans-4-(4-(4-(1-(pentan-3-yl)-1H-pyrazol-4-yl)pyrazolo[1,5-a]pyrazin-6-yl)-1H-pyrazol-1-yl)cyclohexanol (0.028 g, 0.0667 mmol) was added THF (1 mL). 2-Chloroacetic acid (0.00946 g, 0.100 mmol) was added followed by PPh$_3$ (0.0263 g, 0.100 mmol). The solution was cooled to 0° C. and diethyl azodicarboxylate (0.0158 mL, 0.100 mmol) was added as a THF solution (0.5 mL). The solution was protected from light and stirred for 4 hours as it slowly warmed to ambient temperature. The THF was then removed in vacuo and replaced with EtOAc. The solution was washed with a saturated aqueous NaHCO$_3$ solution, dried over Na$_2$SO$_4$, filtered and concentrated. The crude product was dissolved in dioxane (1 mL) and water was added (1 mL). A 1N NaOH solution was added until the pH reached >10 (0.5 mL). The mixture was stirred for 1 hour and the reaction mixture was quenched with 1N KHSO$_4$ (1 mL). The reaction mixture was extracted with EtOAc. The combined organic phases were washed with a saturated aqueous NaHCO$_3$ solution, dried over Na$_2$CO$_3$, filtered and concentrated. The residue was purified over silica gel (40% acetone/hexanes), followed by a second purification by silica gel chromatography (5% MeOH/CH$_2$Cl$_2$) to afford cis-4-(4-(4-(1-(pentan-3-yl)-1H-pyrazol-4-yl)pyrazolo[1,5-a]pyrazin-6-yl)-1H-pyrazol-1-yl)cyclohexanol (10.5 mg, 35% yield) as an off-white solid. Mass spectrum (apci) m/z=420.2 (M+H). $^1$H NMR (CDCl$_3$) δ 8.46 (s, 1H), 8.27 (s, 1H), 8.19 (s, 1H), 8.07 (s, 1H), 8.03 (d, J=2.5 Hz, 1H), 7.95 (s, 1H), 6.95 (dd, J=2.5, 1.0 Hz, 1H), 4.25 (tt, J=11.1, 3.7 Hz, 1H), 4.14 (m, 1H), 4.04 (m, 1H), 2.28 (qd, J=12.9, 3.7 Hz, 2H), 2.09-1.85 (m, 8H), 1.75 (tt, J=13.7, 3.5 Hz, 2H), 0.86 (t, J=7.2 Hz, 6H).

Examples 122 and 123

((1s,3s)-3-((4-(4-(1-(pentan-3-yl)-1H-pyrazol-4-yl)pyrazolo[1,5-a]pyrazin-6-yl)-1H-pyrazol-1-yl)methyl)cyclobutyl)methanol and ((1r,3r)-3-((4-(4-(1-(pentan-3-yl)-1H-pyrazol-4-yl)pyrazolo[1,5-a]pyrazin-6-yl)-1H-pyrazol-1-yl)methyl)cyclobutyl)methanol

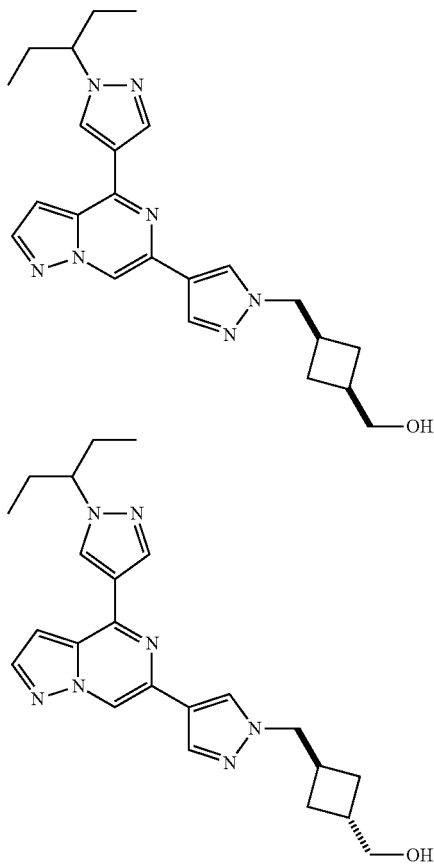

Step A:

To a solution of 4-(1-(pentan-3-yl)-1H-pyrazol-4-yl)-6-(1H-pyrazol-4-yl)pyrazolo[1,5-a]pyrazine (0.100 g, 0.311 mmol) and benzyl 3-((tosyloxy)methyl)cyclobutanecarboxylate (0.233 g, 0.622 mmol) in DMF (1.56 mL, 0.311 mmol) was added cesium carbonate (0.203 g, 0.622 mmol) and the mixture was stirred at 80° C. for 20 hours. The reaction mixture was diluted with water (15 mL) and stirred for 10 minutes. The mixture was extracted with EtOAc and the combined organic extracts were washed with brine, dried over Na$_2$SO$_4$, filtered and concentrated. The residue was purified over silica gel (50% EtOAc/hexanes) to afford benzyl 3-((4-(4-(1-(pentan-3-yl)-1H-pyrazol-4-yl)pyrazolo[1,5-a]pyrazin-6-yl)-1H-pyrazol-1-yl)methyl)cyclobutanecarboxylate (138 mg, 84.7% yield) as a pale orange oil.

Step B:

To a solution of benzyl 3-((4-(4-(1-(pentan-3-yl)-1H-pyrazol-4-yl)pyrazolo[1,5-a]pyrazin-6-yl)-1H-pyrazol-1-yl)methyl)cyclobutanecarboxylate (0.075 g, 0.14 mmol) in THF (1.4 mL, 0.14 mmol) at 0° C. was added diisobutylaluminum hydride (0.46 mL, 0.46 mmol) (1.0M Hexanes). The reaction mixture was stirred for 1 hour and then quenched with saturated aqueous Na/K tartrate solution. The reaction mixture was stirred and the layers were separated. The aqueous phase was extracted with EtOAc. The combined organic extracts were dried over Na$_2$SO$_4$, filtered and concentrated. The residue was purified over silica gel (5% MeOH/CH$_2$Cl$_2$) to afford (3-((4-(4-(1-(pentan-3-yl)-1H-pyrazol-4-yl)pyrazolo[1,5-a]pyrazin-6-yl)-1H-pyrazol-1-yl)methyl)cyclobutyl)methanol (53 mg, 88% yield) as a mixture of the (1s,3s) and (1r, 3r) diastereomers as a white foam.

Step C:

The two diastereomers prepared in Step B were separated by a Chiral Tech IA column (4.6 mm×250 mm, 5 micron) eluting with 20% EtOH in hexanes at 1 mL/min. Peak A (cis conformation (1s, 3s)): retention time=15.5 min; Mass spectrum (apci) m/z=420.2 (M+H); $^1$H NMR (CDCl$_3$) δ 8.47 (s, 1H), 8.29 (s, 1H), 8.19 (s, 1H), 8.05 (d, J=2.4 Hz, 1H), 7.97 (br s, 2H), 6.97 (m, 1H), 4.20 (d, J=7.1 Hz, 2H), 4.06 (tt, J=9.5, 4.7 Hz, 1H), 3.59 (d, J=5.9 Hz, 2H), 2.83 (m, 1H), 2.47 (m, 1H), 2.22 (m, 2H), 1.93 (m, 4H), 1.68 (m, 2H), 0.88 (t, J=7.7 Hz, 6H). Peak B (trans conformation (1r, 3r)): retention time=18.1 min; Mass spectrum (apci) m/z=420.2 (M+H). $^1$H NMR (CDCl$_3$) δ 8.47 (s, 1H), 8.29 (s, 1H), 8.19 (s, 1H), 8.05 (d, J=2.4 Hz, 1H), 7.96 (br s, 2H), 6.97 (m, 1H), 4.29 (d, J=7.1 Hz, 2H), 4.06 (tt, J=9.5, 4.7 9.5 Hz, 1H), 3.71 (d, J=7.1 Hz, 2H), 2.93 (m, 1H), 2.56 (m, 1H), 2.02 (m, 8H), 0.88 (t, J=7.7 Hz, 6H).

Example 124

2-methyl-2-(4-(4-(1-(pentan-3-yl)-1H-pyrazol-4-yl)pyrazolo[1,5-a]pyrazin-6-yl)-1H-pyrazol-1-yl)propan-1-ol

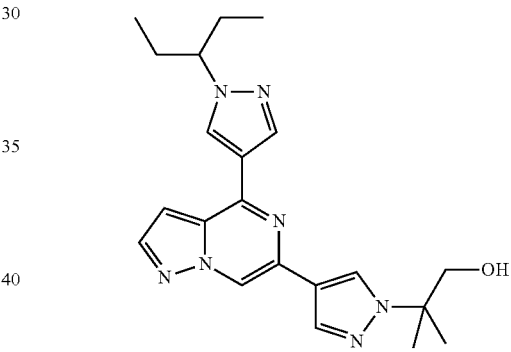

Step A:

To a stirred solution of 4-(1-(pentan-3-yl)-1H-pyrazol-4-yl)-6-(1H-pyrazol-4-yl)pyrazolo[1,5-a]pyrazine (64 mg, 0.1991 mmol) in 600 µL of DMF at room temperature in a capped reaction vial was added ethyl 2-bromo-2-methylpropanoate (32.15 µL, 0.2191 mmol), followed by Cs$_2$CO$_3$ (35.85 mg, 0.5974 mmol). The reaction mixture was capped and heated to 100° C. After 18 hours, another 3 equivalents of cesium carbonate and 1.1 equivalents of ethyl 2-bromo-2-methylpropanoate were added and the reaction was again heated at 100° C. overnight. The reaction mixture was partitioned between ethyl acetate (15 mL) and water (15 mL). The combined organic phases were isolated and washed with water and brine. The combined organic phases were dried over MgSO$_4$, filtered and concentrated. The residue was purified over silica gel (10 to 50% EtOAc in hexanes) to afford ethyl 2-methyl-2-(4-(4-(1-(pentan-3-yl)-1H-pyrazol-4-yl)pyrazolo[1,5-a]pyrazin-6-yl)-1H-pyrazol-1-yl)propanoate (51 mg, 58% yield).

Step B:

To a stirred solution of ethyl 2-methyl-2-(4-(4-(1-(pentan-3-yl)-1H-pyrazol-4-yl)pyrazolo[1,5-a]pyrazin-6-yl)-1H-pyrazol-1-yl)propanoate (51 mg, 0.12 mmol) in 500 µL of anhydrous methanol at room temperature under nitrogen was added NaBH$_4$ (8.1 mg, 0.35 mmol) as a solid. After 1 hour, another 3 equivalents of sodium borohydride was added. The reaction mixture was quenched with 1 mL of saturated ammonium chloride solution and stirred for 5 minutes. The clear solution was diluted with 15 mL of ethyl acetate and shaken. The organic layer was isolated, washed with brine, dried over MgSO₄, filtered and concentrated. The residue was purified over silica gel (20-80% EtOAc in hexanes) to afford 2-methyl-2-(4-(4-(1-(pentan-3-yl)-1H-pyrazol-4-yl)pyrazolo[1,5-a]pyrazin-6-yl)-1H-pyrazol-1-yl)propan-1-ol (28 mg, 55% yield) as a white foam. Mass spectrum (apci) m/z=394.2 (M+H). ¹H NMR (CDCl₃) δ 8.45 (d, J=1.0 Hz, 1H), 8.27 (s, 1H), 8.18 (s, 1H), 8.10 (s, 1H), 8.03 (d, J=2.5 Hz, 1H), 7.95 (s, 1H), 6.95 (dd, J=2.5, 1.0 Hz, 1H), 4.02 (m, 1H), 3.86 (m, 2H), 3.76 (m, 1H), 2.06-1.85 (m, 4H), 1.63 (s, 6H), 0.85 (t, J=7.4 Hz, 6H).

Example 125

(S)-2-(4-(4-(1-(pentan-3-yl)-1H-pyrazol-4-yl)pyrazolo[1,5-a]pyrazin-6-yl)-1H-pyrazol-1-yl)propan-1-ol

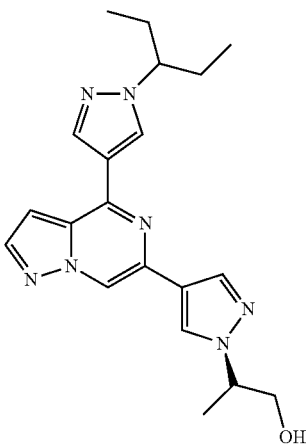

Step A:

To a slurry of 4-(1-(pentan-3-yl)-1H-pyrazol-4-yl)-6-(1H-pyrazol-4-yl)pyrazolo[1,5-a]pyrazine (0.05 g, 0.2 mmol) in DMF (0.5 mL) was added (S)-tert-butyl(2-chloropropoxy)dimethylsilane (0.06 g, 0.3 mmol) and Cs₂CO₃ (0.1 g, 0.3 mmol) and the reaction mixture was heated to 70° C. overnight. The reaction mixture was partitioned between EtOAc and water. The combined organic phases were separated and washed with brine, dried over MgSO₄ and concentrated in vacuo. The residue was purified over silica gel (0-100% EtOAc/CH₂Cl₂) to afford (S)-6-(1-(1-((tert-butyldimethylsilyl)oxy)propan-2-yl)-1H-pyrazol-4-yl)-4-(1-(pentan-3-yl)-1H-pyrazol-4-yl)pyrazolo[1,5-a]pyrazine (0.05 g, 0.1 mmol, 65% yield).

Step B:

To (S)-6-(1-(1-((tert-butyldimethylsilyl)oxy)propan-2-yl)-1H-pyrazol-4-yl)-4-(1-(pentan-3-yl)-1H-pyrazol-4-yl)pyrazolo[1,5-a]pyrazine (0.05 g, 0.1 mmol) was added HCl in isopropyl alcohol (5 M, 2 mL) and the reaction mixture was heated to 80° C. overnight. The reaction mixture was concentrated in vacuo. The resulting material was partitioned between EtOAc and 1N NaOH. The combined organic phases were washed with brine, dried over MgSO₄ and concentrated in vacuo. The residue was purified over silica gel (0-10% MeOH/CH₂Cl₂) to afford (S)-2-(4-(4-(1-(pentan-3-yl)-1H-pyrazol-4-yl)pyrazolo[1,5-a]pyrazin-6-yl)-1H-pyrazol-1-yl)propan-1-ol (0.022 g, 0.058 mmol, 69% yield). Mass spectrum (apci) m/z=380.2 (M+H). ¹H NMR (CDCl₃) δ 8.44 (d, J=0.8 Hz, 1H), 8.25 (s, 1H), 8.18 (s, 1H), 8.02 (m, 2H), 7.98 (s, 1H), 6.94 (dd, J=2.5, 1.0 Hz, 1H), 4.32-4.22 (m, 2H), 4.11-3.94 (m, 2H), 2.06-1.85 (m, 4H), 1.28 (d, J=6.3 Hz, 3H), 0.86 (t, J=7.4 Hz, 6H).

The following compound was prepared according to the procedure described for Example 125.

| Example | Structure | Name | Data |
|---|---|---|---|
| 126 | 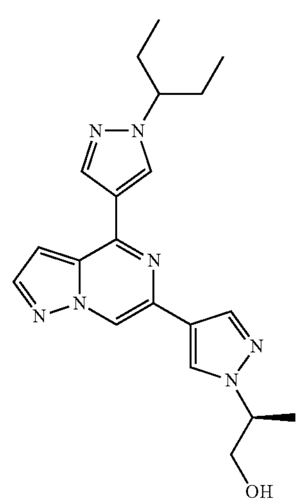 [SMILES: CCC(CC)n1cc(-c2nc(-c3cnn([C@@H](C)CO)c3)cn3nccc23)cn1] | (S)-2-(4-(4-(1-(pentan-3-yl)-1H-pyrazol-4-yl)pyrazolo[1,5-a]pyrazin-6-yl)-1H-pyrazol-1-yl)propan-1-ol | Mass spectrum (apci) m/z = 380.2 (M + H) |

Example 127

(S)-2-((4-(4-(1-(pentan-3-yl)-1H-pyrazol-4-yl)pyrazolo[1,5-a]pyrazin-6-yl)-1H-pyrazol-1-yl)methyl)morpholine trifluoroacetic acid

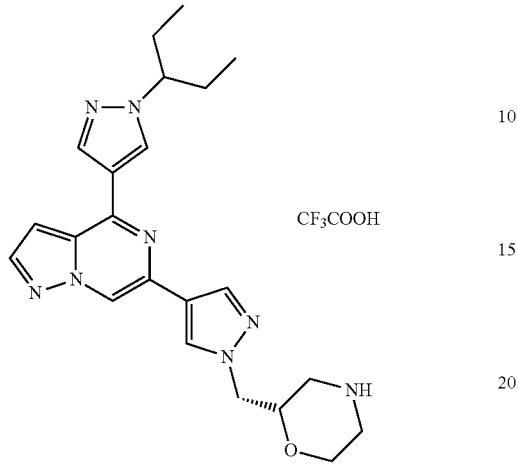

4-(1-(Pentan-3-yl)-1H-pyrazol-4-yl)-6-(1H-pyrazol-4-yl)pyrazolo[1,5-a]pyrazine (40 mg, 0.124 mmol), $Cs_2CO_3$ (122 mg, 0.373 mmol) and (S)-tert-butyl 2-(bromomethyl)morpholine-4-carboxylate (349 mg, 1.24 mmol) were placed in DMF (1 mL) and the reaction mixture was stirred for 24 hours. Water was added and the reaction mixture was extracted with EtOAc. The organic layer was concentrated and the residue was taken up in 10% MeOH in $CH_2Cl_2$. 4 N HCl (2 mL) was added and the reaction mixture was stirred for 1 hour. The reaction mixture was concentrated and the residue was purified by reverse phase chromatography (0-60% ACN:water with 0.1% TFA) to provide (S)-2-((4-(4-(1-(pentan-3-yl)-1H-pyrazol-4-yl)pyrazolo[1,5-a]pyrazin-6-yl)-1H-pyrazol-1-yl)methyl)morpholine (10.2 mg, 0.0243 mmol, 19.5% yield). $^1$H NMR (CDCl$_3$) δ 10.5 (br s, 1H), 9.85 (br s, 1H), 8.49 (s, 1H), 8.28 (s, 1H), 8.20 (s, 1H), 8.05 (d, J=2.5 Hz, 1H), 8.01 (s, 1H), 7.99 (s, 1H), 6.97 (dd, J=2.5, 0.8 Hz, 1H), 4.85 (br s, 2H), 4.36 (m, 2H), 4.24 (m, 1H), 4.10-3.90 (m, 3H), 3.40 (d, J=12.1 Hz, 1H), 3.21 (d, J=12.1 Hz, 1H), 3.03 (m, 1H), 2.82 (t, J=12.3 Hz, 1H), 2.04-1.84 (m, 4H), 0.84 (t, J=7.2 Hz, 6H).

The following compound was prepared according to the procedure described for Example 127.

| Example | Structure | Name | Data |
|---|---|---|---|
| 128 | 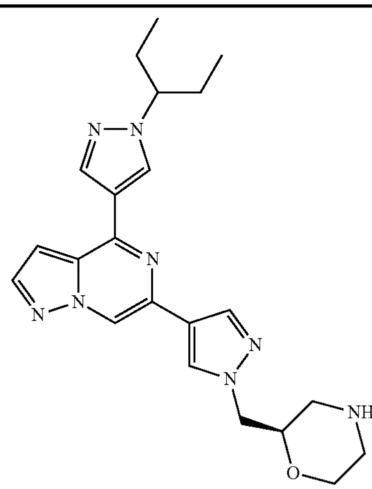 | (R)-2-((4-(4-(1-(pentan-3-yl)-1H-pyrazol-4-yl)pyrazolo[1,5-a]pyrazin-6-yl)-1H-pyrazol-1-yl)methyl)morpholine | Mass spectrum (apci) m/z = 421.3 (M + H) |

Example 129

(S)-2-(dimethylamino)-3-(4-(4-(1-(pentan-3-yl)-1H-pyrazol-4-yl)pyrazolo[1,5-a]pyrazin-6-yl)-1H-pyrazol-1-yl)propan-1-ol

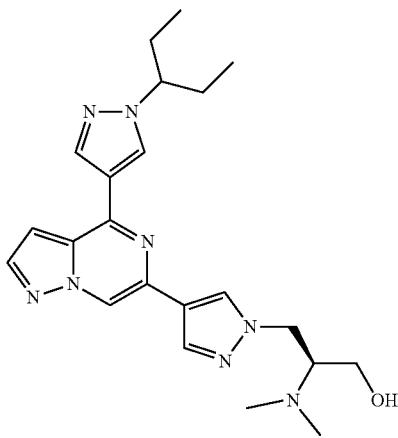 [SMILES: CCC(CC)n1cc(-c2nc(-c3cnn(C[C@@H](CO)N(C)C)c3)cn3nccc23)cn1]

Step A:

To a solution of 4-(1-(pentan-3-yl)-1H-pyrazol-4-yl)-6-(1H-pyrazol-4-yl)pyrazolo[1,5-a]pyrazine (0.100 g, 0.311 mmol) and (R)-tert-butyl 2,2-dimethyl-4-((tosyloxy)methyl) oxazolidine-3-carboxylate (0.240 g, 0.622 mmol) in DMF (1.56 mL, 0.311 mmol) was added $Cs_2CO_3$ (0.203 g, 0.622 mmol) and the mixture was stirred at 80° C. for 16 hours. The reaction mixture was cooled to ambient temperature, diluted with water (15 mL) and stirred for 10 minutes. The reaction mixture was extracted with EtOAc and the combined organic extracts were washed with brine, dried over $Na_2SO_4$, filtered and concentrated. The residue was purified over silica gel (50% EtOAc/hexanes) to afford (S)-tert-butyl 2,2-dimethyl-4-((4-(4-(1-(pentan-3-yl)-1H-pyrazol-4-yl)pyrazolo[1,5-a]pyrazin-6-yl)-1H-pyrazol-1-yl)methyl)oxazolidine-3-carboxylate (158 mg, 95% yield) as a thick colorless foaming oil.

Step B:

A solution of (S)-tert-butyl 2,2-dimethyl-4-((4-(4-(1-(pentan-3-yl)-1H-pyrazol-4-yl)pyrazolo[1,5-a]pyrazin-6-yl)-1H-pyrazol-1-yl)methyl)oxazolidine-3-carboxylate (0.148 g, 0.277 mmol) in acetone (1.38 mL, 0.277 mmol) and HCl (1.85 mL, 5.54 mmol, 3.0 M) was stirred at ambient temperature for 5 hours. The reaction mixture was treated with 3N NaOH (1.8 mL) and saturated aqueous $NaHCO_3$ and then diluted with EtOAc (10 mL) and the layers were separated. The aqueous layer was extracted with EtOAc and the combined organic extracts were dried over $Na_2SO_4$, filtered and concentrated. The crude (S)-2-amino-3-(4-(4-(1-(pentan-3-yl)-1H-pyrazol-4-yl)pyrazolo[1,5-a]pyrazin-6-yl)-1H-pyrazol-1-yl)propan-1-ol (91 mg, 83% yield) was used directly in the next step.

Step C:

To a solution of (S)-2-amino-3-(4-(4-(1-(pentan-3-yl)-1H-pyrazol-4-yl)pyrazolo[1,5-a]pyrazin-6-yl)-1H-pyrazol-1-yl)propan-1-ol (0.043 g, 0.1090 mmol) in dichloroethane (1.5 mL) was added formaldehyde (0.041 mL, 0.55 mmol) (37% aqueous). After stirring for 15 minutes the reaction mixture was treated with $NaBH(OAc)_3$ (0.115 g, 0.545 mmol) and the mixture was stirred for 2 hours at ambient temperature. The reaction mixture was diluted with water and the reaction mixture was extracted with EtOAc. The combined organic layers were dried over $Na_2SO_4$, filtered and concentrated. The residue was purified over silica gel (10% MeOH/$CH_2Cl_2$) to afford (S)-2-(dimethylamino)-3-(4-(4-(1-(pentan-3-yl)-1H-pyrazol-4-yl)pyrazolo[1,5-a]pyrazin-6-yl)-1H-pyrazol-1-yl)propan-1-ol (22 mg, 47% yield). Mass spectrum (apci) m/z=423.3 (M+H). $^1$H NMR ($CDCl_3$) δ 8.46 (d, J=0.8 Hz, 1H), 8.27 (s, 1H), 8.16 (s, 1H), 8.03 (d, J=2.5 Hz, 1H), 7.98 (s, 1H), 7.97 (s, 1H), 6.95 (dd, J=2.5, 1.0 Hz, 1H), 4.42 (dd, J=13.9, 5.7 Hz, 1H), 4.15 (dd, J=13.9, 7.8 Hz, 1H), 4.03 (m, 1H), 3.58 (dd, J=11.2, 4.9 Hz, 1H), 3.47 (dd, J=11.2, 8.2 Hz, 1H), 3.19 (m, 1H), 2.41 (s, 6H), 2.07-1.85 (m, 4H), 0.86 (t, J=7.2 Hz, 6H).

The following compounds were prepared according to the procedure described for Example 129.

| Example | Structure | Name | Data |
|---|---|---|---|
| 130 | 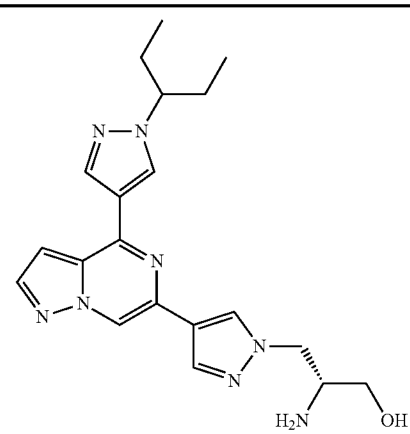 | (R)-2-amino-3-(4-(4-(1-(pentan-3-yl)-1H-pyrazol-4-yl)pyrazolo[1,5-a]pyrazin-6-yl)-1H-pyrazol-1-yl)propan-1-ol | Mass spectrum (apci) m/z = 395.2 (M + H) |

| Example | Structure | Name | Data |
|---------|-----------|------|------|
| 131 | 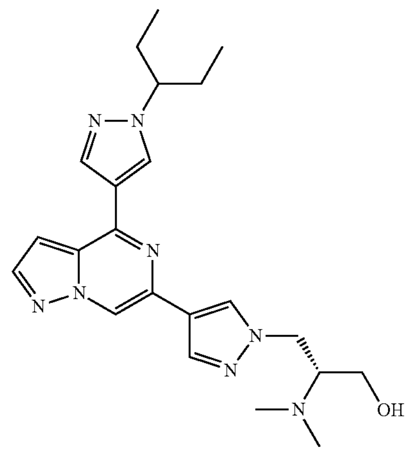 [SMILES: CCC(CC)n1cc(-c2nc(-c3cnn(C[C@H](CO)N(C)C)c3)cn3nccc23)cn1] | (R)-2-(dimethylamino)-3-(4-(4-(1-(pentan-3-yl)-1H-pyrazol-4-yl)pyrazolo[1,5-a]pyrazin-6-yl)-1H-pyrazol-1-yl)propan-1-ol | Mass spectrum (apci) m/z = 423.2 (M + H) |

Examples 132 and 133

(1R,2S,4s)-4-(4-(4-(1-(pentan-3-yl)-1H-pyrazol-4-yl)pyrazolo[1,5-a]pyrazin-6-yl)-1H-pyrazol-1-yl)cyclopentane-1,2-diol and (1R,2S,4r)-4-(4-(4-(1-(pentan-3-yl)-1H-pyrazol-4-yl)pyrazolo[1,5-a]pyrazin-6-yl)-1H-pyrazol-1-yl)cyclopentane-1,2-diol

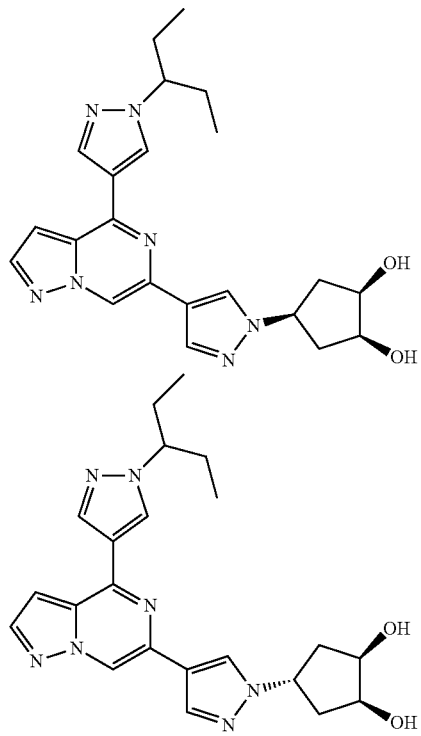

Step A:

To a stirred solution of 4-(1-(pentan-3-yl)-1H-pyrazol-4-yl)-6-(1H-pyrazol-4-yl)pyrazolo[1,5-a]pyrazine (139 mg, 0.433 mmol) in 1.5 mL of DMF at room temperature under nitrogen was added $Cs_2CO_3$ (51.9 mg, 0.865 mmol), followed by cyclopent-3-en-1-yl methanesulfonate (140 mg, 0.865 mmol). The reaction mixture was heated to 80° C. overnight. An additional 2 equivalents of cesium carbonate and cyclopent-3-en-1-yl methanesulfonate were added and the reaction mixture was heated overnight. The reaction mixture was cooled to room temperature and diluted to 30 mL with ethyl acetate. The organic layer was washed with water and brine. The combined organic phases were dried over $MgSO_4$, filtered and concentrated. The residue was purified over silica gel (20-80% EtOAc in hexanes) to afford 6-(1-(cyclopent-3-en-1-yl)-1H-pyrazol-4-yl)-4-(1-(pentan-3-yl)-1H-pyrazol-4-yl)pyrazolo[1,5-a]pyrazine (42 mg, 25% yield).

Step B:

To a stirred solution of 6-(1-(cyclopent-3-en-1-yl)-1H-pyrazol-4-yl)-4-(1-(pentan-3-yl)-1H-pyrazol-4-yl)pyrazolo[1,5-a]pyrazine (42 mg, 0.108 mmol) in 1 mL of 8:1 acetone:water at room temperature under nitrogen was added N-methylmorpholine-N-oxide (22.9 mg, 0.195 mmol) neat as a solid followed by $OsO_4$ (42.5 μL, 0.00542 mmol) (4% water solution) by syringe and the reaction mixture was stirred at room temperature overnight. The reaction mixture was quenched with 0.2 M aqueous $Na_2S_2O_3$ (1 mL) and stirred for 5 minutes. The reaction mixture was diluted with 15 mL of dichloromethane and washed with 0.2 M sodium thiosulfate. The combined organic phases were isolated, dried over $MgSO_4$, filtered and concentrated to a brown oil that was purified over silica gel (0-10% MeOH in dichloromethane) to afford two diastereomers. The faster eluting fraction (Peak A) was (1R,2S,4r)-4-(4-(4-(1-(pentan-3-yl)-1H-pyrazol-4-yl)pyrazolo[1,5-a]pyrazin-6-yl)-1H-pyrazol-1-yl)cyclopentane-1,2-diol (minor isomer): Mass spectrum (apci) m/z=422.2 (M+H). $^1$H NMR ($CDCl_3$) δ 8.44 (d, J=0.8 Hz, 1H), 8.26 (s, 1H), 8.15 (s, 1H), 8.04 (d, J=2.3 Hz, 1H), 8.00 (s, 2H), 6.96 (dd, J=2.3, 1.0 Hz, 1H), 4.79 (tt, J=9.4, 3.3 Hz, 1H), 4.46 (m, 1H), 4.12 (m, 1H), 4.03 (m, 1H), 2.56 (m, 2H), 2.11 (m, 2H), 2.05-1.85 (m, 4H), 0.86 (t, J=7.4 Hz, 6H). The slower eluting fraction (Peak B) was (1R,2S,4s)-4-(4-(4-(1-(pentan-3-yl)-1H-pyrazol-4-yl)pyrazolo[1,5-a]pyrazin-6-yl)-1H-pyrazol-1-yl)cyclopentane-1,2-diol (major isomer): Mass spectrum (apci) m/z=422.2 (M+H). $^1$H NMR ($CDCl_3$) δ 8.45 (d, J=0.8 Hz, 1H), 8.26 (s, 1H), 8.16 (s, 1H), 8.03 (d, J=2.5 Hz, 1H), 7.98 (s, 1H), 7.95 (s, 1H), 6.95 (dd, J=2.3, 0.8 Hz, 1H), 5.05 (m, 1H), 4.51 (m, 2H), 4.03 (m, 1H), 3.72 (m, 1H), 2.44-2.35 (m, 6H), 2.05-1.85 (m, 4H), 0.86 (t, J=7.2 Hz, 6H).

Example 134

N-(2-(4-(4-(1-(pentan-3-yl)-1H-pyrazol-4-yl)pyrazolo[1,5-a]pyrazin-6-yl)-1H-pyrazol-1-yl)ethyl)cyclopropanamine trifluoroacetate

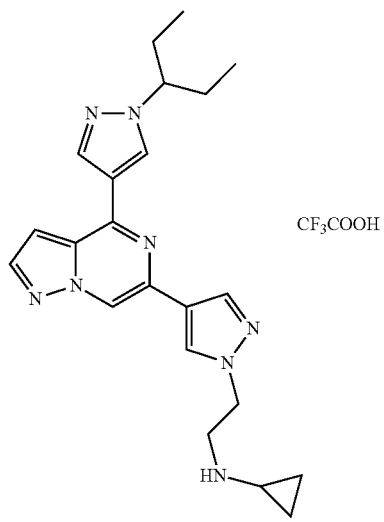 [SMILES: CCC(CC)n1cc(-c2nc(-c3cnn(CCNC4CC4)c3)cn3nccc23)cn1 ; "CF3COOH"]

Step A:
4-(1-(pentan-3-yl)-H-pyrazol-4-yl)-6-(1H-pyrazol-4-yl)pyrazolo[1,5-a]pyrazine (450 mg, 1.40 mmol), Cs$_2$CO$_3$ (1369 mg, 4.20 mmol) and (2-bromoethoxy)(tert-butyl)dimethylsilane (670 mg, 2.80 mmol) were placed in DMF (8 mL) and stirred for 18 hours. Water was added and the mixture was extracted with EtOAc. The combined organic extracts were washed with water. The organic layer was concentrated and the crude 6-(1-(2-((tert-butyldimethylsilyl)oxy)ethyl)-1H-pyrazol-4-yl)-4-(1-(pentan-3-yl)-1H-pyrazol-4-yl)pyrazolo[1,5-a]pyrazine (672 mg, 100% yield) was used in the next step without further purification.

Step B:
6-(1-(2-((tert-butyldimethylsilyl)oxy)ethyl)-1H-pyrazol-4-yl)-4-(1-(pentan-3-yl)-1H-pyrazol-4-yl)pyrazolo[1,5-a]pyrazine (672 mg, 1.40 mmol) was placed in 10% MeOH in CH$_2$Cl$_2$ (20 mL) and 4 N HCl in dioxane (2 mL) as added. The reaction mixture was stirred for 45 minutes. The reaction mixture was adjusted to pH 9 with slow addition of saturated NaHCO$_3$. The reaction mixture was extracted with CH$_2$Cl$_2$, combined and concentrated. The crude material was used in the next step without further purification.

Step C:
2-(4-(4-(1-(Pentan-3-yl)-1H-pyrazol-4-yl)pyrazolo[1,5-a]pyrazin-6-yl)-1H-pyrazol-1-yl)ethanol (512 mg, 1.40 mmol) and Et$_3$N (391 µL, 2.80 mmol) were placed in THF (15 mL). Methanesulfonyl chloride (136 µL, 1.75 mmol) was added and the reaction mixture was stirred for 1 hour. Water was added and the mixture was extracted with CH$_2$Cl$_2$. The combined organic layers were concentrated. The residue was purified over silica gel (1-10% MeOH in CH$_2$Cl$_2$) to provide 2-(4-(4-(1-(pentan-3-yl)-1H-pyrazol-4-yl)pyrazolo[1,5-a]pyrazin-6-yl)-1H-pyrazol-1-yl)ethyl methanesulfonate (481 mg, 1.08 mmol, 77.4% yield).

Step D:
2-(4-(4-(1-(Pentan-3-yl)-1H-pyrazol-4-yl)pyrazolo[1,5-a]pyrazin-6-yl)-1H-pyrazol-1-yl)ethyl methanesulfonate (40 mg, 0.0902 mmol), Cs$_2$CO$_3$ (88.2 mg, 0.271 mmol) and cyclopropanamine (15.4 mg, 0.271 mmol) were placed in DMF (1 mL) and stirred over the weekend. The reaction mixture was concentrated and the crude material was purified by reverse phase chromatography (0-50% CH$_3$CN/water w/0.1% TFA) to provide N-(2-(4-(4-(1-(pentan-3-yl)-1H-pyrazol-4-yl)pyrazolo[1,5-a]pyrazin-6-yl)-1H-pyrazol-1-yl)ethyl)cyclopropanamine trifluoroacetate (20.7 mg, 0.0512 mmol, 56.7% yield)t. Mass spectrum (apci) m/z=405.3 (M+H). $^1$H NMR (CDCl$_3$) δ 8.48 (s, 1H), 8.34 (s, 1H), 8.29 (s, 1H), 8.13 (s, 1H), 8.11 (d, J=2.5 Hz, 1H), 7.94 (s, 1H), 7.10 (m, 1H), 4.61 (m, 2H), 4.06 (m, 1H), 3.73 (m, 2H), 2.70 (m, 1H), 2.05-1.86 (m, 4H), 1.15 (m, 2H), 0.90 (m, 2H), 0.85 (t, J=7.2 Hz, 6H).

The following compounds were prepared according to the procedure described for Example 134.

| Example | Structure | Name | Data |
|---|---|---|---|
| 135 | 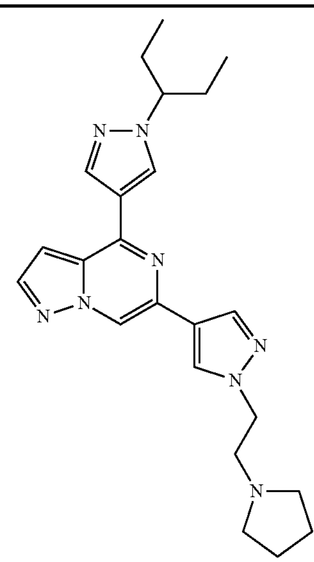 | 4-(1-(pentan-3-yl)-1H-pyrazol-4-yl)-6-(1-(2-(pyrrolidin-1-yl)ethyl)-1H-pyrazol-4-yl)pyrazolo[1,5-a]pyrazine | Mass spectrum (apci) m/z = 419.3 (M + H) |

| Example | Structure | Name | Data |
|---|---|---|---|
| 136 | 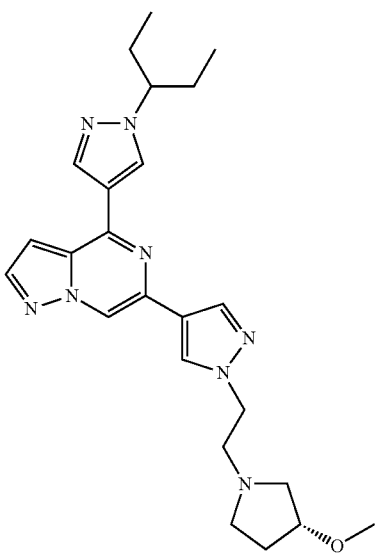 [SMILES: CCC(CC)n1cc(-c2nc(-c3cnn(CCN4CC[C@@H](OC)C4)c3)cn3nccc23)cn1] | (R)-6-(1-(2-(3-methoxypyrrolidin-1-yl)ethyl)-1H-pyrazol-4-yl)-4-(1-(pentan-3-yl)-1H-pyrazol-4-yl)pyrazolo[1,5-a]pyrazine | Mass spectrum (apci) m/z = 449.3 (M + H) |
| 137 | 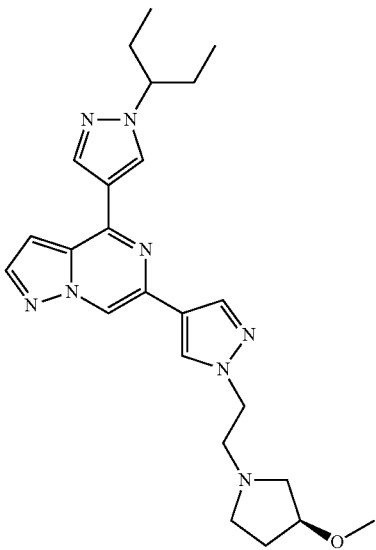 [SMILES: CCC(CC)n1cc(-c2nc(-c3cnn(CCN4CC[C@H](OC)C4)c3)cn3nccc23)cn1] | (S)-6-(1-(2-(3-methoxypyrrolidin-1-yl)ethyl)-1H-pyrazol-4-yl)-4-(1-(pentan-3-yl)-1H-pyrazol-4-yl)pyrazolo[1,5-a]pyrazine | Mass spectrum (apci) m/z = 449.3 (M + H) |

| Example | Structure | Name | Data |
|---|---|---|---|
| 138 | 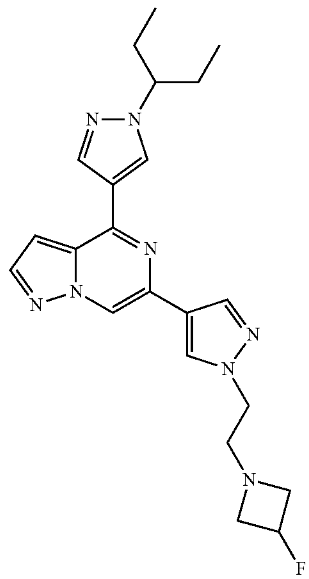 [SMILES: CCC(CC)n1cc(-c2nc(-c3cnn(CCN4CC(F)C4)c3)cn3nccc23)cn1] | 6-(1-(2-(3-fluoroazetidin-1-yl)ethyl)-1H-pyrazol-4-yl)-4-(1-(pentan-3-yl)-1H-pyrazol-4-yl)pyrazolo[1,5-a]pyrazine | Mass spectrum (apci) m/z = 423.2 (M + H) |
| 139 | 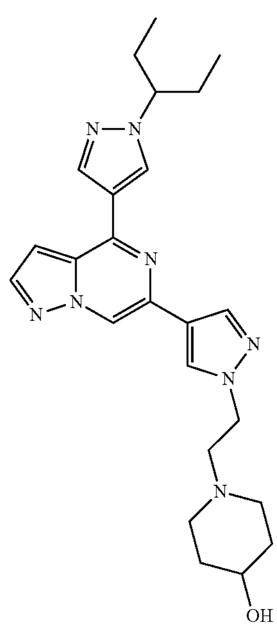 [SMILES: CCC(CC)n1cc(-c2nc(-c3cnn(CCN4CCC(O)CC4)c3)cn3nccc23)cn1] | 1-(2-(4-(4-(1-(pentan-3-yl)-1H-pyrazol-4-yl)pyrazolo[1,5-a]pyrazin-6-yl)-1H-pyrazol-1-yl)ethyl)piperidin-4-ol | Mass spectrum (apci) m/z = 449.3 (M + H) |

-continued

| Example | Structure | Name | Data |
|---|---|---|---|
| 140 | 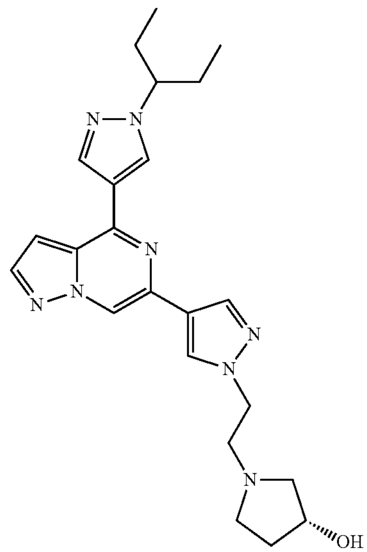 [SMILES: CCC(CC)n1cc(-c2nc(-c3cnn(CCN4CC[C@@H](O)C4)c3)cn3nccc23)cn1] | (R)-1-(2-(4-(4-(1-(pentan-3-yl)-1H-pyrazol-4-yl)pyrazolo[1,5-a]pyrazin-6-yl)-1H-pyrazol-1-yl)ethyl)pyrrolidin-3-ol | Mass spectrum (apci) m/z = 435.2 (M + H) |
| 141 | 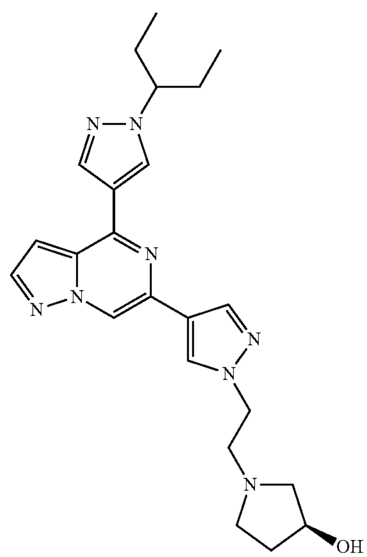 [SMILES: CCC(CC)n1cc(-c2nc(-c3cnn(CCN4CC[C@H](O)C4)c3)cn3nccc23)cn1] | (S)-1-(2-(4-(4-(1-(pentan-3-yl)-1H-pyrazol-4-yl)pyrazolo[1,5-a]pyrazin-6-yl)-1H-pyrazol-1-yl)ethyl)pyrrolidin-3-ol | Mass spectrum (apci) m/z = 435.2 (M + H) |
| 142 | 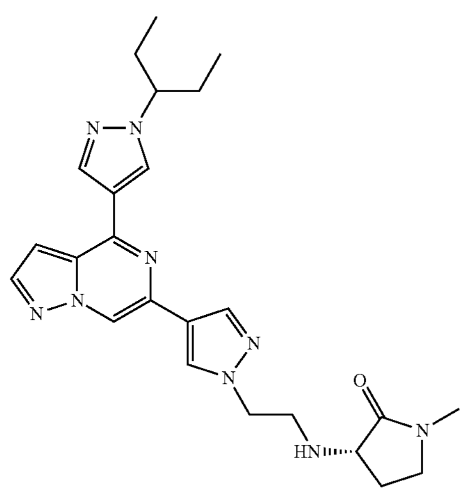 [SMILES: CCC(CC)n1cc(-c2nc(-c3cnn(CCN[C@H]4CCN(C)C4=O)c3)cn3nccc23)cn1] | (S)-1-methyl-3-((2-(4-(4-(1-(pentan-3-yl)-1H-pyrazol-4-yl)pyrazolo[1,5-a]pyrazin-6-yl)-1H-pyrazol-1-yl)ethyl)amino)pyrrolidin-2-one | Mass spectrum (apci) m/z = 462.2 (M + H) |

| Example | Structure | Name | Data |
|---|---|---|---|
| 143 | 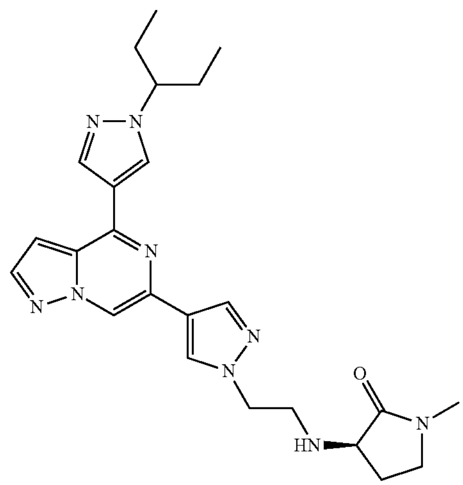 [SMILES: CCC(CC)n1cc(-c2nc(-c3cnn(CCN[C@@H]4CCN(C)C4=O)c3)cn3nccc23)cn1] | (R)-1-methyl-3-((2-(4-(4-(1-(pentan-3-yl)-1H-pyrazol-4-yl)pyrazolo[1,5-a]pyrazin-6-yl)-1H-pyrazol-1-yl)ethyl)amino)pyrrolidin-2-one | Mass spectrum (apci) m/z = 462.3 (M + H) |
| 144 | 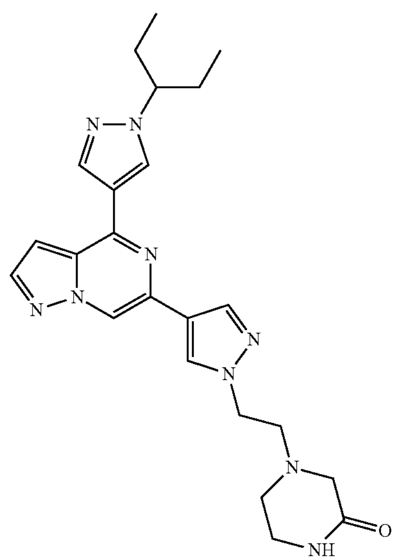 [SMILES: CCC(CC)n1cc(-c2nc(-c3cnn(CCN4CCNC(=O)C4)c3)cn3nccc23)cn1] | 4-(2-(4-(4-(1-(pentan-3-yl)-1H-pyrazol-4-yl)pyrazolo[1,5-a]pyrazin-6-yl)-1H-pyrazol-1-yl)ethyl)piperazin-2-one | Mass spectrum (apci) m/z = 448.2 (M + H) |
| 145 | 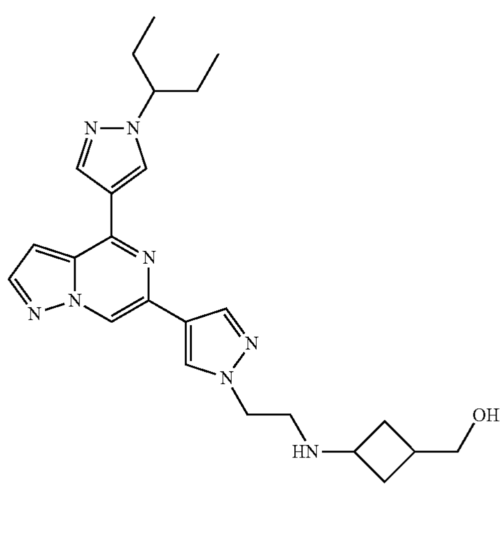 [SMILES: CCC(CC)n1cc(-c2nc(-c3cnn(CCNC4CC(CO)C4)c3)cn3nccc23)cn1] | (3-((2-(4-(4-(1-(pentan-3-yl)-1H-pyrazol-4-yl)pyrazolo[1,5-a]pyrazin-6-yl)-1H-pyrazol-1-yl)ethyl)amino)cyclobutyl)methanol | Mass spectrum (apci) m/z = 449.3 (M + H) |

| Example | Structure | Name | Data |
|---|---|---|---|
| 146 | 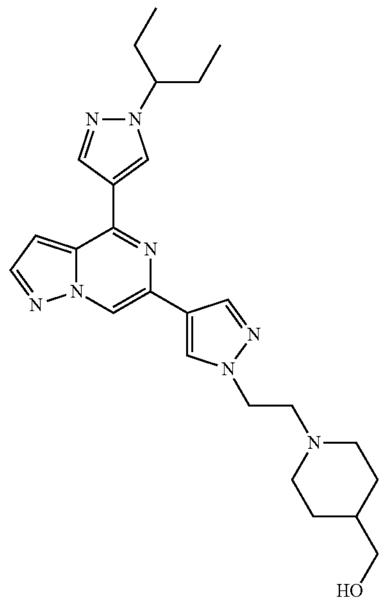 [SMILES: CCC(CC)n1cc(-c2nc(-c3cnn(CCN4CCC(CO)CC4)c3)cn3nccc23)cn1] | (1-(2-(4-(4-(1-(pentan-3-yl)-1H-pyrazol-4-yl)pyrazolo[1,5-a]pyrazin-6-yl)-1H-pyrazol-1-yl)ethyl)piperidin-4-yl)methanol | Mass spectrum (apci) m/z = 463.3 (M + H) |

Example 147

1-(2-(4-(4-(1-(pentan-3-yl)-1H-pyrazol-4-yl)pyrazolo[1,5-a]pyrazin-6-yl)-1H-pyrazol-1-yl)ethyl)piperazin-2-one

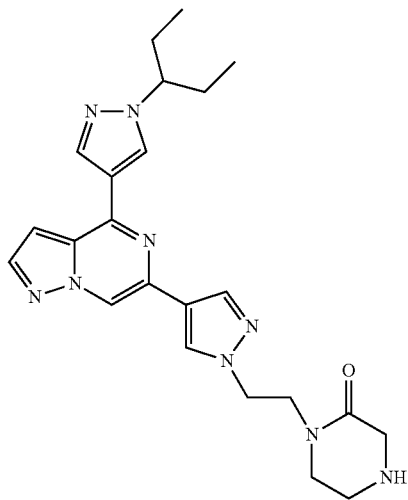 [SMILES: CCC(CC)n1cc(-c2nc(-c3cnn(CCN4CCNCC4=O)c3)cn3nccc23)cn1]

tert-Butyl 3-oxopiperazine-1-carboxylate (0.135 g, 0.676 mmol) was added to a solution of sodium hydride (0.0271 g, 0.676 mmol) in DMF (2.25 mL, 0.225 mmol). 2-(4-(4-(1-(Pentan-3-yl)-1H-pyrazol-4-yl)pyrazolo[1,5-a]pyrazin-6-yl)-1H-pyrazol-1-yl)ethyl methanesulfonate (0.100 g, 0.225 mmol) was slowly added and the reaction mixture was stirred at room temperature for 23 hours. Water (15 mL) was slowly added and the reaction mixture was extracted with EtOAc. The combined organic extracts were dried over Na$_2$SO$_4$ and concentrated. The residue was purified over silica gel (0-10% MeOH in CH$_2$Cl$_2$). The concentrated material was dissolved in 10% MeOH in CH$_2$Cl$_2$ and 6 N HCl in isopropyl alcohol (3 mL) was added and the reaction mixture was stirred for 2 hours and concentrated. The resulting solid was purified over silica gel (0-10% MeOH w/NH$_4$OH in CH$_2$Cl$_2$) to afford 1-(2-(4-(4-(1-(pentan-3-yl)-H-pyrazol-4-yl)pyrazolo[1,5-a]pyrazin-6-yl)-1H-pyrazol-1-yl)ethyl)piperazin-2-one (16.1 mg, 0.0360 mmol, 16.0% yield) as a white foam. Mass spectrum (apci) m/z=448.2 (M+H). $^1$H NMR (CDCl$_3$) δ 8.43 (d, J=1.0 Hz, 1H), 8.26 (s, 1H), 8.18 (s, 1H), 8.04 (d, J=2.3 Hz, 1H), 7.95 (s, 1H), 7.94 (s, 1H), 6.96 (dd, J=2.5, 1.0 Hz, 1H), 4.39 (t, J=6.1 Hz, 2H), 4.03 (m, 1H), 3.75 (t, J=5.9 Hz, 2H), 3.15 (s, 2H), 2.88 (m, 1H), 2.84 (m, 2H), 2.52 (m, 2H), 2.05-1.85 (m, 4H), 0.85 (t, J=7.4 Hz, 6H).

Example 148

(R)-2-methoxy-3-(4-(4-(1-(pentan-3-yl)-1H-pyrazol-4-yl)pyrazolo[1,5-a]pyrazin-6-yl)-1H-pyrazol-1-yl)propan-1-amine

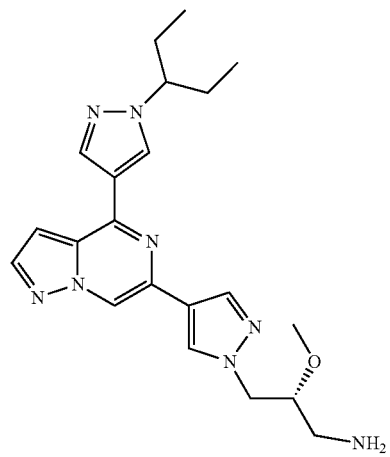 [SMILES: CCC(CC)n1cc(-c2nc(-c3cnn(C[C@@H](CN)OC)c3)cn3nccc23)cn1]

211

Step A:

4-(1-(Pentan-3-yl)-1H-pyrazol-4-yl)-6-(1H-pyrazol-4-yl)pyrazolo[1,5-a]pyrazine (125 mg, 0.389 mmol), 2-(3-bromo-2-methoxypropyl)isoindoline-1,3-dione (145 mg, 0.49 mmol) and Cs$_2$CO$_3$ (380 mg, 1.17 mmol) were heated in DMF (8 mL) to 50° C. for 18 hours. The reaction mixture was cooled and water was added. The reaction mixture was extracted with EtOAc. The combined organic layers were washed with water. The organic layer was concentrated and purified over silica gel (0-5% MeOH in CH$_2$Cl$_2$) to afford 2-(2-methoxy-3-(4-(4-(1-(pentan-3-yl)-1H-pyrazol-4-yl)pyrazolo[1,5-a]pyrazin-6-yl)-1H-pyrazol-1-yl)propyl)isoindoline-1,3-dione (60 mg, 0.111 mmol, 28.6% yield) as a racemic mixture. The racemic material was purified by chiral chromatography to afford 2 peaks that were arbitrarily assigned absolute configuration. Peak A: Arbitrarily assigned the R configuration. Peak B: Arbitrarily assigned the S configuration.

Step B:

(R)-2-(2-methoxy-3-(4-(4-(1-(pentan-3-yl)-1H-pyrazol-4-yl)pyrazolo[1,5-a]pyrazin-6-yl)-1H-pyrazol-1-yl)propyl)isoindoline-1,3-dione (26 mg, 0.048 mmol) [Peak A from previous step] was placed in THF (2 mL). Hydrazine monohydrate (6.0 mg, 0.12 mmol) was added and the reaction mixture was heated to 65° C. for 18 hours. The reaction mixture was cooled and water was added. The reaction mixture was extracted with CH$_2$Cl$_2$ and the combined organic extracts were concentrated. The residue was purified over silica gel (0.5-18% MeOH w/NH$_4$OH in CH$_2$Cl$_2$) to afford (R)-2-methoxy-3-(4-(4-(1-(pentan-3-yl)-1H-pyrazol-4-yl)pyrazolo[1,5-a]pyrazin-6-yl)-1H-pyrazol-1-yl)propan-1-amine (isolated "Peak A") (6.7 mg, 0.016 mmol, 34% yield). Mass spectrum (apci) m/z=409.2 (M+H). $^1$H NMR (CDCl$_3$) δ 8.46 (d, J=0.8 Hz, 1H), 8.27 (s, 1H), 8.17 (s, 1H), 8.03 (m, 2H), 7.99 (s, 1H), 6.95 (dd, J=2.3, 0.8 Hz, 1H), 4.36 (dd, J=14.1, 5.1 Hz, 1H), 4.31 (dd, J=14.1, 6.1 Hz, 1H), 4.03 (m, 1H), 3.69 (pentet, 1H), 3.38 (s, 3H), 2.92 (dd, J=13.3, 4.5 Hz, 1H), 2.75 (dd, J=13.3, 5.5 Hz, 1H), 2.09-1.85 (m, 6H), 0.86 (t, J=7.4 Hz, 6H).

The following compound was prepared according to the procedure described for Example 148.

212

Example 150

2-(4-(4-(1-((1R,2R)-2-methylcyclohexyl)-1H-pyrazol-4-yl)pyrazolo[1,5-a]pyrazin-6-yl)-1H-pyrazol-1-yl)propane-1,3-diol

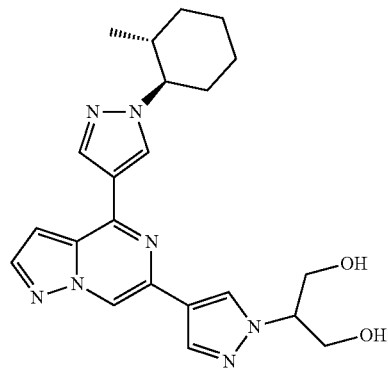 [SMILES: C[C@@H]1CCCC[C@H]1n1cc(-c2nc(-c3cnn(C(CO)CO)c3)cn3nccc23)cn1]

Step A:

4-Chloro-6-(1-(4-methoxybenzyl)-1H-pyrazol-4-yl)pyrazolo[1,5-a]pyrazine hydrochloride (1.2 g, 3.2 mmol), 1-(trans-2-methylcyclohexyl)-4-(4,4,5,5-tetramethyl-1,3,2-dioxaborolan-2-yl)-1H-pyrazole (1.1 g, 3.8 mmol) and K$_2$CO$_3$ (3.2 mL, 6.3 mmol) were dissolved in THF (20 mL) and nitrogen bubbled through the reaction mixture for 3 minutes. XPHOS (0.15 g, 0.32 mmol) and Pd$_2$(dba)$_3$ (0.072 g, 0.079 mmol) were added and the reaction mixture was heated to 60° C. overnight. The reaction mixture was cooled to room temperature, partitioned between water and EtOAc, dried over sodium sulfate, filtered and concentrated. The residue was purified over silica gel (50-75% EtOAc in hexanes) to afford 6-(1-(4-methoxybenzyl)-1H-pyrazol-4-yl)-4-(1-(trans-2-methylcyclohexyl)-1H-pyrazol-4-yl)pyrazolo[1,5-a]pyrazine (1.3 g, 2.8 mmol, 88% yield) as an oil.

Step B:

6-(1-(4-Methoxybenzyl)-1H-pyrazol-4-yl)-4-(1-(trans-2-methylcyclohexyl)-1H-pyrazol-4-yl)pyrazolo[1,5-a]pyra-

| Example | Structure | Name | Data |
| --- | --- | --- | --- |
| 149 | (isolated "Peak B") | (S)-2-methoxy-3-(4-(4-(1-(pentan-3-yl)-1H-pyrazol-4-yl)pyrazolo[1,5-a]pyrazin-6-yl)-1H-pyrazol-1-yl)propan-1-amine | Mass spectrum (apci) m/z = 409.2 (M + H) | zine (1.3 g, 2.78 mmol) was dissolved in TFA (25 mL) and heated to 80° C. for 2.5 hours. The reaction mixture was concentrated and partitioned between EtOAc and 1M NaOH, dried over sodium sulfate, filtered and concentrated. The residue was purified over silica gel (90% EtOAc in hexanes) to afford a racemic mixture of 4-(1-(trans-2-methylcyclohexyl)-1-yl)-6-(1-4-yl)-1H-pyrazol-4-yl)pyrazolo[1,5-a]pyrazine (630 mg, 1.81 mmol, 65.2% yield) as a pale yellow solid.

Step C:

The racemic material (630 mg) prepared in Step B was purified by chiral chromatography (Chiral Tech OJ-H, 22 mm×250 mm, 5 micron, 25% EtOH in hexanes, 23 mL/min) to afford two peaks that were arbitrarily assigned absolute chirality: Peak A (retention time=8.9 min): 4-(1-((1S,2S)-2-methylcyclohexyl)-1H-pyrazol-4-yl)-6-(1H-pyrazol-4-yl)pyrazolo[1,5-a]pyrazine (287 mg, 0.826 mmol, 29.7% yield) and Peak B (retention time=11.3 min): 4-(1-((1R,2R)-2-methylcyclohexyl)-1H-pyrazol-4-yl)-6-(1H-pyrazol-4-yl)pyrazolo[1,5-a]pyrazine (263 mg, 0.757 mmol, 27.2% yield).

Step D:

4-(1-((1R,2R)-2-methylcyclohexyl)-1H-pyrazol-4-yl)-6-(1H-pyrazol-4-yl)pyrazolo[1,5-a]pyrazine (80 mg, 0.23 mmol) was dissolved in DMF (1 mL) and cis-2-phenyl-1,3-dioxan-5-yl methanesulfonate (119 mg, 0.46 mmol) and $Cs_2CO_3$ (225 mg, 0.69 mmol) were added and heated to 80° C. overnight. The reaction mixture was diluted with water (3 mL) and partitioned between water and EtOAc, dried over sodium sulfate, filtered and concentrated. The residue was purified over silica gel to afford 4-(1-((1R,2R)-2-methylcyclohexyl)-1H-pyrazol-4-yl)-6-(1-(cis-2-phenyl-1,3-dioxan-5-yl)-1H-pyrazol-4-yl)pyrazolo[1,5-a]pyrazine (68 mg, 0.13 mmol, 58% yield).

Step E:

4-(1-((1R,2R)-2-methylcyclohexyl)-1H-pyrazol-4-yl)-6-(1-((2R,5r)-2-phenyl-1,3-dioxan-5-yl)-1H-pyrazol-4-yl)pyrazolo[1,5-a]pyrazine (68 mg, 0.13 mmol) was suspended in EtOH (1 mL) and hydrogen chloride (56 μL, 0.67 mmol) was added and the reaction heated to 60° C. for 4 hours. The reaction mixture was partitioned between 1N NaOH and $CH_2Cl_2$, dried over sodium sulfate, filtered and concentrated. The residue was purified over silica gel (6% MeOH in $CH_2Cl_2$) to afford 2-(4-(4-(1-((1R,2R)-2-methylcyclohexyl)-1H-pyrazol-4-yl)pyrazolo[1,5-a]pyrazin-6-yl)-1H-pyrazol-1-yl)propane-1,3-diol (Peak A) (19 mg, 0.045 mmol, 34% yield) as a white solid. Mass spectrum (apci) m/z=422.2 (M+H). $^1$H NMR ($d_6$-DMSO) δ 8.99 (m, 1H), 8.73 (s, 1H), 8.37 (s, 2H), 8.15 (m, 2H), 7.35 (m, 1H), 4.93 (m, 2H), 4.30 (m, 1H), 3.92 (td, J=11.0, 4.9 Hz, 1H), 3.79 (t, J=5.7 Hz, 4H), 2.10-1.67 (m, 6H), 1.39 (m, 2H), 1.17 (m, 1H), 0.65 (d, J=6.5 Hz, 3H).

The following compounds were prepared according to the procedure described for Example 150.

| Example | Structure | Name | Data |
|---|---|---|---|
| 151 | 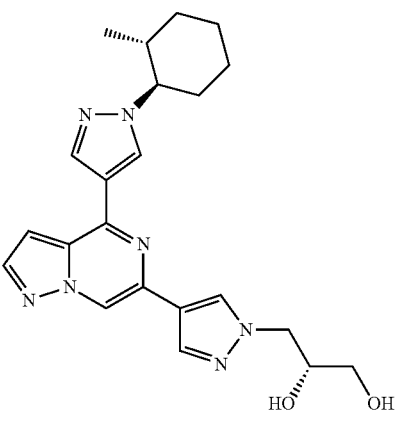 (isolated "Peak B") | (R)-3-(4-(4-(1-((1R,2R)-2-methylcyclohexyl)-1H-pyrazol-4-yl)pyrazolo[1,5-a]pyrazin-6-yl)-1H-pyrazol-1-yl)propane-1,2-diol | Mass spectrum (apci) m/z = 422.2 (M + H) |
| 152 | 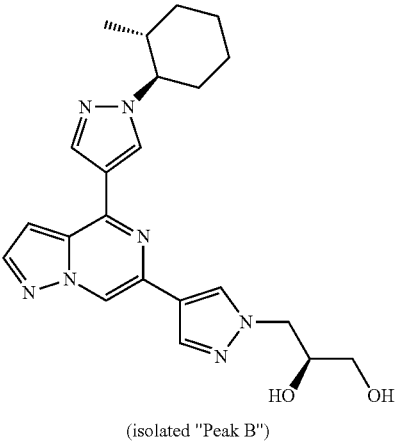 [SMILES: C[C@@H]1CCCC[C@H]1n1cc(-c2nc(-c3cnn(C[C@H](O)CO)c3)cn3nccc23)cn1] (isolated "Peak B") | (S)-3-(4-(4-(1-((1R,2R)-2-methylcyclohexyl)-1H-pyrazol-4-yl)pyrazolo[1,5-a]pyrazin-6-yl)-1H-pyrazol-1-yl)propane-1,2-diol | Mass spectrum (apci) m/z = 422.2 (M + H) |

Example 153 (1R,2R)-2-(4-(4-(1-(pentan-3-yl)-1H-pyrazol-4-yl)pyrazolo[1,5-a]pyrazin-6-yl)-1H-pyrazol-1-yl)cyclopentanol

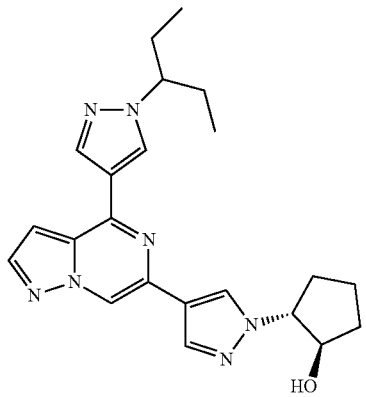 [SMILES: CCC(CC)n1cc(-c2nc(-c3cnn([C@@H]4CCC[C@H]4O)c3)cn3nccc23)cn1]

Step A:

To a stirred solution of 4-(1-(pentan-3-yl)-1H-pyrazol-4-yl)-6-(1H-pyrazol-4-yl)pyrazolo[1,5-a]pyrazine (105 mg, 0.327 mmol) in 1 mL of DMF at room temperature under nitrogen was added NaH (14.4 mg, 0.359 mmol) (60% oil dispersion). After 10 minutes, 6-oxabicyclo[3.1.0]hexane (31.1 µL, 0.359 mmol) was added by syringe. After 3 hour, an additional 1 equivalent each of sodium hydride and 6-oxabicyclo[3.1.0]hexane were added. The reaction mixture was heated to 65° C. overnight. The reaction mixture was cooled to room temperature and quenched with saturated ammonium chloride solution (1 mL). The mixture was partitioned between ethyl acetate (15 mL) and water (15 mL). The combined organic phases were isolated and washed with water and brine. The combined organic phases were dried over MgSO$_4$, filtered and concentrated to afford crude trans-2-(4-(4-(1-(pentan-3-yl)-1H-pyrazol-4-yl)pyrazolo[1,5-a]pyrazin-6-yl)-1H-pyrazol-1-yl)cyclopentanol which was used in the next step without purification.

Step B:

To a stirred solution of crude trans-2-(4-(4-(1-(pentan-3-yl)-1H-pyrazol-4-yl)pyrazolo[1,5-a]pyrazin-6-yl)-1H-pyrazol-1-yl)cyclopentanol (87 mg, 0.21 mmol) in 2.1 mL of dichloromethane at room temperature under nitrogen was added imidazole (15 mg, 0.21 mmol) followed by tert-butyldimethylsilyl chloride (32 mg, 0.21 mmol) and stirred overnight. The reaction mixture was then diluted to 15 mL with dichloromethane and washed with 10% citric acid solution and then with saturated sodium bicarbonate. The combined organic phases were isolated, dried over MgSO$_4$, filtered and concentrated. The residue was purified over silica gel (10-50% EtOAc in hexanes). The purified racemic material was separated by chiral chromatography (Phenomenex Lux-2, 4.6 mm×250 mm, 5 micron, 20% EtOH in hexanes, 1 mL/min) to provide 2 enantiomers, Peak A (4.8 min) Arbitrarily assigned as 6-(1-((1R,2R)-2-((tert-butyldimethylsilyl)oxy)cyclopentyl)-1H-pyrazol-4-yl)-4-(1-(pentan-3-yl)-1H-pyrazol-4-yl)pyrazolo[1,5-a]pyrazine and Peak B (5.5 min). Arbitrarily assigned as 6-(1-((1S,2S)-2-((tert-butyldimethylsilyl)oxy)cyclopentyl)-1H-pyrazol-4-yl)-4-(1-(pentan-3-yl)-1H-pyrazol-4-yl)pyrazolo[1,5-a]pyrazine Step C:

To a stirred solution of 6-(1-((1R,2R)-2-((tert-butyldimethylsilyl)oxy)cyclopentyl)-1H-pyrazol-4-yl)-4-(1-(pentan-3-yl)-1H-pyrazol-4-yl)pyrazolo[1,5-a]pyrazine (19 mg, 0.037 mmol) [Peak A] in 1 mL of THF at room temperature under nitrogen was added tetrabutylammonium fluoride (73 µL, 0.073 mmol) (1M in THF) by syringe. After 45 minutes, the reaction mixture was complete and purified over silica gel (0-5% MeOH in CH$_2$Cl$_2$) to afford (1R,2R)-2-(4-(4-(1-(pentan-3-yl)-1H-pyrazol-4-yl)pyrazolo[1,5-a]pyrazin-6-yl)-1H-pyrazol-1-yl)cyclopentanol (Peak A) (14 mg, 94% yield). Mass spectrum (apci) m/z=406.2 (M+H). $^1$H NMR (CDCl$_3$) δ 8.43 (d, J=0.8 Hz, 1H), 8.25 (s, 1H), 8.16 (s, 1H), 8.02 (d, J=2.3 Hz, 1H), 8.01 (s, 1H), 7.97 (s, 1H), 6.94 (dd, J=2.5, 0.8 Hz, 1H), 4.47 (qd, 7.6 1.6 Hz, 1H), 4.39 (m, 1H), 4.02 (m, 1H), 3.16 (d, J=2.2 Hz, 1H), 2.38 (m, 1H), 2.25-2.11 (m, 2H), 2.06-1.85 (m, 6H), 1.79 (m, 1H), 0.85 (t, J=7.2 Hz, 6H).

The following compounds were prepared according to the procedure described for Example 153.

| Example | Structure | Name | Data |
|---|---|---|---|
| 154 | 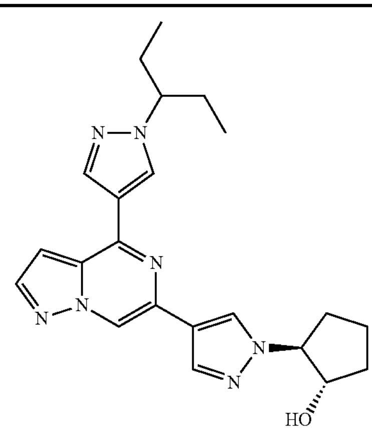 | (1S,2S)-2-(4-(4-(1-(pentan-3-yl)-1H-pyrazol-4-yl)pyrazolo[1,5-a]pyrazin-6-yl)-1H-pyrazol-1-yl)cyclopentanol (isolated "Peak B") | Mass spectrum (apci) m/z = 406.2 (M + H) |

-continued

| Example | Structure | Name | Data |
|---|---|---|---|
| 155 | (isolated "Peak A") | (2S,3S)-3-(4-(4-(1-(pentan-3-yl)-1H-pyrazol-4-yl)pyrazolo[1,5-a]pyrazin-6-yl)-1H-pyrazol-1-yl)butan-2-ol | Mass spectrum (apci) m/z = 394.2 (M + H) |
| 156 | (isolated "Peak B") | (2R,3R)-3-(4-(4-(1-(pentan-3-yl)-1H-pyrazol-4-yl)pyrazolo[1,5-a]pyrazin-6-yl)-1H-pyrazol-1-yl)butan-2-ol | Mass spectrum (apci) m/z = 394.2 (M + H) |
| 157 | (isolated "Peak A") | (2R,3S)-3-(4-(4-(1-(pentan-3-yl)-1H-pyrazol-4-yl)pyrazolo[1,5-a]pyrazin-6-yl)-1H-pyrazol-1-yl)butan-2-ol | Mass spectrum (apci) m/z = 394.2 (M + H) |

-continued

| Example | Structure | Name | Data |
|---|---|---|---|
| 158 | (isolated "Peak B") | (2S,3R)-3-(4-(4-(1-(pentan-3-yl)-1H-pyrazol-4-yl)pyrazolo[1,5-a]pyrazin-6-yl)-1H-pyrazol-1-yl)butan-2-ol | Mass spectrum (apci) m/z = 394.2 (M + H) |
| 159 | (isolated "Peak A") | (3S,4R)-4-(4-(4-(1-(pentan-3-yl)-1H-pyrazol-4-yl)pyrazolo[1,5-a]pyrazin-6-yl)-1H-pyrazol-1-yl)tetrahydrofuran-3-ol | Mass spectrum (apci) m/z = 408.2 (M + H) |
| 160 | (isolated "Peak B") | (3R,4S)-4-(4-(4-(1-(pentan-3-yl)-1H-pyrazol-4-yl)pyrazolo[1,5-a]pyrazin-6-yl)-1H-pyrazol-1-yl)tetrahydrofuran-3-ol | Mass spectrum (apci) m/z = 408.2 (M + H) |

Example 161 trans-3-(4-(4-(1-(pentan-3-yl)-1H-pyrazol-4-yl)pyrazolo[1,5-a]pyrazin-6-yl)-1H-pyrazol-1-yl)cyclobutanol

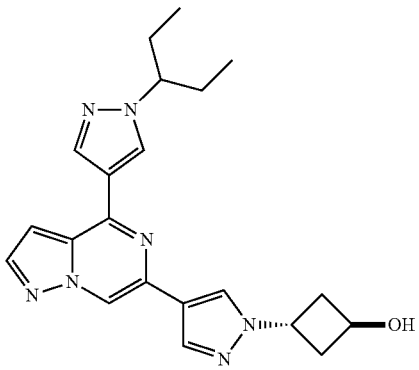 [SMILES: CCC(CC)n1cc(-c2nc(-c3cnn([C@H]4C[C@H](O)C4)c3)cn3nccc23)cn1]

To a solution of trans-3-(4-(4-(1-(pentan-3-yl)-1H-pyrazol-4-yl)pyrazolo[1,5-a]pyrazin-6-yl)-1H-pyrazol-1-yl)cyclobutyl pivalate (0.079 g, 0.17 mmol) in THF (1.1 mL, 0.17 mmol) at 0° C. was added diisobutylaluminum hydride (0.53 mL, 0.53 mmol) (1.0 M Hexanes). The reaction mixture was stirred for 1 hour and then carefully quenched with a saturated aqueous Na/K tartrate solution. The reaction mixture was stirred and the layers were separated. The aqueous phase was extracted with EtOAc. The combined organic extracts were dried over $Na_2SO_4$, filtered and concentrated. The residue was purified over silica gel (EtOAc) to afford trans-3-(4-(4-(1-(pentan-3-yl)-1H-pyrazol-4-yl)pyrazolo[1,5-a]pyrazin-6-yl)-1H-pyrazol-1-yl)cyclobutanol as a white foam. Mass spectrum (apci) m/z=392.2 (M+H). $^1$H NMR ($CDCl_3$) δ 8.45 (d, J=1.0 Hz, 1H), 8.27 (s, 1H), 8.16 (s, 1H), 8.03 (d, J=2.5 Hz, 1H), 8.01 (s, 1H), 7.99 (s, 1H), 6.95 (dd, J=2.3, 1.0 Hz, 1H), 5.05 (m, 1H), 4.79 (m, 1H), 4.03 (m, 1H), 2.93 (m, 2H), 2.58 (m, 2H), 2.06-1.85 (m, 5H), 0.86 (t, J=7.4 Hz, 6H).

Example 162

(1s,3s)-1-methyl-3-(4-(4-(1-(pentan-3-yl)-1H-pyrazol-4-yl)pyrazolo[1,5-a]pyrazin-6-yl)-1H-pyrazol-1-yl)cyclobutanol

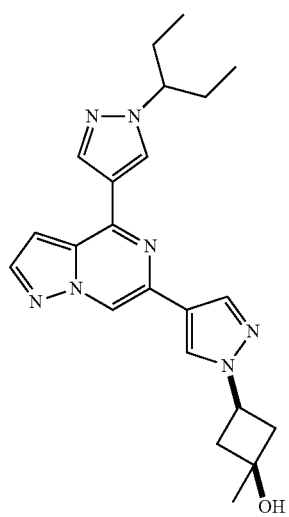

3-(4-(4-(1-(Pentan-3-yl)-1H-pyrazol-4-yl)pyrazolo[1,5-a]pyrazin-6-yl)-1H-pyrazol-1-yl)cyclobutanone (25 mg, 0.0642 mmol) was placed in THF and cooled to 0° C. Methylmagnesium bromide (60.2 μL, 0.0963 mmol) was added and the reaction mixture was stirred at 0° C. for 15 minutes. Water was added slowly and the reaction mixture was extracted with $CH_2Cl_2$. The organic layers were combined and concentrated. The residue was purified over silica gel (0-8% MeOH in $CH_2Cl_2$) and then by reverse phase chromatography (C18, 5-95% $CH_3CN$ in water) to provide (1s,3s)-1-methyl-3-(4-(4-(1-(pentan-3-yl)-1H-pyrazol-4-yl)pyrazolo[1,5-a]pyrazin-6-yl)-1H-pyrazol-1-yl)cyclobutanol (23.8 mg, 0.0587 mmol, 91.4% yield). Mass spectrum (apci) m/z=406.2 (M+H). $^1$H NMR ($CDCl_3$) δ 8.45 (d, J=0.8 Hz, 1H), 8.26 (s, 1H), 8.17 (d, J=0.6 Hz, 1H), 8.03 (m, 2H), 8.00 (s, 1H), 6.95 (dd, J=2.5, 1.0 Hz, 1H), 4.57 (m, 1H), 4.03 (m, 1H), 3.38 (s, 1H), 2.78 (m, 2H), 2.67 (m, 2H), 2.07-1.86 (m, 4H), 1.48 (s, 3H), 0.86 (t, J=7.4 Hz, 6H).

Examples 163 and 164

(1s,3s)-1-(hydroxymethyl)-3-(4-(4-(1-(pentan-3-yl)-1H-pyrazol-4-yl)pyrazolo[1,5-a]pyrazin-6-yl)-1H-pyrazol-1-yl)cyclobutanol and (1r,3r)-1-(hydroxymethyl)-3-(4-(4-(1-(pentan-3-yl)-1H-pyrazol-4-yl)pyrazolo[1,5-a]pyrazin-6-yl)-1H-pyrazol-1-yl)cyclobutanol

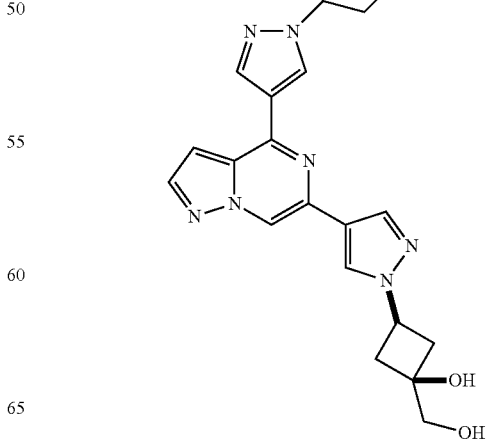

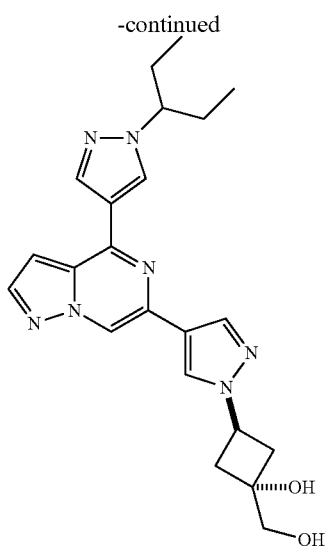

Step A:

Methyltriphenylphosphonium bromide (0.411 g, 1.15 mmol) and potassium 2-methylpropan-2-olate (0.129 g, 1.15 mmol) were placed in THF (7.34 mL, 1.03 mmol) and the reaction mixture was stirred for 2 hours. 3-(4-(4-(1-(Pentan-3-yl)-1H-pyrazol-4-yl)pyrazolo[1,5-a]pyrazin-6-yl)-1H-pyrazol-1-yl)cyclobutanone (0.400 g, 1.03 mmol) was added and the reaction mixture was allowed to continue stirring for 2 hours. Water (20 mL) was added the reaction mixture was extracted with EtOAc. The combined organic layers were dried over $Na_2SO_4$, and concentrated. The residue was purified over silica gel (0-8% MeOH in $CH_2Cl_2$), followed by reverse phase chromatography (C18, 5-95% $CH_3CN$/Water) to afford 6-(1-(3-methylenecyclobutyl)-1H-pyrazol-4-yl)-4-(1-(pentan-3-yl)-1H-pyrazol-4-yl)pyrazolo[1,5-a]pyrazine (0.070 g, 0.181 mmol, 17.6% yield) as a white foam.

Step B:

To a stirred solution of 6-(1-(3-methylenecyclobutyl)-1H-pyrazol-4-yl)-4-(1-(pentan-3-yl)-1H-pyrazol-4-yl)pyrazolo[1,5-a]pyrazine (58 mg, 0.150 mmol) in 1 mL of 8:1 acetone:water at room temperature under nitrogen was added N-methylmorpholine-N-oxide (31.6 mg, 0.269 mmol) followed by $OsO_4$ (58.7 μL, 0.00748 mmol) (4% water solution). The reaction mixture was stirred at room temperature for 1 hour, then quenched with 0.2 M aqueous $Na_2S_2O_3$ (1 mL) and stirred for 5 minutes. The reaction mixture was diluted with 15 mL of dichloromethane and washed mL with 0.2 M sodium thiosulfate. The combined organic phases were isolated, dried over $MgSO_4$, filtered and concentrated and purified over silica gel (0% to 10% MeOH in $CH_2Cl_2$) to afford 2 isomers. Faster eluting peak=Peak A: (1s,3s)-1-(hydroxymethyl)-3-(4-(4-(1-(pentan-3-yl)-1H-pyrazol-4-yl)pyrazolo[,5-a]pyrazin-6-yl)-1H-pyrazol-1-yl)cyclobutanol (7.2 mg, 0.0171 mmol, 11.4% yield) Mass spectrum (apci) m/z=422.2 (M+H). $^1$H NMR ($CDCl_3$) δ 8.46 (s, 1H), 8.27 (s, 1H), 8.17 (s, 1H), 8.04 (s, 1H), 8.03 (d, J=2.5 Hz, 1H), 8.02 (s, 1H), 6.95 (dd, J=2.5, 1.0 Hz, 1H), 4.58 (m, 1H), 4.03 (m, 1H), 3.70 (m, 3H), 2.88 (m, 2H), 2.63 (m, 2H), 2.08-1.86 (m, 5H), 0.86 (t, J=7.4 Hz, 6H); and a slower eluting peak=Peak B: (1r,3r)-1-(hydroxymethyl)-3-(4-(4-(1-(pentan-3-yl)-1H-pyrazol-4-yl)pyrazolo[1,5-a]pyrazin-6-yl)-1H-pyrazol-1-yl)cyclobutanol (17.6 mg, 0.0418 mmol, 27.9% yield). Mass spectrum (apci) m/z=422.2 (M+H). $^1$H NMR ($CDCl_3$) δ 8.45 (s, 1H), 8.27 (s, 1H), 8.16 (s, 1H), 8.03 (d, J=2.2 Hz, 1H), 8.00 (s, 1H), 7.98 (s, 1H), 6.95 (d, J=2.2 Hz, 1H), 5.08 (pentet, J=7.5 Hz, 1H), 4.03 (m, 1H), 3.77 (s, 2H), 2.79 (m, 2H), 2.65 (m, 2H), 2.50 (br s, 1H), 2.12 (br s, 1H), 2.05-1.86 (m, 4H), 0.86 (t, J=7.1 Hz, 6H).

Example 165

(trans-3-(4-(4-(1-(pentan-3-yl)-1H-pyrazol-4-yl)pyrazolo[1,5-a]pyrazin-6-yl)-1H-pyrazol-1-yl)cyclobutyl)methanol

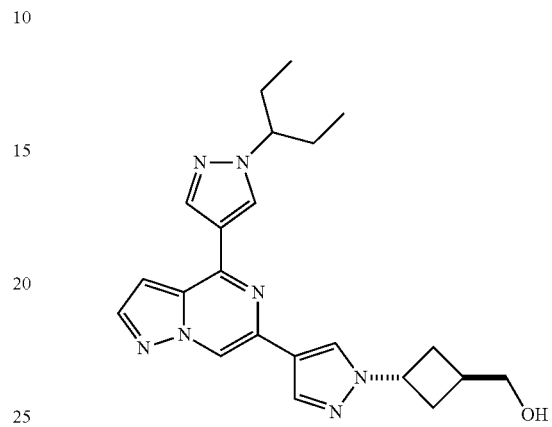

Step A:

To a solution of 4-(1-(pentan-3-yl)-1H-pyrazol-4-yl)-6-(1H-pyrazol-4-yl)pyrazolo[1,5-a]pyrazine (0.100 g, 0.311 mmol) and methyl 3-chlorocyclobutanecarboxylate (0.0925 g, 0.622 mmol) in DMF (1.56 mL, 0.311 mmol) was added cesium carbonate (0.203 g, 0.622 mmol) and the reaction mixture was stirred at 80° C. for 5 hours. The reaction mixture was cooled to ambient temperature, diluted with water (15 mL) and stirred for 10 minutes. The reaction mixture was extracted with EtOAc and the combined extracts were washed with brine, dried over $Na_2SO_4$, filtered and concentrated. The residue was purified over silica gel (50% EtOAc/hexanes) to afford two isomers. Faster eluting peak: trans-methyl 3-(4-(4-(1-(pentan-3-yl)-1H-pyrazol-4-yl)pyrazolo[1,5-a]pyrazin-6-yl)-1H-pyrazol-1-yl)cyclobutanecarboxylate (28 mg, 21% yield) as an off-white foam. Slower eluting peak: cis-methyl 3-(4-(4-(1-(pentan-3-yl)-1H-pyrazol-4-yl)pyrazolo[1,5-a]pyrazin-6-yl)-1H-pyrazol-1-yl)cyclobutanecarboxylate (58 mg, 43% yield) as a thick oil.

Step B:

To a solution of trans-methyl 3-(4-(4-(1-(pentan-3-yl)-1H-pyrazol-4-yl)pyrazolo[1,5-a]pyrazin-6-yl)-1H-pyrazol-1-yl)cyclobutanecarboxylate (0.025 g, 0.058 mmol) in THF (0.58 mL, 0.058 mmol) at 0° C. was added diisobutylaluminum hydride (0.18 mL, 0.18 mmol) (1.0 M Hexanes). The mixture was stirred for 1 hour and then quenched with saturated aqueous Na/K tartrate solution. The reaction mixture was stirred and the layers were separated. The aqueous phase was extracted with EtOAc. The combined organic extracts were dried over $Na_2SO_4$, filtered and concentrated. The residue was purified over silica gel (5% MeOH/$CH_2Cl_2$) to afford ((1r,3r)-3-(4-(4-(1-(pentan-3-yl)-1H-pyrazol-4-yl)pyrazolo[1,5-a]pyrazin-6-yl)-1H-pyrazol-1-yl)cyclobutyl)methanol (20 mg, 85% yield) as an off-white foam. Mass spectrum (apci) m/z=406.2 (M+H). $^1$H NMR ($CDCl_3$) δ 8.46 (d, J=0.8 Hz, 1H), 8.27 (s, 1H), 8.16 (s, 1H), 8.03 (m, 2H), 7.99 (s, 1H), 6.95 (dd, J=2.5, 1.0 Hz, 1H), 4.95 (pentet, J=7.6 Hz, 1H), 4.03 (m, 1H), 3.82 (m, 2H), 2.80 (m, 2H), 2.66 (m, 1H), 2.46 (m, 2H), 2.05-1.85 (m, 4H), 0.86 (t, J=7.4 Hz, 6H).

The following compound was prepared according to the procedure described for Example 165.

| Example | Structure | Name | Data |
|---|---|---|---|
| 166 | 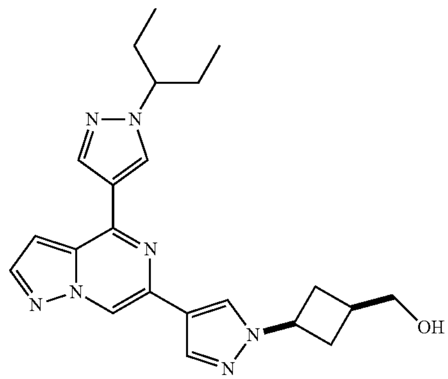 | (cis-3-(4-(4-(1-(pentan-3-yl)-1H-pyrazol-4-yl)pyrazolo[1,5-a]pyrazin-6-yl)-1H-pyrazol-1-yl)cyclobutyl)methanol | Mass spectrum (apci) m/z = 406.2 (M + H) |

Example 167

(1r,3r)-3-(4-(4-(1-(pentan-3-yl)-1H-pyrazol-4-yl)pyrazolo[1,5-a]pyrazin-6-yl)-1H-pyrazol-1-yl)cyclobutanecarboxamide

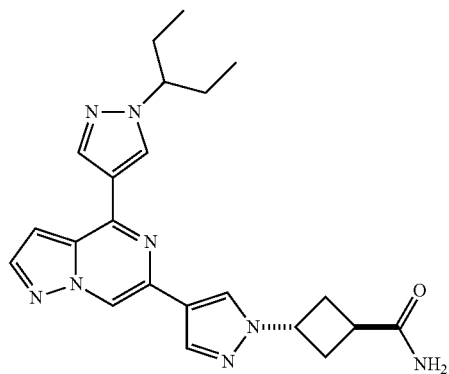

To a vial was added (1r,3r)-methyl 3-(4-(4-(1-(pentan-3-yl)-1H-pyrazol-4-yl)pyrazolo[1,5-a]pyrazin-6-yl)-1H-pyrazol-1-yl)cyclobutanecarboxylate (0.049 g, 0.11 mmol) and 7 N $NH_3$ in methanol (0.81 mL, 5.7 mmol) and the vial was sealed with Teflon lined cap. The mixture was warmed to 60° C. and stirred for 40 hours. Additional 7 N $NH_3$ in methanol (0.81 mL, 5.7 mmol) was added and the mixture was stirred at 80° C. for 48 hours. The mixture was cooled to ambient temperature and diluted with EtOAc. The mixture was washed with brine, dried over $Na_2SO_4$, filtered and concentrated. The residue was purified over silica gel (5% MeOH/$CH_2Cl_2$) to afford (1r,3r)-3-(4-(4-(1-(pentan-3-yl)-1H-pyrazol-4-yl)pyrazolo[1,5-a]pyrazin-6-yl)-1H-pyrazol-1-yl)cyclobutanecarboxamide (21 mg, 44% yield) as an off-white solid. Mass spectrum (apci) m/z=449.2 (M+H). $^1$H NMR ($CDCl_3$) δ 8.46 (s, 1H), 8.26 (s, 1H), 8.17 (s, 1H), 8.03 (d, J=2.5 Hz, 1H), 8.01 (s, 1H), 7.99 (s, 1H), 6.95 (dd, J=2.4, 0.8 Hz, 1H), 5.48 (br d, J=11.1 Hz, 2H), 5.15 (pentet, J=7.8 Hz, 1H), 4.03 (m, 1H), 3.17 (m, 1H), 2.95 (m, 2H), 2.83 (m, 2H), 2.06-1.86 (m, 4H), 0.86 (t, J=7.2 Hz, 6H).

The following compounds were prepared according to the procedure described for Example 167.

| Example | Structure | Name | Data |
|---|---|---|---|
| 168 | 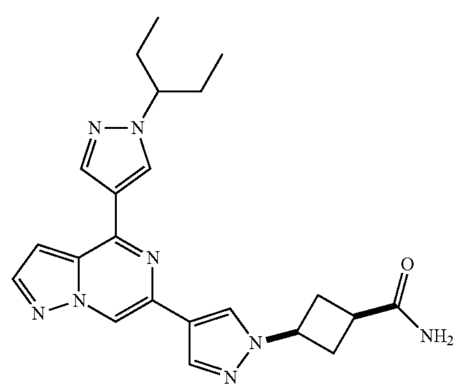 | (1s,3s)-3-(4-(4-(1-(pentan-3-yl)-1H-pyrazol-4-yl)pyrazolo[1,5-a]pyrazin-6-yl)-1H-pyrazol-1-yl)cyclobutanecarboxamide | Mass spectrum (apci) m/z = 406.2 (M + H) |

-continued
| Example | Structure | Name | Data |
|---|---|---|---|
| 169 | 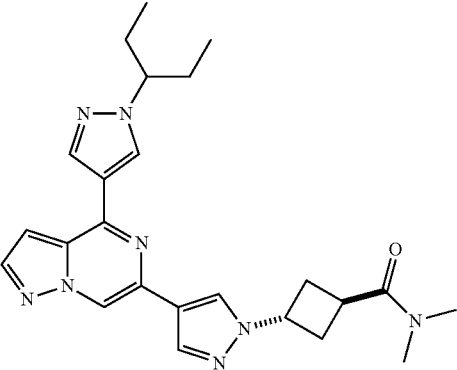 | (1r,3r)-N,N-dimethyl-3-(4-(4-(1-(pentan-3-yl)-1H-pyrazol-4-yl)pyrazolo[1,5-a]pyrazin-6-yl)-1H-pyrazol-1-yl)cyclobutanecarboxamide | Mass spectrum (apci) m/z = 447.3 (M + H) |
| 170 | 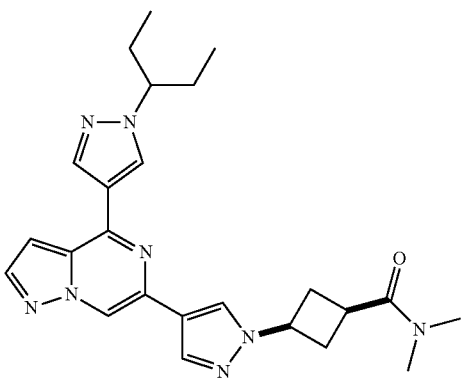 | (1s,3s)-N,N-dimethyl-3-(4-(4-(1-(pentan-3-yl)-1H-pyrazol-4-yl)pyrazolo[1,5-a]pyrazin-6-yl)-1H-pyrazol-1-yl)cyclobutanecarboxamide | Mass spectrum (apci) m/z = 447.2 (M + H) |

Example 171

(1r,3r)-N-(2-hydroxyethyl)-3-(4-(4-(1-(pentan-3-yl)-1H-pyrazol-4-yl)pyrazolo[1,5-a]pyrazin-6-yl)-1H-pyrazol-1-yl)cyclobutanecarboxamide

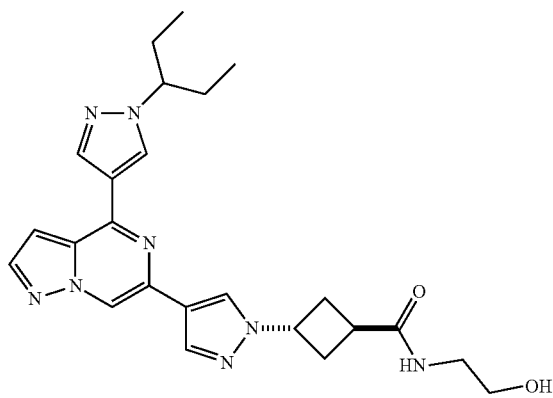

Step A:

To a vial was added (1r,3r)-methyl 3-(4-(4-(1-(pentan-3-yl)-1H-pyrazol-4-yl)pyrazolo[1,5-a]pyrazin-6-yl)-1H-pyrazol-1-yl)cyclobutanecarboxylate (0.049 g, 0.113 mmol) and 2-(tetrahydro-pyran-2-yloxy)-ethylamine (0.0328 g, 0.226 mmol), followed by lithium bis(trimethylsilyl)amide solution (0.170 mL, 0.170 mmol, 1.0M toluene). The reaction mixture was stirred for 2 hours. Additional lithium bis(trimethylsilyl)amide solution (0.170 mL, 0.170 mmol) was added. The reaction mixture was stirred for another 2 hours and quenched by the addition of a saturated aqueous NH$_4$Cl solution. The reaction mixture was ten extracted with EtOAc, and the combined extracts were dried over Na$_2$SO$_4$, filtered and concentrated. The crude product was purified over silica gel (4% MeOH/EtOAc) to afford (1r,3r)-3-(4-(4-(1-(pentan-3-yl)-1H-pyrazol-4-yl)pyrazolo[1,5-a]pyrazin-6-yl)-1H-pyrazol-1-yl)-N-(2-((tetrahydro-2H-pyran-2-yl)oxy)ethyl)cyclobutanecarboxamide (26 mg, 42% yield) as a colorless oil Step B:

(1r,3r)-3-(4-(4-(1-(Pentan-3-yl)-1H-pyrazol-4-yl)pyrazolo[1,5-a]pyrazin-6-yl)-1H-pyrazol-1-yl)-N-(2-((tetrahydro-2H-pyran-2-yl)oxy)ethyl)cyclobutanecarboxamide (0.024 g, 0.044 mmol) was dissolved in MeOH (1.1 mL, 0.044 mmol) and the resulting yellow solution was treated with hydrochloric acid (5 to 6 N solution in 2-propanol; 0.18 mL, 0.88 mmol) and the reaction mixture was stirred for 2 hours. The reaction mixture was treated with 3N NaOH (0.150 mL) and saturated aqueous NaHCO$_3$ until basic. The reaction mixture was diluted with EtOAc (10 mL) and the layers were separated. The reaction mixture was extracted with EtOAc and the combined organic extracts were dried over Na$_2$SO$_4$, filtered and concentrated. The crude product was purified over silica gel (6% MeOH/CH$_2$Cl$_2$) to afford (1r,3r)-N-(2-hydroxyethyl)-3-(4-(4-(1-(pentan-3-yl)-1H-pyrazol-4-yl)pyrazolo[1,5-a]pyrazin-6-yl)-1H-pyrazol-1-yl)cyclobutanecarboxamide (15 mg, 66% yield) as an off-white foam. Mass spectrum (apci) m/z=449.2 (M+H). $^1$H NMR (CDCl$_3$) δ 8.45 (s, 1H), 8.26 (s, 1H), 8.17 (s, 1H), 8.03 (d, J=2.3 Hz, 1H), 8.01 (s, 1H), 8.00 (s, 1H), 6.95 (d, J=2.3 Hz, 1H), 6.03 (t, J=5.1 Hz, 1H), 5.17 (pentet, J=7.8 Hz, 1H), 4.03 (m, 1H), 3.78 (t, J=4.9 Hz, 2H), 3.50 (q, J=5.5 Hz, 2H), 3.12 (m, 1H), 2.99-2.77 (m, 5H), 2.06-1.85 (m, 4H), 0.86 (t, J=7.2 Hz, 6H).

The following compound was prepared according to the procedure described for Example 171.

| Example | Structure | Name | Data |
|---|---|---|---|
| 172 | 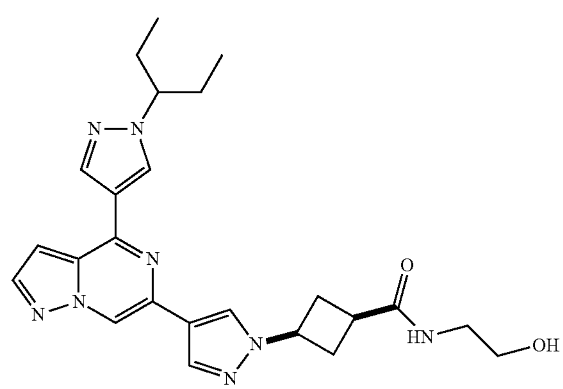 | (1s,3s)-N-(2-hydroxyethyl)-3-(4-(4-(1-(pentan-3-yl)-1H-pyrazol-4-yl)pyrazolo[1,5-a]pyrazin-6-yl)-1H-pyrazol-1-yl)cyclobutanecarboxamide | Mass spectrum (apci) m/z = 463.3 (M + H) |

Example 173

(S)-2-hydroxy-1-(3-(4-(4-(1-(pentan-3-yl)-1H-pyrazol-4-yl)pyrazolo[1,5-a]pyrazin-6-yl)-1H-pyrazol-1-yl)azetidin-1-yl)propan-1-one

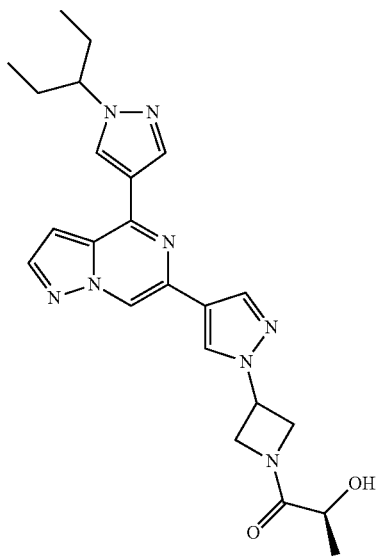 [SMILES: CCC(CC)n1cc(-c2nc(-c3cnn(C4CN(C(=O)[C@H](C)O)C4)c3)cn3nccc23)cn1]

Step A:

6-(1-(Azetidin-3-yl)-1H-pyrazol-4-yl)-4-(1-(pentan-3-yl)-1H-pyrazol-4-yl)pyrazolo[1,5-a]pyrazine (30 mg, 0.080 mmol) was dissolved in CH$_2$Cl$_2$ (1 mL) and pyridine (25.7 µL, 0.32 mmol) was added, followed by (S)-1-chloro-1-oxopropan-2-yl acetate (20.2 µL, 0.16 mmol). After stirring for 1 hour, the reaction mixture was quenched with water (0.1 mL) and concentrated. The residue was purified by reverse phase chromatography (C18, 10-95% CH$_3$CN in water) to afford (S)-1-oxo-1-(3-(4-(4-(1-(pentan-3-yl)-1H-pyrazol-4-yl)pyrazolo[1,5-a]pyrazin-6-yl)-1H-pyrazol-1-yl)azetidin-1-yl)propan-2-yl acetate (25 mg, 64% yield).

Step B:

(S)-1-Oxo-1-(3-(4-(4-(1-(pentan-3-yl)-1H-pyrazol-4-yl)pyrazolo[1,5-a]pyrazin-6-yl)-1H-pyrazol-1-yl)azetidin-1-yl)propan-2-yl acetate (27 mg, 0.055 mmol) was dissolved in MeOH (2 mL). K$_2$CO$_3$ (2 mg, 0.014 mmol) was added and the reaction mixture was stirred at room temperature for 1 hour. The reaction mixture was diluted with Et$_2$O (20 mL), filtered and concentrated to afford (S)-2-hydroxy-1-(3-(4-(4-(1-(pentan-3-yl)-1H-pyrazol-4-yl)pyrazolo[1,5-a]pyrazin-6-yl)-1H-pyrazol-1-yl)azetidin-1-yl)propan-1-one (21 mg, 85% yield) as a colorless glass. Mass spectrum (apci) m/z=449.2 (M+H). $^1$H NMR (CDCl$_3$) δ 8.47 (s, 1H), 8.27 (s, 1H), 8.16 (d, J=2.7 Hz, 1H), 8.09 (s, 1H), 8.05 (m, 2H), 6.97 (dd, J=2.5, 1.0 Hz, 1H), 5.27 (m, 1H), 4.75-4.51 (m, 4H), 4.29 (m, 1H), 4.04 (m, 1H), 3.32 (br s, 1H), 2.06-1.86 (m, 4H), 1.40 (m, 3H), 0.86 (t, J=7.4 Hz, 6H).

The following compound was prepared according to the procedure described for Example 173.

| Example | Structure | Name | Data |
|---|---|---|---|
| 174 | 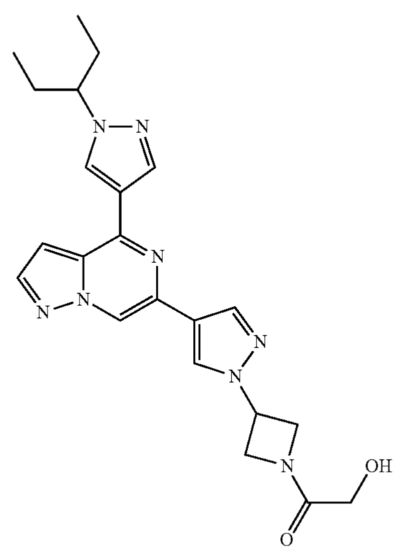 [SMILES: CCC(CC)n1cc(-c2nc(-c3cnn(C4CN(C(=O)CO)C4)c3)cn3nccc23)cn1] | 2-hydroxy-1-(3-(4-(4-(1-(pentan-3-yl)-1H-pyrazol-4-yl)pyrazolo[1,5-a]pyrazin-6-yl)-1H-pyrazol-1-yl)azetidin-1-yl)ethanone | Mass spectrum (apci) m/z = 435.2 (M + H) |

Example 175

(R)-2-hydroxy-1-(3-(4-(4-(1-(pentan-3-yl)-1H-pyrazol-4-yl)pyrazolo[1,5-a]pyrazin-6-yl)-1H-pyrazol-1-yl)azetidin-1-yl)propan-1-one

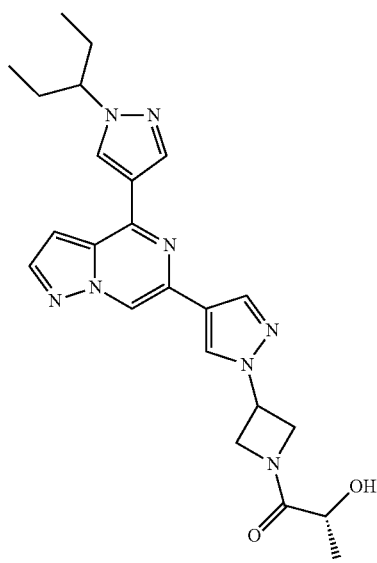 [SMILES: CCC(CC)n1cc(-c2nc(-c3cnn(C4CN(C(=O)[C@@H](C)O)C4)c3)cn3nccc23)cn1]

6-(1-(Azetidin-3-yl)-1H-pyrazol-4-yl)-4-(1-(pentan-3-yl)-1H-pyrazol-4-yl)pyrazolo[1,5-a]pyrazine (0.05 g, 0.133 mmol) and D-lactic acid (0.0150 g, 0.166 mmol) were added to DMF (1.90 mL, 0.133 mmol). (2-(7-Aza-1H-benzotriazol-1-yl)-1,1,3,3-tetramethyluronium hexafluorophosphate) (0.0657 g, 0.173 mmol) was added and the reaction mixture was allowed to stir for 24 hours. Water (10 mL) was added and the reaction mixture was extracted with EtOAc. The combined organic layers were dried over $Na_2SO_4$, and concentrated. The crude mixture was purified over silica gel (0-6% MeOH w/$NH_4OH$ in $CH_2Cl_2$) to afford (R)-2-hydroxy-1-(3-(4-(4-(1-(pentan-3-yl)-1H-pyrazol-4-yl)pyrazolo[1,5-a]pyrazin-6-yl)-1H-pyrazol-1-yl)azetidin-1-yl)propan-1-one (0.0092 g, 0.0205 mmol, 15.4% yield) as a white solid. Mass spectrum (apci) m/z=449.2 (M+H). $^1$H NMR ($CDCl_3$) δ 8.47 (s, 1H), 8.27 (s, 1H), 8.16 (d, J=2.7 Hz, 1H), 8.09 (s, 1H), 8.05 (m, 2H), 6.97 (dd, J=2.5, 1.0 Hz, 1H), 5.27 (m, 1H), 4.75-4.51 (m, 4H), 4.29 (m, 1H), 4.04 (m, 1H), 3.32 (dd, J=11.2, 6.5 Hz, 1H), 2.06-1.86 (m, 4H), 1.40 (t, J=6.7 Hz, 3H), 0.86 (t, J=7.4 Hz, 6H).

The following compounds were prepared according to the procedure described for Example 175.

| Example | Structure | Name | Data |
|---|---|---|---|
| 176 | 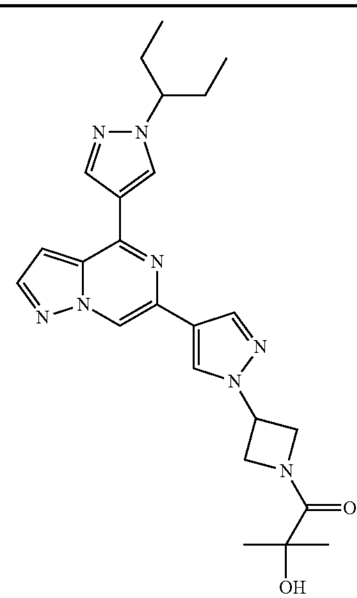 | 2-hydroxy-2-methyl-1-(3-(4-(4-(1-(pentan-3-yl)-1H-pyrazol-4-yl)pyrazolo[1,5-a]pyrazin-6-yl)-1H-pyrazol-1-yl)azetidin-1-yl)propan-1-one | Mass spectrum (apci) m/z = 463.3 (M + H) |

-continued
| Example | Structure | Name | Data |
|---|---|---|---|
| 177 | 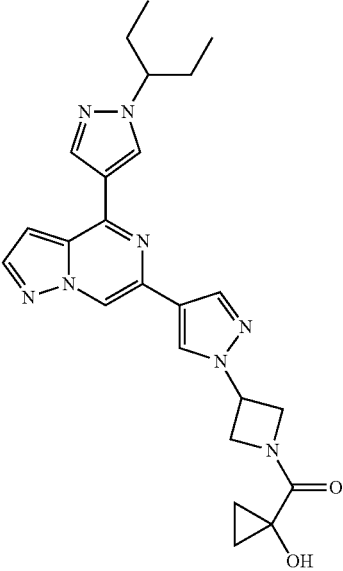 [SMILES: CCC(CC)n1cc(-c2nc(-c3cnn(C4CN(C(=O)C5(O)CC5)C4)c3)cn3nccc23)cn1] | (1-hydroxycyclopropyl)(3-(4-(4-(1-(pentan-3-yl)-1H-pyrazol-4-yl)pyrazolo[1,5-a]pyrazin-6-yl)-1H-pyrazol-1-yl)azetidin-1-yl)methanone | Mass spectrum (apci) m/z = 461.2 (M + H) |
| 178 | 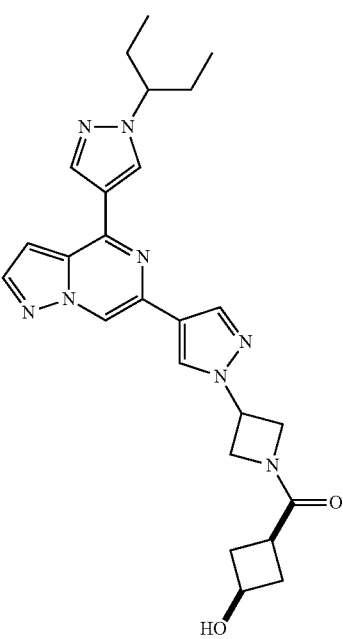 | (cis-3-hydroxycyclobutyl)(3-(4-(4-(1-(pentan-3-yl)-1H-pyrazol-4-yl)pyrazolo[1,5-a]pyrazin-6-yl)-1H-pyrazol-1-yl)azetidin-1-yl)methanone | Mass spectrum (apci) m/z = 475.2 (M + H) |

-continued

| Example | Structure | Name | Data |
|---|---|---|---|
| 179 | 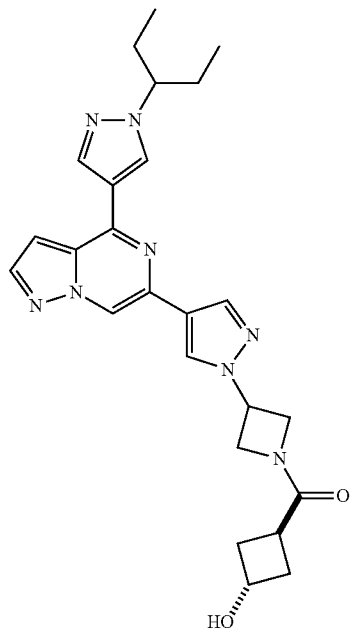 | (trans-3-hydroxycyclobutyl)(3-(4-(4-(1-(pentan-3-yl)-1H-pyrazol-4-yl)pyrazolo[1,5-a]pyrazin-6-yl)-1H-pyrazol-1-yl)azetidin-1-yl)methanone | Mass spectrum (apci) m/z = 475.2 (M + H) |

Example 180

2-(3-hydroxyazetidin-1-yl)-1-(3-(4-(4-(1-(pentan-3-yl)-1H-pyrazol-4-yl)pyrazolo[1,5-a]pyrazin-6-yl)-1H-pyrazol-1-yl)azetidin-1-yl)ethanone

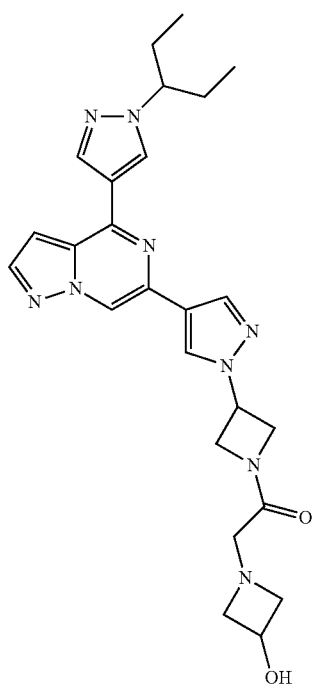 [SMILES: CCC(CC)n1cc(-c2nc(-c3cnn(C4CN(C(=O)CN5CC(O)C5)C4)c3)cn3nccc23)cn1]

6-(1-(Azetidin-3-yl)-1H-pyrazol-4-yl)-4-(1-(pentan-3-yl)-1H-pyrazol-4-yl)pyrazolo[1,5-a]pyrazine (0.050 g, 0.1328 mmol) and triethylamine (0.2036 mL, 1.461 mmol) were added to DMF (1 mL) and 2-chloroacetyl chloride (0.01321 mL, 0.1660 mmol) was added. The reaction mixture was stirred for 1.5 hours. Azetidin-3-ol hydrochloride (0.1164 g, 1.063 mmol) was added and the reaction mixture was stirred for an additional 2 hours. Water (10 mL) was added and the reaction mixture was extracted with EtOAc. The combined organic layers were dried over $Na_2SO_4$, and concentrated. The mixture was purified over silica gel (0-10% MeOH w/$NH_4OH$ in $CH_2Cl_2$) to afford 2-(3-hydroxyazetidin-1-yl)-1-(3-(4-(4-(1-(pentan-3-yl)-1H-pyrazol-4-yl)pyrazolo[1,5-a]pyrazin-6-yl)-1H-pyrazol-1-yl)azetidin-1-yl)ethanone (0.0027 g, 0.005515 mmol, 4.152% yield) as a white solid. Mass spectrum (apci) m/z=490.2 (M+H). $^1$H NMR ($CDCl_3$) δ 8.47 (d, J=1.0 Hz, 1H), 8.27 (s, 1H), 8.17 (s, 1H), 8.10 (s, 1H), 8.05 (d, J=2.3 Hz, 1H), 8.03 (s, 1H), 6.97 (dd, J=2.3, 1.0 Hz, 1H), 5.21 (m, 1H), 4.68 (d, J=6.7 Hz, 2H), 4.58-4.45 (m, 3H), 4.04 (m, 1H), 3.83 (m, 2H), 3.27 (d, J=4.5 Hz, 2H), 3.16 (m, 2H), 2.05-1.85 (m, 4H), 0.86 (t, J=7.4 Hz, 6H).

The following compound was prepared according to the procedure described for Example 180.

| Example | Structure | Name | Data |
|---|---|---|---|
| 181 | 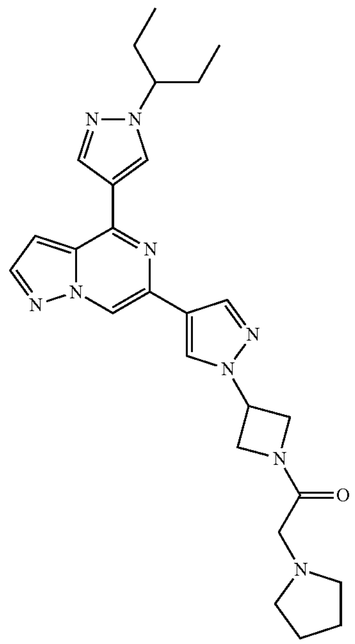 [SMILES: CCC(CC)n1cc(-c2nc(-c3cnn(C4CN(C(=O)CN5CCCC5)C4)c3)cn3nccc23)cn1] | 1-(3-(4-(4-(1-(pentan-3-yl)-1H-pyrazol-4-yl)pyrazolo[1,5-a]pyrazin-6-yl)-1H-pyrazol-1-yl)azetidin-1-yl)-2-(pyrrolidin-1-yl)ethanone | Mass spectrum (apci) m/z = 488.3 (M + H) |

Example 182

N,N-dimethyl-2-oxo-2-(3-(4-(4-(1-(pentan-3-yl)-1H-pyrazol-4-yl)pyrazolo[1,5-a]pyrazin-6-yl)-1H-pyrazol-1-yl)azetidin-1-yl)acetamide

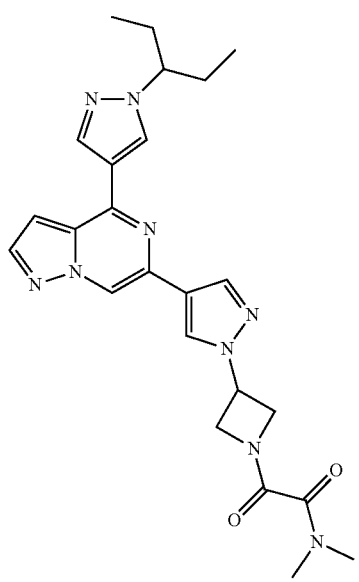 [SMILES: CCC(CC)n1cc(-c2nc(-c3cnn(C4CN(C(=O)C(=O)N(C)C)C4)c3)cn3nccc23)cn1]

6-(1-(Azetidin-3-yl)-1H-pyrazol-4-yl)-4-(1-(pentan-3-yl)-1H-pyrazol-4-yl)pyrazolo[1,5-a]pyrazine (48 mg, 0.13 mmol) was stirred in $CH_2Cl_2$ (2 mL) and 2-(dimethylamino)-2-oxoacetic acid (45 mg, 0.38 mmol), O-(Benzotriazol-1-yl)-N,N,N',N'-tetramethyluronium tetrafluoroborate (49 mg, 0.15 mmol) and diisopropylethylamine (26.7 µL, 0.15 mmol) were added. The reaction mixture was stirred at room temperature overnight. The reaction mixture was quenched with water and partitioned between 5% isopropyl alcohol in $CH_2Cl_2$ and 0.1 M NaOH with brine. The organic layer was washed with a citric acid/brine mixture, dried over sodium sulfate, filtered and concentrated. The residue was purified by reverse phase chromatography (C18, 10 to 95% $CH_3CN$ in water) to afford N,N-dimethyl-2-oxo-2-(3-(4-(4-(1-(pentan-3-yl)-1H-pyrazol-4-yl)pyrazolo[1,5-a]pyrazin-6-yl)-1H-pyrazol-1-yl)azetidin-1-yl)acetamide (17 mg, 28% yield) as a colorless glass. Mass spectrum (apci) m/z=476.3 (M+H). $^1$H NMR ($CDCl_3$) δ 8.47 (d, J=1.0 Hz, 1H), 8.26 (s, 1H), 8.17 (s, 1H), 8.11 (s, 1H), 8.04 (m, 2H), 6.97 (dd, J=2.5, 1.0 Hz, 1H), 5.25 (m, 1H), 4.89 (ddd, J=11.0, 8.2, 1.4 Hz, 1H), 4.77 (dd, J=10.4, 5.5 Hz, 1H), 4.64 (ddd, J=11.0, 8.2, 1.4 Hz, 1H), 4.57 (dd, J=11.2, 5.7 Hz, 1H), 4.04 (m, 1H), 3.21 (s, 3H), 3.00 (s, 3H), 2.06-1.85 (m, 4H), 0.86 (t, J=7.4 Hz, 6H).

Example 183

(S)-3-amino-2-methyl-4-(4-(4-(1-(pentan-3-yl)-1H-pyrazol-4-yl)pyrazolo[1,5-a]pyrazin-6-yl)-1H-pyrazol-1-yl)butan-2-ol

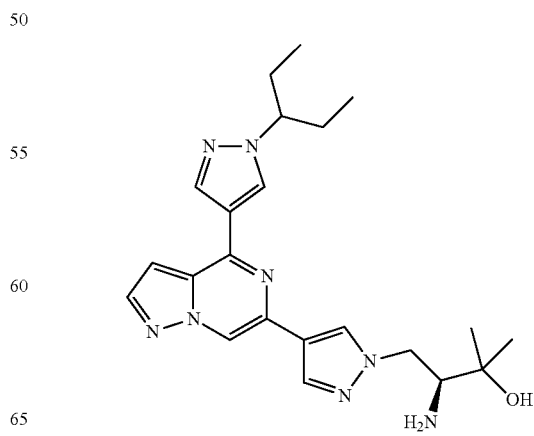

241

Step A:

To a solution of 4-(1-(pentan-3-yl)-1H-pyrazol-4-yl)-6-(1H-pyrazol-4-yl)pyrazolo[1,5-a]pyrazine (0.100 g, 0.311 mmol) and N-(tert-butoxycarbonyl)-3-iodo-L-alanine methyl ester (0.205 g, 0.622 mmol) in DMF (1.6 mL) was added $Cs_2CO_3$ (0.203 g, 0.622 mmol) and the mixture was stirred at 85° C. for 16 hours. The reaction mixture was cooled to ambient temperature, diluted with water (15 mL) and stirred for 10 minutes. The mixture was extracted with EtOAc and the combined extracts were washed with brine, dried over $Na_2SO_4$, filtered and concentrated. The residue was purified over silica gel (70% EtOAc/hexanes) to afford (S)-methyl 2-((tert-butoxycarbonyl)amino)-3-(4-(4-(1-(pentan-3-yl)-1H-pyrazol-4-yl)pyrazolo[1,5-a]pyrazin-6-yl)-1H-pyrazol-1-yl)propanoate (100 mg, 62% yield) as a white foam.

Step B:

To a solution of (S)-methyl 2-((tert-butoxycarbonyl)amino)-3-(4-(4-(1-(pentan-3-yl)-1H-pyrazol-4-yl)pyrazolo[1,5-a]pyrazin-6-yl)-1H-pyrazol-1-yl)propanoate (0.095 g, 0.18 mmol) in THF (0.91 mL, 0.18 mmol) at 0° C. was added methylmagnesium bromide (0.30 mL, 0.91 mmol) (3.0M $Et_2O$) and the mixture was stirred at 0° C. for 2 hours and then at ambient temperature for 2 hours. The reaction mixture was quenched by the addition of saturated aqueous $NH_4Cl$ (5 mL) and extracted with EtOAc (3×10 mL). The combined organic layers were dried over $Na_2SO_4$, filtered and concentrated. The residue was purified over silica gel (EtOAc) to afford (S)-tert-butyl (3-hydroxy-3-methyl-1-(4-(4-(1-(pentan-3-yl)-1H-pyrazol-4-yl)pyrazolo[1,5-a]pyrazin-6-yl)-1H-pyrazol-1-yl)butan-2-yl)carbamate (70 mg, 74% yield) as a light yellow solid.

Step C:

To a solution of (S)-tert-butyl (3-hydroxy-3-methyl-1-(4-(4-(1-(pentan-3-yl)-1H-pyrazol-4-yl)pyrazolo[1,5-a]pyrazin-6-yl)-1H-pyrazol-1-yl)butan-2-yl)carbamate (0.066 g, 0.13 mmol) in EtOH (1.3 mL, 0.13 mmol) and THF (1.3 mL, 0.13 mmol) was added hydrochloric acid, 5 to 6 N solution in 2-propanol (0.51 mL, 2.5 mmol) and the mixture was stirred at ambient temperature for 7 hours. The reaction mixture was treated with 3N NaOH (1 mL) and then saturated aqueous $NaHCO_3$ was added until the reaction mixture was basic. The reaction mixture was diluted with EtOAc (10 mL) and the layers were separated. The aqueous layer was extracted with EtOAc and the combined organic extracts were dried over $Na_2SO_4$, filtered and concentrated. The residue was purified over silica gel (5-8% MeOH with $NH_4OH/CH_2Cl_2$) to afford (S)-3-amino-2-methyl-4-(4-(4-(1-(pentan-3-yl)-1H-pyrazol-4-yl)pyrazolo[1,5-a]pyrazin-6-yl)-1H-pyrazol-1-yl)butan-2-ol (44 mg, 82% yield) as a white foam. Mass spectrum (apci) m/z=423.2 (M+H). $^1H$ NMR ($CDCl_3$) δ 8.46 (d, J=1.0 Hz, 1H), 8.27 (s, 1H), 8.17 (s, 1H), 8.03 (m, 2H), 7.99 (s, 1H), 6.96 (dd, J=2.3, 0.8 Hz, 1H), 4.47 (dd, J=13.7, 3.1 Hz, 1H), 4.03 (m, 2H), 3.21 (dd, J=10.0, 3.3 Hz, 1H), 3.15 (br s, 1H), 2.07-1.86 (m, 4H), 1.32 (s, 3H), 1.29 (s, 3H), 0.86 (t, J=7.2 Hz, 6H).

242

Example 184

4-((4-(4-(1-(pentan-3-yl)-1H-pyrazol-4-yl)pyrazolo[1,5-a]pyrazin-6-yl)-1H-pyrazol-1-yl)methyl)piperidin-4-ol

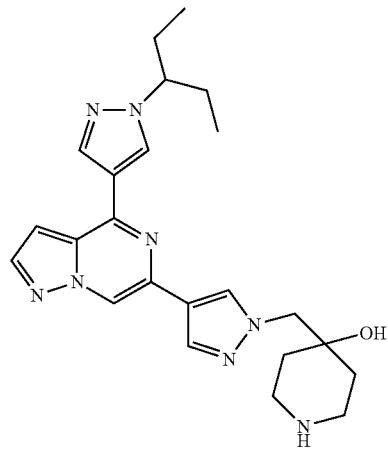 [SMILES: CCC(CC)n1cc(-c2nc(-c3cnn(CC4(O)CCNCC4)c3)cn3nccc23)cn1]

Step A:

To a stirred solution of 4-(1-(pentan-3-yl)-1H-pyrazol-4-yl)-6-(1H-pyrazol-4-yl)pyrazolo[1,5-a]pyrazine (80 mg, 0.249 mmol) in 1 mL of DMF at room temperature under nitrogen was added NaH (11.9 mg, 0.299 mmol) (60% oil dispersion). After 10 minutes, tert-butyl 1-oxa-6-azaspiro[2.5]octane-6-carboxylate (69.0 mg, 0.324 mmol) was added. The reaction mixture was heated to 65° C. and stirred overnight. The reaction mixture was quenched with saturated ammonium chloride solution (1 mL) and then partitioned between ethyl acetate and water. The combined organic phases were isolated, washed with brine, dried over $MgSO_4$, filtered and concentrated. The residue was purified over silica gel (20-80% ethyl acetate in hexanes) to afford tert-butyl 4-hydroxy-4-((4-(4-(1-(pentan-3-yl)-1H-pyrazol-4-yl)pyrazolo[1,5-a]pyrazin-6-yl)-1H-pyrazol-1-yl)methyl)piperidine-1-carboxylate (66 mg, 50% yield) as a yellow solid.

Step B:

To a stirred solution of tert-butyl 4-hydroxy-4-((4-(4-(1-(pentan-3-yl)-1H-pyrazol-4-yl)pyrazolo[1,5-a]pyrazin-6-yl)-1H-pyrazol-1-yl)methyl)piperidine-1-carboxylate (66 mg, 0.12 mmol) in 1 mL of dichloromethane at 0° C. in an open flask was added TFA (1 mL) and the reaction mixture was stirred for 1 hour. The reaction mixture was concentrated to dryness under a stream of nitrogen and the residue was stirred in a mixture of dichloromethane (15 mL) and 20% sodium carbonate solution (15 mL) for 5 minutes. The organic phases were isolated and the aqueous phase was extracted with dichloromethane. The combined organic layers were dried over $MgSO_4$, filtered and concentrated. The residue was purified over silica gel (eluent—gradient of 0%-20%-50% MeOH in $CH_2Cl_2$ with 2% $NH_{40}OH$) and the product was isolated and concentrated to dryness. The silica gel had dissolved in this high methanol chromatography solvent. The crude product was filtered first through paper with dichloromethane and then through a membrane filter. After concentration, 4-((4-(4-(1-(pentan-3-yl)-1H-pyrazol-4-yl)pyrazolo[1,5-a]pyrazin-6-yl)-1H-pyrazol-1-yl)methyl)piperidin-4-ol (39 mg, 69% yield) was isolated as a tan solid.

243

Mass spectrum (apci) m/z=435.2 (M+H). ¹H NMR (CDCl₃) δ 8.46 (d, J=1.0 Hz, 1H), 8.26 (s, 1H), 8.17 (s, 1H), 8.03 (d, J=2.3 Hz, 1H), 8.01 (s, 2H), 6.96 (dd, J=2.3, 1.0 Hz, 1H), 5.30 (s, 1H), 4.17 (s, 2H), 4.03 (m, 1H), 3.06 (m, 2H), 2.93 (dt, J=12.3, 3.9 Hz, 2H), 2.06-1.85 (m, 4H), 1.63 (m, 2H), 1.49 (m, 2H), 0.85 (t, J=7.2 Hz, 6H).

Example 185

1-(4-hydroxy-4-((4-(4-(1-(pentan-3-yl)-1H-pyrazol-4-yl)pyrazolo[1,5-a]pyrazin-6-yl)-1H-pyrazol-1-yl)methyl)piperidin-1-yl)ethanone

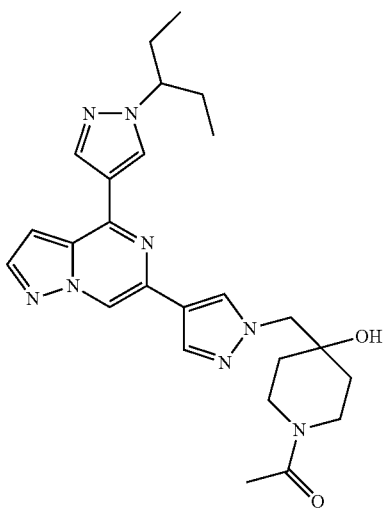 [SMILES: CCC(CC)n1cc(-c2nc(-c3cnn(CC4(O)CCN(C(C)=O)CC4)c3)cn3nccc23)cn1]

To a stirred solution of 4-((4-(4-(1-(pentan-3-yl)-1H-pyrazol-4-yl)pyrazolo[1,5-a]pyrazin-6-yl)-1H-pyrazol-1-yl)methyl)piperidin-4-ol (20 mg, 0.046 mmol) in 460 µL of dioxane and 460 µL of 20% sodium carbonate at 0° C. was added acetyl chloride (4.9 µL, 0.069 mmol). After 1 hour, an additional 3 equivalents of acetyl chloride was added. The reaction mixture was warmed to room temperature and stirred for another hour. The reaction mixture was partitioned between ethyl acetate and water. The combined organic phases were washed with brine, dried over MgSO₄, filtered and concentrated. The residue was purified over silica gel (0-10% methanol in CH₂Cl₂) to afford 1-(4-hydroxy-4-((4-(4-(1-(pentan-3-yl)-1H-pyrazol-4-yl)pyrazolo[1,5-a]pyrazin-6-yl)-1H-pyrazol-1-yl)methyl)piperidin-1-yl)ethanone (5 mg, 21% yield). Mass spectrum (apci) m/z=477.2 (M+H). ¹H NMR (CDCl₃) δ 8.47 (d, J=1.0 Hz, 1H), 8.27 (s, 1H), 8.16 (s, 1H), 8.04 (d, J=2.5 Hz, 1H), 8.02 (d, J=0.6 Hz, 1H), 7.98 (s, 1H), 6.96 (dd, J=2.3, 0.8 Hz, 1H), 4.42 (m, 1H), 4.15 (s, 2H), 4.03 (m, 1H), 3.62 (m, 1H), 3.49 (m, 1H), 3.05 (m, 1H), 2.10 (s, 3H), 2.05-1.86 (m, 4H), 1.52 (m, 4H), 0.86 (t, J=7.4 Hz, 6H).

244

Example 186

2-amino-1-(3-(4-(4-(1-(pentan-3-yl)-1H-pyrazol-4-yl)pyrazolo[1,5-a]pyrazin-6-yl)-1H-pyrazol-1-yl)azetidin-1-yl)ethanone

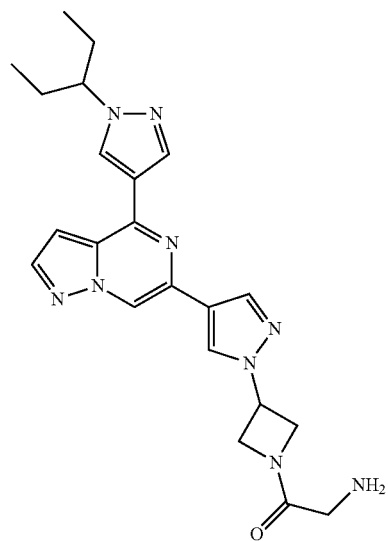 [SMILES: CCC(CC)n1cc(-c2nc(-c3cnn(C4CN(C(=O)CN)C4)c3)cn3nccc23)cn1]

6-(1-(Azetidin-3-yl)-1H-pyrazol-4-yl)-4-(1-(pentan-3-yl)-1H-pyrazol-4-yl)pyrazolo[1,5-a]pyrazine (75 mg, 0.20 mmol), Et₃N (83.3 µL, 0.60 mmol) and 2,5-dioxopyrrolidin-1-yl 2-((tert-butoxycarbonyl)amino)acetate (81.4 mg, 0.30 mmol) were placed in CH₂Cl₂ (5 mL) and stirred for 1 hour. Water was added and the reaction mixture was extracted with CH₂Cl₂. The combined organic layers were concentrated. The residue was taken up in 10% MeOH in CH₂Cl₂ and 4 N HCl in dioxane (2 mL) was added, and the reaction mixture was stirred for 2 hours. Saturated aqueous NaHCO₃ was added and the reaction mixture was extracted with 10% MeOH in CH₂Cl₂. The combined organic layers were concentrated. The residue was purified over silica gel (0-14% MeOH in CH₂Cl₂) followed by reverse phase (5-60% CH₃CN:water w/0.1% TFA) to provide the produce as the TFA salt. The TFA salt was taken up in 10% MeOH in CH₂Cl₂ and saturated aqueous NaHCO₃ was added. The layers were separated and the organic layer was dried, filtered and concentrated to provide 2-amino-1-(3-(4-(4-(1-(pentan-3-yl)-1H-pyrazol-4-yl)pyrazolo[1,5-a]pyrazin-6-yl)-1H-pyrazol-1-yl)azetidin-1-yl)ethanone (20.8 mg, 24% yield). Mass spectrum (apci) m/z=434.2 (M+H). ¹H NMR (CDCl₃) δ 8.47 (d, J=1.0 Hz, 1H), 8.27 (s, 1H), 8.17 (s, 1H), 8.10 (s, 1H), 8.04 (m, 2H), 6.97 (dd, J=2.3, 1.0 Hz, 1H), 5.24 (m, 1H), 4.65-4.49 (m, 4H), 4.04 (m, 1H), 3.35 (d, J=4.7 Hz, 2H), 2.07-1.85 (m, 4H), 0.86 (t, J=7.4 Hz, 6H).

Example 187

2-(methylamino)-1-(3-(4-(4-(1-(pentan-3-yl)-1H-pyrazol-4-yl)pyrazolo[1,5-a]pyrazin-6-yl)-1H-pyrazol-1-yl)azetidin-1-yl)ethanone bis(2,2,2-trifluoroacetate)

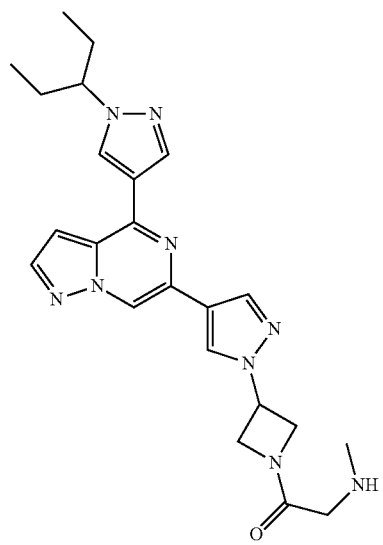 [SMILES: CCC(CC)n1cc(-c2nc(-c3cnn(C4CN(C(=O)CNC)C4)c3)cn3nccc23)cn1]

Step A:

6-(1-(Azetidin-3-yl)-1H-pyrazol-4-yl)-4-(1-(pentan-3-yl)-1H-pyrazol-4-yl)pyrazolo[1,5-a]pyrazine (60 mg, 0.16 mmol), Et$_3$N (66 µL, 0.48 mmol) and 2,5-dioxopyrrolidin-1-yl 2-((tert-butoxycarbonyl)amino)acetate (65 mg, 0.24 mmol) were placed in CH$_2$Cl$_2$ (3 mL) and stirred for 1 hour. Water was added and the mixture was extracted with CH$_2$Cl$_2$. The organic layers were combined and concentrated. The residue was purified by reverse phase chromatography (C18, 10-95% CH$_3$CN in water) to afford tert-butyl (2-oxo-2-(3-(4-(4-(1-(pentan-3-yl)-1H-pyrazol-4-yl)pyrazolo[1,5-a]pyrazin-6-yl)-1H-pyrazol-1-yl)azetidin-1-yl)ethyl)carbamate (65 mg, 76% yield).

Step B:

tert-Butyl (2-oxo-2-(3-(4-(4-(1-(pentan-3-yl)-1H-pyrazol-4-yl)pyrazolo[1,5-a]pyrazin-6-yl)-1H-pyrazol-1-yl)azetidin-1-yl)ethyl)carbamate (46 mg, 0.086 mmol) was dissolved in DMF (2 mL) and 60% NaH (6.9 mg, 0.17 mmol) was added and stirred for 2 hours. MeI (5.9 µL, 0.095 mmol) was added and stirred at room temperature overnight. The reaction mixture was quenched with water and extracted with EtOAc. The combined organic extracts were washed with water, dried over sodium sulfate, filtered and concentrated. The residue was purified by reverse phase chromatography (C18, 10-95% CH$_3$CN in water) to afford tert-butyl methyl(2-oxo-2-(3-(4-(4-(1-(pentan-3-yl)-1H-pyrazol-4-yl)pyrazolo[1,5-a]pyrazin-6-yl)-1H-pyrazol-1-yl)azetidin-1-yl)ethyl)carbamate (23 mg, 48.7% yield).

Step C:

tert-Butyl methyl(2-oxo-2-(3-(4-(4-(1-(pentan-3-yl)-1H-pyrazol-4-yl)pyrazolo[1,5-a]pyrazin-6-yl)-1H-pyrazol-1-yl)azetidin-1-yl)ethyl)carbamate (22 mg, 0.040 mmol) was dissolved in CH$_2$Cl$_2$ (1 mL) and TFA (0.6 mL) was added and the reaction mixture was stirred for 1 hour. The reaction mixture was concentrated and placed under high vacuum to afford 2-(methylamino)-1-(3-(4-(4-(1-(pentan-3-yl)-1H-pyrazol-4-yl)pyrazolo[1,5-a]pyrazin-6-yl)-1H-pyrazol-1-yl)azetidin-1-yl)ethanone bis(2,2,2-trifluoroacetate) (27 mg, 99% yield) as a yellow foam. Mass spectrum (apci) m/z=448.2 (M+H).

Example 188

(3R,4R)-4-(4-(4-(1-(pentan-3-yl)-1H-pyrazol-4-yl)pyrazolo[1,5-a]pyrazin-6-yl)-1H-pyrazol-1-yl)piperidin-3-ol

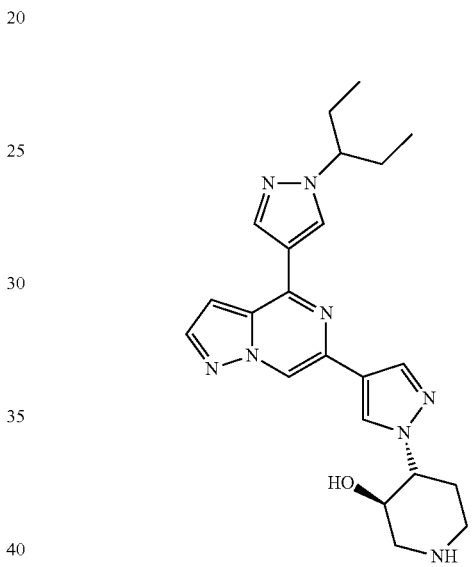

Step A:

To a slurry of 4-(1-(pentan-3-yl)-1H-pyrazol-4-yl)-6-(1H-pyrazol-4-yl)pyrazolo[1,5-a]pyrazine (0.10 g, 0.31 mmol) in DMF (0.5 mL) was added Cs$_2$CO$_3$ (0.20 g, 0.62 mmol) and (1R,6S)-tert-butyl 7-oxa-3-azabicyclo[4.1.0]heptane-3-carboxylate (0.12 g, 0.62 mmol) and the reaction mixture was heated at 70° C. overnight. The reaction mixture was partitioned between EtOAc and water. The combined organic phases were washed with brine, dried over MgSO$_4$ and concentrated in vacuo. The residue was purified over silica gel (0-100% EtOAc/CH$_2$Cl$_2$) to afford 2 spots. The top spot was determined to be (3R,4R)-tert-butyl 3-hydroxy-4-(4-(4-(1-(pentan-3-yl)-1H-pyrazol-4-yl)pyrazolo[1,5-a]pyrazin-6-yl)-1H-pyrazol-1-yl)piperidine-1-carboxylate (50 mg, 31% yield).

Step B:

To a solution of (3R,4R)-tert-butyl 3-hydroxy-4-(4-(4-(1-(pentan-3-yl)-1H-pyrazol-4-yl)pyrazolo[1,5-a]pyrazin-6-yl)-1H-pyrazol-1-yl)piperidine-1-carboxylate (0.050 g, 0.096 mmol) in CH$_2$Cl$_2$ was added TFA (to a final concentration of 1:1) and the reaction mixture was stirred at room temperature for 1 hour. The reaction mixture was concentrated in vacuo and azeotroped with EtOAc until a solid formed. The solid was collected to give (3R,4R)-4-(4-(4-(1-(pentan-3-yl)-1H-pyrazol-4-yl)pyrazolo[1,5-a]pyrazin-6-yl)-1H-pyrazol-1-yl)piperidin-3-ol (0.034 g, 0.081 mmol, 84% yield). Mass spectrum (apci) m/z=421.2 (M+H). ¹H NMR (CD₂Cl₂) δ 8.40 (d, J=0.8 Hz, 1H), 8.19 (s, 1H), 8.14 (s, 1H), 8.04 (s, 1H), 7.94 (d, J=2.3 Hz, 1H), 7.93 (s, 1H), 6.90 (dd, J=2.5, 1.0 Hz, 1H), 3.97 (m, 2H), 3.81 (td, J=9.8, 4.9 Hz, 1H), 3.27 (ddd, J=12.1, 4.9, 1.0 Hz, 1H), 3.12 (m, 1H), 2.67 (td, J=12.5, 2.7 Hz, 1H), 2.52 (dd, J=12.1, 10.0, 1H), 2.17 (m, 1H), 2.03-1.77 (m, 6H), 0.78 (t, J=7.4 Hz, 6H).

Example 189

(1S,2R)-2-(4-(4-(1-(pentan-3-yl)-1H-pyrazol-4-yl)pyrazolo[1,5-a]pyrazin-6-yl)-1H-pyrazol-1-yl)cyclopentanol

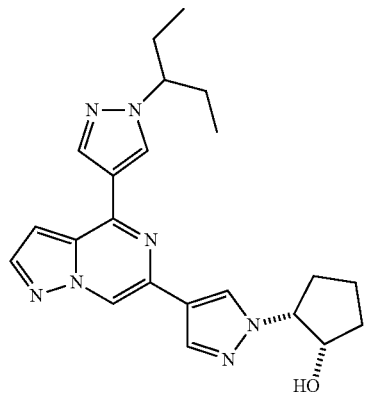

Step A:

To a stirred solution of trans-2-(4-(4-(1-(pentan-3-yl)-1H-pyrazol-4-yl)pyrazolo[1,5-a]pyrazin-6-yl)-1H-pyrazol-1-yl)cyclopentanol (90 mg, 0.22 mmol) in 2.2 mL THF at room temperature under nitrogen was added 4-nitrobenzoic acid (37 mg, 0.22 mmol) and PPh₃ (58 mg, 0.22 mmol). Diisopropyl azodicarboxylate (43 µL, 0.22 mmol) was added and the reaction mixture was stirred at room temperature overnight. The reaction mixture was concentrated to dryness and the crude material was purified over silica gel (0-50% EtOAc in hexanes) to afford 2-(4-(4-(1-(pentan-3-yl)-1H-pyrazol-4-yl)pyrazolo[1,5-a]pyrazin-6-yl)-1H-pyrazol-1-yl) cyclopentyl 4-nitrobenzoate as a racemic mixture. The racemate was separated on a Chiral Tech OJ-H column (4.6 mm×250 mm, 1:1 EtOH/hexanes, 1 mL/min): Peak A: 10.1 min. Arbitrarily assigned as (1S,2R) and Peak B: 14.5 min. Arbitrarily assigned as (1R,2S).

Step B:

To a stirred solution of (1S,2R)-2-(4-(4-(1-(pentan-3-yl)-1H-pyrazol-4-yl)pyrazolo[1,5-a]pyrazin-6-yl)-1H-pyrazol-1-yl)cyclopentyl 4-nitrobenzoate (26 mg, 0.0469 mmol) [Peak A from previous reaction] in 1 mL of methanol at room temperature under nitrogen was added 2M aqueous K₂CO₃ (70.3 µL, 0.141 mmol) and the reaction mixture was stirred overnight. The reaction mixture was concentrated and partitioned between ethyl acetate and water with stirring. The layers were separated, and the organic layer was extracted with brine, dried over MgSO₄, filtered and concentrated to afford (1S,2R)-2-(4-(4-(1-(pentan-3-yl)-1H-pyrazol-4-yl)pyrazolo[1,5-a]pyrazin-6-yl)-1H-pyrazol-1-yl) cyclopentanol (Peak A) (17 mg, 85% yield) as a clear oil. Mass spectrum (apci) m/z=406.2 (M+H). ¹H NMR (CDCl₃) δ 8.45 (d, J=1.0 Hz, 1H), 8.26 (s, 1H), 8.16 (s, 1H), 8.07 (s, 1H), 8.03 (d, J=2.3 Hz, 1H), 8.00 (s, 1H), 6.95 (dd, J=2.5, 1.0 Hz, 1H), 4.52 (m, 2H), 4.03 (m, 1H), 3.53 (br s, 1H), 2.35 (m, 1H), 2.23 (m, 1H), 2.11 (m, 1H), 2.05-1.85 (m, 6H), 1.77 (m, 1H), 0.86 (t, J=7.2 Hz, 6H).

The following compound was prepared according to the procedure described for Example 189.

| Example | Structure | Name | Data |
|---|---|---|---|
| 190 | (isolated "Peak B") | (1R,2S)-2-(4-(4-(1-(pentan-3-yl)-1H-pyrazol-4-yl)pyrazolo[1,5-a]pyrazin-6-yl)-1H-pyrazol-1-yl)cyclopentanol | Mass spectrum (apci) m/z = 406.2 (M + H) |

Example 191

2,2-dimethyl-3-(4-(4-(1-(pentan-3-yl)-1H-pyrazol-4-yl)pyrazolo[1,5-a]pyrazin-6-yl)-1H-pyrazol-1-yl)propan-1-ol

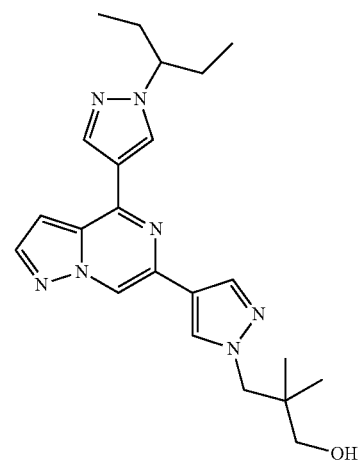 [SMILES: CCC(CC)n1cc(-c2nc(-c3cnn(CC(C)(C)CO)c3)cn3nccc23)cn1]

Step A:

To a solution of 4-(1-(pentan-3-yl)-1H-pyrazol-4-yl)-6-(1H-pyrazol-4-yl)pyrazolo[1,5-a]pyrazine (50 mg, 0.16 mmol) and methyl 2,2-dimethyl-3-((methylsulfonyl)oxy)propanoate (65 mg, 0.31 mmol) in DMA (2 mL) was added cesium carbonate (101 mg, 0.31 mmol). The mixture was stirred in a screw-cap vial at 100° C. overnight. The reaction mixture was partitioned between water and EtOAc, and the aqueous layer was extracted with EtOAc (2×10 mL). The combined organic phases were washed with water and brine, dried over $Na_2SO_4$, filtered and concentrated to afford methyl 2,2-dimethyl-3-(4-(4-(1-(pentan-3-yl)-1H-pyrazol-4-yl)pyrazolo[1,5-a]pyrazin-6-yl)-1H-pyrazol-1-yl)propanoate (42 mg, 62% yield) as a white foam.

Step B:

To a solution of methyl 2,2-dimethyl-3-(4-(4-(1-(pentan-3-yl)-1H-pyrazol-4-yl)pyrazolo[1,5-a]pyrazin-6-yl)-1H-pyrazol-1-yl)propanoate (42 mg, 0.10 mmol) in methanol (1 mL) at 0° C. was added sodium borohydride (100 mg, 2.65 mmol). The reaction mixture was allowed to warm slowly to room temperature overnight. The reaction mixture was treated with saturated aqueous $NH_4Cl$ (10 mL) and stirred for 10 minutes, then extracted with $CH_2Cl_2$. The combined organic phases were washed with brine (5 mL), dried over $Na_2SO_4$ and concentrated. The residue was purified over silica gel (20% acetone/$CH_2Cl_2$) to afford 2,2-dimethyl-3-(4-(4-(1-(pentan-3-yl)-1H-pyrazol-4-yl)pyrazolo[1,5-a]pyrazin-6-yl)-1H-pyrazol-1-yl)propan-1-ol (25.5 mg, 65% yield) as a colorless glass. Mass spectrum (apci) m/z=408.2 (M+H). $^1$H NMR (CDCl$_3$) δ 8.46 (d, J=1.0 Hz, 1H), 8.27 (s, 1H), 8.16 (s, 1H), 8.03 (d, J=2.3 Hz, 1H), 7.98 (s, 1H), 7.93 (s, 1H), 6.95 (dd, J=2.3, 1.0 Hz, 1H), 4.08 (s, 2H), 4.03 (m, 1H), 3.67 (t, J=6.8 Hz, 1H), 3.25 (d, J=6.6 Hz, 2H), 2.06-1.86 (m, 4H), 1.00 (s, 6H), 0.86 (t, J=7.2 Hz, 6H).

The following compound was prepared according to the procedure described for Example 191.

| Example | Structure | Name | Data |
| --- | --- | --- | --- |
| 192 | 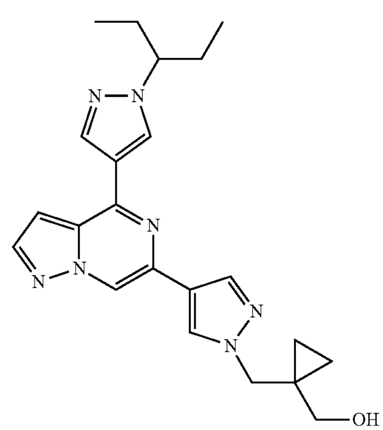 [SMILES: CCC(CC)n1cc(-c2nc(-c3cnn(CC4(CO)CC4)c3)cn3nccc23)cn1] | (1-((4-(4-(1-(pentan-3-yl)-1H-pyrazol-4-yl)pyrazolo[1,5-a]pyrazin-6-yl)-1H-pyrazol-1-yl)methyl)cyclopropyl)methanol | Mass spectrum (apci) m/z = 406.3 (M + H) |

Example 193

(2R)-3-(4-(4-(1-(1,1,1-trifluorobutan-2-yl)-1H-pyrazol-4-yl)pyrazolo[1,5-a]pyrazin-6-yl)-1H-pyrazol-1-yl)propane-1,2-diol

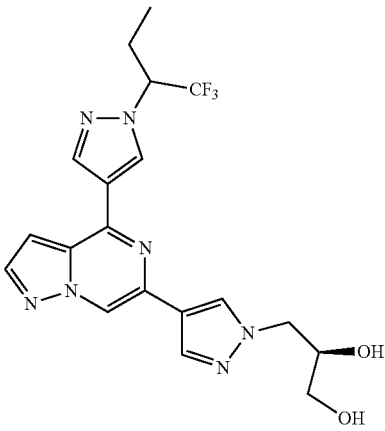 [SMILES: CCC(n1cc(-c2nc(-c3cnn(C[C@@H](O)CO)c3)cn3nccc23)cn1)C(F)(F)F]

Step A:

A solution of 6-(1-(4-methoxybenzyl)-1H-pyrazol-4-yl)-4-(1H-pyrazol-4-yl)pyrazolo[1,5-a]pyrazine (250 mg, 0.67 mmol) and 1,1,1-trifluorobutan-2-yl methanesulfonate (208 mg, 1.0 mmol) in DMA (5 mL) was treated with cesium carbonate (439 mg, 1.35 mmol) then stirred at 80° C. in a sealed tube overnight. The reaction mixture was treated with an additional 200 mg of 1,1,1-trifluorobutan-2-yl methanesulfonate and stirred at 80° C. The reaction mixture was partitioned between water and EtOAc and the aqueous layer was extracted with EtOAc. The combined organic phases were washed with water, and brine, dried over $Na_2SO_4$, filtered and concentrated. The residue was purified over silica gel (10% acetone/$CH_2Cl_2$) to afford 6-(1-(4-methoxybenzyl)-1H-pyrazol-4-yl)-4-(1-(1,1,1-trifluorobutan-2-yl)-1H-pyrazol-4-yl)pyrazolo[1,5-a]pyrazine as a pale yellow gum.

Step B:

6-(1-(4-Methoxybenzyl)-1H-pyrazol-4-yl)-4-(1-(1,1,1-trifluorobutan-2-yl)-1H-pyrazol-4-yl)pyrazolo[1,5-a]pyrazine (29 mg, 0.06 mmol) was treated with TFA (1 mL) and stirred at 60° C. overnight. The mixture was concentrated and then partitioned between $CH_2Cl_2$ and 1N NaOH. The aqueous phase was extracted with $CH_2Cl_2$ and the combined organic phases were washed with brine, dried over $Na_2SO_4$, filtered and concentrated. The residue was purified over silica gel (2.5% MeOH/$CH_2Cl_2$) to afford 6-(1H-pyrazol-4-yl)-4-(1-(1,1,1-trifluorobutan-2-yl)-1H-pyrazol-4-yl)pyrazolo[1,5-a]pyrazine (12 mg, 55% yield) as a white solid.

Step C:

To a solution of 6-(1H-pyrazol-4-yl)-4-(1-(1,1,1-trifluorobutan-2-yl)-1H-pyrazol-4-yl)pyrazolo[1,5-a]pyrazine (12 mg, 0.03 mmol) in DMA (1 mL) was added (S)-4-(chloromethyl)-2,2-dimethyl-1,3-dioxolane (9 μL, 0.07 mmol) followed by cesium carbonate (22 mg, 0.07 mmol). The reaction mixture was stirred at 70° C. overnight. Additional (S)-4-(chloromethyl)-2,2-dimethyl-1,3-dioxolane (50 μL) was added and the reaction mixture stirred overnight at 70° C. The reaction mixture was partitioned between water and EtOAc and the aqueous layer extracted with EtOAc. The combined organic phases were washed with water and brine, dried over $Na_2SO_4$, filtered and concentrated. The residue was purified over silica gel (10% acetone/$CH_2Cl_2$) to afford 6-(1-(((R)-2,2-dimethyl-1,3-dioxolan-4-yl)methyl)-1H-pyrazol-4-yl)-4-(1-(1,1,1-trifluorobutan-2-yl)-1H-pyrazol-4-yl)pyrazolo[1,5-a]pyrazine (8 mg, 50.6% yield) as a colorless glass.

Step D:

6-(1-(((R)-2,2-dimethyl-1,3-dioxolan-4-yl)methyl)-H-pyrazol-4-yl)-4-(1-(1,1,1-trifluorobutan-2-yl)-1H-pyrazol-4-yl)pyrazolo[1,5-a]pyrazine (8 mg, 0.02 mmol) was dissolved in isopropyl alcohol (1 mL) and concentrated HCl (1 drop) was added. The reaction mixture was stirred at 60° C. for 2 hours. The cooled reaction mixture was concentrated and partitioned between 2N NaOH and $CH_2Cl_2$. The aqueous layer was extracted with $CH_2Cl_2$ and the combined organic phases were washed with brine, dried over $Na_2SO_4$ and concentrated to afford (2R)-3-(4-(4-(1-(1,1,1-trifluorobutan-2-yl)-1H-pyrazol-4-yl)pyrazolo[1,5-a]pyrazin-6-yl)-1H-pyrazol-1-yl)propane-1,2-diol (4.7 mg, 64% yield) as a white solid. Mass spectrum (apci) m/z=436.2 (M+H). $^1$H NMR (CDCl$_3$) δ 8.50 (d, J=0.8 Hz, 1H), 8.32 (s, 1H), 8.28 (s, 1H), 8.06 (m, 2H), 8.00 (s, 1H), 6.95 (dd, J=2.5, 0.8 Hz, 1H), 4.73 (m, 1H), 4.40-4.29 (m, 2H), 4.13 (m, 1H), 3.68-3.58 (m, 2H), 2.41-2.18 (m, 2H), 0.98 (t, J=7.2 Hz, 3H).

Examples 194 and 195

(R)-3-(4-(4-(1-((R)-4,4,4-trifluorobutan-2-yl)-1H-pyrazol-4-yl)pyrazolo[1,5-a]pyrazin-6-yl)-1H-pyrazol-1-yl)propane-1,2-diol hydrochloride and (R)-3-(4-(4-(1-((S)-4,4,4-trifluorobutan-2-yl)-1H-pyrazol-4-yl)pyrazolo[1,5-a]pyrazin-6-yl)-1H-pyrazol-1-yl) propane-1,2-diol hydrochloride

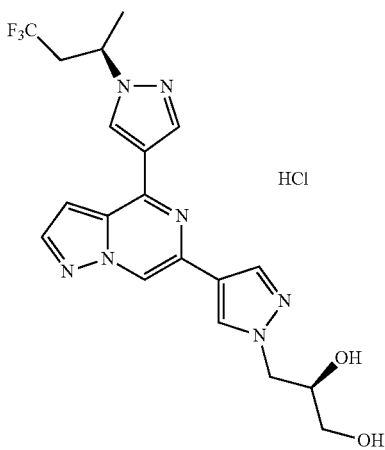

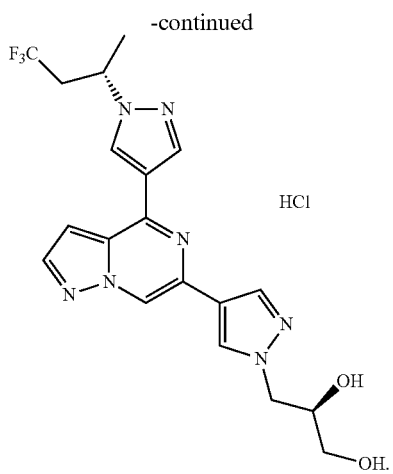

Step A:

A mixture of 4-chloro-6-(1-(4-methoxybenzyl)-1H-pyrazol-4-yl)pyrazolo[1,5-a]pyrazine hydrochloride (60 mg, 0.159 mmol), 4-(4,4,5,5-tetramethyl-1,3,2-dioxaborolan-2-yl)-1-(4,4,4-trifluorobutan-2-yl)-1H-pyrazole (55.8 mg, 0.183 mmol), Pd$_2$dba$_3$ (14.6 mg, 0.0159 mmol), XPHOS (15.2 mg, 0.0319 mmol) in 2M K$_2$CO$_3$ (239 μL, 0.478 mmol) and dioxane (797 μL, 0.159 mmol) was degassed with nitrogen and heated to 80° C. overnight. The reaction mixture was partitioned between water and EtOAc, dried over Na$_2$SO$_4$, filtered and concentrated. The residue was purified over silica gel (10-50% EtOAc in CH$_2$Cl$_2$) to afford 6-(1-(4-methoxybenzyl)-1H-pyrazol-4-yl)-4-(1-(4,4,4-trifluorobutan-2-yl)-1H-pyrazol-4-yl)pyrazolo[1,5-a]pyrazine (60 mg, 78.1% yield).

Step B:

A solution of 6-(1-(4-methoxybenzyl)-1H-pyrazol-4-yl)-4-(1-(4,4,4-trifluorobutan-2-yl)-1H-pyrazol-4-yl)pyrazolo[1,5-a]pyrazine (60 mg, 0.12 mmol) in TFA (1246 μL, 0.12 mmol). Triflic acid (11 μL, 0.12 mmol) was added and the reaction mixture was heated at 80° C. for 24 hours. The reaction mixture was concentrated and taken on to next step without purification.

Step C:

6-(1H-Pyrazol-4-yl)-4-(1-(4,4,4-trifluorobutan-2-yl)-1H-pyrazol-4-yl)pyrazolo[1,5-a]pyrazine (60 mg, 0.166 mmol) was dissolved in DMF (0.8 mL) and Cs$_2$CO$_3$ (108 mg, 0.332 mmol) and (S)-(−)-4-(Chloromethyl)-2,2-dimethyl-1,3-dioxolane (27.5 mg, 0.183 mmol) were added. The reaction mixture was heated to 80° C. overnight. The reaction mixture was partitioned between water and EtOAc, washed with water and brine, dried over Na$_2$SO$_4$, filtered and concentrated. The residue was purified over silica gel to afford 6-(1-(((R)-2,2-dimethyl-1,3-dioxolan-4-yl)methyl)-1H-pyrazol-4-yl)-4-(1-(4,4,4-trifluorobutan-2-yl)-1H-pyrazol-4-yl)pyrazolo[1,5-a]pyrazine as a diastereomeric mixture.

Step D:

Diastereomeric separation of the mixture prepared in Step C was achieved by a Chiral Tech IA column, eluting with 30% EtOH in hexanes to afford 2 peaks: 6-(1-(((R)-2,2-dimethyl-1,3-dioxolan-4-yl)methyl)-1H-pyrazol-4-yl)-4-(1-((R)-4,4,4-trifluorobutan-2-yl)-1H-pyrazol-4-yl)pyrazolo[1,5-a]pyrazine (first eluting peak) and 6-(1-(((R)-2,2-dimethyl-1,3-dioxolan-4-yl)methyl)-1H-pyrazol-4-yl)-4-(1-((S)-4,4,4-trifluorobutan-2-yl)-1H-pyrazol-4-yl)pyrazolo[1,5-a]pyrazine (second eluting peak). Absolute stereochemistry was arbitrarily assigned.

Step E:

The purified diastereomers isolated in Step D were separately dissolved in MeOH (1 mL) and treated with 20 μL concentrated HCl for 4 hours. The solutions were concentrated to separately afford (R)-3-(4-(4-(1-((R)-4,4,4-trifluorobutan-2-yl)-1H-pyrazol-4-yl)pyrazolo[1,5-a]pyrazin-6-yl)-1H-pyrazol-1-yl)propane-1,2-diol hydrochloride salt (Peak A) (6.2 mg, 65% yield); Mass spectrum (apci) m/z=436.1 (M+H); and (R)-3-(4-(4-(1-((S)-4,4,4-trifluorobutan-2-yl)-1H-pyrazol-4-yl)pyrazolo[1,5-a]pyrazin-6-yl)-1H-pyrazol-1-yl)propane-1,2-diol hydrochloride salt (Peak B) (5.5 mg, 72% yield). Mass spectrum (apci) m/z=436.1 (M+H).

The following compounds were prepared according to the procedure described for Examples 194 and 195.

| Example | Structure | Name | Data |
|---|---|---|---|
| 196 | 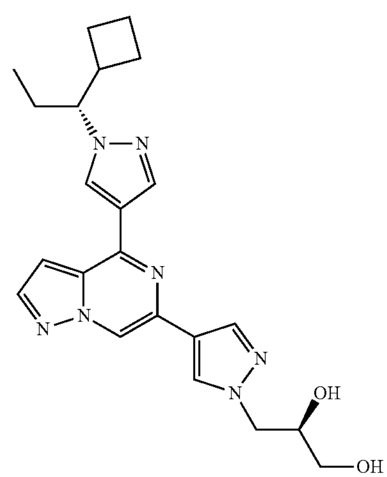 | (R)-3-(4-(4-(1-((R)-1-cyclobutylpropyl)-1H-pyrazol-4-yl)pyrazolo[1,5-a]pyrazin-6-yl)-1H-pyrazol-1-yl)propane-1,2-diol | Mass spectrum (apci) m/z = 422.2 (M + H) |

(isolated "Peak A")

| Example | Structure | Name | Data |
|---|---|---|---|
| 197 | 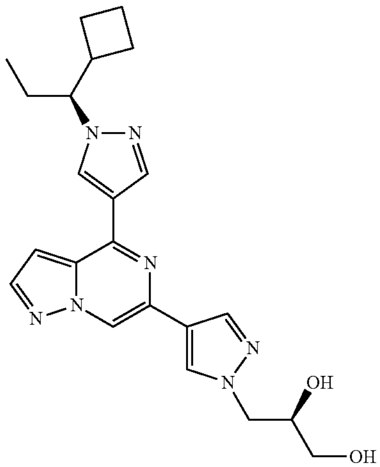 | (R)-3-(4-(4-(1-((S)-1-cyclobutylpropyl)-1H-pyrazol-4-yl)pyrazolo[1,5-a]pyrazin-6-yl)-1H-pyrazol-1-yl)propane-1,2-diol (isolated "Peak B") | Mass spectrum (apci) m/z = 422.2 (M + H) |

Examples 198 and 199

(R)-3-(4-(4-(1-((S)-2,2-difluoropentan-3-yl)-1H-pyrazol-4-yl)pyrazolo[1,5-a]pyrazin-6-yl)-1H-pyrazol-1-yl)propane-1,2-diol and (R)-3-(4-(4-(1-((R)-2,2-difluoropentan-3-yl)-1H-pyrazol-4-yl)pyrazolo[1,5-a]pyrazin-6-yl)-1H-pyrazol-1-yl)propane-1,2-diol

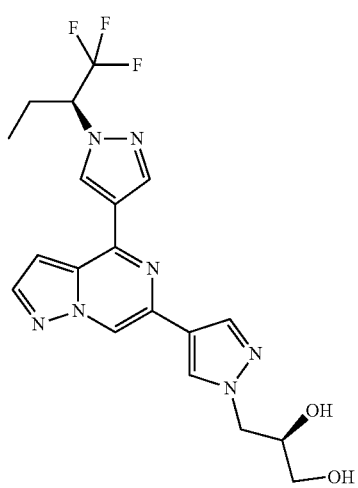

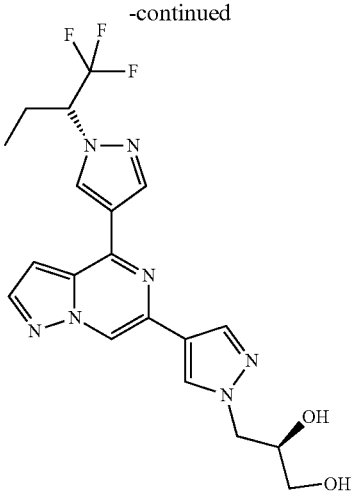

Step A:

A mixture of 4-chloro-6-(1-(4-methoxybenzyl)-1H-pyrazol-4-yl)pyrazolo[1,5-a]pyrazine hydrochloride (500 mg, 1.33 mmol), 3-(4-(4,4,5,5-tetramethyl-1,3,2-dioxaborolan-2-yl)-1H-pyrazol-1-yl)pentan-2-one (481 mg, 1.73 mmol), $Pd_2dba_3$ (122 mg, 0.133 mmol), XPHOS (127 mg, 0.266 mmol) in 2M $K_2CO_3$ (1993 µL, 3.99 mmol) and dioxane (6645 µL, 1.33 mmol) was degassed with nitrogen and heated at 80° C. overnight. The reaction mixture was partitioned between water and EtOAc, dried over sodium sulfate, filtered and concentrated. The residue was purified over silica gel (0-100% EtOAc in $CH_2Cl_2$) to afford 3-(4-(6-(1-(4-methoxybenzyl)-1H-pyrazol-4-yl)pyrazolo[1,5-a]pyrazin-4-yl)-1H-pyrazol-1-yl)pentan-2-one.

Step B:

To a solution of 3-(4-(6-(1-(4-methoxybenzyl)-1H-pyrazol-4-yl)pyrazolo[1,5-a]pyrazin-4-yl)-1H-pyrazol-1-yl)pentan-2-one (350 mg, 0.768 mmol) in $CH_2Cl_2$ (3842 µL, 0.768 mmol) in a Teflon bottle (50 mL) at 0° C. was added Diethylaminosulfur trifluoride (DAST) (305 µl, 2.31 mmol) and the resulting mixture was heated to 40° C. for 3 hours.

The reaction mixture was transferred to a glass round bottom flask and concentrated. The residue was purified over silica gel (0-5% MeOH in CH₂Cl₂) to afford 4-(1-(2,2-difluoropentan-3-yl)-1H-pyrazol-4-yl)-6-(1-(4-methoxybenzyl)-1H-pyrazol-4-yl)pyrazolo[1,5-a]pyrazine (300 mg, 82% yield).

Step C:

4-(1-(2,2-Difluoropentan-3-yl)-1H-pyrazol-4-yl)-6-(1-(4-methoxybenzyl)-1H-pyrazol-4-yl)pyrazolo[1,5-a]pyrazine (60 mg, 0.125 mmol) was heated in TFA (2 mL) with trifluoromethanesulfonic acid (100 μL) to 50° C. for 2 hours. The reaction mixture was concentrated and used in the next step without purification.

Step D:

A suspension of 4-(1-(2,2-difluoropentan-3-yl)-1H-pyrazol-4-yl)-6-(1H-pyrazol-4-yl)pyrazolo[1,5-a]pyrazine (50 mg, 0.140 mmol), (S)-(-)-4-(Chloromethyl)-2,2-dimethyl-1,3-dioxolane (28.7 μL, 0.210 mmol), Cs₂CO₃ (137 mg, 0.420 mmol) in DMF (0.7 mL) was heated at 60° C. for 3 days. The reaction mixture was partitioned between water and EtOAc, washed with water and brine, dried over sodium sulfate, filtered and concentrated. The residue was purified over silica gel to afford (2R)-3-(4-(4-(1-(2,2-difluoropentan-3-yl)-1H-pyrazol-4-yl)pyrazolo[1,5-a]pyrazin-6-yl)-1H-pyrazol-1-yl)propane-1,2-diol (22 mg, 36% yield) as a diastereomeric mixture.

Step E:

The diastereomers prepared in Step D were separated by chiral chromatography (Chiral Tech IA column, 4.6 mm×250 mm, 5 micron, 25% EtOH in hexanes, 1 mL/min). The absolute chirality of the isolated compounds was arbitrarily assigned. Peak A: 7 mg; retention time=16.7 min; Mass spectrum (apci) m/z=432.2 (M+H). ¹H NMR (CDCl₃) δ 8.47 (s, 1H), 8.28 (s, 1H), 8.24 (s, 1H), 8.04 (m, 2H), 7.99 (s, 1H), 6.93 (m, 1H), 4.43 (m, 1H), 4.35 (d, J=5.3 Hz, 2H), 4.17 (pentet, J=4.9 Hz, 1H), 3.73-3.63 (m, 2H), 3.55 (br s, 1H), 2.31-2.12 (m, 2H), 1.65-1.50 (m, 3H), 0.92 (t, J=7.2 Hz, 3H). Peak B: 6 mg; retention time=18.1 min retention time; Mass spectrum (apci) m/z=432.2 (M+H). ¹H NMR (CDCl₃) δ 8.47 (s, 1H), 8.28 (s, 1H), 8.24 (s, 1H), 8.04 (m, 2H), 7.99 (s, 1H), 6.93 (m, 1H), 4.43 (m, 1H), 4.35 (d, J=5.1 Hz, 2H), 4.17 (pentet, J=4.7 Hz, 1H), 3.72-3.63 (m, 2H), 3.55 (br s, 1H), 2.47 (br s, 1H), 2.32-2.13 (m, 2H), 1.65-1.50 (m, 3H), 0.92 (t, J=7.4 Hz, 3H).

Example 200

(S)-4-(4-(4-(1-(pentan-3-yl)-1H-pyrazol-4-yl)pyrazolo[1,5-a]pyrazin-6-yl)-1H-pyrazol-1-yl)butane-1,3-diol

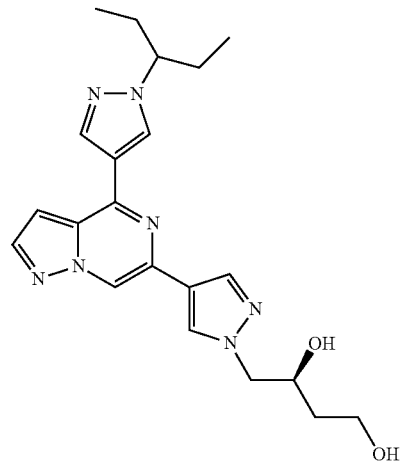 [SMILES: CCC(CC)n1cc(-c2nc(-c3cnn(C[C@@H](O)CCO)c3)cn3nccc23)cn1]

Step A:
To the solid 4-(1-(pentan-3-yl)-1H-pyrazol-4-yl)-6-(1H-pyrazol-4-yl)pyrazolo[1,5-a]pyrazine (0.40 g, 1.2 mmol) and Cs₂CO₃ (0.81 g, 2.5 mmol) was added DMF (5 mL) followed by 4-(chloromethyl)-1,3-dioxane (0.34 g, 2.5 mmol) and the reaction mixture was stirred at 80° C. overnight. The reaction mixture was poured into water and extracted into EtOAc. The combined organic phases were washed with brine, dried over MgSO₄ and concentrated in vacuo. The residue was purified over silica gel (0-100% EtOAc in CH₂Cl₂) to afford 6-(1-((1,3-dioxan-4-yl)methyl)-1H-pyrazol-4-yl)-4-(1-(pentan-3-yl)-1H-pyrazol-4-yl)pyrazolo[1,5-a]pyrazine (0.4 g, 0.95 mmol, 76% yield).

Step B:
To 6-(1-((1,3-dioxan-4-yl)methyl)-1H-pyrazol-4-yl)-4-(1-(pentan-3-yl)-1H-pyrazol-4-yl)pyrazolo[1,5-a]pyrazine (0.4 g, 0.9 mmol) was added 5M HCl in isopropyl alcohol and the reaction mixture was heated to 80° C. overnight. The reaction mixture was concentrated in vacuo and the residue was partitioned between EtOAc and 1N NaOH. The combined organic phases were washed with brine, dried over MgSO₄ and concentrated in vacuo. The material purified over silica gel (0-10% MeOH/CH₂Cl₂) and precipitated from CH₃CN to afford 4-(4-(4-(1-(pentan-3-yl)-1H-pyrazol-4-yl)pyrazolo[1,5-a]pyrazin-6-yl)-1H-pyrazol-1-yl)butane-1,3-diol (0.2 g, 0.5 mmol, 51% yield).

Step C:
To a solution of 4-(4-(4-(1-(pentan-3-yl)-1H-pyrazol-4-yl)pyrazolo[1,5-a]pyrazin-6-yl)-1H-pyrazol-1-yl)butane-1,3-diol (0.187 g, 0.457 mmol) in CH₂Cl₂ (5 mL) was added 1H-imidazole (0.124 g, 1.83 mmol) and tert-butylchlorodimethylsilane (0.206 g, 1.37 mmol) and the reaction mixture was stirred overnight. The reaction mixture was washed with 1N HCl, brine, dried over MgSO₄ and concentrated in vacuo. The material was purified over silica gel (0-50% EtOAc/CH₂Cl₂) to afford 6-(1-(2,4-bis((tert-butyldimethylsilyl)oxy)butyl)-1H-pyrazol-4-yl)-4-(1-(pentan-3-yl)-1H-pyrazol-4-yl)pyrazolo[1,5-a]pyrazine (0.10 g, 0.157 mmol, 34.3% yield) as an enantiomeric mixture.

Step D:

The enantiomers prepared in Step C were separated by chiral chromatography (Chiral Tech AS-H column, 4.6 mm×250 mm, 5 micron, 15% EtOH in hexanes, 1 mL/min). Peak A, 5.6 min retention time. Peak B, 6.9 min retention time. Peak A was arbitrarily assigned as (S)-6-(1-(2,4-bis((tert-butyldimethylsilyl)oxy)butyl)-1H-pyrazol-4-yl)-4-(1-(pentan-3-yl)-1H-pyrazol-4-yl)pyrazolo[1,5-a]pyrazine.

Step E:

To (S)-6-(1-(2,4-bis((tert-butyldimethylsilyl)oxy)butyl)-1H-pyrazol-4-yl)-4-(1-(pentan-3-yl)-1H-pyrazol-4-yl)pyrazolo[1,5-a]pyrazine (0.010 g, 0.016 mmol) was added 5M HCl in isopropyl alcohol and the reaction mixture was heated to 60° C. for 2 hours. The reaction mixture was concentrated in vacuo and the residue was partitioned between EtOAc and basic water. The combined organic phases were washed with brine, dried over $MgSO_4$ and concentrated in vacuo. The residue was purified over silica gel (0-10% MeOH/$CH_2C2$) to afford (S)-4-(4-(4-(1-(pentan-3-yl)-1H-pyrazol-4-yl)pyrazolo[1,5-a]pyrazin-6-yl)-1H-pyrazol-1-yl)butane-1,3-diol (Peak A) (0.0041 g, 0.010 mmol, 64% yield). Mass spectrum (apci) m/z=410.2 (M+H). $^1$H NMR ($CDCl_3$) δ 8.45 (d, J=0.8 Hz, 1H), 8.26 (s, 1H), 8.25 (s, 1H), 8.07 (s, 1H), 8.05 (d, J=2.5 Hz, 1H). 7.98 (s, 1H), 6.98 (dd, J=2.3, 0.8 Hz, 1H), 4.35 (br s, 1H), 4.31 (dd, J=13.5, 2.7 Hz, 1H), 4.21 (dd, J=13.7, 7.4 Hz, 1H), 4.04 (m, 1H), 3.91 (t, J=5.3 Hz, 2H), 2.06-1.85 (m, 4H), 1.81-1.74 (m, 2H), 0.86 (t, J=7.2 Hz, 6H).

The following compound was prepared according to the procedure described for Example 200.

Example 202

(R)-2-methyl-3-(4-(4-(1-(pentan-3-yl)-1H-pyrazol-4-yl)pyrazolo[1,5-a]pyrazin-6-yl)-1H-pyrazol-1-yl)propane-1,2-diol

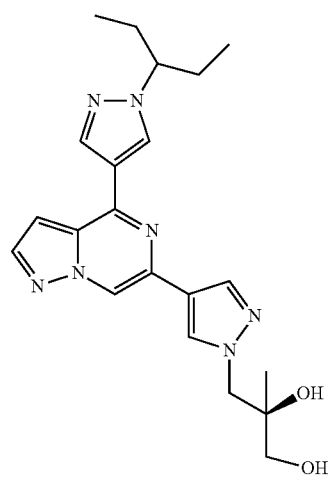 [SMILES: CCC(CC)n1cc(-c2nc(-c3cnn(C[C@@](C)(O)CO)c3)cn3nccc23)cn1]

Step A:

4-(1-(Pentan-3-yl)-1H-pyrazol-4-yl)-6-(1H-pyrazol-4-yl)pyrazolo[1,5-a]pyrazine (250 mg, 0.778 mmol), $Cs_2CO_3$ (760 mg, 2.33 mmol) and (2,2,4-trimethyl-1,3-dioxolan-4-yl)methyl methanesulfonate (174 mg, 0.778 mmol) were placed in DMF (8 mL) and heated to 70° C. for 18 hours. Water was added and the reaction mixture was extracted with EtOAc. The organic layers were combined and washed with water. The organic layer was concentrated and the residue was purified over silica gel (0-60 EtOAc in hexanes) to afford 4-(1-(pentan-3-yl)-H-pyrazol-4-yl)-6-(1-((2,2,4-trimethyl-1,3-dioxolan-4-yl)methyl)-1H-pyrazol-4-yl)pyrazolo[1,5-a]pyrazine (325 mg, 0.723 mmol, 92.9% yield) as an isomeric mixture.

| Example | Structure | Name | Data |
|---|---|---|---|
| 201 | (isolated "Peak B") | (R)-4-(4-(4-(1-(pentan-3-yl)-1H-pyrazol-4-yl)pyrazolo[1,5-a]pyrazin-6-yl)-1H-pyrazol-1-yl)butane-1,3-diol | Mass spectrum (apci) m/z = 422.2 (M + H) |

Step B:
4-(1-(Pentan-3-yl)-1H-pyrazol-4-yl)-6-(1-((2,2,4-trimethyl-1,3-dioxolan-4-yl)methyl)-1H-pyrazol-4-yl)pyrazolo[1,5-a]pyrazine (325 mg, 0.723 mmol) was purified by chiral chromatography on a Chiral Tech IA column (4.6 mm×250 mm, 5 micron), eluting with 20% EtOH:80% hexanes at 1 mL/min. Peak A (14.9 min), arbitrarily assigned as the R isomer; and Peak B (20.9 min), arbitrarily assigned as the S isomer.

Step C:
To a solution of (R)-4-(1-(pentan-3-yl)-1H-pyrazol-4-yl)-6-(1-((2,2,4-trimethyl-1,3-dioxolan-4-yl)methyl)-1H-pyrazol-4-yl)pyrazolo[1,5-a]pyrazine (107 mg, 0.238 mmol) [Peak A from previous step] in 5 mL of isopropyl alcohol was added 6 drops of HCl and the reaction mixture was stirred for 1 hour at 70° C. The reaction mixture was concentrated and taken up in $CH_2Cl_2$. Saturated bicarbonate was added and the reaction mixture was extracted with $CH_2Cl_2$. The organic layers were combined and concentrated. The residue was purified over silica gel (0-9% MeOH in $CH_2Cl_2$) to provide (R)-2-methyl-3-(4-(4-(1-(pentan-3-yl)-1H-pyrazol-4-yl)pyrazolo[1,5-a]pyrazin-6-yl)-1H-pyrazol-1-yl)propane-1,2-diol (Peak A) (73.9 mg, 0.180 mmol, 75.8% yield). Mass spectrum (apci) m/z=410.2 (M+H). $^1$H NMR (CDCl$_3$) δ 8.46 (d, J=0.8 Hz, 1H), 8.26 (s, 1H), 8.16 (s, 1H), 8.03 (m, 2H), 8.02 (s, 1H), 6.96 (dd, J=2.3, 0.8 Hz, 1H), 4.34 (d, J=14.1 Hz, 1H), 4.18 (d, J=14.1 Hz, 1H), 4.03 (m, 1H), 3.57 (s, 1H), 3.52 (dd, J=11.5, 6.7 Hz, 1H), 3.39 (dd, J=11.3, 6.7 Hz, 1H), 2.80 (t, J=6.7 Hz, 1H), 2.05-1.85 (m, 4H), 1.22 (s, 3H), 0.86 (t, J=7.4 Hz, 6H).

The following compound was prepared according to the procedure described for Example 202.

Example 204

(R)-3-(4-(4-(1-((R)-1-((S)-2,2-difluorocyclopropyl)propyl)-1H-pyrazol-4-yl)pyrazolo[1,5-a]pyrazin-6-yl)-1H-pyrazol-1-yl)propane-1,2-diol

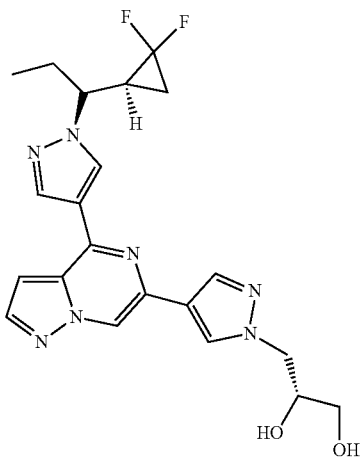

Step A:
A pressure tube equipped with a stir bar was charged with 4-chloro-6-(1H-pyrazol-4-yl)pyrazolo[1,5-a]pyrazine (0.100 g, 0.455 mmol) and 3 mL of dioxane. To this was added 1-(1-(2,2-difluorocyclopropyl)propyl)-4-(4,4,5,5-tetramethyl-1,3,2-dioxaborolan-2-yl)-1H-pyrazole (0.284 g, 0.911 mmol, 2 mL in dioxane), Pd$_2$dba$_3$ (0.0417 g, 0.0455 mmol), XPhos (0.0868 g, 0.182 mmol) and K$_2$CO$_3$ (0.911 mL, 1.82 mmol, 2M). The tube was sealed and warmed to 100° C. for 16 hours. The mixture was partitioned between water and EtOAc and filtered through GF/F filter paper. The filtrate was extracted with EtOAc, and the combined organic extracts were dried over sodium sulfate and concentrated under reduced pressure. The residue was purified over silica gel (EtOAc) to afford 4-(1-(1-(2,2-difluorocyclopropyl)propyl)-1H-pyrazol-4-yl)-6-(1H-pyrazol-4-yl)pyrazolo[1,5-a]pyrazine (52 mg, 31% yield) as a tan solid.

| Example | Structure | Name | Data |
| --- | --- | --- | --- |
| 203 | (isolated "Peak B") | (S)-2-methyl-3-(4-(4-(1-(pentan-3-yl)-1H-pyrazol-4-yl)pyrazolo[1,5-a]pyrazin-6-yl)-1H-pyrazol-1-yl)propane-1,2-diol | Mass spectrum (apci) m/z = 410.2 (M + H) |

Step B:

A round bottom flask equipped with a stir bar and nitrogen inlet was charged with 4-(1-(1-(2,2-difluorocyclopropyl)propyl)-1H-pyrazol-4-yl)-6-(1H-pyrazol-4-yl)pyrazolo[1,5-a]pyrazine (0.052 g, 0.141 mmol), 2 mL of DMA and cesium carbonate (0.138 g, 0.422 mmol). To this was added (S)-4-(chloromethyl)-2,2-dimethyl-1,3-dioxolane (0.042 g, 0.282 mmol) and the reaction mixture was warmed to 70° C. for 6 hours. The reaction mixture was diluted with water and extracted with EtOAc. The combined organic extracts were washed with brine, dried over sodium sulfate and concentrated under reduced pressure. The residue was purified over silica gel (EtOAc) to afford 35 mg of the product as a diastereomeric mixture.

Step C:

The diastereomers prepared in Step B were separated by chiral chromatography (Chiral Tech OJ-H, 2.1 cm×250 mm, 20% EtOH in hexanes, 24 mL/min) to afford 2 peaks that were arbitrarily assigned chirality. Peak A (retention time=16 min), arbitrarily assigned as 4-(1-((1R)-1-(2,2-difluorocyclopropyl)propyl)-1H-pyrazol-4-yl)-6-(1-(((R)-2,2-dimethyl-1,3-dioxolan-4-yl)methyl)-1H-pyrazol-4-yl)pyrazolo[1,5-a]pyrazine; and Peak B (retention time=20 min), arbitrarily assigned as 4-(1-((1R)-1-(2,2-difluorocyclopropyl)propyl)-1H-pyrazol-4-yl)-6-(1-(((R)-2,2-dimethyl-1,3-dioxolan-4-yl)methyl)-1H-pyrazol-4-yl)pyrazolo[1,5-a]pyrazine.

Step X:

A microwave reaction tube was charged with 4-(1-((1R)-1-(2,2-difluorocyclopropyl)propyl)-1H-pyrazol-4-yl)-6-(1-(((R)-2,2-dimethyl-1,3-dioxolan-4-yl)methyl)-1H-pyrazol-4-yl)pyrazolo[1,5-a]pyrazine (0.012 mg, 0.025 mmol) [Peak A from previous step] and isopropyl alcohol (1 mL). To this was added a couple of drops of concentrated HCl. The tube was sealed and the reaction mixture was warmed to 60° C. for 3 hours. The reaction mixture was concentrated under reduced pressure and the crude material was taken up in 25% isopropyl alcohol/$CH_2Cl_2$ and 10% aqueous $K_2CO_3$. The mixture was extracted with 25% isopropyl alcohol/$CH_2Cl_2$, and the combined organic extracts were dried over sodium sulfate, filtered and concentrated under reduced pressure to afford (R)-3-(4-(4-(1-((R)-1-((S)-2,2-difluorocyclopropyl)propyl)-1H-pyrazol-4-yl)pyrazolo[1,5-a]pyrazin-6-yl)-1H-pyrazol-1-yl)propane-1,2-diol (Peak A") (7 mg, 64% yield) as a solid. Mass spectrum (apci) m/z=444.2 (M+H). $^1$H NMR ($CD_3OD$) δ 8.70 (d, J=0.8 Hz, 1H), 8.63 (s, 1H), 8.38 (s, 1H), 8.28 (s, 1H), 8.10 (s, 1H), 8.07 (d, J=2.5 Hz, 1H), 7.20 (dd, J=2.3, 0.8 Hz, 1H), 4.37 (dd, J=13.9, 4.1 Hz, 1H), 4.20 (dd, J=14.1, 7.6 Hz, 1H), 4.05 (m, 2H), 3.60-3.51 (m, 2H), 2.38-2.13 (m, 2H), 2.09-1.97 (m, 1H), 1.59-1.48 (m, 1H), 1.37-1.25 (m, 2H), 0.92 (t, J=7.4 Hz, 3H).

The following compounds were prepared according to the procedure described for Example 204.

| Example | Structure | Name | Data |
|---|---|---|---|
| 205 | 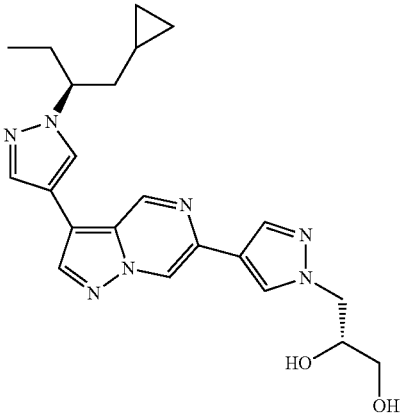<br>(isolated "Peak A") | (R)-3-(4-(4-(1-((S)-1-cyclopropylbutan-2-yl)-1H-pyrazol-4-yl)pyrazolo[1,5-a]pyrazin-6-yl)-1H-pyrazol-1-yl)propane-1,2-diol | Mass spectrum (apci) m/z = 422.2 (M + H) |
| 206 | 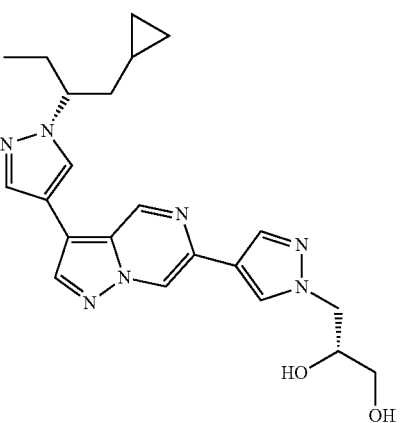<br>(isolated "Peak B") | (R)-3-(4-(4-(1-((R)-1-cyclopropylbutan-2-yl)-1H-pyrazol-4-yl)pyrazolo[1,5-a]pyrazin-6-yl)-1H-pyrazol-1-yl)propane-1,2-diol | Mass spectrum (apci) m/z = 422.2 (M + H) |

Example 207

(R)-3-(4-(4-(1-((1S,2R)-2-ethylcyclopentyl)-1H-pyrazol-4-yl)pyrazolo[1,5-a]pyrazin-6-yl)-1H-pyrazol-1-yl)propane-1,2-diol

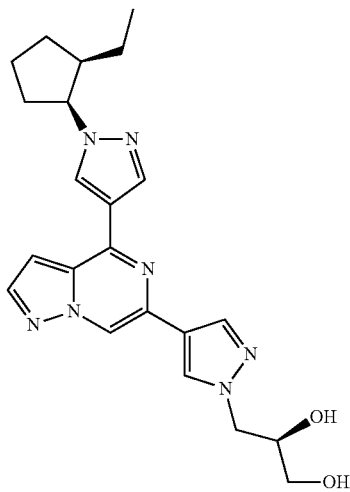 [SMILES: CC[C@@H]1CCC[C@@H]1n1cc(-c2nc(-c3cnn(C[C@@H](O)CO)c3)cn3nccc23)cn1]

Step A:

In 8 mL of DMF were combined 4-(4,4,5,5-tetramethyl-1,3,2-dioxaborolan-2-yl)-1H-pyrazole (1.72 g, 8.84 mmol), 1-cyclobutylpropyl methanesulfonate (1.7 g, 8.84 mmol), and $Cs_2CO_3$ (3.02 g, 9.28 mmol) and the reaction mixture was sparged with argon for 5 minutes before vessel was sealed and heated to 100° C. over the weekend. The reaction mixture was poured into saturated sodium bicarbonate and extracted with EtOAc. The combined organic layers were washed with 1:1 bicarbonate:water and brine, and the aqueous layer was extracted with EtOAc. The combined organic layers were dried over $MgSO_4$, filtered, and concentrated under reduced pressure. The crude material was purified by silica gel chromatography eluting 3% acetone in $CH_2Cl_2$ to afford an inseparable mixture of 1-(1-cyclobutylpropyl)-4-(4,4,5,5-tetramethyl-1,3,2-dioxaborolan-2-yl)-1H-pyrazole and 1-(trans-2-ethylcyclopentyl)-4-(4,4,5,5-tetramethyl-1,3,2-dioxaborolan-2-yl)-1H-pyrazole (0.353 g, 14% yield).

Step B:

In 5 mL of THF were combined the mixture of 1-(1-cyclobutylpropyl)-4-(4,4,5,5-tetramethyl-1,3,2-dioxaborolan-2-yl)-1H-pyrazole and 1-(trans-2-ethylcyclopentyl)-4-(4,4,5,5-tetramethyl-1,3,2-dioxaborolan-2-yl)-1H-pyrazole (0.353 g, 1.22 mmol). 4-Chloro-6-(1-(4-methoxybenzyl)-1H-pyrazol-4-yl)pyrazolo[1,5-a]pyrazine hydrochloride (0.458 g, 1.22 mmol), $Pd_2(dba)_3$ (0.0557 g, 0.0608 mmol), and XPhos (0.116 g, 0.243 mmol) were added and the reaction mixture was sparged with argon for 2 minutes. $K_2CO_3$ (2.43 mL, 4.87 mmol) was added and the reaction mixture was sparged for another 3 minutes before the vessel was sealed and heated to 70° C. overnight. The reaction mixture was diluted with EtOAc (30 mL) and 10 mL of water, and the organic layer was collected and dried over $MgSO_4$, filtered, and concentrated under reduced pressure. The residue was purified over silica gel (20% acetone in $CH_2Cl_2$), followed by reverse phase chromatography (C18, 5 to 95% $CH_3CN$ in water) to afford 4-(1-(2-ethylcyclopentyl)-1H-pyrazol-4-yl)-6-(1-(4-methoxybenzyl)-1H-pyrazol-4-yl)pyrazolo[1,5-a]pyrazine (0.150 g, 0.321 mmol, 26.4% yield).

Step C:

4-(1-(2-Ethylcyclopentyl)-1H-pyrazol-4-yl)-6-(1-(4-methoxybenzyl)-1H-pyrazol-4-yl)pyrazolo[1,5-a]pyrazine (0.150 g, 0.321 mmol) was dissolved in 1 mL of TFA and the reaction mixture was heated to 80° C. overnight and then concentrated under reduced pressure. The residue was taken up in 1M NaOH and extracted with EtOAc. The combined organic layers were washed with brine (10 mL), dried over $MgSO_4$, filtered, and removed under reduced pressure to provide 4-(1-(2-ethylcyclopentyl)-1H-pyrazol-4-yl)-6-(1H-pyrazol-4-yl)pyrazolo[1,5-a]pyrazine as a racemic mixture.

Step D:

The racemic mixture prepared in Step C was purified by chiral chromatography (Chiral Tech OD-H, 4.6 mm×250 mm, 5 micron, 10% EtOH in hexanes, 1 mL/min) to afford two peaks that were arbitrarily assigned. Peak A (retention time=14.4 min): 4-(1-((1S,2R)-2-ethylcyclopentyl)-1H-pyrazol-4-yl)-6-(1H-pyrazol-4-yl)pyrazolo[1,5-a]pyrazine, and Peak B (retention time=17.1 min): 4-(1-((1R,2S)-2-ethylcyclopentyl)-1H-pyrazol-4-yl)-6-(1H-pyrazol-4-yl)pyrazolo[1,5-a]pyrazine Step E:

To a solution of 4-(1-((1S,2R)-2-ethylcyclopentyl)-1H-pyrazol-4-yl)-6-(1H-pyrazol-4-yl)pyrazolo[1,5-a]pyrazine (7 mg, 0.02 mmol) in DMA (0.5 mL) was added (S)-4-(chloromethyl)-2,2-dimethyl-1,3-dioxolane (14 µL, 0.10 mmol) followed by cesium carbonate (13 mg, 0.04 mmol). The mixture was stirred at 70° C. in a sealed screw-cap vial overnight. The mixture was partitioned between water (5 mL) and EtOAc (5 mL) and the aqueous layer extracted with EtOAc. The combined organic phases were washed with water and brine, then dried over $Na_2SO_4$, filtered and concentrated to afford 6-(1-(((R)-2,2-dimethyl-1,3-dioxolan-4-yl)methyl)-1H-pyrazol-4-yl)-4-(1-((1S,2R)-2-ethylcyclopentyl)-1H-pyrazol-4-yl)pyrazolo[1,5-a]pyrazine as a colorless glass.

Step F:

6-(1-(((R)-2,2-dimethyl-1,3-dioxolan-4-yl)methyl)-1H-pyrazol-4-yl)-4-(1-((1S,2R)-2-ethylcyclopentyl)-1H-pyrazol-4-yl)pyrazolo[1,5-a]pyrazine (9 mg, 0.02 mmol) was dissolved in isopropyl alcohol (1 mL) and concentrated HCl (1 drop) was added. The mixture was stirred at 60° C. for 2 hours. The cooled mixture was concentrated and the residue was partitioned between 2N NaOH and $CH_2Cl_2$. The aqueous layer was extracted with $CH_2Cl_2$ and the combined organic extracts were washed with brine, dried over $Na_2SO_4$, filtered and concentrated. The residue was purified over silica gel (2-5% MeOH/$CH_2Cl_2$) to afford (R)-3-(4-(4-(1-((1S,2R)-2-ethylcyclopentyl)-1H-pyrazol-4-yl)pyrazolo[1,5-a]pyrazin-6-yl)-1H-pyrazol-1-yl)propane-1,2-diol (Peak A) (3.8 mg, 46% yield) as a white solid. Mass spectrum (apci) m/z=422.2 (M+H). $^1$H NMR (CDCl$_3$) δ 8.46 (d, J=0.8 Hz, 1H), 8.22 (s, 1H), 8.14 (s, 1H), 8.06 (s, 1H), 8.03 (s, J=2.5 Hz, 1H), 7.99 (s, 1H), 6.94 (dd, J=2.4, 0.8 Hz, 1H), 4.81 (td, J=7.2, 5.1 Hz, 1H), 4.39-4.27 (m, 2H), 4.11 (m, 1H), 3.66-3.56 (m, 2H), 2.40-2.22 (m, 2H), 2.16-2.05 (m, 2H), 2.02-1.94 (m, 1H), 1.83-1.57 (m, 2H), 1.17-1.09 (m, 1H), 0.94-0.82 (m, 4H).

The following compound was prepared according to the procedure described for Example 207.

| Example | Structure | Name | Data |
|---|---|---|---|
| 208 | 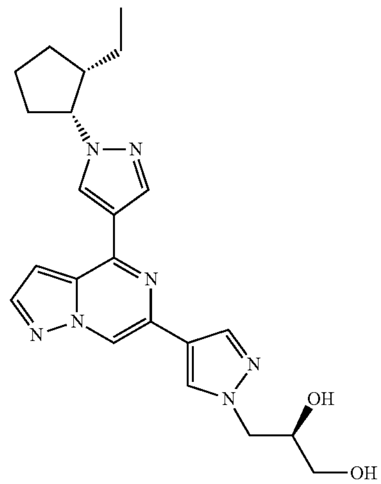 | (R)-3-(4-(4-(1-((1R,2S)-2-ethylcyclopentyl)-1H-pyrazol-4-yl)pyrazolo[1,5-a]pyrazin-6-yl)-1H-pyrazol-1-yl)propane-1,2-diol (isolated "Peak B") | Mass spectrum (apci) m/z = 422.2 (M + H) |

Example 209

(R)-3-(4-(4-(1-((R)-1,1,1-trifluoropentan-3-yl)-1H-pyrazol-4-yl)pyrazolo[1,5-a]pyrazin-6-yl)-1H-pyrazol-1-yl)propane-1,2-diol

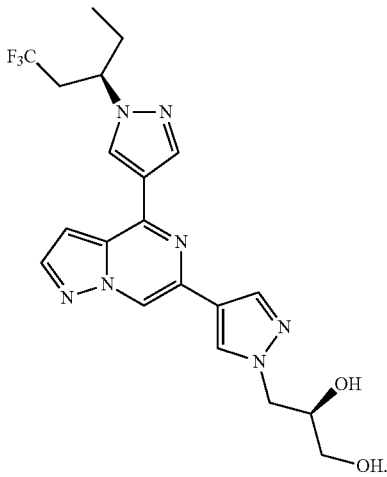 [SMILES: CC[C@H](CC(F)(F)F)n1cc(-c2nc(-c3cnn(C[C@@H](O)CO)c3)cn3nccc23)cn1]

Step A:
A mixture of 4-chloro-6-(1-(4-methoxybenzyl)-1H-pyrazol-4-yl)pyrazolo[1,5-a]pyrazine hydrochloride (0.322 g, 0.855 mmol), 4-(4,4,5,5-tetramethyl-1,3,2-dioxaborolan-2-yl)-1-(1,1,1-trifluoropentan-3-yl)-1H-pyrazole (0.272 g, 0.855 mmol), Pd$_2$dba$_3$ (0.0783 g, 0.0855 mmol), XPhos (0.0815 g, 0.171 mmol) in 2M K$_2$CO$_3$ (1.28 mL, 2.56 mmol) and dioxane (4.27 mL, 0.855 mmol) was degassed with nitrogen and heated at 100° C. for 2 hours. The reaction mixture was partitioned between EtOAc and brine. The aqueous layer was extracted with EtOAc. The combined organic layers were dried over sodium sulfate, filtered and concentrated. The residue was purified over silica gel (10-80% EtOAc in hexanes) to afford 6-(1-(4-methoxybenzyl)-1H-pyrazol-4-yl)-4-(1-(1,1,1-trifluoropentan-3-yl)-1H-pyrazol-4-yl)pyrazolo[1,5-a]pyrazine (339 mg, 80% yield).

Step B:
A solution of 6-(1-(4-methoxybenzyl)-1H-pyrazol-4-yl)-4-(1-(1,1,1-trifluoropentan-3-yl)-1H-pyrazol-4-yl)pyrazolo[1,5-a]pyrazine (339 mg, 0.684 mmol) in TFA (6842 µL, 0.684 mmol) was heated at 80° C. for 30 minutes. Triflic acid (60.8 µL, 0.684 mmol) was added and the reaction heated overnight. The reaction mixture was concentrated, partitioned between EtOAc and saturated aqueous NaHCO$_3$, dried over sodium sulfate, filtered and concentrated to afford crude 6-(1H-pyrazol-4-yl)-4-(1-(1,1,1-trifluoropentan-3-yl)-1H-pyrazol-4-yl)pyrazolo[1,5-a]pyrazine, which was taken on to the next step without further purification.

Step C:
A suspension of 6-(1H-pyrazol-4-yl)-4-(1-(1,1,1-trifluoropentan-3-yl)-1H-pyrazol-4-yl)pyrazolo[1,5-a]pyrazine (300 mg, 0.799 mmol), (S)-(–)-4-(Chloromethyl)-2,2-dimethyl-1,3-dioxolane (120 µL, 0.879 mmol), Cs$_2$CO$_3$ (521 mg, 1.60 mmol) in DMF (3996 µL, 0.799 mmol) was heated at 60° C. for 1 day. The reaction mixture was diluted with EtOAc and then washed with water. The organic layer was dried over sodium sulfate and concentrated to afford 6-(1-((-2,2-dimethyl-1,3-dioxolan-4-yl)methyl)-1H-pyrazol-4-yl)-4-(1-(1,1,1-trifluoropentan-3-yl)-1H-pyrazol-4-yl)pyrazolo[1,5-a]pyrazine as a mixture of diastereomers. The diastereomers were separated by chiral chromatography (Chiral Tech IA column, 4.6 mm×250 mm, 5 micron, 15% EtOH in hexanes, 1 mL/min) to afford Peak A (retention time=21.5 min), arbitrarily assigned as R stereochemistry; and Peak B (retention time=24.3 min), arbitrarily assigned as S stereochemistry.

Step D:
A solution of 6-(1-(((R)-2,2-dimethyl-1,3-dioxolan-4-yl)methyl)-1H-pyrazol-4-yl)-4-(1-(1,1,1-trifluoropentan-3-yl)-1H-pyrazol-4-yl)pyrazolo[1,5-a]pyrazine (42 mg, 0.086 mmol) [Peak A from previous step] and concentrated HCl (3 drops) in methanol was heated at 65° C. for 1 hour. The mixture was concentrated and purified by reverse phase chromatography (C18, 5 to 95% CH$_3$CN in water) to afford (R)-3-(4-(4-(1-((R)-1,1,1-trifluoropentan-3-yl)-1H-pyrazol-4-yl)pyrazolo[1,5-a]pyrazin-6-yl)-1H-pyrazol-1-yl)propane-1,2-diol (Peak A) (33 mg, 86% yield). Mass spectrum (apci) m/z=450.2 (M+H). 1H NMR (CD$_3$OD) δ 8.63 (s, 1H), 8.55 (s, 1H), 8.37 (s, 1H), 8.25 (s, 1H), 8.08 (s, 1H), 8.06 (s, J=2.5 Hz, 1H), 7.14 (dd, J=2.5, 0.8 Hz, 1H), 4.62 (m, 1H), 4.39 (dd, J=14.1, 4.3 Hz, 1H), 4.23 (dd, J=14.1, 7.4 Hz, 1H), 4.07 (m, 1H), 3.62-3.52 (m, 2H), 3.11-2.96 (m, 1H), 2.80-2.66 (m, 1H), 2.15-1.91 (m, 2H), 0.85 (t, J=7.2 Hz, 3H).

The following compounds were prepared according to the procedure described for Example 209.

| Example | Structure | Name | Data |
|---|---|---|---|
| 210 | 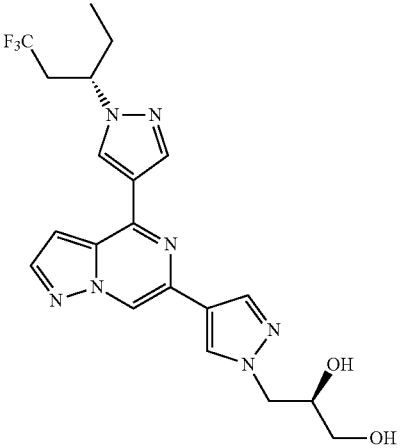 (isolated "Peak B") | (R)-3-(4-(4-(1-((S)-1,1,1-trifluoropentan-3-yl)-1H-pyrazol-4-yl)pyrazolo[1,5-a]pyrazin-6-yl)-1H-pyrazol-1-yl)propane-1,2-diol | Mass spectrum (apci) m/z = 450.2 (M + H) |
| 211 | 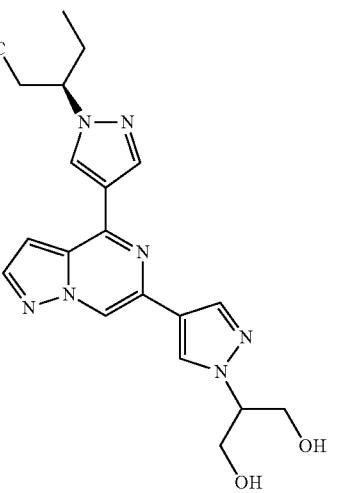 (isolated "Peak A") | (R)-2-(4-(4-(1-(1,1,1-trifluoropentan-3-yl)-1H-pyrazol-4-yl)pyrazolo[1,5-a]pyrazin-6-yl)-1H-pyrazol-1-yl)propane-1,3-diol | Mass spectrum (apci) m/z = 450.2 (M + H) |
| 212 | 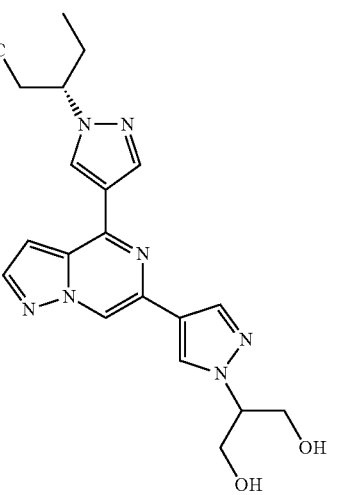 (isolated "Peak B") | (S)-2-(4-(4-(1-(1,1,1-trifluoropentan-3-yl)-1H-pyrazol-4-yl)pyrazolo[1,5-a]pyrazin-6-yl)-1H-pyrazol-1-yl)propane-1,3-diol | Mass spectrum (apci) m/z = 450.2 (M + H) |

Example 213

(R)-3-(4-(4-(1-((R)-1-cyclopropylpropyl)-1H-pyrazol-4-yl)pyrazolo[1,5-a]pyrazin-6-yl)-1H-pyrazol-1-yl)propane-1,2-diol

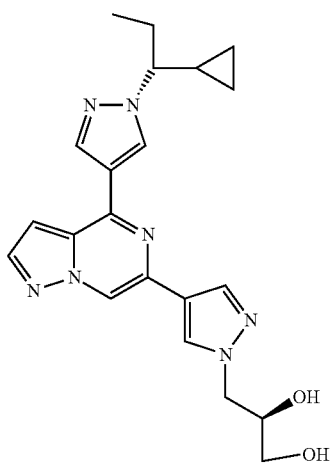

Step A:

In 80 mL of THF were combined 4-chloro-6-(1H-pyrazol-4-yl)pyrazolo[1,5-a]pyrazine (6.5 g, 30 mmol), 1-(1-cyclopropylpropyl)-4-(4,4,5,5-tetramethyl-1,3,2-dioxaborolan-2-yl)-1H-pyrazole (12 g, 44 mmol), dicyclohexyl(2',4',6'-triisopropyl-[1,1'-biphenyl]-2-yl)phosphine (2.8 g, 5.9 mmol), and $Pd_2(dba)_3$ (1.4 g, 1.5 mmol). The reaction mixture was sparged with argon for 3 minutes. To the reaction mixture was added potassium carbonate (44 mL, 89 mmol) by syringe and the reaction mixture was sparged for another 5 minutes before the vessel was sealed and heated to 75° C. for 5 hours. The cooled reaction mixture was extracted with EtOAc and $CH_2Cl_2$. The organic layer was passed over a plug of 1:1 Celite®:$MgSO_4$ and concentrated under reduced pressure to yield a thick oil. This oil was triturated with 10 volumes of $CH_2Cl_2$ (65 mL) and the resulting solids were washed with $CH_2Cl_2$ (30 mL). The filtrate was concentrated and purified over silica gel (15-30% acetone in $CH_2Cl_2$) to afford a racemic mixture of 4-(1-(1-cyclopropylpropyl)-1H-pyrazol-4-yl)-6-(1H-pyrazol-4-yl)pyrazolo[1,5-a]pyrazine (4.9 g, 13 mmol, 45% yield) as a light yellow foam.

Step B:

The racemic mixture prepared in Step A was separated by chiral SFC chromatography (IA column, 2.0×25 cm, 20% MeOH (0.1% DEA) in $CO_2$, 100 bar, 70 mL/min) to afford 2 compounds. Peak A: (S)-4-(1-(1-cyclopropylpropyl)-1H-pyrazol-4-yl)-6-(1H-pyrazol-4-yl)pyrazolo[1,5-a]pyrazine: 5.2 min retention time. Peak B: (R)-4-(1-(1-cyclopropylpropyl)-1H-pyrazol-4-yl)-6-(1H-pyrazol-4-yl)pyrazolo[1,5-a]pyrazine, 6.1 min retention time. Absolute stereochemistry was arbitrarily assigned.

Step C:

To a solution of (R)-4-(1-(1-cyclopropylpropyl)-1H-pyrazol-4-yl)-6-(1H-pyrazol-4-yl)pyrazolo[1,5-a]pyrazine (1.1 g, 3.3 mmol) in DMF (20 mL) was added $Cs_2CO_3$ (2.2 g, 6.6 mmol) and (S)-4-(chloromethyl)-2,2-dimethyl-1,3-dioxolane (0.90 mL, 6.6 mmol) and the reaction mixture was heated to 70° C. overnight. The reaction mixture was diluted with EtOAc and washed with water and brine, dried over $MgSO_4$, filtered and concentrated in vacuo. The residue was purified over silica gel (0-50% EtOAc/$CH_2Cl_2$ as eluent) to afford 4-(1-((R)-1-cyclopropylpropyl)-1H-pyrazol-4-yl)-6-(1-(((R)-2,2-dimethyl-1,3-dioxolan-4-yl)methyl)-1H-pyrazol-4-yl)pyrazolo[1,5-a]pyrazine (1.1 g, 2.5 mmol, 74% yield).

Step D:

To a solution of 4-(1-((R)-1-cyclopropylpropyl)-1H-pyrazol-4-yl)-6-(1-(((R)-2,2-dimethyl-1,3-dioxolan-4-yl)methyl)-1H-pyrazol-4-yl)pyrazolo[1,5-a]pyrazine (1.1 g, 2.5 mmol) in isopropyl alcohol (20 mL) was added 5 drops of concentrated HCl and the reaction mixture was heated to 70° C. for 5 hours. The reaction mixture was concentrated in vacuo and the residue was partitioned between basic water and EtOAc. The combined organic phases were washed with brine, dried over $MgSO_4$ and concentrated in vacuo. The residue was purified over silica gel (0-10% MeOH/ETOAc) to afford (R)-3-(4-(4-(1-((R)-1-cyclopropylpropyl)-1H-pyrazol-4-yl)pyrazolo[1,5-a]pyrazin-6-yl)-1H-pyrazol-1-yl)propane-1,2-diol (Peak B) (0.79 g, 1.9 mmol, 79% yield). Mass spectrum (apci) m/z=408.2 (M+H). $^1$H NMR ($d_6$-DMSO) δ 8.99 (d, J=0.8 Hz, 1H), 8.72 (d, J=0.6 Hz, 1H), 8.37 (s, 1H), 8.33 (d, J=0.6 Hz, 1H), 8.16 (d, J=2.5 Hz, 1H), 8.15 (d, J=0.6 Hz, 1H), 7.35 (dd, J=2.5, 1.0 Hz, 1H), 5.04 (d, J=5.3 Hz, 1H), 4.76 (t, J=5.7 Hz, 1H), 4.28 (dd, J=13.7, 3.9 Hz, 1H), 4.04 (dd, J=13.7, 7.8 Hz, 1H), 3.88 (m, 1H), 3.51 (td, J=9.2, 5.1 Hz, 1H), 3.44-3.33 (m, 2H), 2.16-1.95 (m, 2H), 1.40 (m, 1H), 0.79 (t, J=7.2 Hz, 3H), 0.67 (m, 1H), 0.46-0.30 (m, 3H).

The following compounds were prepared according to the procedure described for Example 213.

| Example | Structure | Name | Data |
|---|---|---|---|
| 214 | 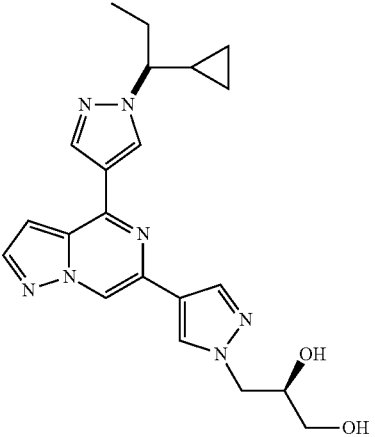<br>(isolated "Peak A") | (R)-3-(4-(4-(1-((S)-1-cyclopropylpropyl)-1H-pyrazol-4-yl)pyrazolo[1,5-a]pyrazin-6-yl)-1H-pyrazol-1-yl)propane-1,2-diol | Mass spectrum (apci) m/z = 408.2 (M + H) |
| 215 | 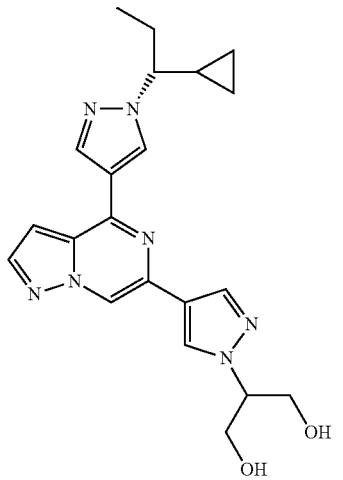<br>(isolated "Peak B") | (R)-2-(4-(4-(1-(1-cyclopropylpropyl)-1H-pyrazol-4-yl)pyrazolo[1,5-a]pyrazin-6-yl)-1H-pyrazol-1-yl)propane-1,3-diol | Mass spectrum (apci) m/z = 408.2 (M + H) |

Example 216

(R)-3-(4-(4-(1-(dicyclopropylmethyl)-1H-pyrazol-4-yl)pyrazolo[1,5-a]pyrazin-6-yl)-1H-pyrazol-1-yl)propane-1,2-diol

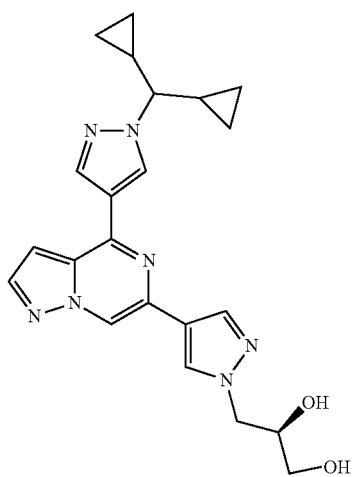 [SMILES: OC[C@H](O)Cn1cc(-c2cn3nccc3c(-c3cnn(C(C4CC4)C4CC4)c3)n2)cn1]

Step A:

To a solution of 1-(dicyclopropylmethyl)-4-(4,4,5,5-tetramethyl-1,3,2-dioxaborolan-2-yl)-1H-pyrazole (1.3 g, 4.6 mmol) in THF (40 mL) was added sodium hydrogen carbonate (7.6 mL, 11 mmol) and 4-chloro-6-(1H-pyrazol-4-yl)pyrazolo[1,5-a]pyrazine (0.5 g, 2.3 mmol) and the reaction mixture was purged with $N_2$ for 20 minutes. To the reaction mixture was added 100 mg each of $Pd_2(dba)_3$ and XPhos and the reaction mixture was heated to 83° C. for 4 hours. The cooled reaction mixture was partitioned between EtOAc and water, washed with brine, dried over $MgSO_4$ and concentrated in vacuo. The residue was purified over silica gel (20-100% EtOAc in $CH_2Cl_2$) to afford 4-(1-(dicyclopropylmethyl)-1H-pyrazol-4-yl)-6-(1H-pyrazol-4-yl)pyrazolo[1,5-a]pyrazine.

Step B:

To a solution of 4-(1-(dicyclopropylmethyl)-1H-pyrazol-4-yl)-6-(1H-pyrazol-4-yl)pyrazolo[1,5-a]pyrazine (0.10 g, 0.29 mmol) in DMF (4 mL) was added (S)-4-(chloromethyl)-2,2-dimethyl-1,3-dioxolane (0.087 g, 0.58 mmol) and $Cs_2CO_3$ (0.19 g, 0.58 mmol) and the reaction mixture was stirred overnight at 80° C. The reaction mixture was partitioned between EtOAc and water. The combined organic phases were washed with brine, dried over $MgSO_4$ and concentrated in vacuo. The residue was purified over silica gel (0-100% EtOAc/$CH_2Cl_2$) to afford (R)-4-(1-(dicyclopropylmethyl)-1H-pyrazol-4-yl)-6-(1-((2,2-dimethyl-1,3-dioxolan-4-yl)methyl)-1H-pyrazol-4-yl)pyrazolo[1,5-a]pyrazine (0.05 g, 0.11 mmol, 38% yield)

Step C:

To a solution of (R)-4-(1-(dicyclopropylmethyl)-1H-pyrazol-4-yl)-6-(1-((2,2-dimethyl-1,3-dioxolan-4-yl)methyl)-1H-pyrazol-4-yl)pyrazolo[1,5-a]pyrazine (0.050 g, 0.109 mmol) in isopropyl alcohol (10 mL) was added concentrated HCl (3 drops) and the reaction mixture was stirred overnight at room temperature. The reaction mixture was concentrated in vacuo and the residue was partitioned between EtOAc and 1N NaOH. The combined organic phases were washed with brine, dried over $MgSO_4$ and concentrated in vacuo. The residue was purified over silica gel (0-10% MeOH/$CH_2Cl_2$) to afford (R)-3-(4-(4-(1-(dicyclopropylmethyl)-1H-pyrazol-4-yl)pyrazolo[1,5-a]pyrazin-6-yl)-1H-pyrazol-1-yl)propane-1,2-diol (0.0193 g, 0.0460 mmol, 42.3% yield). Mass spectrum (apci) m/z=420.2 (M+H). $^1$H NMR ($CDCl_3$) δ 8.43 (d, J=0.8 Hz, 1H), 8.32 (s, 1H), 8.22 (s, 1H), 8.04 (s, 1H), 8.02 (d, J=2.5 Hz, 1H), 7198 (s, 1H), 6.95 (dd, J=2.5, 1.0 Hz, 1H), 4.35 (s, 1H), 4.33 (d, J=1.2 Hz, 1H), 4.16 (pentet, J=5.3 Hz, 1H), 3.71-3.63 (m, 2H), 3.13 (t, J=8.6 Hz, 1H), 1.48-1.39 (m, 2H), 0.77 (m, 2H), 0.58 (m, 2H), 0.53-0.39 (m, 4H).

Example 217

(R)-3-(4-(4-(1-(cis-2-methylcyclobutyl)-1H-pyrazol-4-yl)pyrazolo[1,5-a]pyrazin-6-yl)-1H-pyrazol-1-yl)propane-1,2-diol

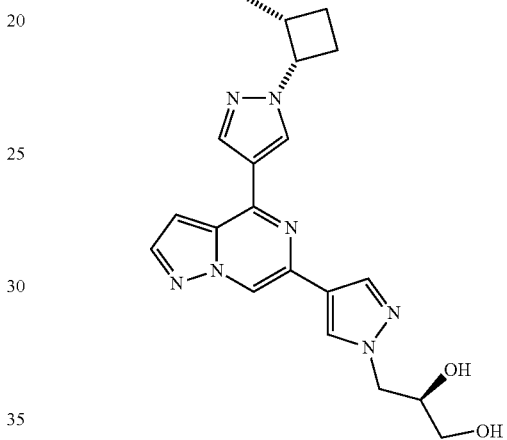

Step A:

To a stirred solution of 1-(cis-2-methylcyclobutyl)-4-(4,4,5,5-tetramethyl-1,3,2-dioxaborolan-2-yl)-1H-pyrazole (91 mg, 0.35 mmol) in 1 mL of dioxane in a capped reaction vial was added 4-chloro-6-(1H-pyrazol-4-yl)pyrazolo[1,5-a]pyrazine (76 mg, 0.35 mmol), 2-(Dicyclohexylphosphino)-2',4',6'-tri-i-propyl-1,1'-biphenyl (17 mg, 0.035 mmol) and 2M aqueous $K_2CO_3$ (347 µL, 0.69 mmol). The reaction mixture was sparged with argon for 5 minutes and then $Pd_2(dba)_3$ (16 mg, 0.017 mmol) was added. The vial was capped and heated to 80° C. overnight. The reaction mixture was cooled to room temperature and partitioned between dichloromethane (15 mL) and water (15 mL). The combined organic phases were isolated and the aqueous phase was extracted with dichloromethane. The combined organic layers were dried over $MgSO_4$, filtered and concentrated. The residue was purified over silica gel (10-75% EtOAc in hexanes) to afford 4-(1-(cis-2-methylcyclobutyl)-1H-pyrazol-4-yl)-6-(1H-pyrazol-4-yl)pyrazolo[1,5-a]pyrazine (17 mg, 15% yield) as a yellow solid.

Step B:

To a stirred solution of 4-(1-(cis-2-methylcyclobutyl)-1H-pyrazol-4-yl)-6-(1H-pyrazol-4-yl)pyrazolo[1,5-a]pyrazine (17 mg, 0.05323 mmol) in 400 µL of DMF at room temperature in a capped reaction vial was added neat $Cs_2CO_3$ (34.69 mg, 0.1065 mmol) as a solid followed by (S)-4-(chloromethyl)-2,2-dimethyl-1,3-dioxolane (14.54 µL, 0.1065 mmol). The reaction mixture was capped and heated to 80° C. for 4 hours. The reaction mixture was cooled to room temperature and diluted with 15 mL of ethyl acetate.

The organic phase was washed with water and brine. The combined organic phases were isolated, dried over MgSO$_4$, filtered and concentrated. The residue was purified over silica gel (10-60% EtOAc in hexanes) to afford 6-(1-(((R)-2,2-dimethyl-1,3-dioxolan-4-yl)methyl)-1H-pyrazol-4-yl)-4-(1-(cis-2-methylcyclobutyl)-1H-pyrazol-4-yl)pyrazolo[1,5-a]pyrazine (11 mg, 47% yield).

Step C:

To a stirred suspension of 6-(1-(((R)-2,2-dimethyl-1,3-dioxolan-4-yl)methyl)-1H-pyrazol-4-yl)-4-(1-(cis-2-methylcyclobutyl)-1H-pyrazol-4-yl)pyrazolo[1,5-a]pyrazine (11 mg, 0.025 mmol) in 500 μL of isopropyl alcohol in a capped flask at room temperature was added HCl (10 μL, 0.051 mmol, 5M in isopropyl alcohol). The reaction mixture was heated to 60° C. for 3 hours. The reaction mixture was cooled to room temperature, dried under a stream of nitrogen and then stirred into a mixture of dichloromethane (10 mL) and 20% sodium carbonate solution (10 mL). After 5 minutes, the layers were separated and the aqueous layer was extracted with dichloromethane. The combined organic layers were dried over MgSO$_4$, filtered and concentrated. The residue was purified over silica gel (0-10% methanol in CH$_2$Cl$_2$) to afford (R)-3-(4-(4-(1-(cis-2-methylcyclobutyl)-1H-pyrazol-4-yl)pyrazolo[1,5-a]pyrazin-6-yl)-1H-pyrazol-1-yl)propane-1,2-diol (4 mg, 37% yield) as a white foam. Mass spectrum (apci) m/z=394.2 (M+H). $^1$H NMR (CDCl$_3$) δ 8.45 (d, J=0.8 Hz, 1H), 8.25 (s, 1H), 8.21 (s, 1H), 8.03 (m, 2H), 7.99 (s, 1H), 6.95 (dd, J=2.5, 1.0 Hz, 1H), 5.01 (q, J=8.0 Hz, 1H), 4.35 (d, J=5.3 Hz, 2H), 4.17 (pentet, J=4.9 Hz, 1H), 3.72-3.64 (m, 2H), 3.57 (br s, 1H), 2.99-2.85 (m, 2H), 2.62-2.53 (m, 1H), 2.49 (br s, 1H), 2.18 (dq, J=11.3, 8.4 Hz, 1H), 1.67 (m, 1H), 0.91 (d, J=7.0 Hz, 3H).

Example 218

(S)-1-(4-(4-(1-((R)-1-cyclopropylpropyl)-1H-pyrazol-4-yl)pyrazolo[1,5-a]pyrazin-6-yl)-1H-pyrazol-1-yl)propan-2-ol

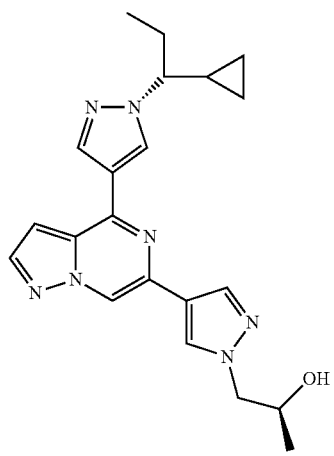

Step A:

To a solution of (R)-4-(1-(1-cyclopropylpropyl)-1H-pyrazol-4-yl)-6-(1H-pyrazol-4-yl)pyrazolo[1,5-a]pyrazine (0.15 g, 0.45 mmol) [peak B from chiral chromatography in Example 285; chirality arbitrarily assigned] in THF (4 mL) was added 60% sodium hydride (0.036 g, 0.90 mmol) followed by (S)-2-methyloxirane (0.052 g, 0.90 mmol) and the reaction mixture was stirred overnight at room temperature. The reaction mixture was diluted with water and extracted into EtOAc. The combined organic phases were washed with brine, dried over MgSO$_4$ and concentrated in vacuo. The residue was purified over silica gel (0->100% EtOAc in CH$_2$Cl$_2$) to afford crude (S)-1-(4-(4-(1-((R)-1-cyclopropylpropyl)-1H-pyrazol-4-yl)pyrazolo[1,5-a]pyrazin-6-yl)-1H-pyrazol-1-yl)propan-2-ol (0.1 g, 55% yield).

Step B:

To a solution of (S)-1-(4-(4-(1-((R)-1-cyclopropylpropyl)-1H-pyrazol-4-yl)pyrazolo[1,5-a]pyrazin-6-yl)-1H-pyrazol-1-yl)propan-2-ol (0.1 g, 0.3 mmol) in CH$_2$Cl$_2$ was added 1H-imidazole (0.03 g, 0.5 mmol) and tert-butylchlorodimethylsilane (0.08 g, 0.5 mmol) and the reaction mixture was stirred overnight at room temperature. The reaction mixture was washed with HCl (1N), brine, dried over MgSO$_4$ and concentrated in vacuo. The residue was purified over silica gel (0-50% EtOAc/CH$_2$Cl$_2$) to afford 6-(1-((S)-2-((tert-butyldimethylsilyl)oxy)propyl)-1H-pyrazol-4-yl)-4-(1-((R)-1-cyclopropylpropyl)-1H-pyrazol-4-yl)pyrazolo[1,5-a]pyrazine (0.50 g, 39% yield).

Step C:

To a solution of 6-(1-((S)-2-((tert-butyldimethylsilyl)oxy)propyl)-1H-pyrazol-4-yl)-4-(1-((R)-1-cyclopropylpropyl)-1H-pyrazol-4-yl)pyrazol[1,5-a]pyrazine (0.050 g, 0.099 mmol) in isopropyl alcohol (10 mL) was added 4 drops of concentrated HCl and the reaction mixture was stirred at room temperature for 3 hours. The reaction mixture was concentrated in vacuo and the residue was partitioned between EtOAc and 0.1 M NaOH. The combined organic phases were washed with brine, dried over MgSO$_4$ and concentrated in vacuo. The residue was purified over silica gel (0-5% MeOH/CH$_2$Cl$_2$) to afford (S)-1-(4-(4-(1-((R)-1-cyclopropylpropyl)-1H-pyrazol-4-yl)pyrazolo[1,5-a]pyrazin-6-yl)-1H-pyrazol-1-yl)propan-2-ol (0.015 g, 0.038 mmol, 39% yield). Mass spectrum (apci) m/z=392.2 (M+H). $^1$H NMR (CDCl$_3$) δ 8.43 (d, J=1.0 Hz, 1H), 8.24 (s, 1H), 8.23 (s, 1H), 8.02 (m, 2H), 7.98 (s, 1H), 6.94 (dd, J=2.3, 1.0 Hz, 1H), 4.32-4.22 (m, 2H), 4.08 (m, 1H), 3.40 (m, 1H), 2.21-2.03 (m, 2H), 1.42-1.32 (m, 1H), 1.28 (d, J=6.3 Hz, 3H), 0.91 (t, J=7.4 Hz, 3H), 0.82-0.74 (m, 1H), 0.62-0.54 (m, 1H), 0.46-0.34 (m, 2H).

What is claimed is:

1. A method for treating an autoimmune disease or inflammatory disease associated with a JAK kinase in a subject in need thereof, which comprises administering to said subject a therapeutically effective amount of a compound of Formula I

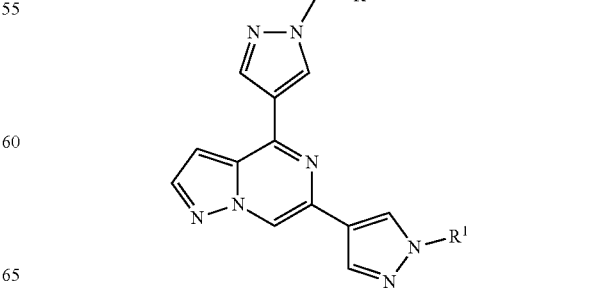

I or a stereoisomer or pharmaceutically acceptable salt or solvate thereof, wherein:

$R^1$ is hydroxy(1-6C)alkyl, $HOCH_2$(cyclopropylidine)$CH_2$—, (1-4C alkoxy)(1-6C)hydroxyalkyl, (hydroxy)trifluoro(1-6C)alkyl, dihydroxy(2-6C)alkyl, $H_2N$(3-6C)hydroxyalkyl, (1-3C alkyl)NH(3-6C)hydroxyalkyl, (1-3C alkyl)$_2$N(3-6C)hydroxyalkyl, $H_2N$(1-4C alkoxy)(3-6C)alkyl, $Cyc^1(CH_2)_m$—, $hetCyc^1$, $hetCyc^2CH_2$—, $R^aR^bNC(=O)CH_2$—, $hetCyl^{3a}$(1-3C)alkyl, $hetCyc^{3b}$(2-3C)hydroxyalkyl, $R^cR^dN$(2-3C)alkyl, (1-3C alkyl)$_2NSO_2$(2-3C)alkyl, $hetCyc^4$, (1-6C)alkyl or $CH_3SO_2$(1-6C)alkyl, $Cyc^1$ is a 4-6 membered cycloalkyl substituted with 1-2 substituents independently selected from the group consisting of HO, $HOCH_2$—, (1-3C)alkyl, $H_2NHC(=O)$—, (1-3C alkyl)$_2NC(=O)$—, and $HOCH_2CH_2NHC(=O)$—;

m is 0 or 1;

$hetCyc^1$ is a 4-6 membered heterocyclic ring having a ring heteroatom selected from N, O and S wherein the S is optionally oxidized to $SO_2$, wherein said heterocyclic ring is optionally substituted with a substituent selected from the group consisting of OH, (1-3C alkyl)C(=O)—, (1-3C alkyl)$SO_2$—, (1-3C alkyl)NHC(=O)— and $NH_2CH_2C(=O)$—;

$hetCyc^2$ is a 4-6 membered heterocyclic ring having a ring S atom; wherein the S is oxidized to $SO_2$;

$R^a$ and $R^b$ are independently H or (1-3C)alkyl, or $R^a$ and $R^b$ together with the nitrogen atom to which they are attached form a 4-6 membered ring optionally having a ring oxygen atom;

$hetCyc^{3a}$ and $hetCyc^{3b}$ are independently a 4-6 membered heterocyclic ring having 1-2 ring heteroatoms independently selected from N and O, wherein said heterocyclic ring is optionally substituted with 1-2 substituents independently selected from the group consisting of halogen, OH, (1-4C)alkoxy, $HOCH_2$—, (1-3C alkyl)C(=O)— and oxo;

$R^c$ is H or (1-3C)alkyl;

$R^d$ is (1-3C)alkyl, (1-3C alkyl)$SO_2$—, $hetCyc^a$, or (3-6C)cycloalkyl optionally substituted with $HOCH_2$—;

$hetCyc^a$ is a 5-6 membered azacyclic ring optionally substituted with 1-2 substituents independently selected from oxo and (1-3C)alkyl;

$hetCyc^4$ is azetidinyl substituted with $((CH_3)_2N)_2P(=O)$— or Y—C(=O)—;

Y is $R^eR^fN(CH_2)_n$—, $hetCyc^bCH_2$—, $Cyc^2$, hydroxy(1-3C)alkyl, (1-3C alkyl)$_2NC(=O)$—, (1-3C)alkyl$SO_2$— or (1-3C)alkyl;

n is 0 or 1;

$R^e$ and $R^f$ are independently H or (1-3C)alkyl;

$hetCyc^b$ is a 4-5 membered azacyclic ring optionally substituted with OH;

$Cyc^2$ is a (3-6C)cycloalkyl optionally substituted with OH;

$R^2$ is (1-6C)alkyl, trifluoro(1-6C)alkyl, difluoro(1-6C)alkyl, fluoro(1-6C)alkyl, hydroxy(1-6C)alkyl, (1-6C)alkoxy, (3-6C)cycloalkyl (optionally substituted with one or two halogens), (3-6C)cycloalkylCH$_2$—, HOC(=O)— or phenyl, and $R^3$ is (1-6C)alkyl or (3-6C)cycloalkyl, or $R^2$ and $R^3$ together with the carbon atom to which they are attached form a 3-7 membered cycloalkyl ring optionally substituted with one or two substituents independently selected from OH, (1-6C)alkyl and hydroxy(1-6C)alkyl, or $R^2$ and $R^3$ together with the carbon atom to which they are attached form a 4-membered saturated azacyclic ring substituted with $SO_2CF_3$; and $R^4$ is hydrogen or (1-6C)alkyl.

2. The method according to claim 1, wherein $R^1$ is hydroxy(1-6C)alkyl, $HOCH_2$(cyclopropylidine)$CH_2$—, (1-4C alkoxy)(1-6C)hydroxyalkyl, (hydroxy)trifluoro(1-6C)alkyl, dihydroxy(2-6C)alkyl, $H_2N$(3-6C)hydroxyalkyl, (1-3C alkyl)NH(3-6C)hydroxyalkyl, (1-3C alkyl)$_2$N(3-6C)hydroxyalkyl, $H_2N$(1-4C alkoxy)(3-6C)alkyl, $Cyc^1(CH_2)_m$—, $hetCyc^1$, $hetCyc^2CH_2$—, $R^aR^bNC(=O)CH_2$—, $hetCyc^{3a}$(1-3C)alkyl, $hetCyc^{3b}$(2-3C)hydroxyalkyl, $R^cR^dN$(2-3C alkyl)-, (1-3C alkyl)$_2NSO_2$(2-3C alkyl)- or $hetCyc^4$.

3. The method according to claim 1, wherein $R^1$ is hydroxy(1-6C)alkyl, $HOCH_2$(cyclopropylidine)$CH_2$—, (1-4C alkoxy)(1-6C)hydroxyalkyl, (hydroxy)trifluoro(1-6C)alkyl, dihydroxy(2-6C)alkyl, $H_2N$(3-6C)hydroxyalkyl, (1-3C alkyl)NH(3-6C)hydroxyalkyl, (1-3C alkyl)$_2$N(3-6C)hydroxyalkyl or $H_2N$(1-4C alkoxy)(3-6C)alkyl.

4. The method according to claim 1, wherein $R^1$ is dihydroxy(2-6C)alkyl, $H_2N$(3-6C)hydroxyalkyl, (1-3C alkyl)$_1$NH(3-6C)hydroxyalkyl or (1-3C alkyl)$_2$N(3-6C)hydroxyalkyl.

5. The method according to claim 1, wherein $R^1$ is dihydroxy(2-6C)alkyl.

6. The method according to claim 1, wherein $R^1$ is $H_2N$(3-6C)hydroxyalkyl, (1-3C alkyl)NH(3-6C)hydroxyalkyl or (1-3C alkyl)$_2$N(3-6C)hydroxyalkyl.

7. The method according to claim 1, wherein $R^2$ is (1-6C)alkyl, trifluoro(1-6C)alkyl, difluoro(1-6C)alkyl, fluoro(1-6C)alkyl, hydroxy(1-6C)alkyl, (1-6C)alkoxy, (3-6C)cycloalkyl (optionally substituted with one or two halogens), (3-6C)cycloalkylCH$_2$—, HOC(=O)— or phenyl;

$R^3$ is (1-6C)alkyl or (3-6C)cycloalkyl; and $R^4$ is hydrogen or (1-6C)alkyl.

8. The method according to claim 7, wherein:

$R^2$ is (1-6C)alkyl;

$R^3$ is (1-6C)alkyl; and $R^4$ is hydrogen.

9. The method according to claim 1, wherein:

$R^2$ and $R^3$ together with the carbon atom to which they are attached form a 3-7 membered cycloalkyl ring optionally substituted by one or two groups independently selected from OH, (1-6C)alkyl and hydroxy(1-6C)alkyl; and $R^4$ is hydrogen or (1-6C)alkyl.

10. The method according to claim 1, wherein:

$R^2$ and $R^3$ together with the carbon atom to which they are attached form a 4-membered saturated azacyclic ring substituted with $SO_2CF_3$; and $R^4$ is hydrogen or (1-6C)alkyl.

11. The method according to claim 1, wherein the compound of Formula I or the pharmaceutically acceptable salt thereof is selected from 4-(1-(1-ethoxyethyl)-1H-pyrazol-4-yl)-6-(1-methyl-1H-pyrazol-4-yl)pyrazolo[1,5-a]pyrazine;

4-(1-cycloheptyl-1H-pyrazol-4-yl)-6-(1-methyl-1H-pyrazol-4-yl)pyrazolo[1,5-a]pyrazine;

4-(2-(4-(4-(1-(pentan-3-yl)-1H-pyrazol-4-yl)pyrazolo[1,5-a]pyrazin-6-1H-pyrazol-1-yl)ethyl)morpholine;

4-(1-(pentan-3-yl)-1H-pyrazol-4-yl)-6-(1-((tetrahydro-2H-pyran-4-yl)methyl)-1H-pyrazol-4-yl)pyrazolo[1,5-a]pyrazine;

N,N-dimethyl-2-(4-(4-(1-(pentan-3-yl)-1H-pyrazol-4-yl)pyrazolo[1,5-a]pyrazin-6-yl)-1H-pyrazol-1-yl)acetamide;

1-morpholino-2-(4-(4-(1-(pentan-3-yl)-1H-pyrazol-4-yl)pyrazolo[1,5-a]pyrazin-6-yl)-1H-pyrazol-1-yl)ethanone;

6-(1-(3-(methylsulfonyl)propyl)-1H-pyrazol-4-yl)-4-(1-(pentan-3-yl)-1H-pyrazol-4-yl)pyrazolo[1,5-a]pyrazine;

5-((4-(4-(1-(pentan-3-yl)-1H-pyrazol-4-yl)pyrazolo[1,5-a]pyrazin-6-yl)-1H-pyrazol-1-yl)methyl)oxazolidin-2-one;

N-methyl-N-(2-(4-(4-(1-(pentan-3-yl)-1H-pyrazol-4-yl)pyrazolo[1,5-a]pyrazin-6-yl)-1H-pyrazol-1-yl)ethyl)methanesulfonamide;

N,N-dimethyl-2-(4-(4-(1-(pentan-3-yl)-1H-pyrazol-4-yl)pyrazolo[1,5-a]pyrazin-6-yl)-1H-pyrazol-1-yl)ethanamine;

4-((4-(4-(1-(pentan-3-yl)-1H-pyrazol-4-yl)pyrazolo[1,5-a]pyrazin-6-yl)-1H-pyrazol-1-yl)methyl)tetrahydro-2H-thiopyran 1,1-dioxide;

N,N-dimethyl-3-(4-(4-(1-(pentan-3-yl)-1H-pyrazol-4-yl)pyrazolo[1,5-a]pyrazin-6-yl)-1H-pyrazol-1-yl)propan-1-amine;

3-(4-(4-(1-(pentan-3-yl)-1H-pyrazol-4-yl)pyrazolo[1,5-a]pyrazin-6-yl)-1H-pyrazol-1-yl)thietane 1,1-dioxide;

(R)-2-methyl-3-(4-(4-(1-(pentan-3-yl)-1H-pyrazol-4-yl)pyrazolo[1,5-a]pyrazin-6-yl)-1H-pyrazol-1-yl)propan-1-ol;

(S)-2-methyl-3-(4-(4-(1-(pentan-3-yl)-1H-pyrazol-4-yl)pyrazolo[1,5-a]pyrazin-6-yl)-1H-pyrazol-1-yl)propan-1-ol;

(3-((4-(4-(1-(pentan-3-yl)-1H-pyrazol-4-yl)pyrazolo[1,5-a]pyrazin-6-yl)-1H-pyrazol-1-yl)methyl)oxetan-3-yl)methanol;

(S)-5-((4-(4-(1-(pentan-3-yl)-1H-pyrazol-4-yl)pyrazolo[1,5-a]pyrazin-6-yl)-1H-pyrazol-1-yl)methyl)pyrrolidin-2-one;

(R)-5-((4-(4-(1-(pentan-3-yl)-1H-pyrazol-4-yl)pyrazolo[1,5-a]pyrazin-6-yl)-1H-pyrazol-1-yl)methyl)pyrrolidin-2-one;

3-(4-(4-(1-(pentan-3-yl)-1H-pyrazol-4-yl)pyrazolo[1,5-a]pyrazin-6-yl)-1H-pyrazol-1-yl)propan-1-ol;

2-(4-(4-(1-(pentan-3-yl)-1H-pyrazol-4-yl)pyrazolo[1,5-a]pyrazin-6-yl)-1H-pyrazol-1-yl)ethanol;

(R)-4-(4-(4-(1-(sec-butyl)-1H-pyrazol-4-yl)pyrazolo[1,5-a]pyrazin-6-yl)-1H-pyrazol-1-yl)tetrahydro-2H-thiopyran 1,1-dioxide;

6-(1-(2-(methylsulfonyl)ethyl)-1H-pyrazol-4-yl)-4-(1-(pentan-3-yl)-1H-pyrazol-4-yl)pyrazolo[1,5-a]pyrazine;

N,N-dimethyl-2-(4-(4-(1-(pentan-3-yl)-1H-pyrazol-4-yl)pyrazolo[1,5-a]pyrazin-6-yl)-1H-pyrazol-1-yl)ethanesulfonamide;

4-(1-(pentan-3-yl)-1H-pyrazol-4-yl)-6-(1-(piperidin-4-yl)-1H-pyrazol-4-yl)pyrazolo[1,5-a]pyrazine;

4-(1-isopropyl-1H-pyrazol-4-yl)-6-(1-(piperidin-4-yl)-1H-pyrazolo-4-yl)pyrazolo[1,5-a]pyrazine;

(R)-4-(1-(pentan-3-yl)-1H-pyrazol-4-yl)-6-(1-(pyrrolidin-2-ylmethyl)-1H-pyrazol-4-yl)pyrazolo[1,5-a]pyrazine;

(S)-4-(1-(pentan-3-yl)-1H-pyrazol-4-yl)-6-(1-(pyrrolidin-2-ylmethyl)-1H-pyrazol-4-yl)pyrazolo[1,5-a]pyrazine;

(R)-4-(1-(pentan-3-yl)-1H-pyrazol-4-yl)-6-(1-(piperidin-3-yl)-1H-pyrazol-4-yl)pyrazolo[1,5-a]pyrazine;

(S)-3-((4-(4-(1-(pentan-3-yl)-1H-pyrazol-4-yl)pyrazolo[1,5-a]pyrazin-6-yl)-1H-pyrazol-1-yl)methyl)morpholine;

1-(4-(4-(4-(1-(pentan-3-yl)-1H-pyrazol-4-yl)pyrazolo[1,5-a]pyrazin-6-yl)-1H-pyrazol-1-yl)piperidin-1-yl)ethanone;

6-(1-(1-(methylsulfonyl)piperidin-4-yl)-1H-pyrazol-4-yl)-4-(1-(pentan-3-yl)-1H-pyrazol-4-yl)pyrazolo[1,5-a]pyrazine;

N-methyl-4-(4-(4-(1-(pentan-3-yl)-1H-pyrazol-4-yl)pyrazolo[1,5-a]pyrazin-6-yl)-1H-pyrazol-1-yl)piperidine-1-carboxamide;

2-amino-1-(4-(4-(4-(1-(pentan-3-yl)-1H-pyrazol-4-yl)pyrazolo[1,5-a]pyrazine-6-yl)-1H-pyrazol-1-yl)piperidin-1-yl)ethanone;

6-(1-(1-(methylsulfonyl)azetidin-3-yl)-1H-pyrazol-4-yl)-4-(1-(pentan-3-yl)-1H-pyrazol-4-yl)pyrazolo[1,5-a]pyrazine;

1-(3-(4-(4-(1-(pentan-3-yl)-1H-pyrazol-4-yl)pyrazolo[1,5-a]pyrazin-6-yl)-1H-pyrazol-1-yl)azetidin-1-yl)ethanone;

N-methyl-3-(4-(4-(1-(pentan-3-yl)-1H-pyrazol-4-yl)pyrazolo[1,5-a]pyrazin-6-yl)-1H-pyrazol-1-yl)azetidine-1-carboxamide;

N,N-dimethyl-3-(4-(4-(1-(pentan-3-yl)-1H-pyrazol-4-yl)pyrazolo[1,5-a]pyrazin-6-yl)-1H-pyrazol-1-yl)azetidine-1-carboxamide;

Bis-N,N-dimethyl-P-(3-(4-(4-(1-(pentan-3-yl)-1H-pyrazol-4-yl)pyrazolo[1,5-a]pyrazin-6-yl)-1H-pyrazol-1-yl)azetidin-1-yl)phosphonic amide;

2-methyl-1-(3-(4-(4-(1-(pentan-3-yl)-1H-pyrazol-4-yl)pyrazolo[1,5-a]pyrazin-6-yl)-1H-pyrazol-1-yl)azetidin-1-yl)propan-1-one;

cyclopropyl(3-(4-(4-(1-(pentan-3-yl)-1H-pyrazol-4-yl)pyrazolo[1,5-a]pyrazin-6-yl)-1H-pyrazol-1-yl)azetidin-1-yl)methanone;

2-(4-(6-(1-methyl-1H-pyrazol-4-yl)pyrazolo[1,5-a]pyrazine-4-yl)-1H-pyrazol-1-yl)butanoic acid;

2-(4-(6-(1-methyl-1H-pyrazol-4-yl)pyrazolo[1,5-a]pyrazin-4-yl)-1H-pyrazol-1-yl)butan-1-ol;

2-(4-(6-(1-methyl-1H-pyrazol-4-yl)pyrazolo[1,5-a]pyrazin-4-yl)-1H-pyrazol-1-yl)propan-1-ol;

3-(4-(6-(1-methyl-1H-pyrazol-4-yl)pyrazolo[1,5-a]pyrazin-4-yl)-1H-pyrazol-1-yl)pentan-1-ol;

4-(1-(3-ethyl-1-((trifluoromethyl)sulfonyl)azetidin-3-yl)-1H-pyrazol-4-yl)-6-(1-methyl-1H-pyrazol-4-yl)pyrazolo[1,5-a]pyrazine;

6-(1-methyl-1H-pyrazol-4-yl)-4-(1-(1-methylcyclopentyl)-1H-pyrazol-4-yl)pyrazolo[1,5-a]pyrazine;

6-(1-methyl-1H-pyrazol-4-yl)-4-(1-(3-methylpentan-3-yl)-1H-pyrazol-4-yl)pyrazolo[1,5-a]pyrazine;

(2-(4-(6-(1-methyl-1H-pyrazol-4-yl)pyrazolo[1,5-a]pyrazin-4-yl)-1H-pyrazol-1-yl)cyclopentyl)methanol;

6-(1-methyl-1H-pyrazol-4-yl)-4-(1-(2-methylcycloheptyl)-1H-pyrazol-4-yl)pyrazolo[1,5-a]pyrazine;

2-(4-(6-(1-methyl-1H-pyrazol-4-yl)pyrazolo[1,5-a]pyrazin-4-yl)-1H-pyrazol-1-yl)cyclopentanol;

(R)-3-(4-(4-(1-(pentan-3-yl)-1H-pyrazol-4-yl)pyrazolo[1,5-a]pyrazin-6-yl)-1H-pyrazol-1-yl)propane-1,2-diol;

(S)-3-(4-(4-(1-(pentan-3-yl)-1H-pyrazol-4-yl)pyrazolo[1,5-a]pyrazin-6-yl)-1H-pyrazol-1-yl)propane-1,2-diol;

(S)-3-methyl-1-(4-(4-(1-(pentan-3-yl)-1H-pyrazol-4-yl)pyrazolo[1,5-a]pyrazin-6-yl)-1H-pyrazol-1-yl)butane-2,3-diol;

(R)-3-methyl-1-(4-(4-(1-(pentan-3-yl)-1H-pyrazol-4-yl)pyrazolo[1,5-a]pyrazin-6-yl)-1H-pyrazol-1-yl)butane-2,3-diol;

3-(4-(4-(1-(pentan-3-yl)-1H-pyrazol-4-yl)pyrazolo[1,5-a]pyrazin-6-yl)-1H-pyrazol-1-yl)propane-1,2-diol;

(2R,3R)-1-(4-(4-(1-(pentan-3-yl)-1H-pyrazol-4-yl)pyrazolo[1,5-a]pyrazin-6-yl)-1H-pyrazol-1-yl)butane-2,3-diol;

2-methyl-3-(4-(4-(1-(pentan-3-yl)-1H-pyrazol-4-yl)pyrazolo[1,5-a]pyrazin-6-yl)-1H-pyrazol-1-yl)propane-1,2-diol, 2-((4-(4-(1-(pentan-3-yl)-1H-pyrazol-4-yl)pyrazolo[1,5-a]pyrazin-6-yl)-1H-pyrazol-1-yl)methyl)propane-1,3-diol, (S)-4-(4-(4-(1-(pentan-3-yl)-1H-pyrazol-4-yl)pyrazolo[1,5-a]pyrazin-6-yl)-1H-pyrazol-1-yl)butane-1,2-diol;

4-(4-(4-(1-(pentan-3-yl)-1H-pyrazol-4-yl)pyrazolo[1,5-a]pyrazin-6-yl)-1H-pyrazol-1-yl)butane-1,3-diol;

(R)-4-(4-(4-(1-(pentan-3-yl)-1H-pyrazol-4-yl)pyrazolo[1,5-a]pyrazin-6-yl)-1H-pyrazol-1-yl)butane-1,2-diol;

(2S,3S)-1-(4-(4-(1-(pentan-3-yl)-1H-pyrazol-4-yl)pyrazolo[1,5-a]pyrazin-6-yl)-1H-pyrazol-1-yl)butane-2,3-diol;

(2R)-3-(4-(4-(1-(1-phenylpropyl)-1H-pyrazol-4-yl)pyrazolo[1,5-a]pyrazin-6-yl)-1H-pyrazol-1-yl)propane-1,2-diol;

(2R)-3-(4-(4-(1-(sec-butyl)-1H-pyrazol-4-yl)pyrazolo[1,5-a]pyrazin-6-yl)-1H-pyrazol-1-yl)propane-1,2-diol;

(R)-3-(4-(4-(1-((S)-sec-butyl)-1H-pyrazol-4-yl)pyrazolo[1,5-a]pyrazin-6-yl)-1H-pyrazol-1-yl)propane-1,2-diol;

(R)-3-(4-(4-(1-((R)-sec-butyl)-1H-pyrazol-4-yl)pyrazolo[1,5-a]pyrazin-6-yl)-1H-pyrazol-1-yl)propane-1,2-diol;

(S)-3-(4-(4-(1-((S)-sec-butyl)-1H-pyrazol-4-yl)pyrazolo[1,5-a]pyrazin-6-yl)-1H-pyrazol-1-yl)propane-1,2-diol;

(S)-3-(4-(4-(1-((R)-sec-butyl)-1H-pyrazol-4-yl)pyrazolo[1,5-a]pyrazin-6-yl)-1H-pyrazol-1-yl)propane-1,2-diol;

(R)-3-(4-(4-(1-((S)-pentan-2-yl)-1H-pyrazol-4-yl)pyrazolo[1,5-a]pyrazin-6-yl)-1H-pyrazol-1-yl)propane-1,2-diol;

(R)-3-(4-(4-(1-((R)-pentan-2-yl)-1H-pyrazol-4-yl)pyrazolo[1,5-a]pyrazin-6-yl)-1H-pyrazol-1-yl)propane-1,2-diol;

(S)-3-(4-(4-(1-((R)-pentan-2-yl)-1H-pyrazol-4-yl)pyrazolo[1,5-a]pyrazin-6-yl)-1H-pyrazol-1-yl)propane-1,2-diol;

(R)-3-(4-(4-(1-((S)-4-methylpentan-2-yl)-1H-pyrazol-4-yl)pyrazolo[1,5-a]pyrazin-6-yl)-1H-pyrazol-1-yl)propane-1,2-diol;

(S)-3-(4-(4-(1-((S)-4-methylpentan-2-yl)-1H-pyrazol-4-yl)pyrazolo[1,5-a]pyrazin-6-yl)-1H-pyrazol-1-yl)propane-1,2-diol;

(R)-3-(4-(4-(1-((R)-4-methylpentan-2-yl)-1H-pyrazol-4-yl)pyrazolo[1,5-a]pyrazin-6-yl)-1H-pyrazol-1-yl)propane-1,2-diol;

(S)-3-(4-(4-(1-((R)-4-methylpentan-2-yl)-1H-pyrazol-4-yl)pyrazolo[1,5-a]pyrazin-6-yl)-1H-pyrazol-1-yl)propane-1,2-diol;

(2R)-3-(4-(4-(1-(1-(3,3-difluorocyclobutyl)propyl)-1H-pyrazol-4-yl)pyrazolo[1,5-a]pyrazin-6-yl)-1H-pyrazol-1-yl)propane-1,2-diol;

(R)-3-(4-(4-(1-((S)-3-methylbutan-2-yl)-1H-pyrazol-4-yl)pyrazolo[1,5-a]pyrazin-6-yl)-1H-pyrazol-1-yl)propane-1,2-diol;

2-(4-(4-(1-(pentan-3-yl)-1H-pyrazol-4-yl)pyrazolo[1,5-a]pyrazin-6-yl)-1H-pyrazol-1-yl)propane-1,3-diol;

(S)-2-(4-(4-(1-(pentan-2-yl)-1H-pyrazol-4-yl)pyrazolo[1,5-a]pyrazin-6-yl)-1H-pyrazol-1-yl)propane-1,3-diol;

(R)-2-(4-(4-(1-(pentan-2-yl)-1H-pyrazol-4-yl)pyrazolo[1,5-a]pyrazin-6-yl)-1H-pyrazol-1-yl)propane-1,3-diol;

(S)-2-(4-(4-(1-(sec-butyl)-1H-pyrazol-4-yl)pyrazolo[1,5-a]pyrazin-6-yl)-1H-pyrazol-1-yl)propane-1,3-diol;

(R)-2-(4-(4-(1-(sec-butyl)-1H-pyrazol-4-yl)pyrazolo[1,5-a]pyrazin-6-yl)-1H-pyrazol-1-yl)propane-1,3-diol;

(S)-3-(4-(4-(1-((S)-pentan-2-yl)-1H-pyrazol-4-yl)pyrazolo[1,5-a]pyrazin-6-yl)-1H-pyrazol-1-yl)propane-1,2-diol;

(S)-2-(4-(4-(1-(4-methylpentan-2-yl)-1H-pyrazol-4-yl)pyrazolo[1,5-a]pyrazin-6-yl)-1H-pyrazol-1-yl)propane-1,3-diol;

(R)-2-(4-(4-(1-(4-methylpentan-2-yl)-1H-pyrazol-4-yl)pyrazolo[1,5-a]pyrazin-6-yl)-1H-pyrazol-1-yl)propane-1,3-diol;

(2S,3S)-3-(4-(4-(1-(pentan-3-yl)-1H-pyrazol-4-yl)pyrazolo[1,5-a]pyrazin-6-yl)-1H-pyrazol-1-yl)butane-1,2-diol;

(2S,3R)-3-(4-(4-(1-(pentan-3-yl)-1H-pyrazol-4-yl)pyrazolo[1,5-a]pyrazin-6-yl)-1H-pyrazol-1-yl)butane-1,2-diol;

(2R,3S)-3-(4-(4-(1-(pentan-3-yl)-1H-pyrazol-4-yl)pyrazolo[1,5-a]pyrazin-6-yl)-1H-pyrazol-1-yl)butane-1,2-diol, (2R,3R)-3-(4-(4-(1-(pentan-3-yl)-1H-pyrazol-4-yl)pyrazolo[1,5-a]pyrazin-6-yl)-1H-pyrazol-1-yl)butane-1,2-diol;

(R)-3-(4-(4-(1-((1R,2S)-2-methylcyclopentyl)-1H-pyrazol-4-yl)pyrazolo[1,5-a]pyrazin-6-yl)-1H-pyrazol-1-yl)propane-1,2-diol;

(R)-3-(4-(4-(1-((1S,2R)-2-methylcyclopentyl)-1H-pyrazol-4-yl)pyrazolo[1,5-a]pyrazin-6-yl)-1H-pyrazol-1-yl)propane-1,2-diol;

(R)-3-(4-(4-(1-(S)-2,2-dimethylcyclopentyl)-1H-pyrazol-4-yl)pyrazolo[1,5-a]pyrazin-6-yl)-1H-pyrazol-1-yl)propane-1,2-diol;

(R)-3-(4-(4-(1-((R)-2,2-dimethylcyclopentyl)-1H-pyrazol-4-yl)pyrazolo[1,5-a]pyrazin-6-yl)-1H-pyrazol-1-yl)propane-1,2-diol;

N-isopropyl-2-(4-(4-(1-(pentan-3-yl)-1H-pyrazol-4-yl)pyrazolo[1,5-a]pyrazin-6-yl)-1H-pyrazol-1-yl)acetamide;

1-amino-3-(4-(4-(1-(pentan-3-yl)-1H-pyrazol-4-yl)pyrazolo[1,5-a]pyrazin-6-yl)-1H-pyrazol-1-yl)propan-2-ol;

(R)-1-(dimethylamino)-3-(4-(4-(1-(pentan-3-yl)-1H-pyrazol-4-yl)pyrazolo[1,5-a]pyrazin-6-yl)-1H-pyrazol-1-yl)propan-2-ol;

(R)-1-(methylamino)-3-(4-(4-(1-(pentan-3-yl)-1H-pyrazol-4-yl)pyrazolo[1,5-a]pyrazin-6-yl)-1H-pyrazol-1-yl)propan-2-ol;

(S)-1-(dimethylamino)-3-(4-(4-(1-(pentan-3-yl)-1H-pyrazol-4-yl)pyrazolo[1,5-a]pyrazin-6-yl)-1H-pyrazol-1-yl)propan-2-ol;

(S)-1-(methylamino)-3-(4-(4-(1-(pentan-3-yl)-1H-pyrazol-4-yl)pyrazolo[1,5-a]pyrazin-6-yl)-1H-pyrazol-1-yl)propan-2-ol;

(R)-1-(3-methoxyazetidin-1-yl)-3-(4-(4-(1-(pentan-3-yl)-1H-pyrazol-4-yl)pyrazolo[1,5-a]pyrazin-6-yl)-1H-pyrazol-1-yl)propan-2-ol;

(S)-1-(3-methoxyazetidin-1-yl)-3-(4-(4-(1-(pentan-3-yl)-1H-pyrazol-4-yl)pyrazolo[1,5-a]pyrazin-6-yl)-1H-pyrazol-1-yl)propan-2-ol;

(R)-1-(4-(4-(1-(pentan-3-yl)-1H-pyrazol-4-yl)pyrazolo[1,5-a]pyrazin-6-yl)-1H-pyrazol-1-yl)-3-(pyrrolidin-1-yl)propan-2-ol;

(S)-1-(4-(4-(1-(pentan-3-yl)-1H-pyrazol-4-yl)pyrazolo[1,5-a]pyrazin-6-yl)-1H-pyrazol-1-yl)-3-(pyrrolidin-1-yl)propan-2-ol;
(R)-1-methoxy-3-(4-(4-(1-(pentan-3-yl)-1H-pyrazol-4-yl)pyrazolo[1,5-a]pyrazin-6-yl)-1H-pyrazol-1-yl)propan-2-ol;
(S)-1-methoxy-3-(4-(4-(1-(pentan-3-yl)-1H-pyrazol-4-yl)pyrazolo[1,5-a]pyrazin-6-yl)-1H-pyrazol-1-yl)propan-2-ol;
(R)-1-(4-(4-(1-(pentan-3-yl)-1H-pyrazol-4-yl)pyrazolo[1,5-a]pyrazin-6-yl)-1H-pyrazol-1-yl)propan-2-ol;
(S)-1-(4-(4-(1-(pentan-3-yl)-1H-pyrazol-4-yl)pyrazolo[1,5-a]pyrazin-6-yl)-1H-pyrazol-1-yl)propan-2-ol;
4,4,4-trifluoro-1-(4-(4-(1-(pentan-3-yl)-1H-pyrazol-4-yl)pyrazolo[1,5-a]pyrazin-6-yl)-1H-pyrazol-1-yl)butan-2-ol;
3,3-dimethyl-1-(4-(4-(1-(pentan-3-yl)-1H-pyrazol-4-yl)pyrazolo[1,5-a]pyrazin-6-yl)-1H-pyrazol-1-yl)butan-2-ol;
3-methyl-1-(4-(4-(1-(pentan-3-yl)-1H-pyrazol-4-yl)pyrazolo[1,5-a]pyrazin-6-yl)-1H-pyrazol-1-yl)butan-2-ol;
(S)-1-(4-(4-(1-(pentan-3-yl)-1H-pyrazol-4-yl)pyrazolo[1,5-a]pyrazin-6-yl)-1H-pyrazol-1-yl)butan-2-ol;
(R)-1-(4-(4-(1-(pentan-3-yl)-1H-pyrazol-4-yl)pyrazolo[1,5-a]pyrazin-6-yl)-1H-pyrazol-1-yl)butan-2-ol;
4-((4-(4-(1-(pentan-3-yl)-1H-pyrazol-4-yl)pyrazolo[1,5-a]pyrazin-6-yl)-1H-pyrazol-1-yl)methyl)tetrahydro-2H-pyran-4-ol;
2-methyl-1-(4-(4-(1-(pentan-3-yl)-1H-pyrazol-4-yl)pyrazolo[1,5-a]pyrazin-6-yl)-1H-pyrazol-1-yl)propan-2-ol;
trans-4-(4-(4-(1-(pentan-3-yl)-1H-pyrazol-4-yl)pyrazolo[1,5-a]pyrazin-6-yl)-1H-pyrazol-1-yl)cyclohexanol;
cis-3-(4-(4-(1-(pentan-3-yl)-1H-pyrazol-4-yl)pyrazolo[1,5-a]pyrazin-6-yl)-1H-pyrazol-1-yl)cyclobutanol;
(1s,3s)-3-((4-(4-(1-(pentan-3-yl)-1H-pyrazol-4-yl)pyrazolo[1,5-a]pyrazin-6-yl)-1H-pyrazol-1-yl)methyl)cyclobutanol;
cis-4-(4-(4-(1-(pentan-3-yl)-1H-pyrazol-4-yl)pyrazolo[1,5-a]pyrazin-6-yl)-1H-pyrazol-1-yl)cyclohexanol;
((1s,3s)-3-((4-(4-(1-(pentan-3-yl)-1H-pyrazol-4-yl)pyrazolo[1,5-a]pyrazin-6-yl)-1H-pyrazol-1-yl)methyl)cyclobutyl)methanol;
((1r,3r)-3-((4-(4-(1-(pentan-3-yl)-1H-pyrazol-4-yl)pyrazolo[1,5-a]pyrazin-6-yl)-1H-pyrazol-1-yl)methyl)cyclobutyl)methanol;
2-methyl-2-(4-(4-(1-(pentan-3-yl)-1H-pyrazol-4-yl)pyrazolo[1,5-a]pyrazin-6-yl)-1H-pyrazol-1-yl)propan-1-ol;
(S)-2-(4-(4-(1-(pentan-3-yl)-1H-pyrazol-4-yl)pyrazolo[1,5-a]pyrazin-6-yl)-1H-pyrazol-1-yl)propan-1-ol;
(S)-2-(4-(4-(1-(pentan-3-yl)-1H-pyrazol-4-yl)pyrazolo[1,5-a]pyrazin-6-yl)-1H-pyrazol-1-yl)propan-1-ol;
(S)-2-((4-(4-(1-(pentan-3-yl)-1H-pyrazol-4-yl)pyrazolo[1,5-a]pyrazin-6-yl)-1H-pyrazol-1-yl)methyl)morpholine;
(R)-2-((4-(4-(1-(pentan-3-yl)-1H-pyrazol-4-yl)pyrazolo[1,5-a]pyrazin-6-yl)-1H-pyrazol-1-yl)methyl)morpholine;
(S)-2-(dimethylamino)-3-(4-(4-(1-(pentan-3-yl)-1H-pyrazol-4-yl)pyrazolo[1,5-a]pyrazin-6-yl)-1H-pyrazol-1-yl)propan-1-ol,
(R)-2-amino-3-(4-(4-(1-(pentan-3-yl)-1H-pyrazol-4-yl)pyrazolo[1,5-a]pyrazin-6-yl)-1H-pyrazol-1-yl)propan-1-ol;
(R)-2-(dimethyl amino)-3-(4-(4-(1-(pentan-3-yl)-1H-pyrazol-4-yl)pyrazolo[1,5-a]pyrazin-6-yl)-1H-pyrazol-1-yl)propan-1-ol;
(1R,2S,4s)-4-(4-(4-(1-(pentan-3-yl)-1H-pyrazol-4-yl)pyrazolo[1,5-a]pyrazin-6-yl)-1H-pyrazol-1-yl)cyclopentane-1,2-diol;
(1R,2S,4r)-4-(4-(4-(1-(pentan-3-yl)-1H-pyrazol-4-yl)pyrazolo[1,5-a]pyrazin-6-yl)-1H-pyrazol-1-yl)cyclopentane-1,2-diol;
N-(2-(4-(4-(1-(pentan-3-yl)-1H-pyrazol-4-yl)pyrazolo[1,5-a]pyrazin-6-yl)-1H-pyrazol-1-yl)ethyl)cyclopropanamine;
4-(1-(pentan-3-yl)-1H-pyrazol-4-yl)-6-(1-(2-(pyrrolidin-1-yl)ethyl)-1H-pyrazol-4-yl)pyrazolo[1,5-a]pyrazine;
(R)-6-(1-(2-(3-methoxypyrrolidin-1-yl)ethyl)-1H-pyrazol-4-yl)-4-(1-(pentan-3-yl)-1H-pyrazol-4-yl)pyrazolo[1,5-a]pyrazine;
(S)-6-(1-(2-(3-methoxypyrrolidin-1-yl)ethyl)-1H-pyrazol-4-yl)-4-(1-(pentan-3-yl)-1H-pyrazol-4-yl)pyrazolo[1,5-a]pyrazine;
6-(1-(2-(3-fluoroazetidin-1-yl)ethyl)-1H-pyrazol-4-yl)-4-(1-(pentan-3-yl)-1H-pyrazol-4-yl)pyrazolo[1,5-a]pyrazine;
1-(2-(4-(4-(1-(pentan-3-yl)-1H-pyrazol-4-yl)pyrazolo[1,5-a]pyrazin-6-yl)-1H-pyrazol-1-yl)ethyl)piperidin-4-ol;
(R)-1-(2-(4-(4-(1-(pentan-3-yl)-1H-pyrazol-4-yl)pyrazolo[1,5-a]pyrazin-6-yl)-1H-pyrazol-1-yl)ethyl)pyrrolidin-3-ol;
(S)-1-(2-(4-(4-(1-(pentan-3-yl)-1H-pyrazol-4-yl)pyrazolo[1,5-a]pyrazin-6-yl)-1H-pyrazol-1-yl)ethyl)pyrrolidin-3-ol;
(S)-1-methyl-3-((2-(4-(4-(1-(pentan-3-yl)-1H-pyrazol-4-yl)pyrazolo[1,5-a]pyrazin-6-yl)-1H-pyrazol-1-yl)ethyl)amino)pyrrolidin-2-one;
(R)-1-methyl-3-((2-(4-(4-(1-(pentan-3-yl)-1H-pyrazol-4-yl)pyrazolo[1,5-a]pyrazin-6-yl)-1H-pyrazol-1-yl)ethyl)amino)pyrrolidin-2-one;
4-(2-(4-(4-(1-(pentan-3-yl)-1H-pyrazol-4-yl)pyrazolo[1,5-a]pyrazin-6-yl)-1H-pyrazol-1-yl)ethyl)piperazin-2-one;
(3-((2-(4-(4-(1-(pentan-3-yl)-1H-pyrazol-4-yl)pyrazolo[1,5-a]pyrazin-6-yl)-1H-pyrazol-1-yl)ethyl)amino)cyclobutyl)methanol;
(1-(2-(4-(4-(1-(pentan-3-yl)-1H-pyrazol-4-yl)pyrazolo[1,5-a]pyrazin-6-yl)-1H-pyrazol-1-yl)ethyl)piperidin-4-yl)methanol;
1-(2-(4-(4-(1-(pentan-3-yl)-1H-pyrazol-4-yl)pyrazolo[1,5-a]pyrazin-6-yl)-1H-pyrazol-1-yl)ethyl)piperazin-2-one;
(R)-2-methoxy-3-(4-(4-(1-(pentan-3-yl)-1H-pyrazol-4-yl)pyrazolo[1,5-a]pyrazin-6-yl)-1H-pyrazol-1-yl)propan-1-amine;
(S)-2-methoxy-3-(4-(4-(1-(pentan-3-yl)-1H-pyrazol-4-yl)pyrazolo[1,5-a]pyrazin-6-yl)-1H-pyrazol-1-yl)propan-1-amine;
2-(4-(4-(1-((1R,2R)-2-methylcyclohexyl)-1H-pyrazol-4-yl)pyrazolo[1,5-a]pyrazin-6-yl)-1H-pyrazol-1-yl)propane-1,3-diol;
(R)-3-(4-(4-(1-((1R,2R)-2-methylcyclohexyl)-1H-pyrazol-4-yl)pyrazolo[1,5-a]pyrazin-6-yl)-1H-pyrazol-1-yl)propane-1,2-diol;
(S)-3-(4-(4-(1-((1R,2R)-2-methylcyclohexyl)-1H-pyrazol-4-yl)pyrazolo[1,5-a]pyrazin-6-yl)-1H-pyrazol-1-yl)propane-1,2-diol;
(1R,2R)-2-(4-(4-(1-(pentan-3-yl)-1H-pyrazol-4-yl)pyrazolo[1,5-a]pyrazin-6-yl)-1H-pyrazol-1-yl)cyclopentanol;

(1S,2S)-2-(4-(4-(1-(pentan-3-yl)-1H-pyrazol-4-yl)pyrazolo[1,5-a]pyrazin-6-yl)-1H-pyrazol-1-yl)cyclopentanol;
(2S,3S)-3-(4-(4-(1-(pentan-3-yl)-1H-pyrazol-4-yl)pyrazolo[1,5-a]pyrazin-6-yl)-1H-pyrazol-1-yl)butan-2-ol;
(2R,3R)-3-(4-(4-(1-(pentan-3-yl)-1H-pyrazol-4-yl)pyrazolo[1,5-a]pyrazin-6-yl)-1H-pyrazol-1-yl)butan-2-ol;
(2R,3S)-3-(4-(4-(1-(pentan-3-yl)-1H-pyrazol-4-yl)pyrazolo[1,5-a]pyrazin-6-yl)-1H-pyrazol-1-yl)butan-2-ol;
(2S,3R)-3-(4-(4-(1-(pentan-3-yl)-1H-pyrazol-4-yl)pyrazolo[1,5-a]pyrazin-6-yl)-1H-pyrazol-1-yl)butan-2-ol;
(3S,4R)-4-(4-(4-(1-(pentan-3-yl)-1H-pyrazol-4-yl)pyrazolo[1,5-a]pyrazin-6-yl)-1H-pyrazol-1-yl)tetrahydrofuran-3-ol;
(3R,4S)-4-(4-(4-(1-(pentan-3-yl)-1H-pyrazol-4-yl)pyrazolo[1,5-a]pyrazin-6-yl)-1H-pyrazol-1-yl)tetrahydrofuran-3-ol;
trans-3-(4-(4-(1-(pentan-3-yl)-1H-pyrazol-4-yl)pyrazolo[1,5-a]pyrazin-6-yl)-1H-pyrazol-1-yl)cyclobutanol;
(1s,3s)-1-methyl-3-(4-(4-(1-(pentan-3-yl)-1H-pyrazol-4-yl)pyrazolo[1,5-a]pyrazin-6-yl)-1H-pyrazol-1-yl)cyclobutanol;
(1s,3s)-1-(hydroxymethyl)-3-(4-(4-(1-(pentan-3-yl)-1H-pyrazol-4-yl)pyrazolo[1,5-a]pyrazin-6-yl)-1H-pyrazol-1-yl)cyclobutanol;
(1r,3r)-1-(hydroxymethyl)-3-(4-(4-(1-(pentan-3-yl)-1H-pyrazol-4-yl)pyrazolo[1,5-a]pyrazin-6-yl)-1H-pyrazol-1-yl)cyclobutanol;
(trans-3-(4-(4-(1-(pentan-3-yl)-1H-pyrazol-4-yl)pyrazolo[1,5-a]pyrazin-6-yl)-1H-pyrazol-1-yl)cyclobutyl)methanol;
(cis-3-(4-(4-(1-(pentan-3-yl)-1H-pyrazol-4-yl)pyrazolo[1,5-a]pyrazin-6-yl)-1H-pyrazol-1-yl)cyclobutyl)methanol;
(1r,3r)-3-(4-(4-(1-(pentan-3-yl)-1H-pyrazol-4-yl)pyrazolo[1,5-a]pyrazin-6-yl)-1H-pyrazol-1-yl)cyclobutanecarboxamide;
(1s,3s)-3-(4-(4-(1-(pentan-3-yl)-1H-pyrazol-4-yl)pyrazolo[1,5-a]pyrazin-6-yl)-1-pyrazol-1-yl)cyclobutanecarboxamide;
(1r,3r)-N,N-dimethyl-3-(4-(4-(1-(pentan-3-yl)-1H-pyrazol-4-yl)pyrazolo[1,5-a]pyrazin-6-yl)-1H-pyrazol-1-yl)cyclobutanecarboxamide;
(1s,3s)-N,N-dimethyl-3-(4-(4-(1-(pentan-3-yl)-1H-pyrazol-4-yl)pyrazolo[1,5-a]pyrazin-6-yl)-1H-pyrazol-1-yl)cyclobutanecarboxamide;
(1r,3r)-N-(2-hydroxyethyl)-3-(4-(4-(1-(pentan-3-yl)-1H-pyrazol-4-yl)pyrazolo[1,5-a]pyrazin-6-yl)-1H-pyrazol-1-yl)cyclobutanecarboxamide;
(1s,3s)-N-(2-hydroxyethyl)-3-(4-(4-(1-(pentan-3-yl)-1H-pyrazol-4-yl)pyrazolo[1,5-a]pyrazin-6-yl)-1H-pyrazol-1-yl)cyclobutanecarboxamide;
(S)-2-hydroxy-1-(3-(4-(4-(1-(pentan-3-yl)-1H-pyrazol-4-yl)pyrazolo[1,5-a]pyrazin-6-yl)-1H-pyrazol-1-yl)azetidin-1-yl)propan-1-one;
2-hydroxy-1-(3-(4-(4-(1-(pentan-3-yl)-1H-pyrazol-4-yl)pyrazolo[1,5-a]pyrazin-6-yl)-1H-pyrazol-1-yl)azetidin-1-yl)ethanone;
(R)-2-hydroxy-1-(3-(4-(4-(1-(pentan-3-yl)-1H-pyrazol-4-yl)pyrazolo[1,5-a]pyrazin-6-yl)-1H-pyrazol-1-yl)azetidin-1-yl)propan-1-one;
2-hydroxy-2-methyl-1-(3-(4-(4-(1-(pentan-3-yl)-1H-pyrazol-4-yl)pyrazolo[1,5-a]pyrazin-6-yl)-1H-pyrazol-1-yl)azetidin-1-yl)propan-1-one;
(1-hydroxycyclopropyl(3-(4-(4-(1-(pentan-3-yl)-1H-pyrazol-4-yl)pyrazolo[1,5-a]pyrazin-6-yl)-1H-pyrazol-1-yl)azetidin-1-yl)methanone;
(cis-3-hydroxycyclobutyl)(3-(4-(4-(1-(pentan-3-yl)-1H-pyrazol-4-yl)pyrazolo[1,5-a]pyrazin-6-yl)-1H-pyrazol-1-yl)azetidin-1-yl)methanone;
(trans-3-hydroxycyclobutyl)(3-(4-(4-(1-(pentan-3-yl)-1H-pyrazol-4-yl)pyrazolo[1,5-a]pyrazin-6-yl)-1H-pyrazol-1-yl)azetidin-1-yl)methanone;
2-(3-hydroxyazetidin-1-yl)-1-(3-(4-(4-(1-(pentan-3-yl)-1H-pyrazol-4-yl)pyrazolo[1,5-a]pyrazin-6-yl)-1H-pyrazol-1-yl)azetidin-1-yl)ethanone;
1-(3-(4-(4-(1-(pentan-3-yl)-1H-pyrazol-4-yl)pyrazolo[1,5-a]pyrazin-6-yl)-1H-pyrazol-1-yl)azetidin-1-yl)-2-(pyrrolidin-1-yl)ethanone;
N,N-dimethyl-2-oxo-2-(3-(4-(4-(1-(pentan-3-yl)-1H-pyrazol-4-yl)pyrazolo[1,5-a]pyrazin-6-yl)-1H-pyrazol-1-yl)azetidin-1-yl)acetamide;
(S)-3-amino-2-methyl-4-(4-(4-(1-(pentan-3-yl)-1H-pyrazol-4-yl)pyrazolo[1,5-a]pyrazin-6-yl)-1H-pyrazol-1-yl)butan-2-ol;
4-((4-(4-(1-(pentan-3-yl)-1H-pyrazol-4-yl)pyrazolo[1,5-a]pyrazin-6-yl)-1H-pyrazol-1-yl)methyl)piperidin-4-ol;
1-(4-hydroxy-4-((4-(4-(1-(pentan-3-yl)-1H-pyrazol-4-yl)pyrazolo[1,5-a]pyrazin-6-yl)-1H-pyrazol-1-yl)methyl)piperidin-1-yl)ethanone;
2-amino-1-(3-(4-(4-(1-(pentan-3-yl)-1H-pyrazol-4-yl)pyrazolo[1,5-a]pyrazin-6-yl)-1H-pyrazol-1-yl)azetidin-1-yl)ethanone;
2-(methyl amino)-1-(3-(4-(4-(1-(pentan-3-yl)-1H-pyrazol-4-yl)pyrazolo[1,5-a]pyrazin-6-yl)-1H-pyrazol-1-yl)azetidin-1-yl)ethanone;
(3R,4R)-4-(4-(4-(1-(pentan-3-yl)-1H-pyrazol-4-yl)pyrazolo[1,5-a]pyrazin-6-yl)-1H-pyrazol-1-yl)piperidin-3-ol;
(1S,2R)-2-(4-(4-(1-(pentan-3-yl)-1H-pyrazol-4-yl)pyrazolo[1,5-a]pyrazin-6-yl)-1H-pyrazol-1-yl)cyclopentanol;
(1R,2S)-2-(4-(4-(1-(pentan-3-yl)-1H-pyrazol-4-yl)pyrazolo[1,5-a]pyrazin-6-yl)-1H-pyrazol-1-yl)cyclopentanol;
2,2-dimethyl-3-(4-(4-(1-(pentan-3-yl)-1H-pyrazol-4-yl)pyrazolo[1,5-a]pyrazin-6-yl)-1H-pyrazol-1-yl)propan-1-ol;
(1-((4-(4-(1-(pentan-3-yl)-1H-pyrazol-4-yl)pyrazolo[1,5-a]pyrazin-6-yl)-1H-pyrazol-1-yl)methyl)cyclopropyl)methanol;
(2R)-3-(4-(4-(1-(1,1,1-trifluorobutan-2-yl)-1H-pyrazol-4-yl)pyrazolo[1,5-a]pyrazin-6-yl)-1H-pyrazol-1-yl)propane-11,2-diol;
(R)-3-(4-(4-(1-((R)-4,4,4-trifluorobutan-2-yl)-1H-pyrazol-4-yl)pyrazolo[1,5-a]pyrazin-6-yl)-1H-pyrazol-1-yl)propane-1,2-diol;
(R)-3-(4-(4-(1-((S)-4,4,4-trifluorobutan-2-yl)-1H-pyrazol-4-yl)pyrazolo[1,5-a]pyrazin-6-yl)-1H-pyrazol-1-yl)propane-1,2-diol;
(R)-3-(4-(4-(1-((R)-1-cyclobutylpropyl)-1H-pyrazol-4-yl)pyrazolo[1,5-a]pyrazin-6-yl)-1H-pyrazol-1-yl)propane-1,2-diol;
(R)-3-(4-(4-(1-((S)-1-cyclobutylpropyl)-1H-pyrazol-4-yl)pyrazolo[1,5-a]pyrazin-6-yl)-1H-pyrazol-1-yl)propane-1,2-diol;
(R)-3-(4-(4-(1-((S)-2,2-difluoropentan-3-yl)-1H-pyrazol-4-yl)pyrazolo[1,5-a]pyrazin-6-yl)-1H-pyrazol-1-yl)propane-1,2-diol;
(R)-3-(4-(4-(1-((R)-2,2-difluoropentan-3-yl)-1H-pyrazol-4-yl)pyrazolo[1,5-a]pyrazin-6-yl)-1H-pyrazol-1-yl)propane-1,2-diol (S)-4-(4-(4-(1-(pentan-3-yl)-1H-pyrazol-4-yl)pyrazolo[1,5-a]pyrazin-6-yl)-1H-pyrazol-1-yl)butane-1,3-diol,
(R)-4-(4-(4-(1-(pentan-3-yl)-1H-pyrazol-4-yl)pyrazolo[1,5-a]pyrazin-6-yl)-1H-pyrazol-1-yl)butane-1,3-diol;
(R)-2-methyl-3-(4-(4-(1-(pentan-3-yl)-1H-pyrazol-4-yl)pyrazolo[1,5-a]pyrazin-6-yl)-1H-pyrazol-1-yl)propane-1,2-diol;
(S)-2-methyl-3-(4-(4-(1-(pentan-3-yl)-1H-pyrazol-4-yl)pyrazolo[1,5-a]pyrazin-6-yl)-1H-pyrazol-1-yl)propane-1,2-diol;
(R)-3-(4-(4-(1-((R)-1-((S)-2,2-difluorocyclopropyl)propyl)-1H-pyrazol-4-yl)pyrazolo[1,5-a]pyrazin-6-yl)-1H-pyrazol-1-yl)propane-1,2-diol;
(R)-3-(4-(4-(1-((S)-1-cyclopropylbutan-2-yl)-1H-pyrazol-4-yl)pyrazolo[1,5-a]pyrazin-6-yl)-1H-pyrazol-1-yl)propane-1,2-diol;
(R)-3-(4-(4-(1-((R)-1-cyclopropylbutan-2-yl)-1H-pyrazol-4-yl)pyrazolo[1,5-a]pyrazin-6-yl)-1H-pyrazol-1-yl)propane-1,2-diol;
(R)-3-(4-(4-(1-((1S,2R)-2-ethylcyclopentyl)-1H-pyrazol-4-yl)pyrazolo[1,5-a]pyrazin-6-yl)-1H-pyrazol-1-yl)propane-1,2-diol;
(R)-3-(4-(4-(1-((1R,2S)-2-ethylcyclopentyl)-1H-pyrazol-4-yl)pyrazolo[1,5-a]pyrazin-6-yl)-1H-pyrazol-1-yl)propane-1,2-diol;
(R)-3-(4-(4-(1-((R)-1,1,1-trifluoropentan-3-yl)-1H-pyrazol-4-yl)pyrazolo[1,5-a]pyrazin-6-yl)-1H-pyrazol-1-yl)propane-1,2-diol;
(R)-3-(4-(4-(1-((S)-1,1,1-trifluoropentan-3-yl)-1H-pyrazol-4-yl)pyrazolo[1,5-a]pyrazin-6-yl)-1H-pyrazol-1-yl)propane-1,2-diol;
(R)-2-(4-(4-(1-(1,1,1-trifluoropentan-3-yl)-1H-pyrazol-4-yl)pyrazolo[1,5-a]pyrazin-6-yl)-1H-pyrazol-1-yl)propane-1,3-diol;
(S)-24(4-(4-(1-(1,1,1-trifluoropentan-3-yl)-1H-pyrazol-4-yl)pyrazolo[1,5-a]pyrazin-6-yl)-1H-pyrazol-1-yl)propane-1,3-diol;
(R)-3-(4-(4-(1-((R)-1-cyclopropylpropyl)-1H-pyrazol-4-yl)pyrazolo[1,5-a]pyrazin-6-yl)-1H-pyrazol-1-yl)propane-1,2-diol;
(R)-3-(4-(4-(1-((S)-1-cyclopropylpropyl)-1H-pyrazol-4-yl)pyrazolo[1,5-a]pyrazin-6-yl)-1H-pyrazol-1-yl)propane-1,2-diol;
(R)-2-(4-(4-(1-(1-cyclopropylpropyl)-1H-pyrazol-4-yl)pyrazolo[1,5-a]pyrazin-6-yl)-1H-pyrazol-1-yl)propane-1,3-diol;
(R)-3-(4-(4-(1-(dicyclopropylmethyl)-1H-pyrazol-4-yl)pyrazolo[1,5-a]pyrazin-6-yl)-1H-pyrazol-1-yl)propane-1,2-diol;
(R)-3-(4-(4-(1-(cis-2-methylcyclobutyl)-1H-pyrazol-4-yl)pyrazolo[1,5-a]pyrazin-6-yl)-1H-pyrazol-1-yl)propane-1,2-diol; and
(S)-1-(4(4-((1-((R)-1-cyclopropylpropyl)-1H-pyrazol-4-yl)pyrazolo[1,5-a]pyrazin-6-yl)-1H-pyrazol-1-yl)propan-2-ol;

and pharmaceutically acceptable salts thereof.

12. The method according to claim 11, wherein the pharmaceutically acceptable salt is a trifluoroacetic acid salt or a hydrochloric acid salt.

13. The method according to claim 11, wherein the compuund of Formula I or the pharmaceuitcally acceptable salt thereof is selected from:

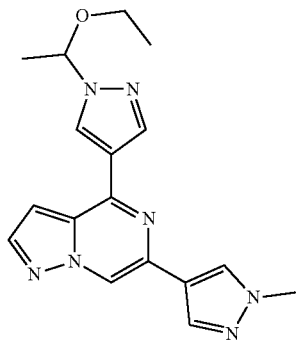

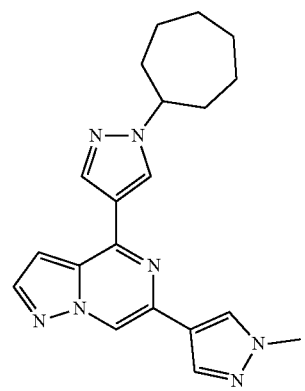

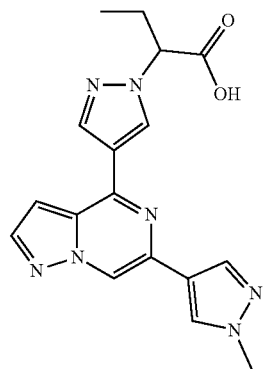

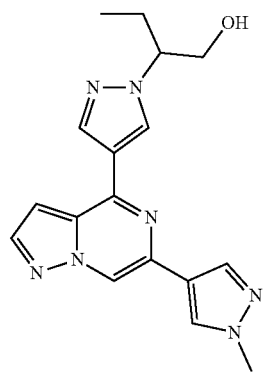

291
-continued
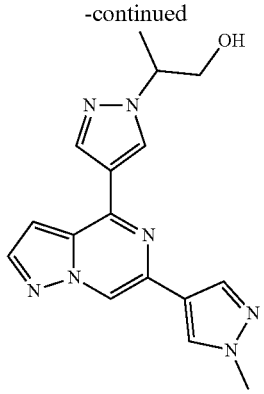
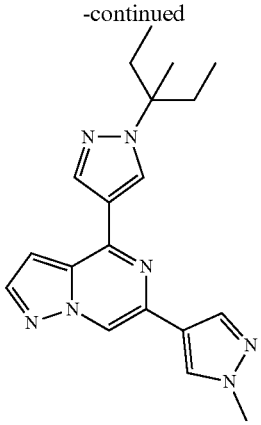
292
-continued
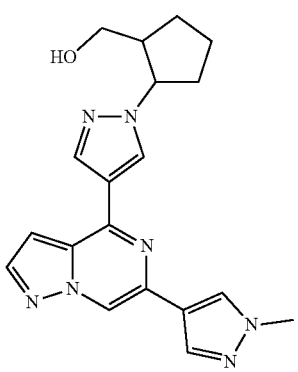
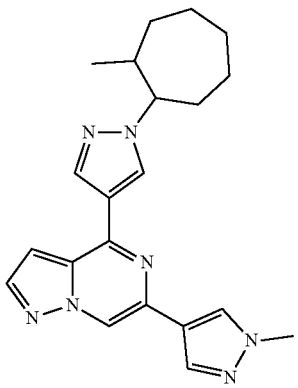
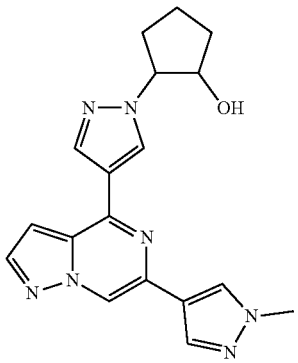
and pharmaceutically acceptable salts thereof.
14. The method according to claim 11, wherein the compound of Formula I or the pharmaceutically acceptable salt thereof is selected from:

293
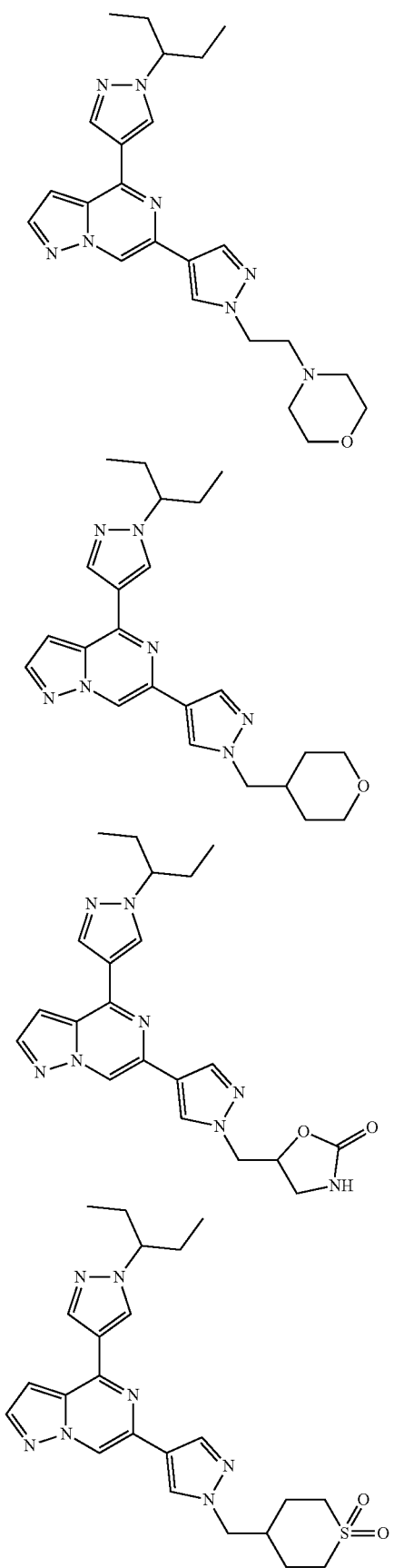
294
-continued
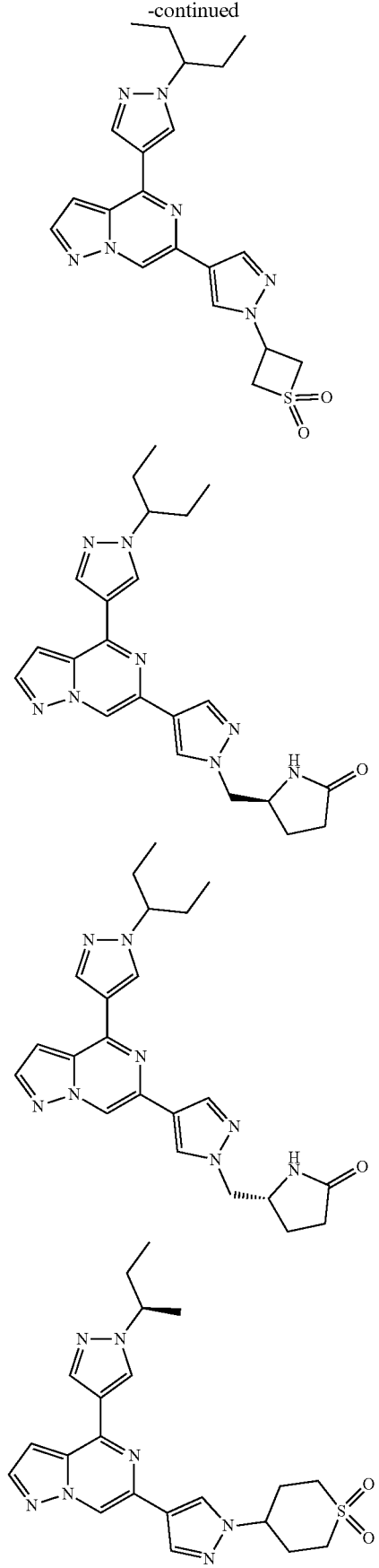

295
-continued
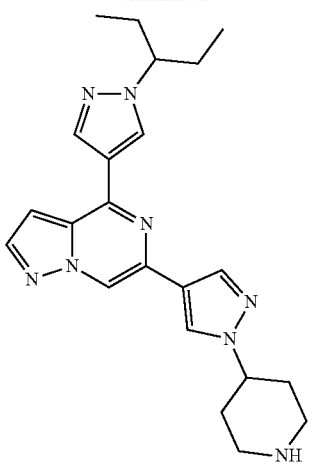
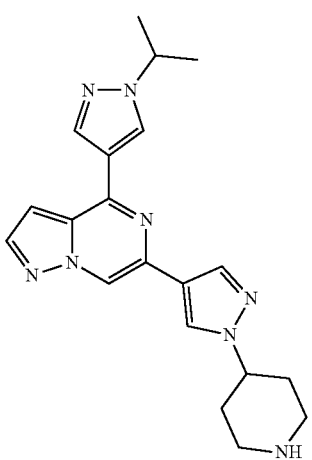
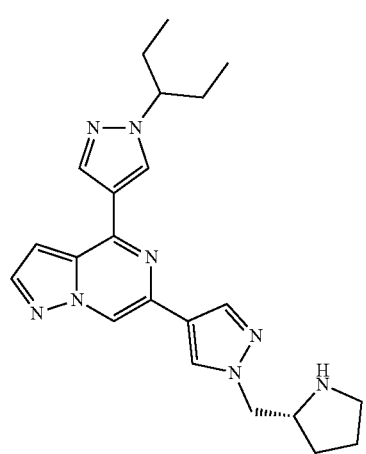
296
-continued
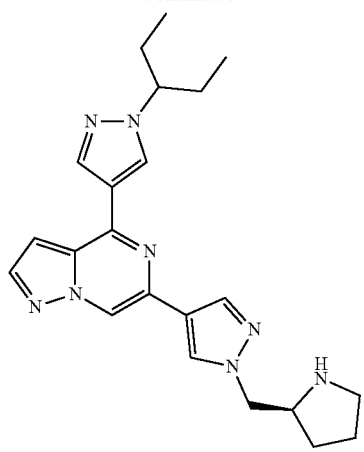
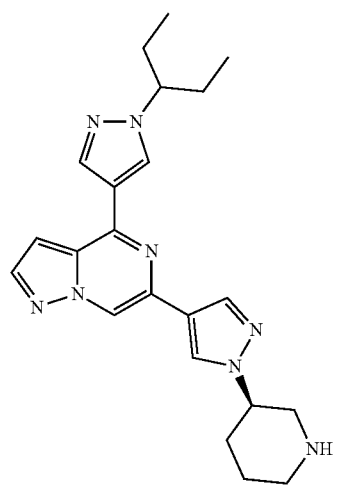
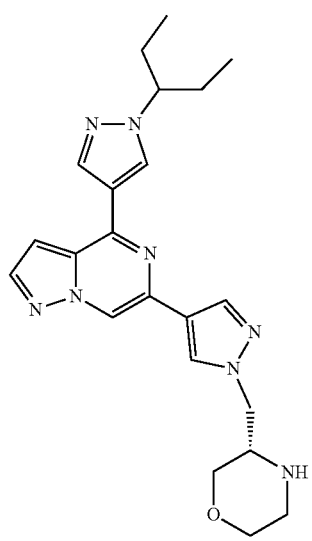

297
-continued
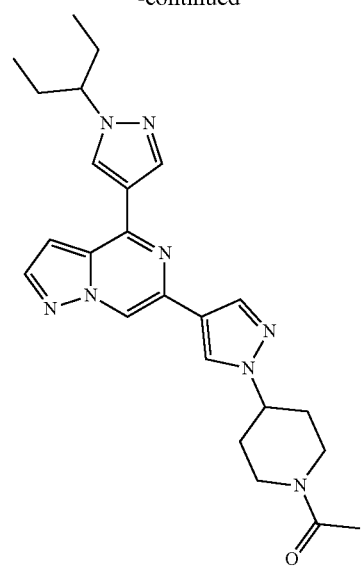
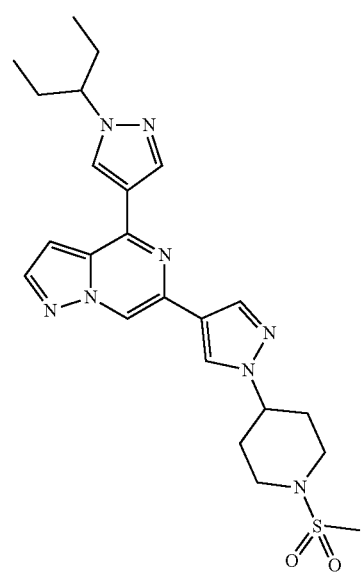
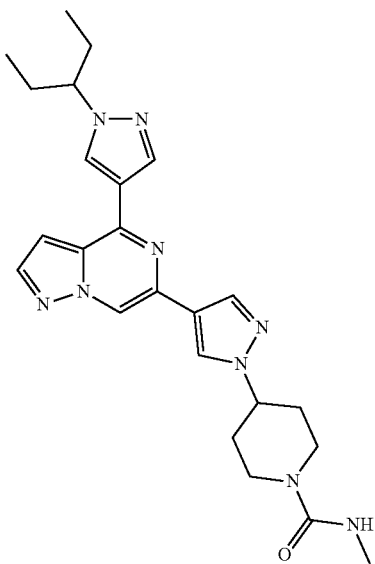
298
-continued
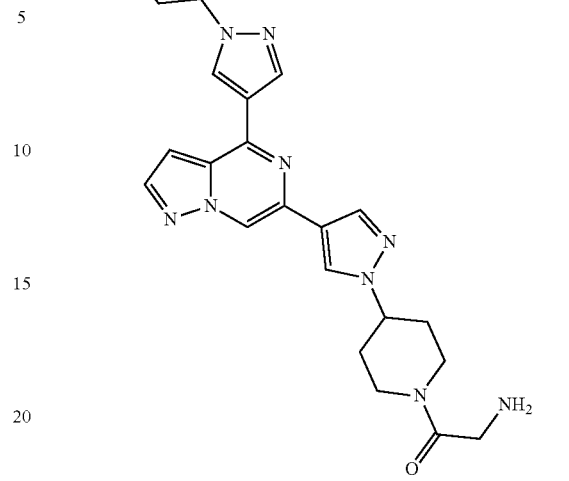
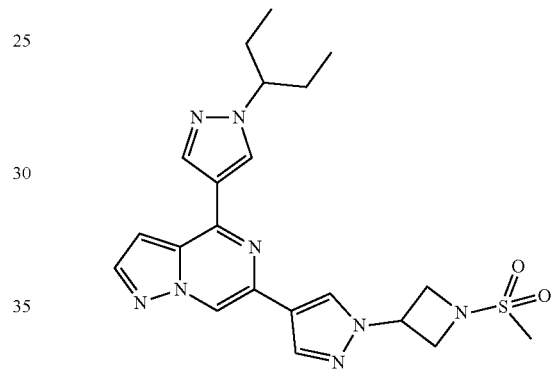
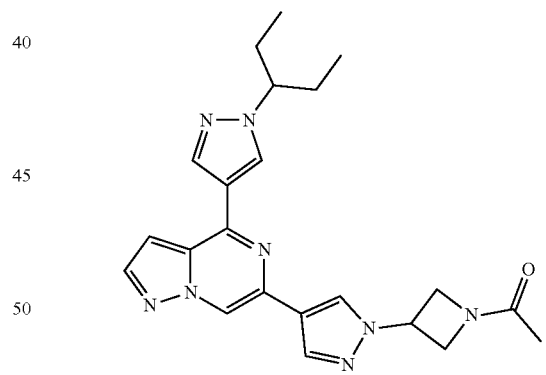
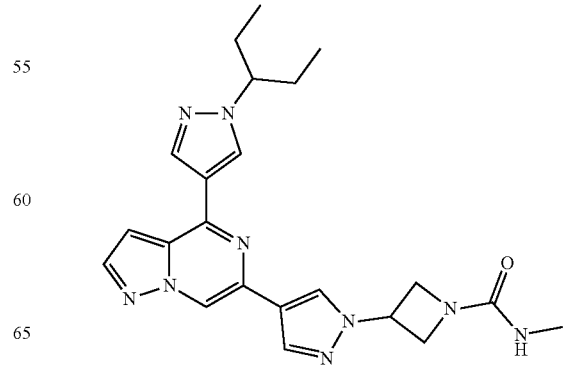

299
-continued
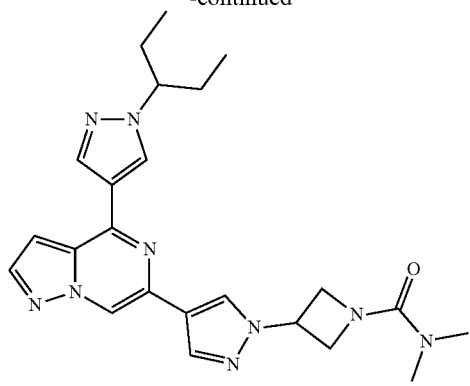
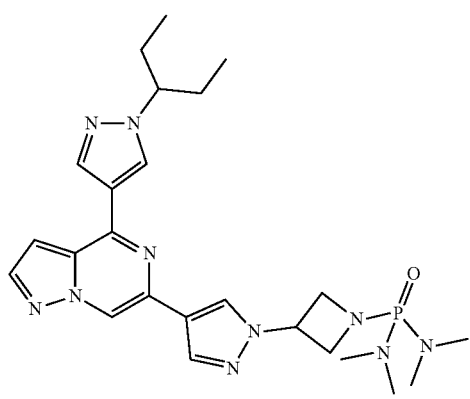
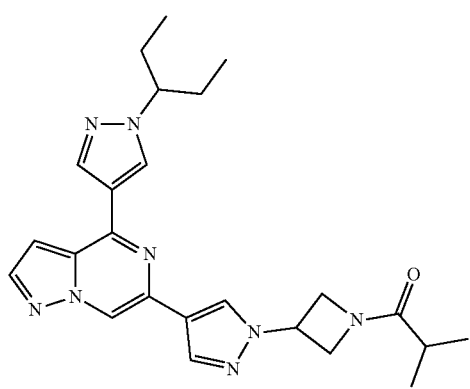
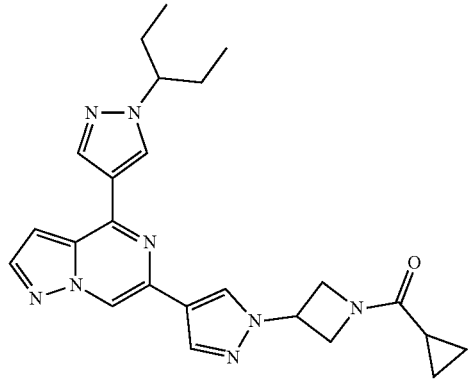
300
-continued
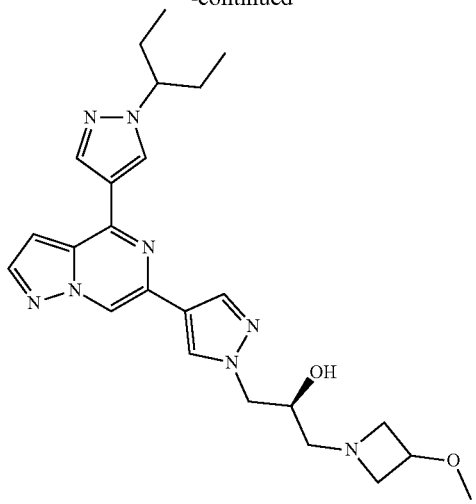
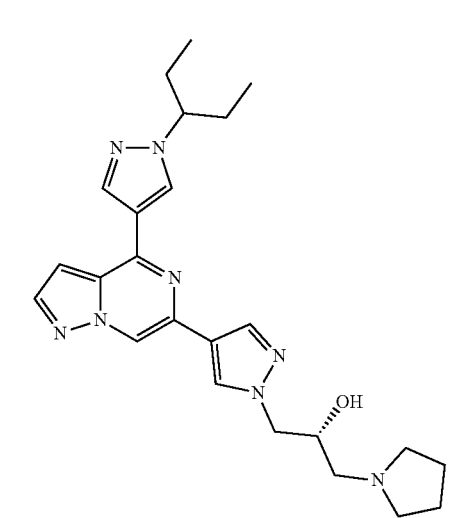
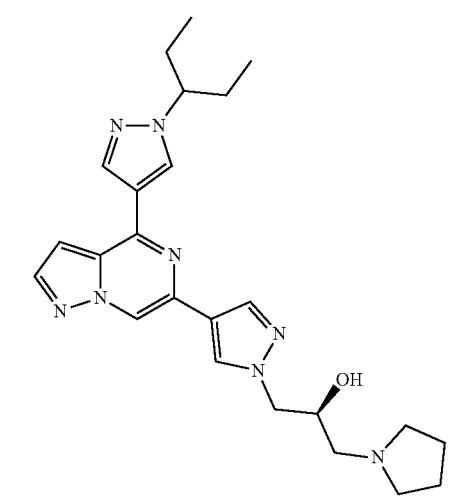

-continued
| 301 | 302 |
|---|---|
| 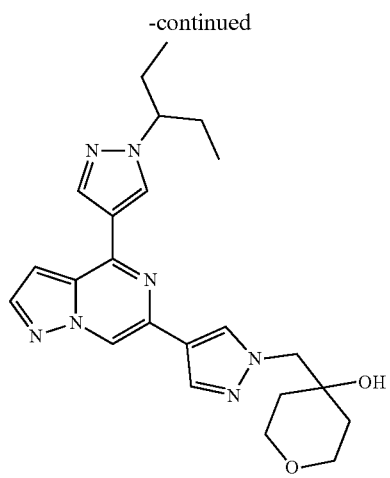 | 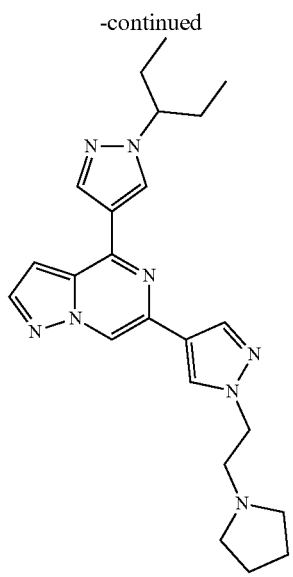 |
| 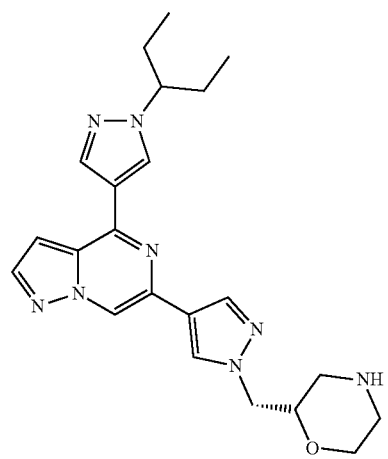 | 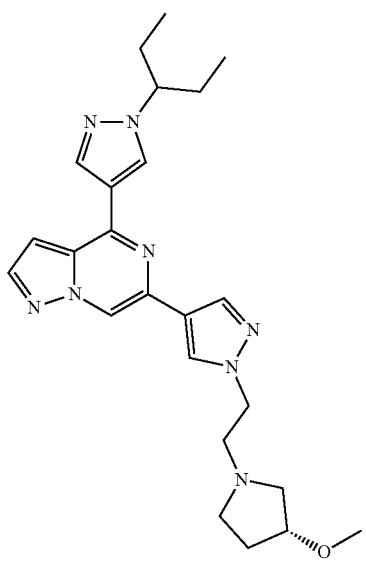 |
| 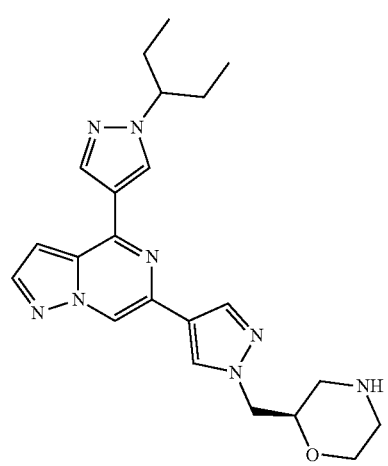 | 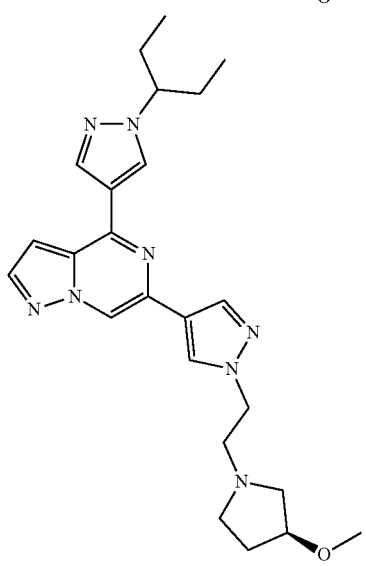 |

303
-continued
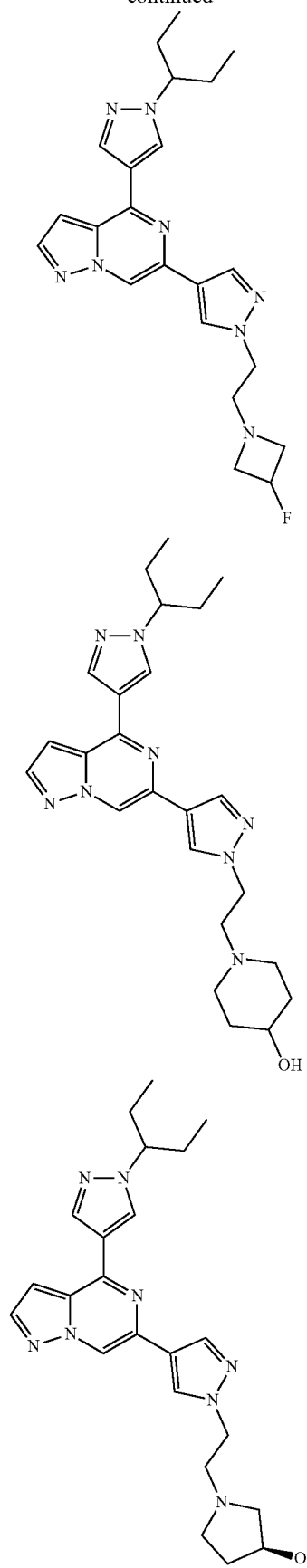
304
-continued
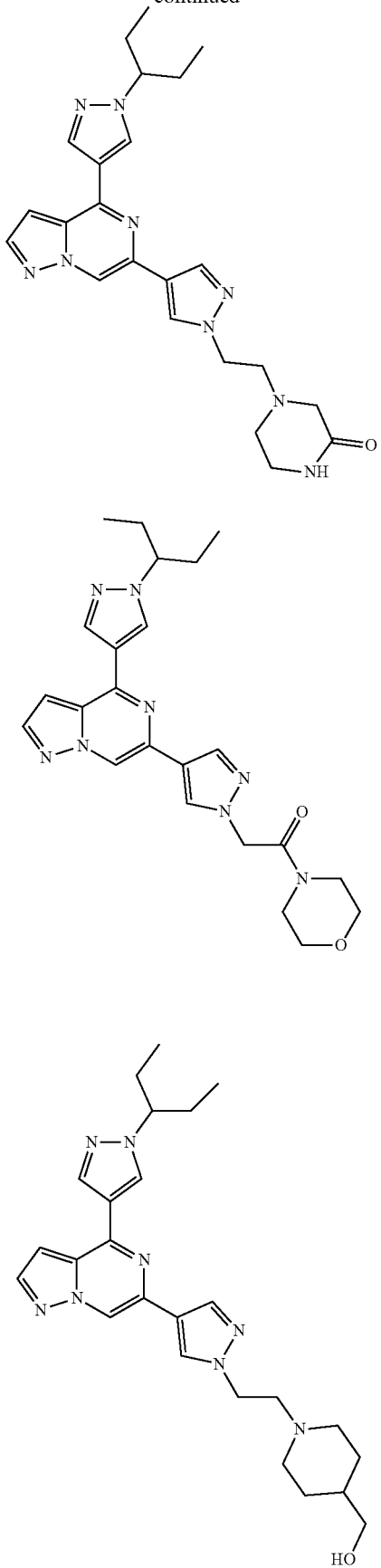

305
-continued
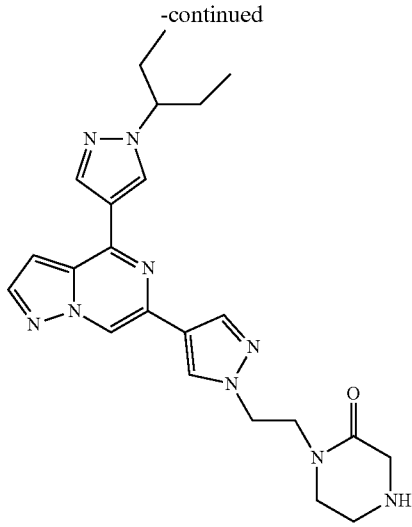
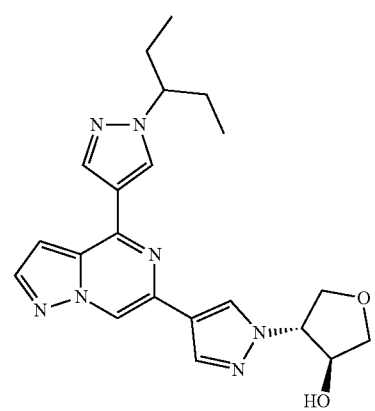
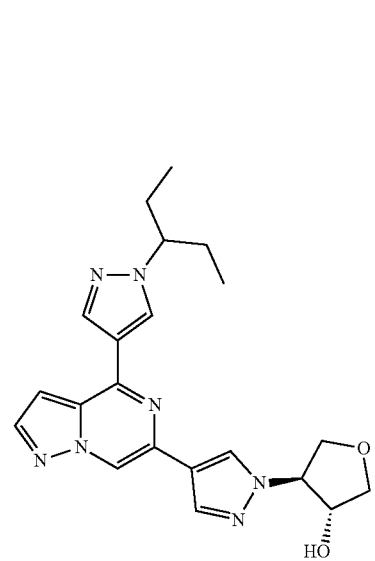
306
-continued
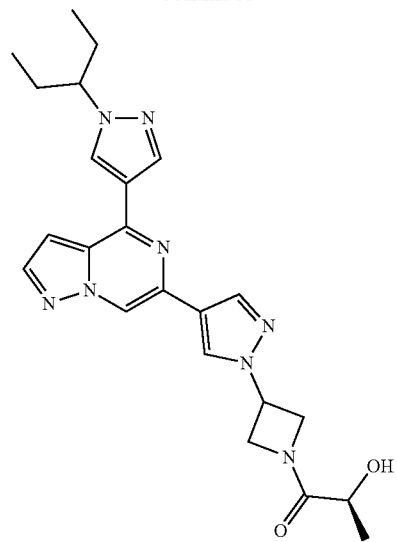
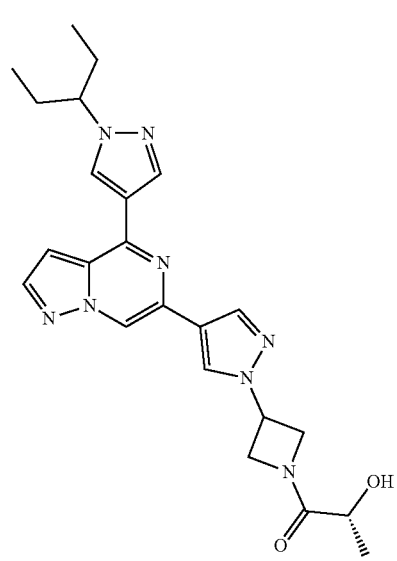

307
-continued
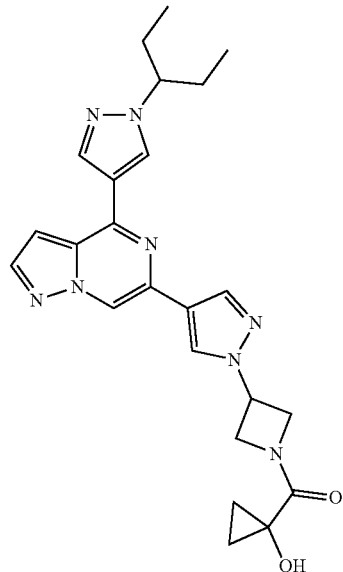
308
-continued
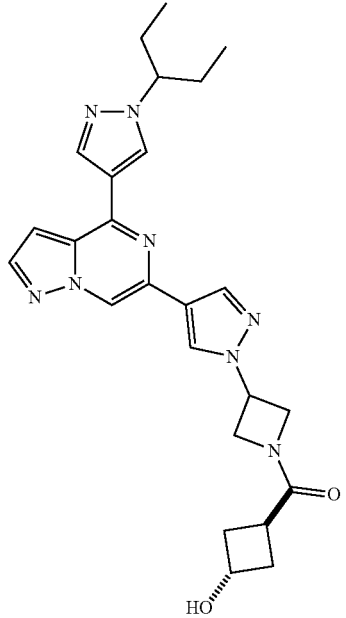
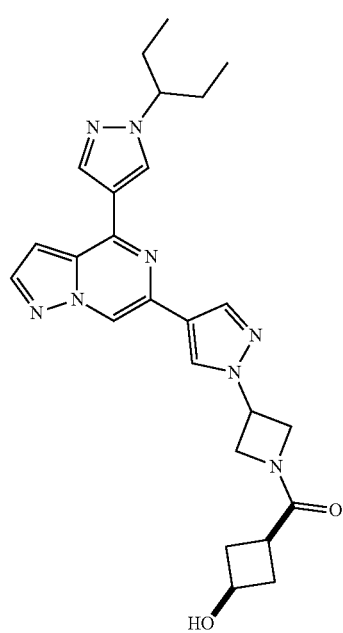
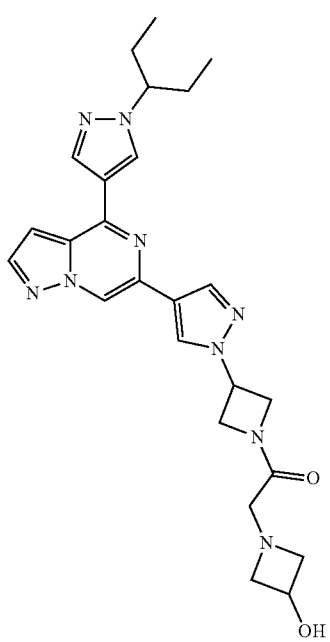

309
-continued
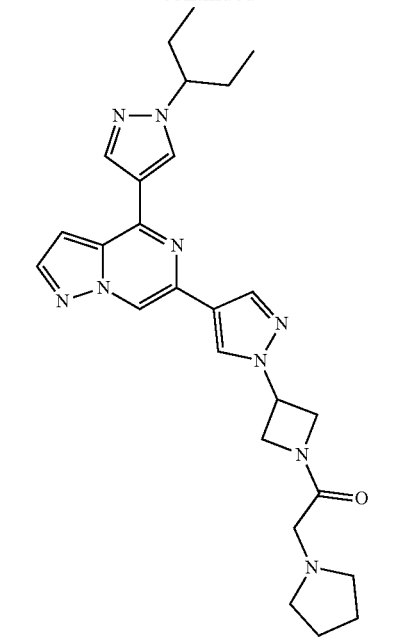
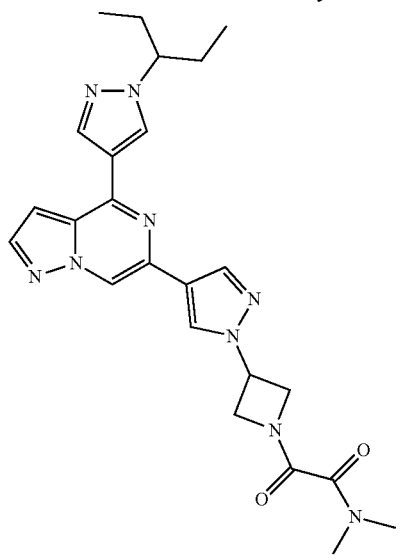
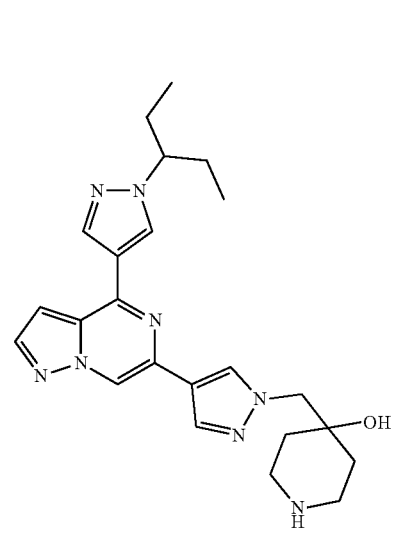
310
-continued
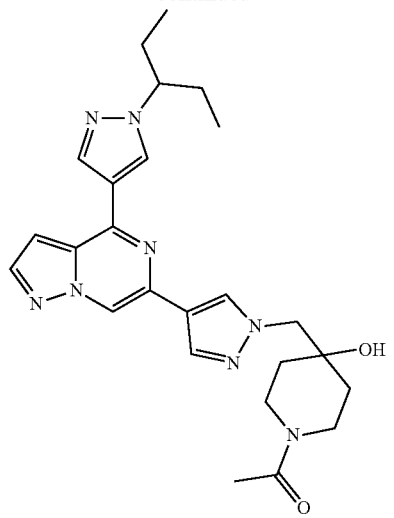
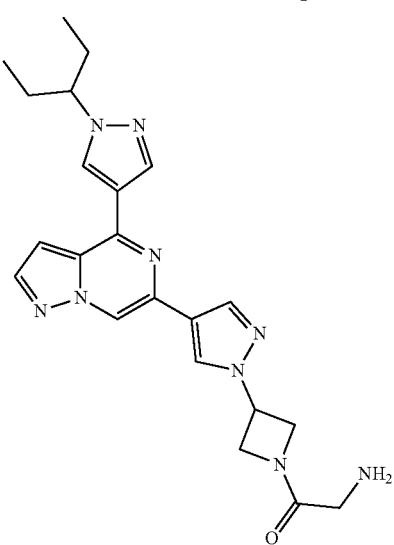
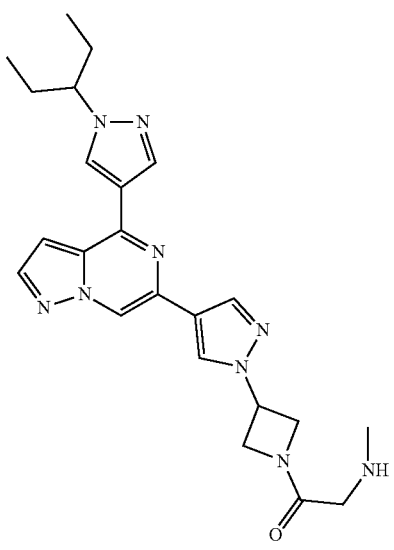

311
-continued
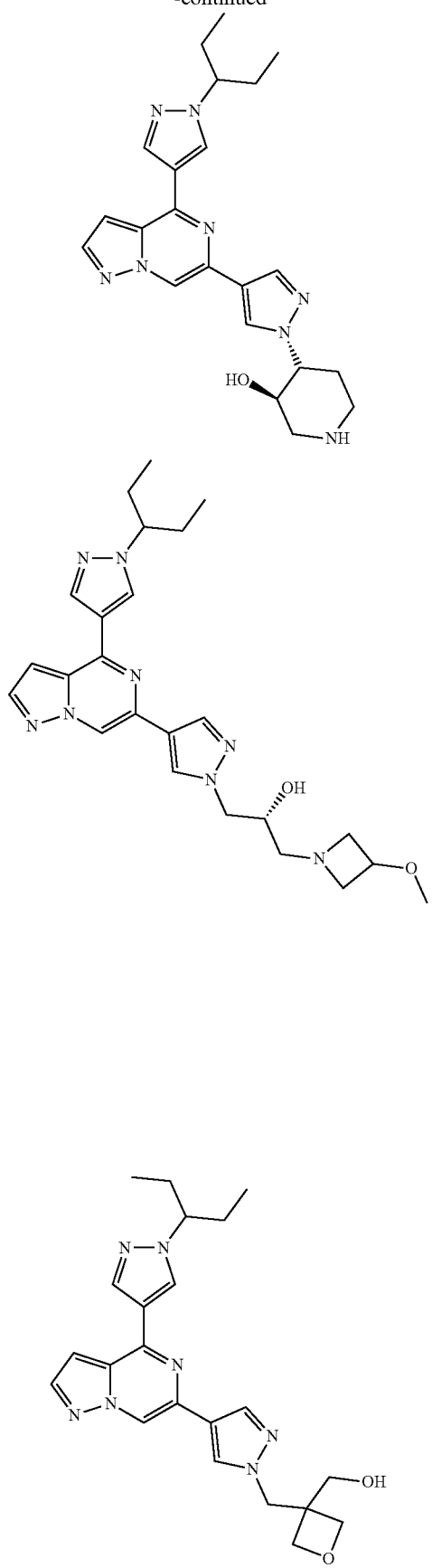
312
-continued
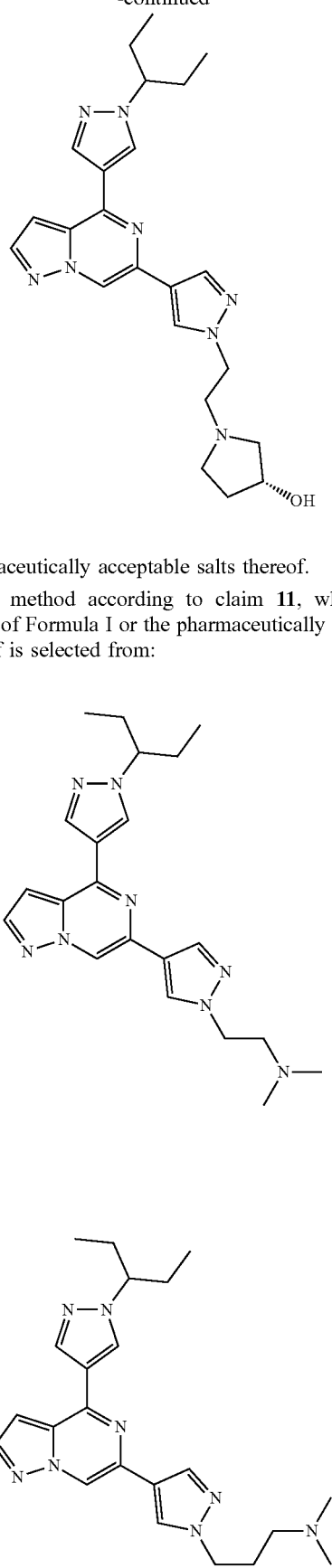
and pharmaceutically acceptable salts thereof.
15. The method according to claim 11, wherein the compound of Formula I or the pharmaceutically acceptable salt thereof is selected from:

313
-continued
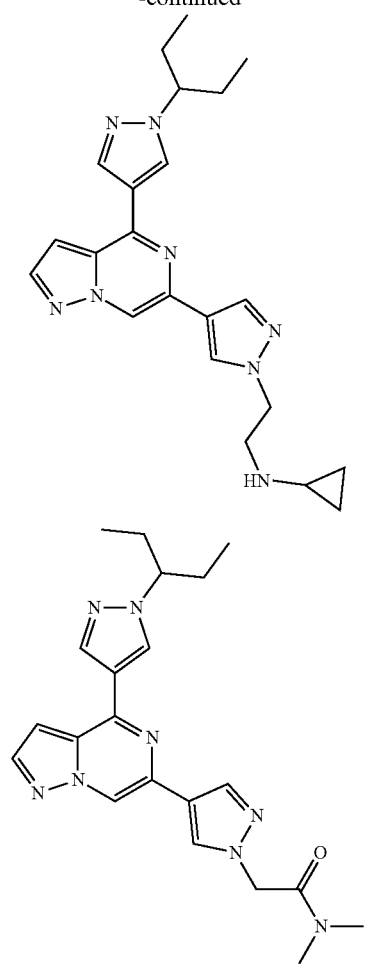
314
-continued
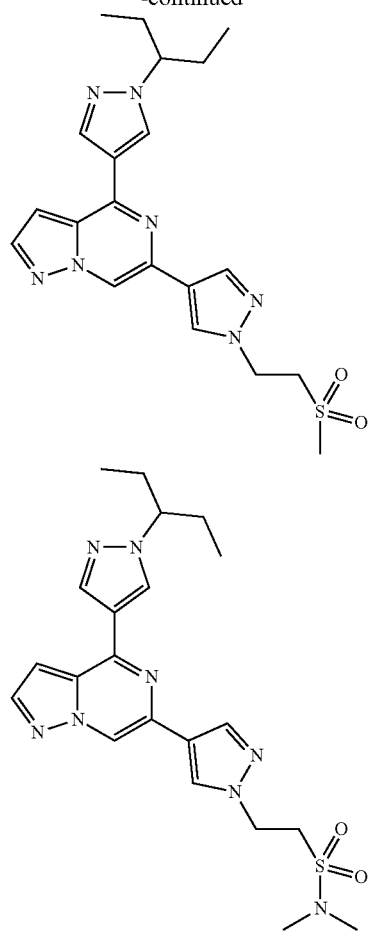
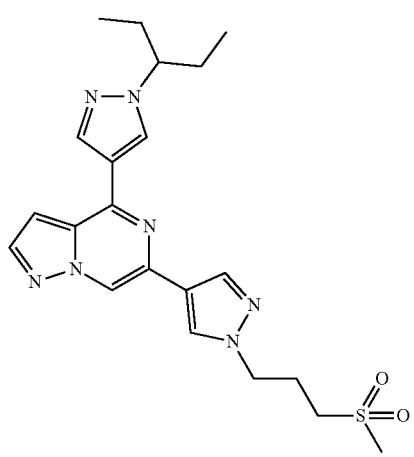
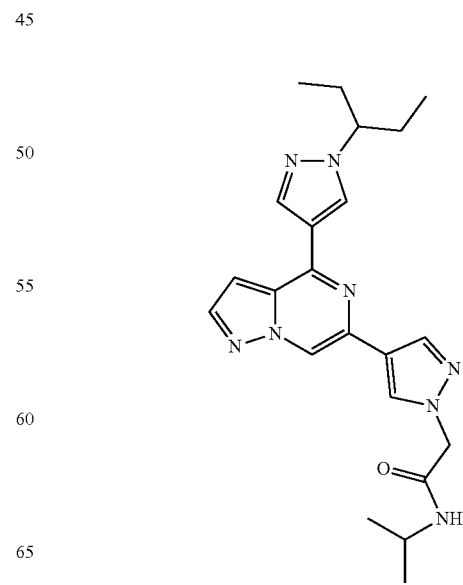

315
-continued
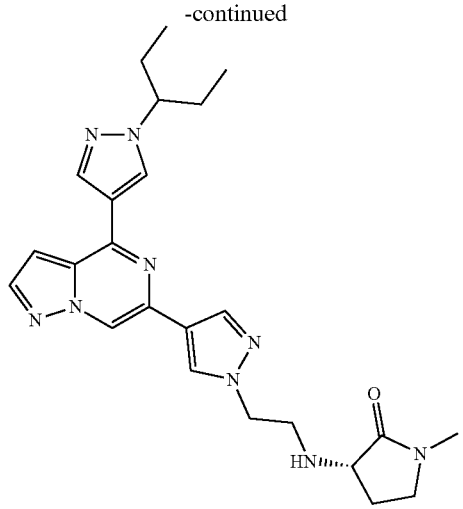
and pharmaceutically acceptable salts thereof.
16. The method according to claim 11, wherein the compound of Formula I or the pharmaceutically acceptable salt thereof is selected from:
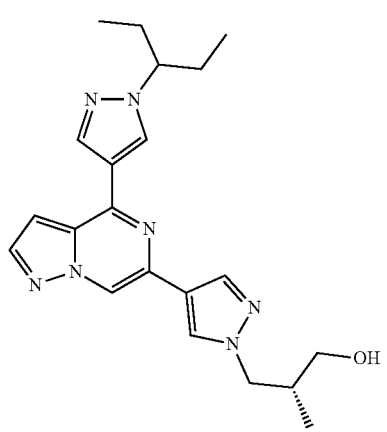
316
-continued
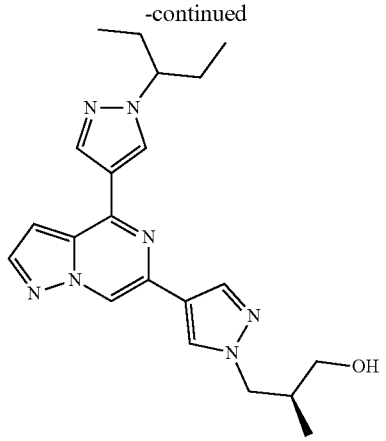
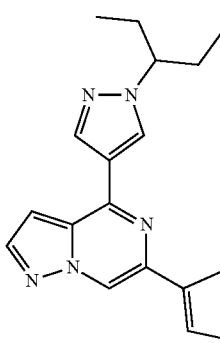
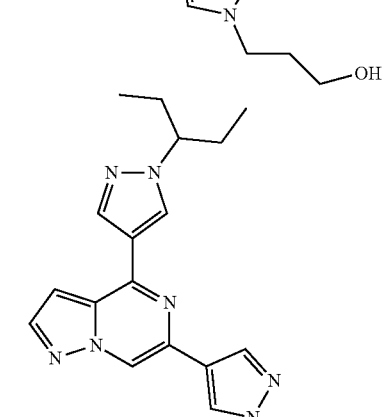
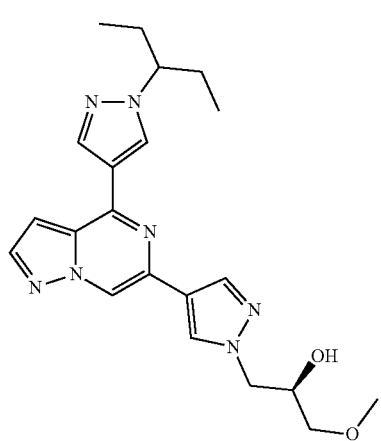

317
-continued
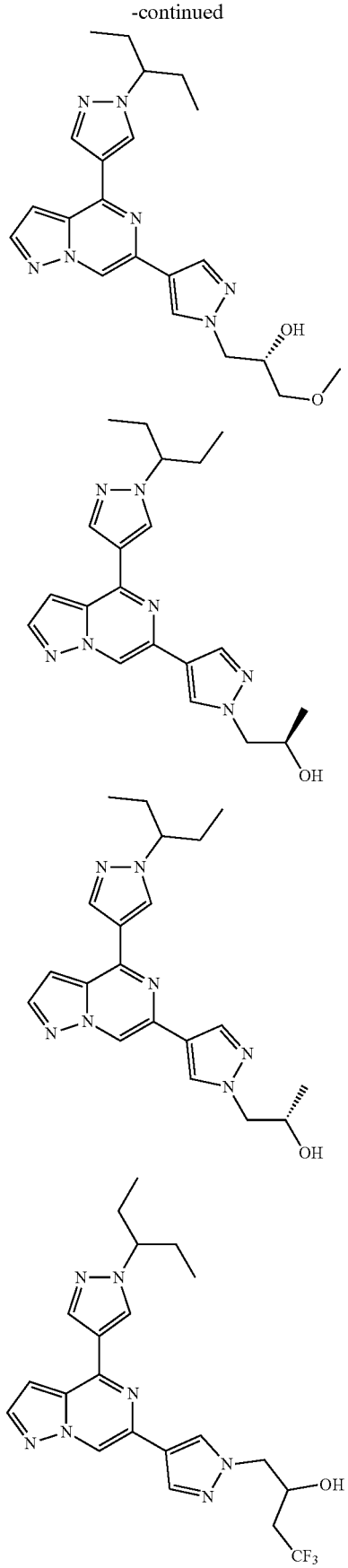
318
-continued
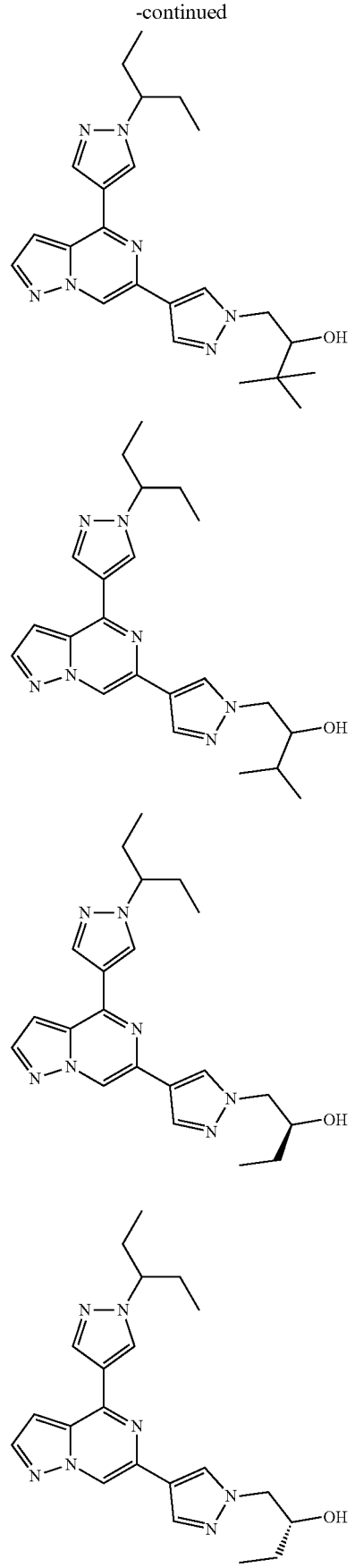

319
-continued
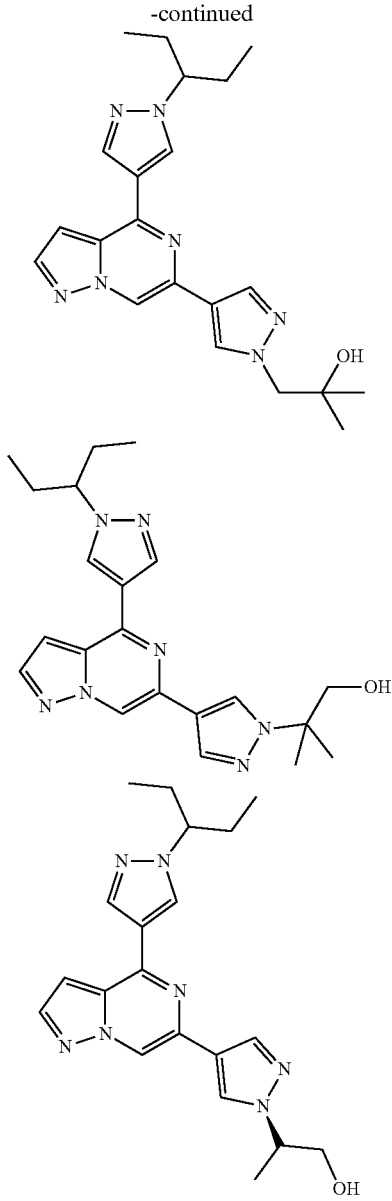
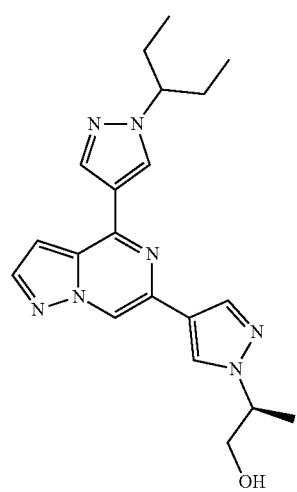
320
-continued
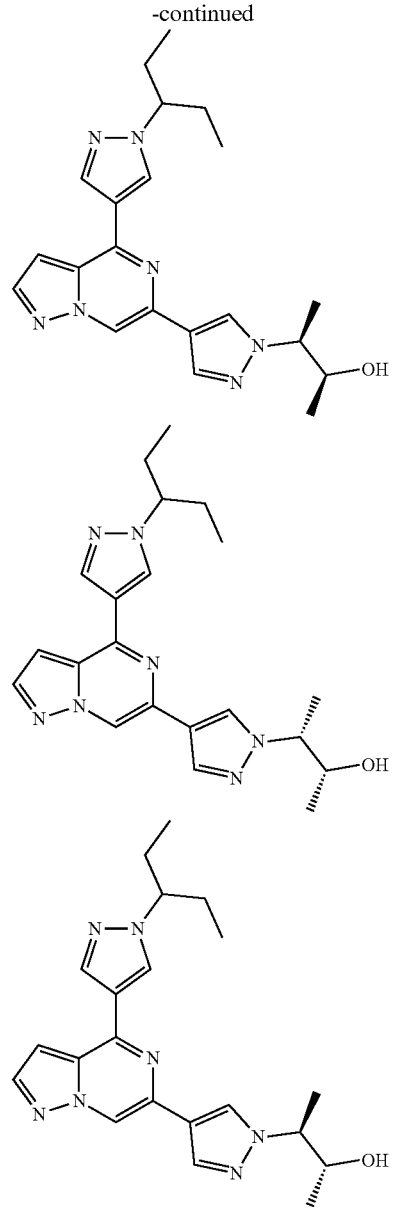
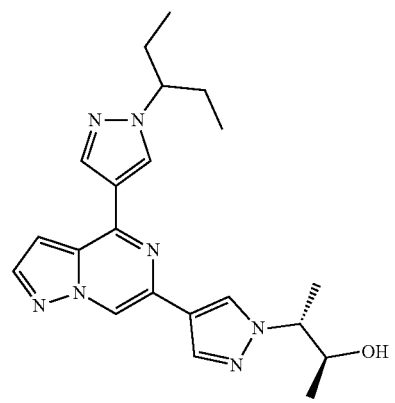

-continued
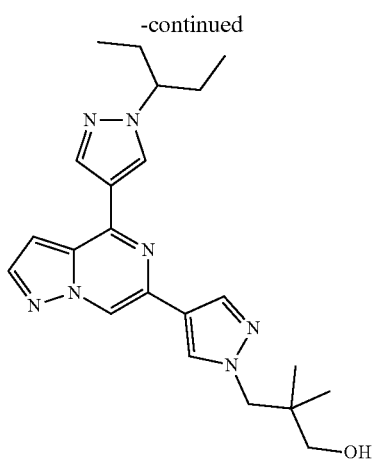
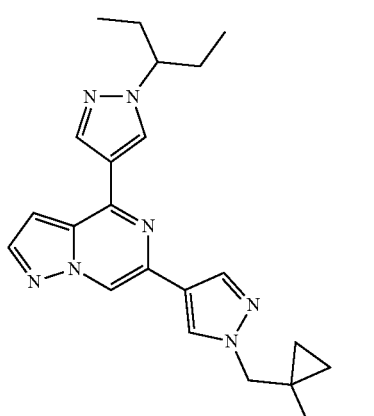
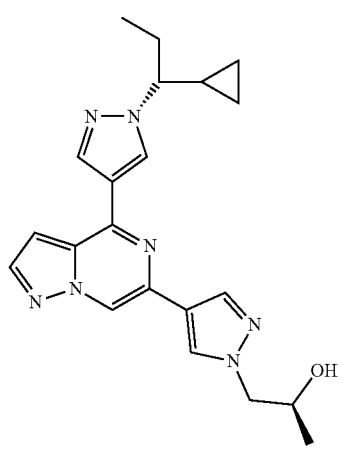
and pharmaceutically acceptable salts thereof.
17. The method according to claim 11, wherein the compound of Formula I or the pharmaceutically acceptable salt thereof is selected from:
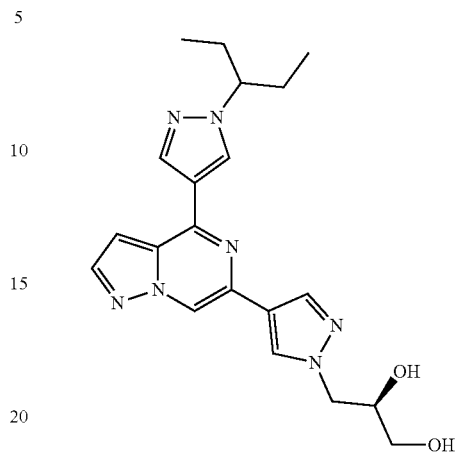
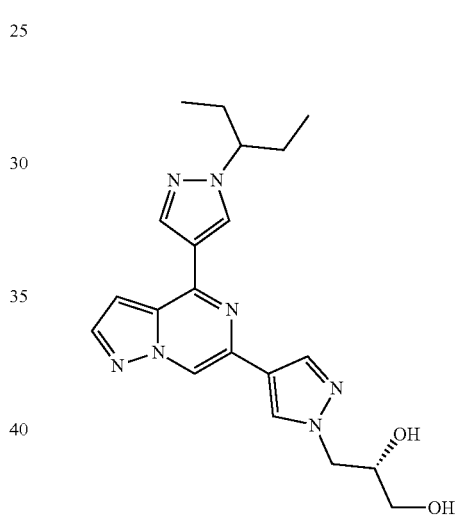
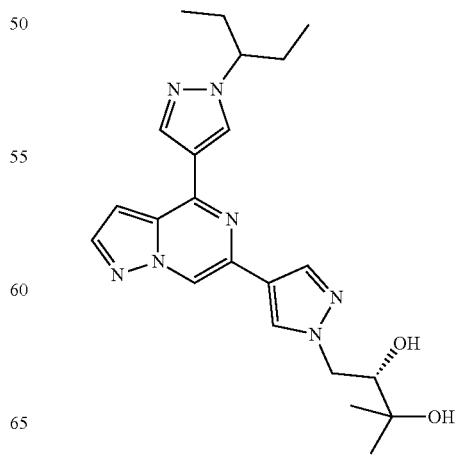

323
-continued
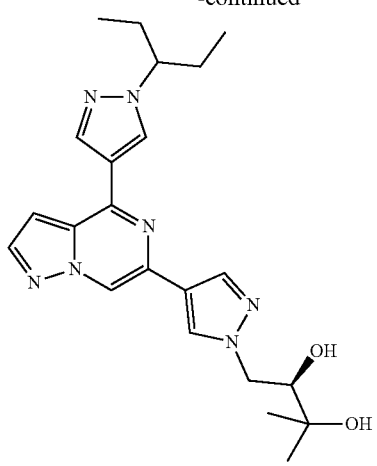
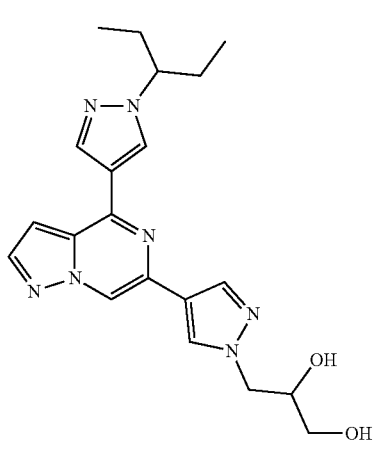
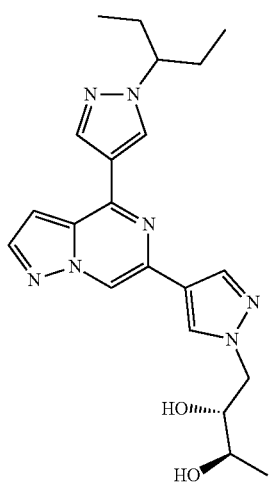
324
-continued
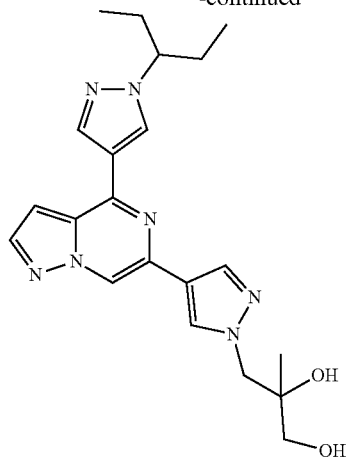
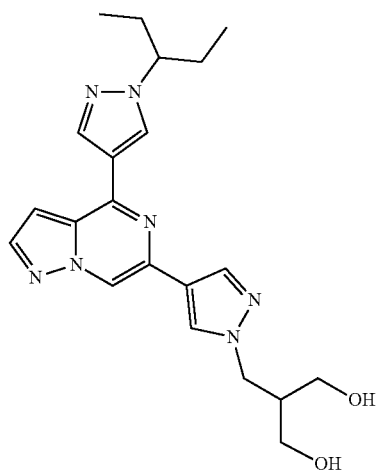
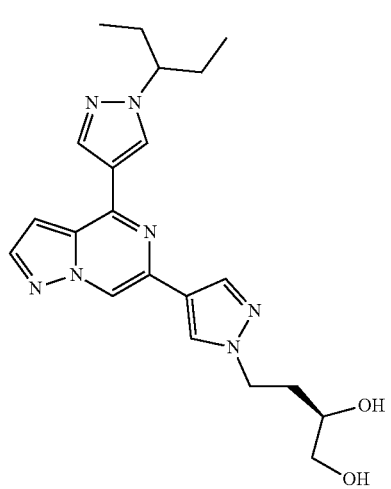

325
-continued
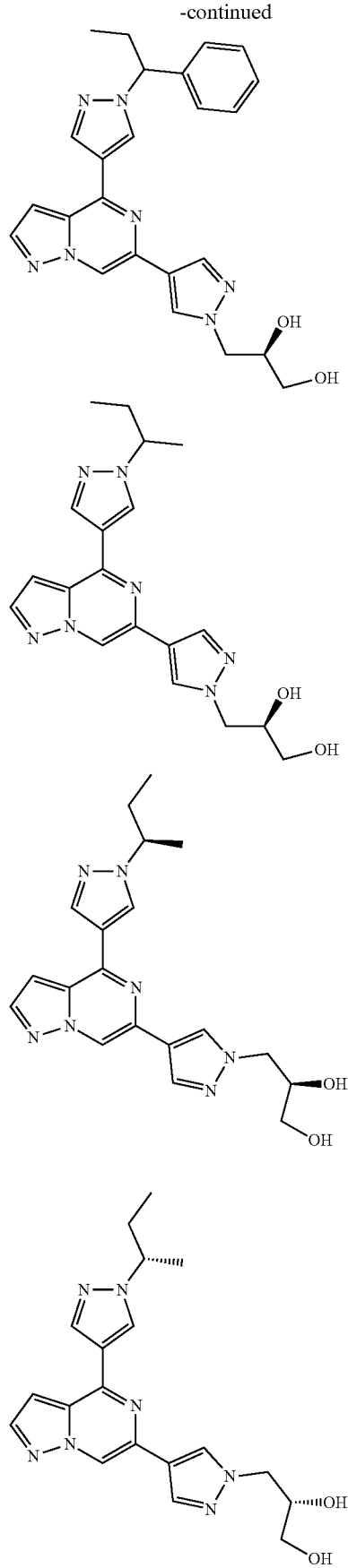
326
-continued
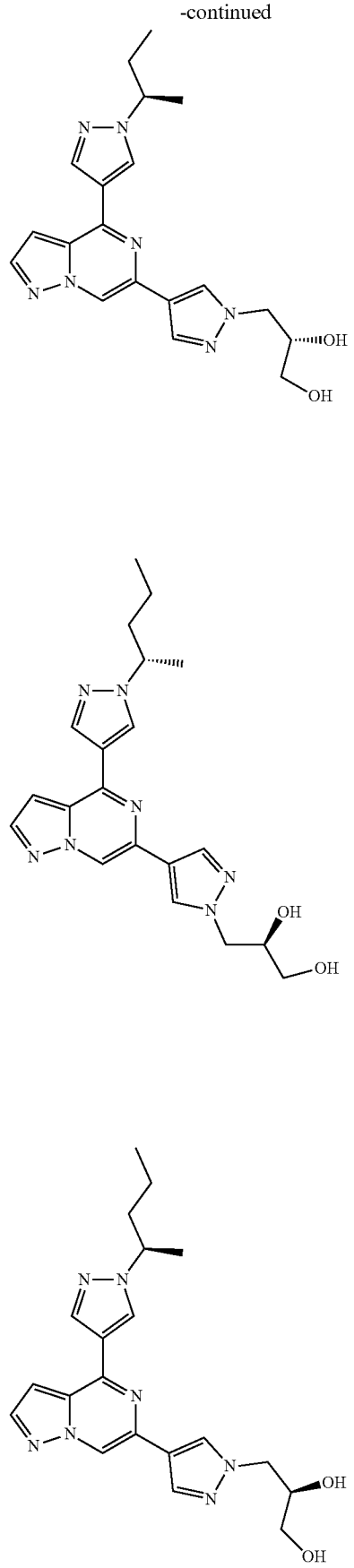

327
-continued
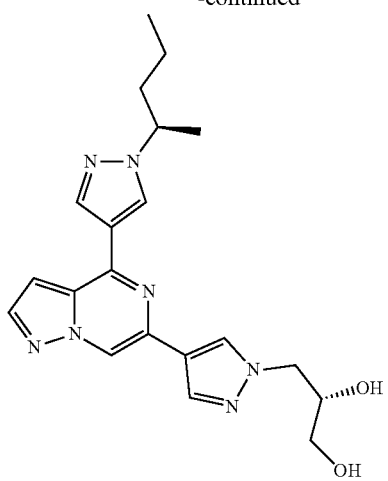
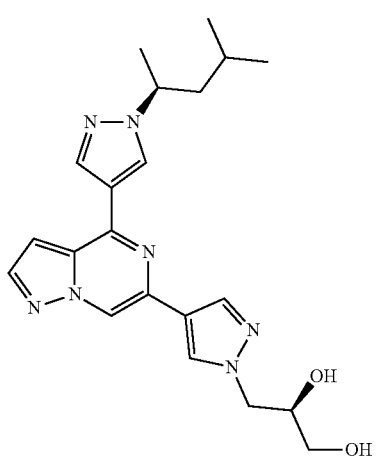
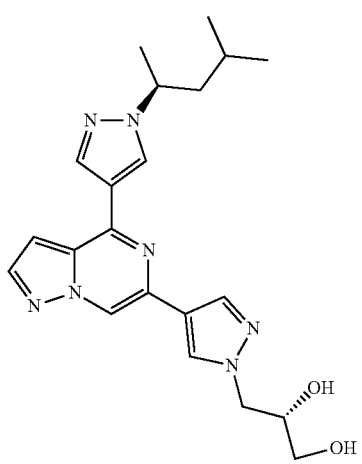
328
-continued
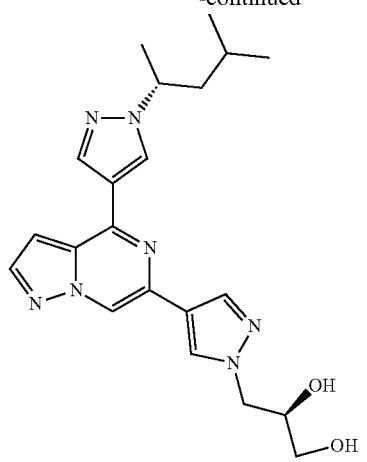
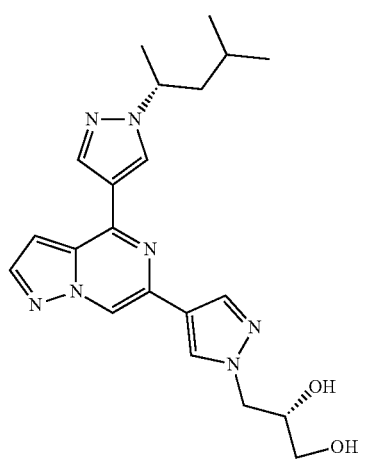
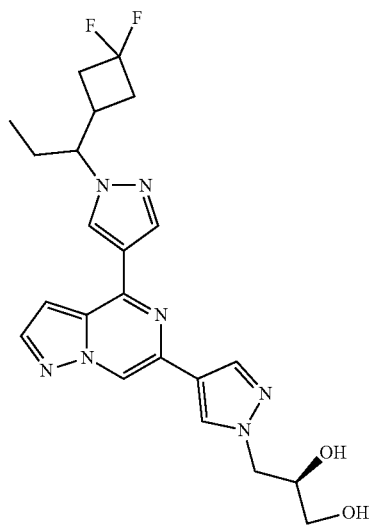

329
-continued
330
-continued
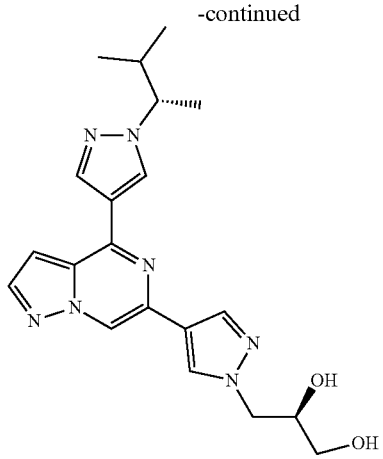
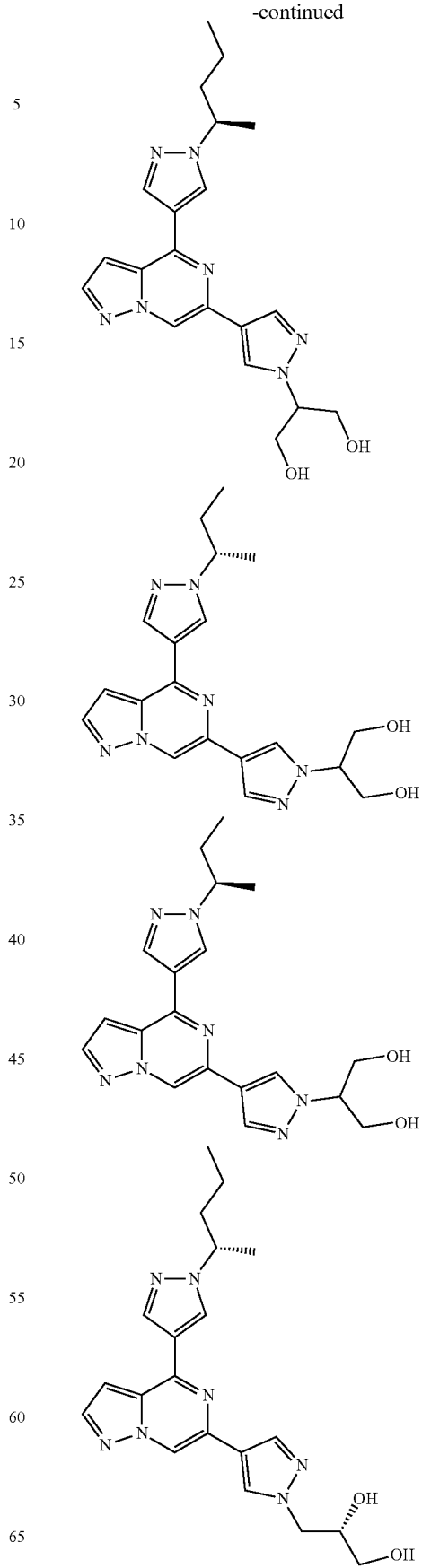

331
-continued
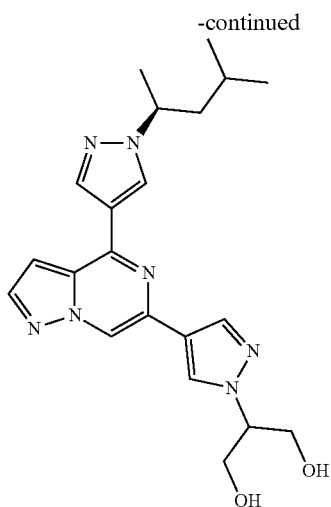
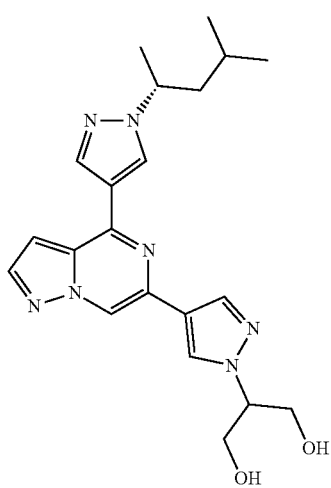
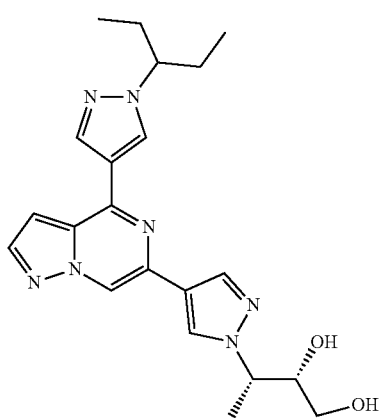
332
-continued
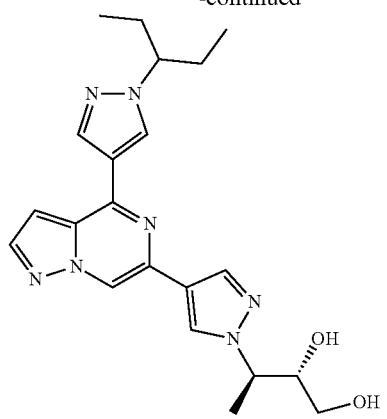
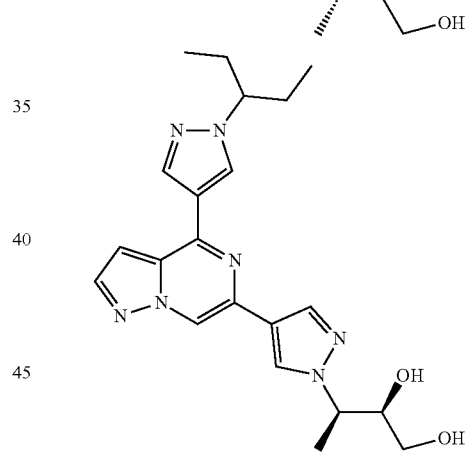
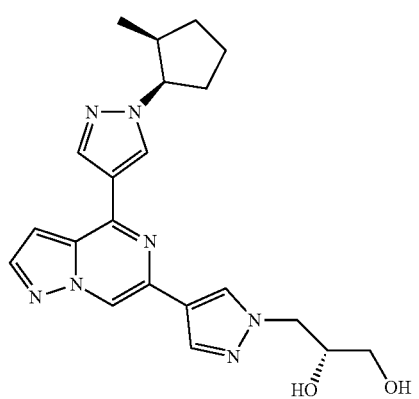

333
-continued
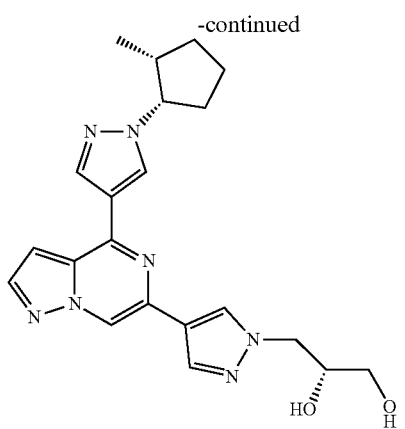
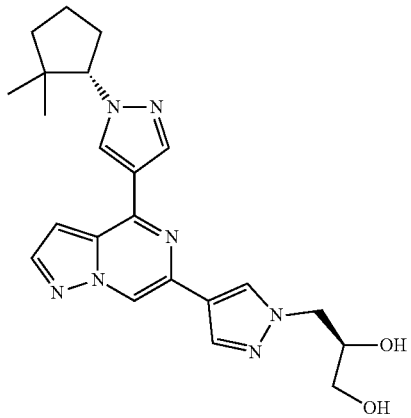
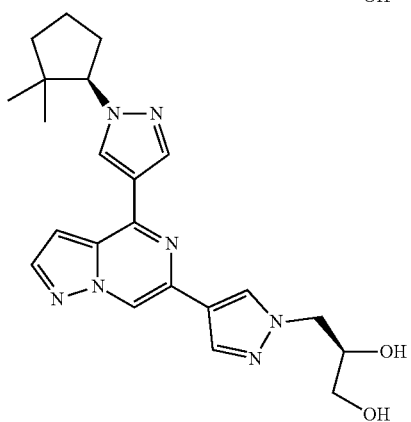
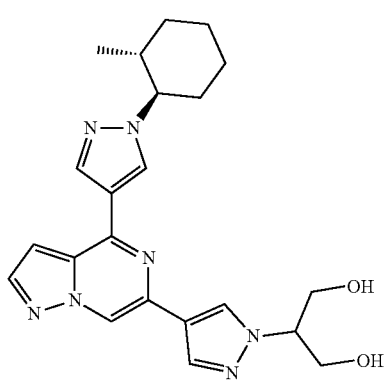
334
-continued
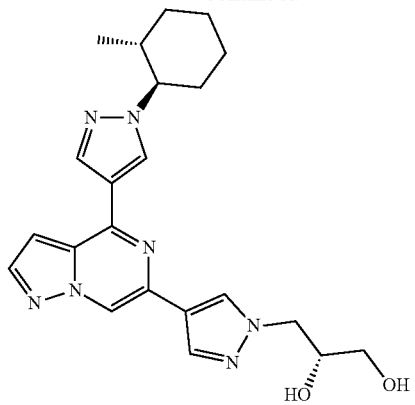
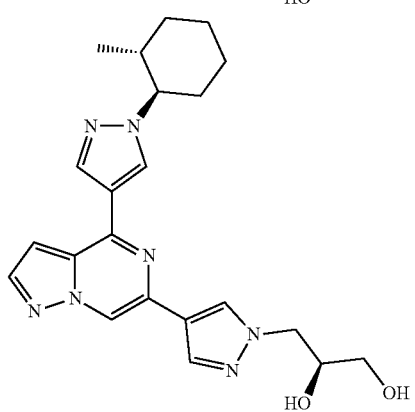
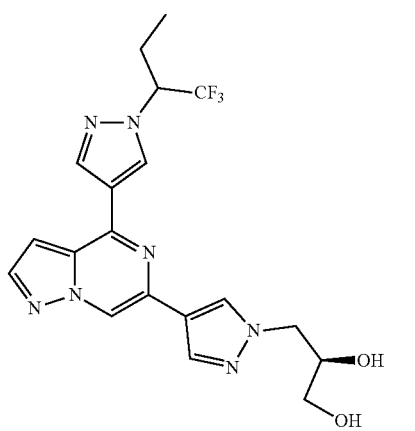

335
-continued
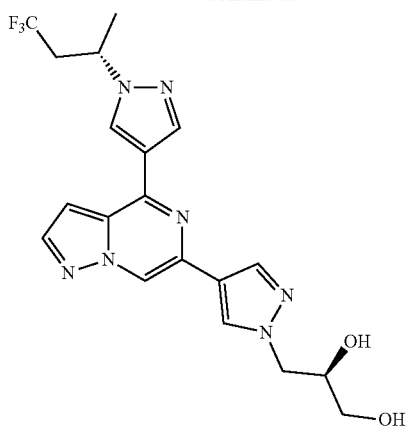
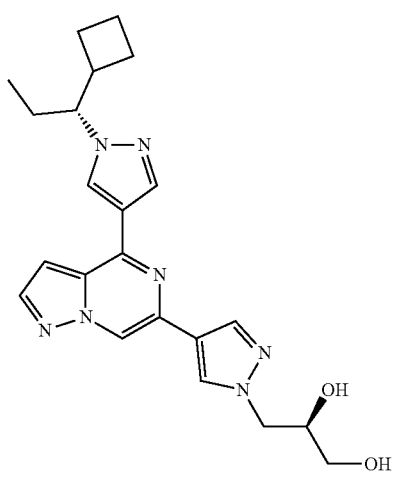
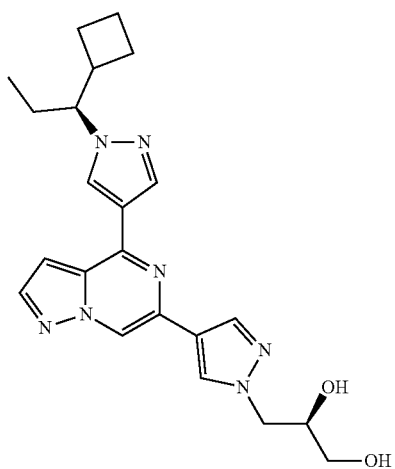
336
-continued
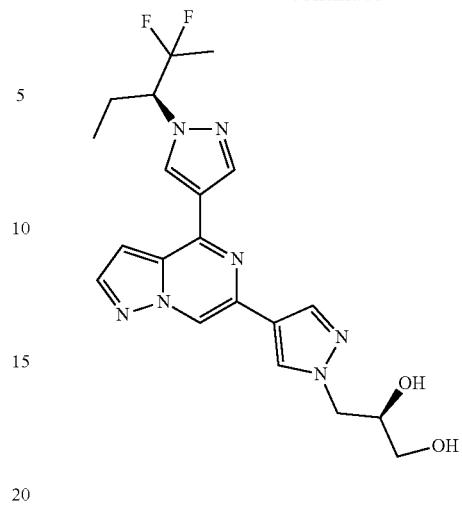
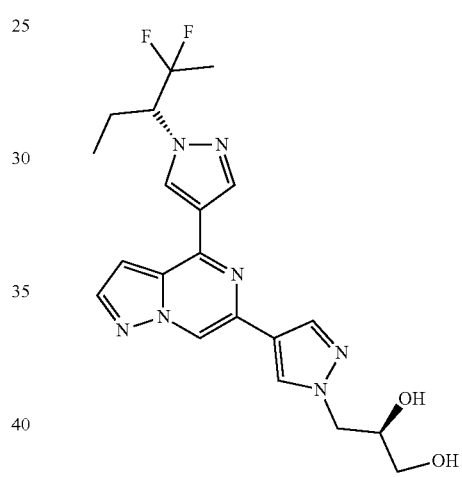
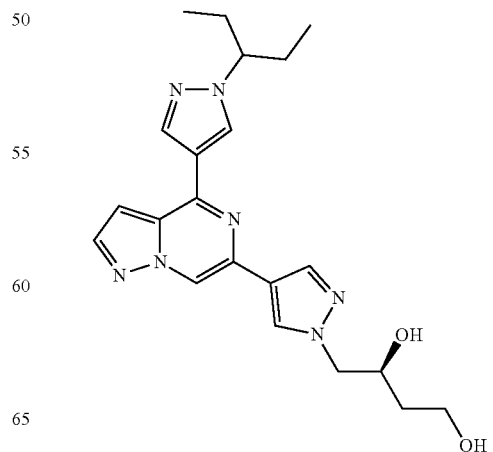

337
-continued
338
-continued
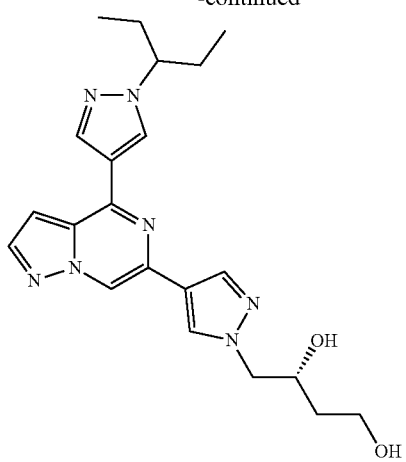
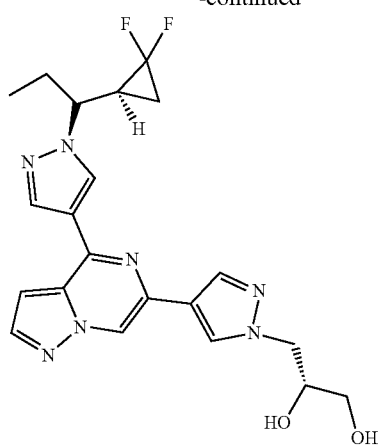
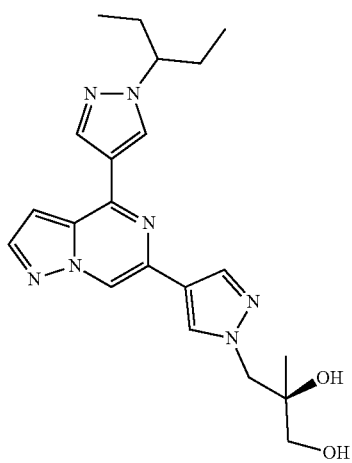
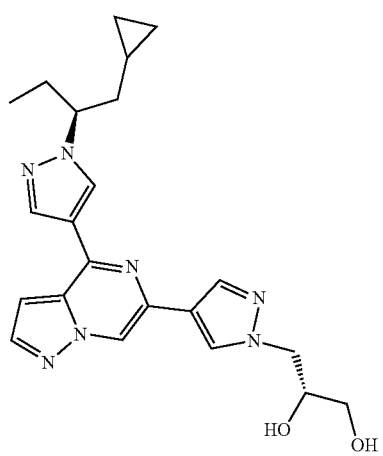
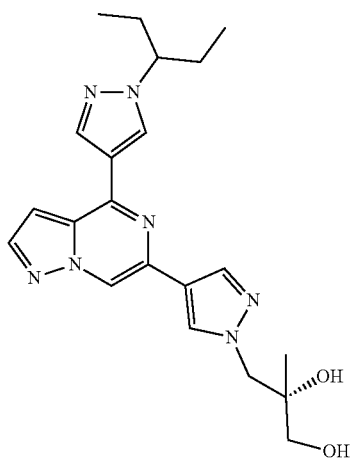
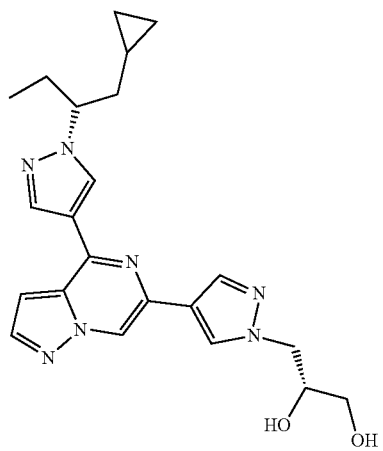

339
-continued
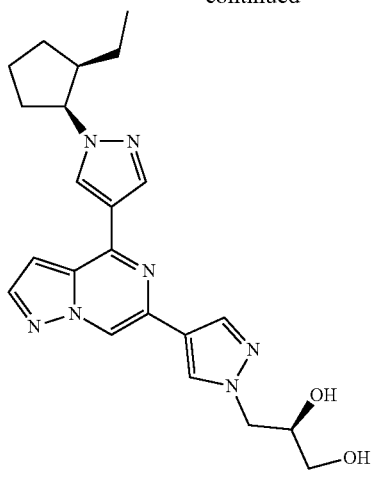
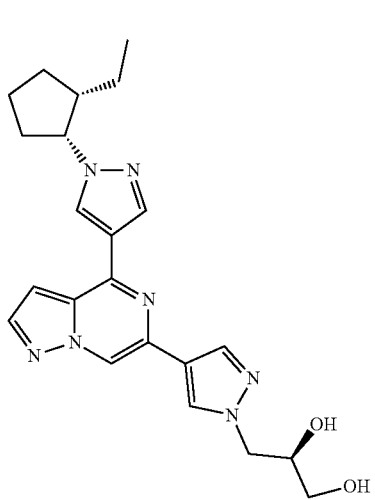
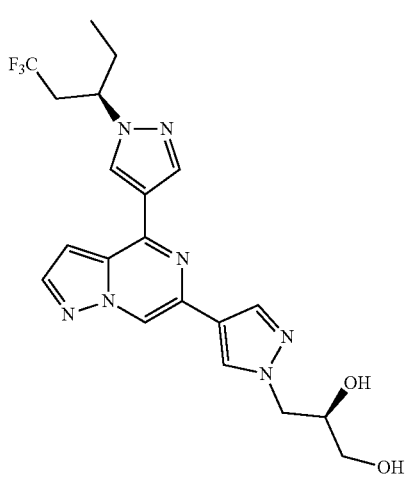
340
-continued
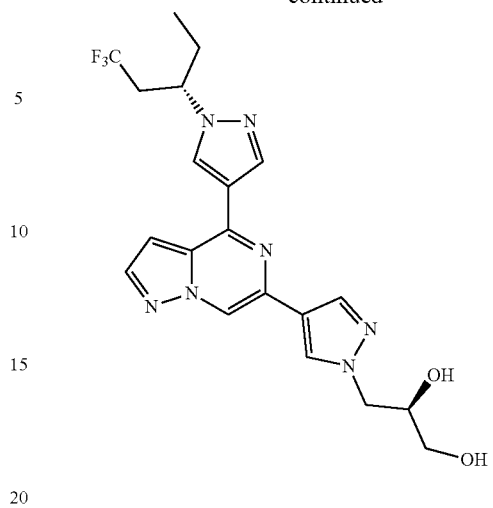
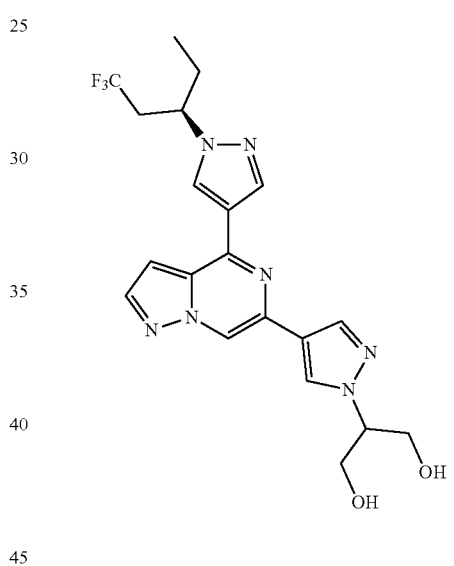
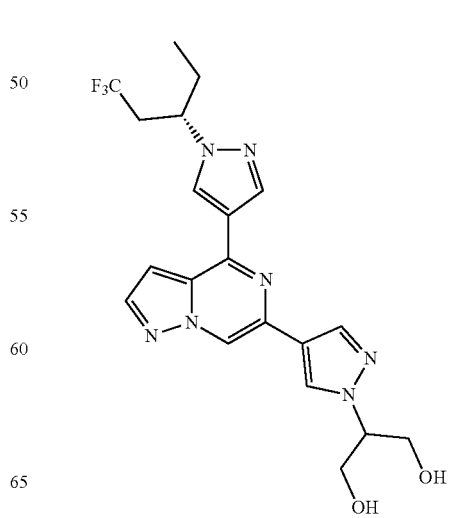

341
-continued
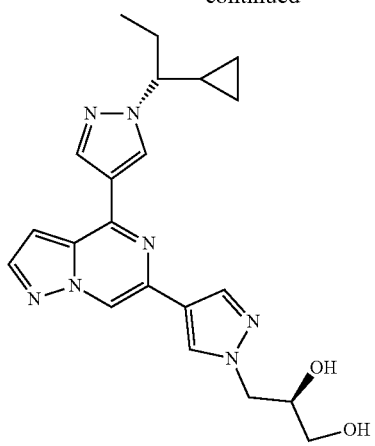
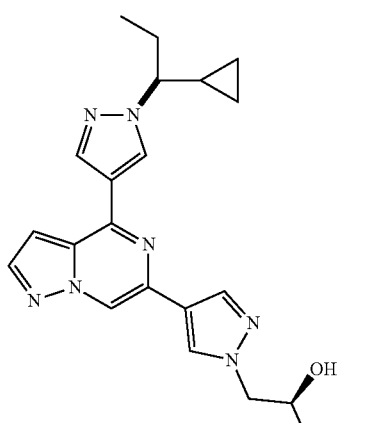
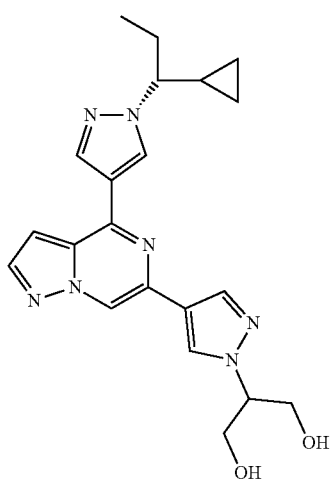
342
-continued
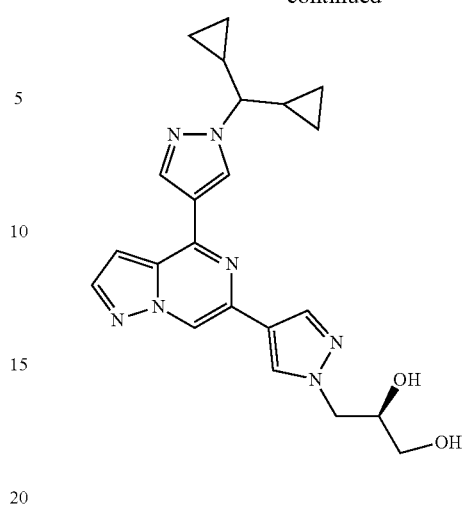
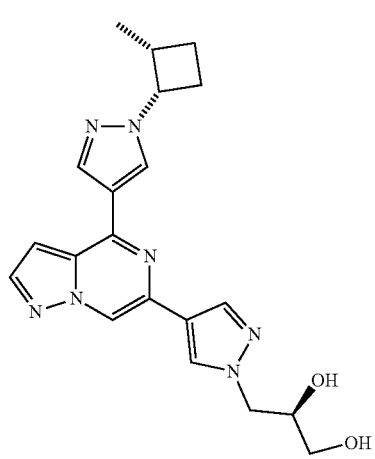
and pharmaceutically acceptable salts thereof.
18. The method according to claim 11, wherein the compound of Formula I or the pharmaceutically acceptable salt thereof is selected from:
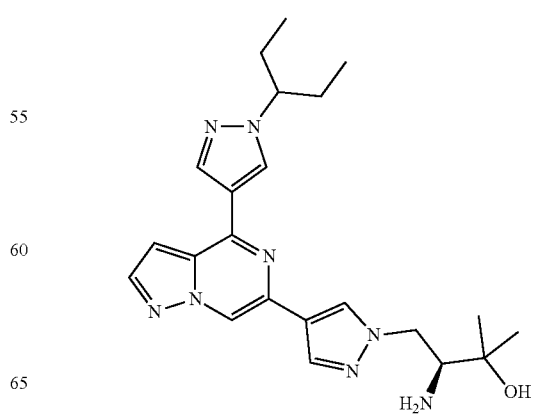

343
-continued
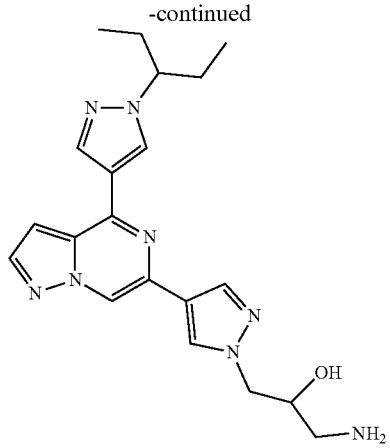
344
-continued
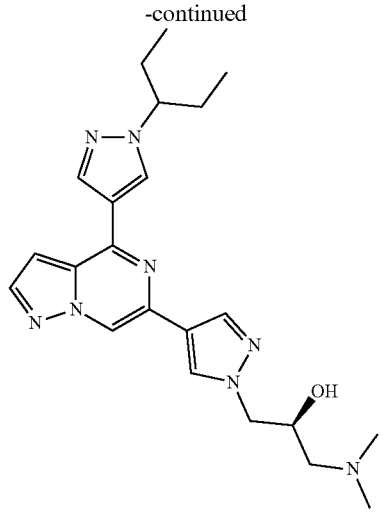
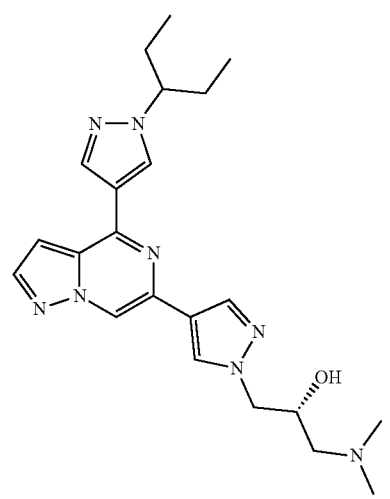
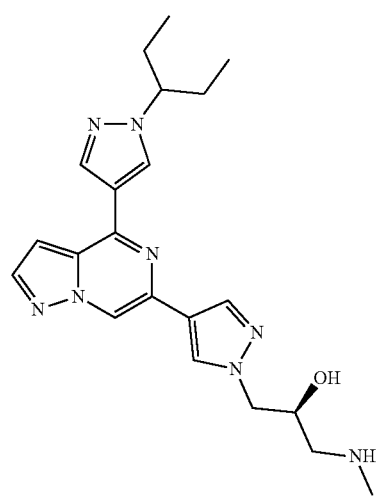
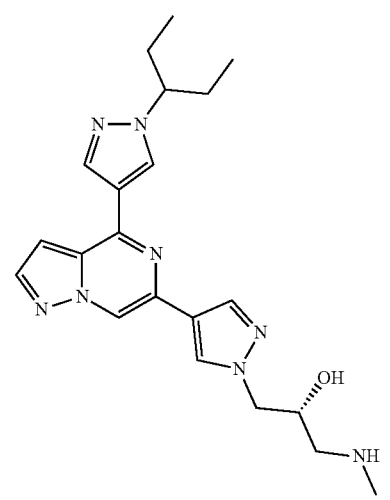
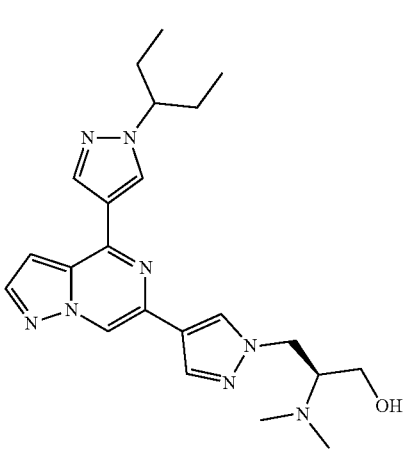

345
-continued
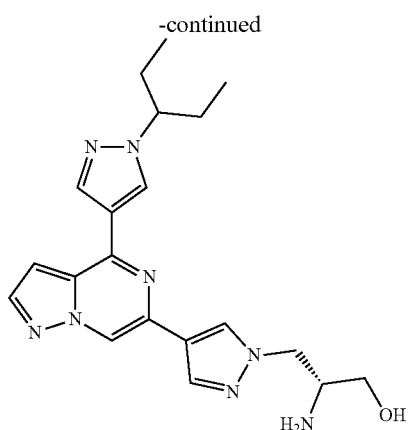
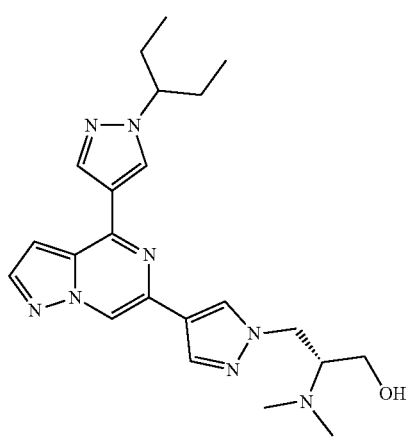
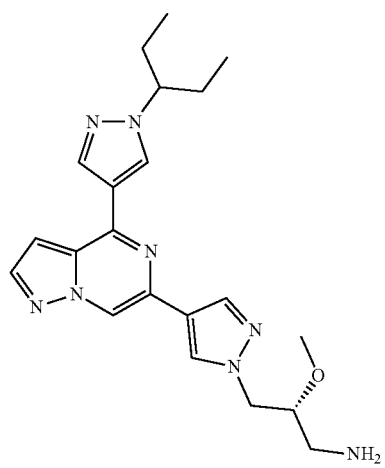
346
-continued
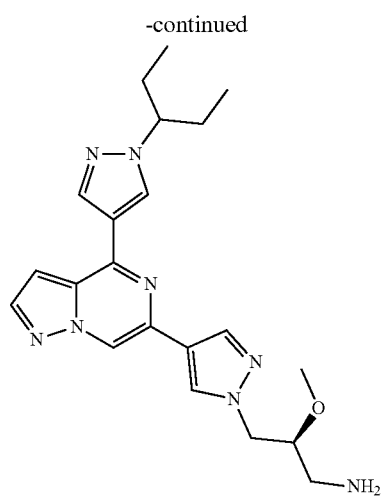
and pharmaceutically acceptable salts thereof.
19. The method according to claim 11, wherein the compound of Formula I or the pharmaceutically acceptable salt thereof is selected from:
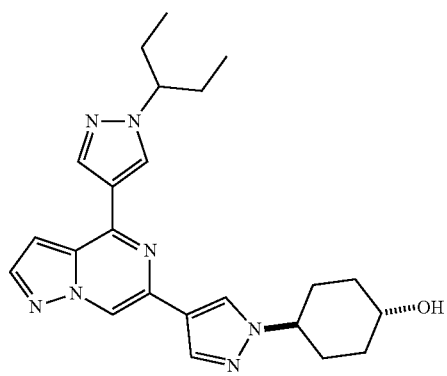
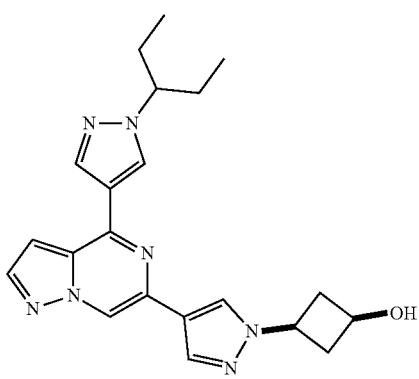

347
-continued
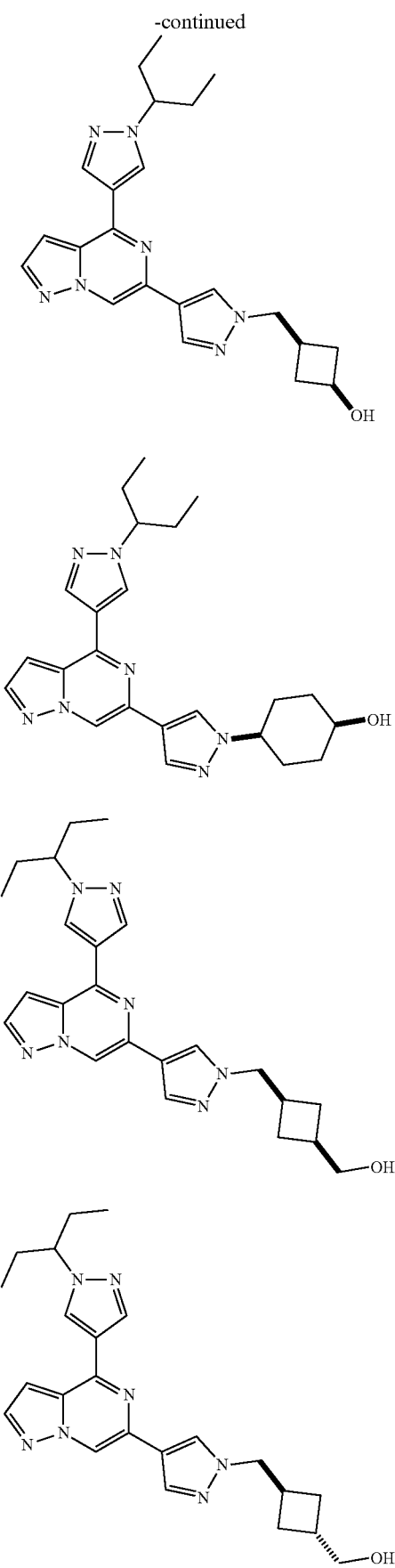
348
-continued
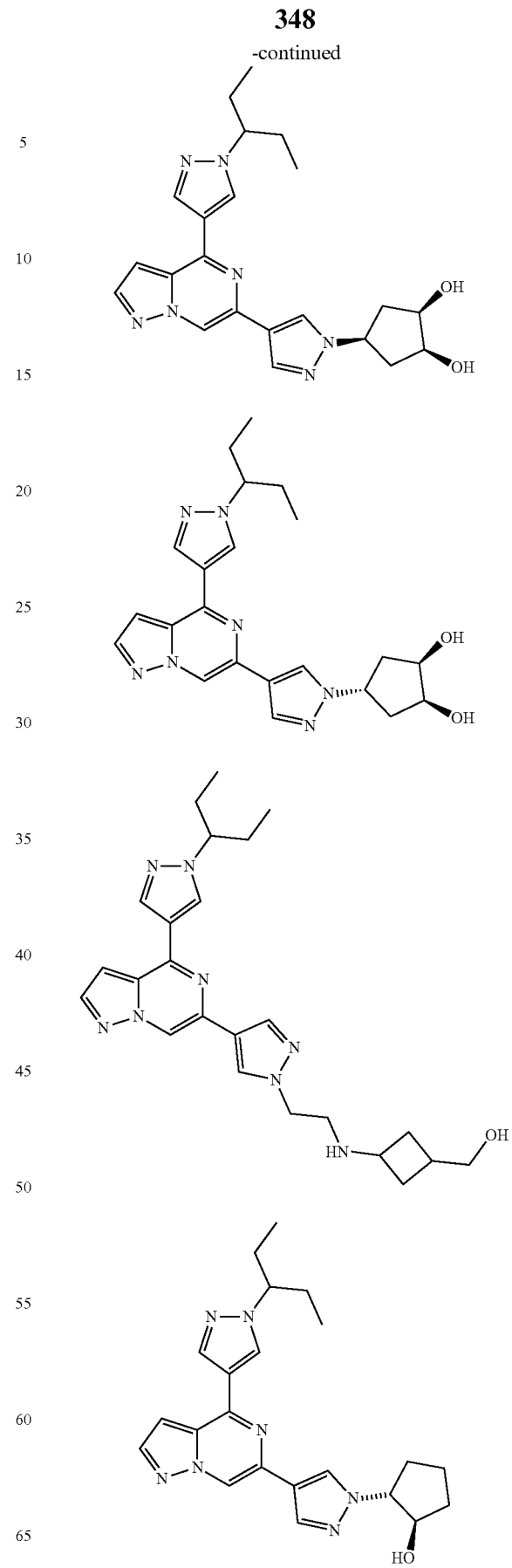

349
-continued
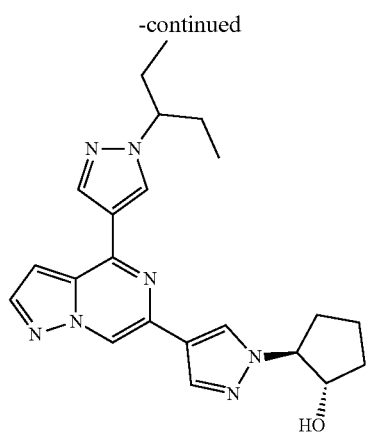
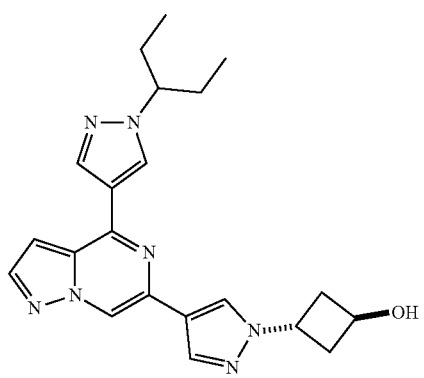
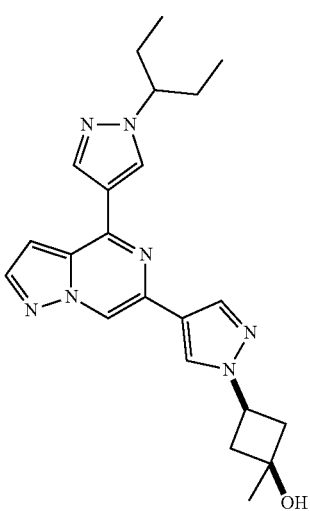
350
-continued
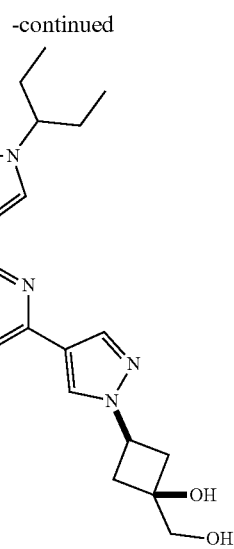
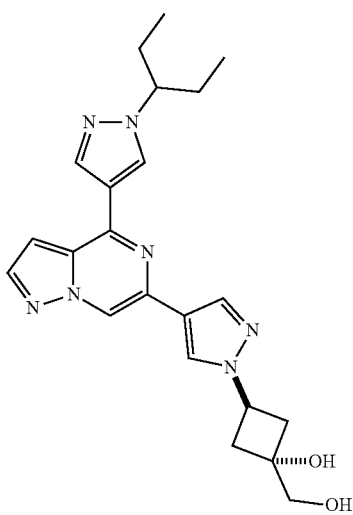
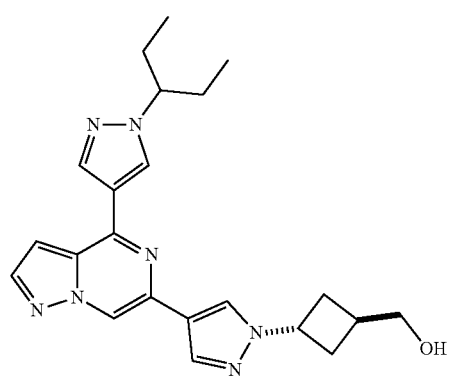

| 351 | 352 |
|---|---|
| -continued | -continued |
| 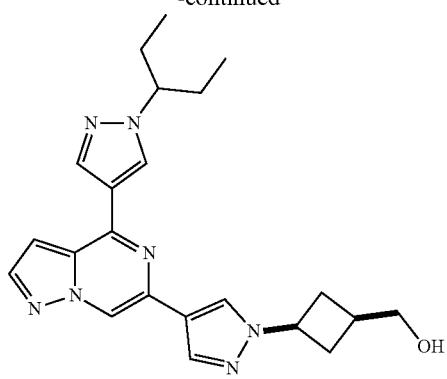 | 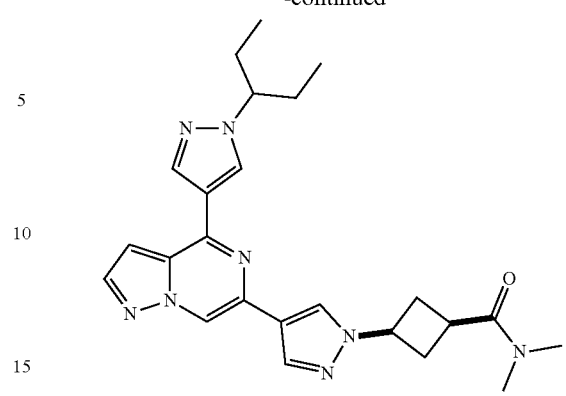 |
| 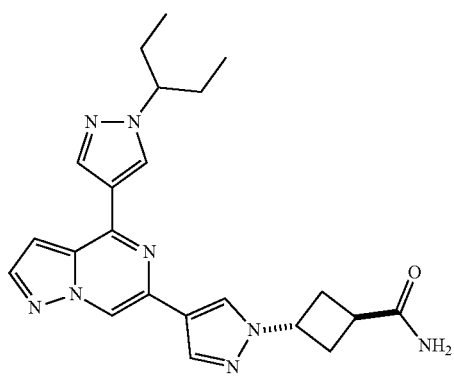 | 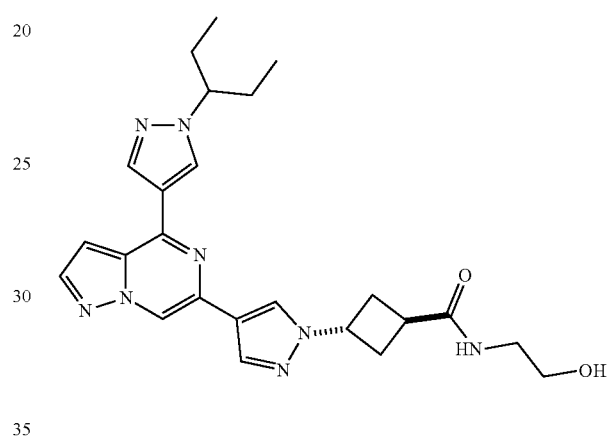 |
| 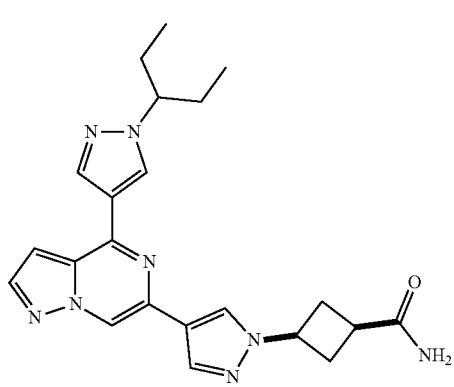 | 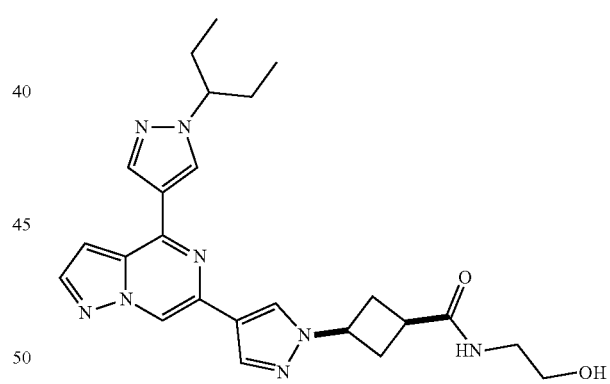 |
| 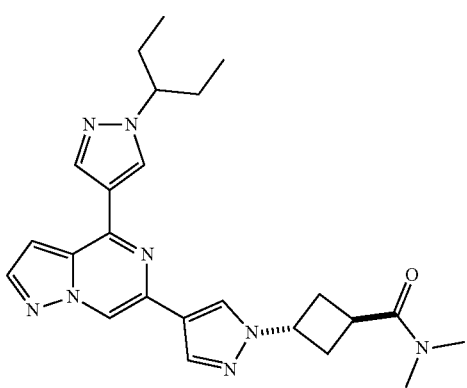 | 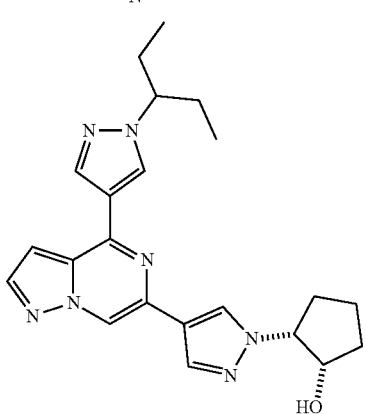 |

-continued and pharmaceutically acceptable salts thereof.

20. The method according to claim 1, wherein the disease or disorder is selected from:
   (i) arthritis;
   (ii) intestinal inflammations;
   (iii) airways diseases;
   (iv) allergic reactions;
   (v) eye diseases, disorders or conditions;
   (vi) skin diseases, conditions or disorders;
   (vii) sepsis, systemic inflammatory response syndrome, and neutropenic fever;
   (viii) fibrosis;
   (ix) gout;
   (x) lupus and manifestations of lupus;
   (xi) neurodegenerative diseases;
   (xii) diabetes and complications from diabetes; metabolic syndrome and obesity;
   (xii) axial spondyloarthorpathy (axial SpA); and
   (xiv) interferon type 1 activation disorders.

21. The method of claim 20, wherein the disease or disorder is selected from:
   (i) arthritis;
   (ii) intestinal inflammations;
   (vi) skin diseases; and
   (x) lupus and manifestations or lupus.

22. The method according to claim 1, wherein said compound of Formula I is formulated for oral administration.

23. The method according to claim 22, wherein said compound of Formula I is formulated as a tablet or capsule.

24. The method according to claim 1, further comprising administering an additional therapy or therapeutic agent.

25. The method according to claim 24, wherein the additional therapeutic agent is selected from the group consisting of cyclosporin A, rapamycin, tacrolimus, leflunomide, deoxyspergualin, mycophenolate, daclizumab, OKT3, AtGam, aspirin, acetaminophen, ibuprofen, naproxen, piroxicam, antiinflammatory steroids, methotrexate, statins, anti-TNF agents, abatacept, cyclophosphamide, mycophenolic acid, hydroxychloroquine, and metformin.

* * * * *